US008895580B2

(12) United States Patent
Beshore et al.

(10) Patent No.: US 8,895,580 B2
(45) Date of Patent: Nov. 25, 2014

(54) QUINOLINONE-PYRAZOLONE M1 RECEPTOR POSITIVE ALLOSTERIC MODULATORS

(75) Inventors: Douglas C. Beshore, Lower Gwynedd, PA (US); Scott D. Kuduk, Harleysville, PA (US); Robert M. DiPardo, Lansdale, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 142 days.

(21) Appl. No.: 13/499,335

(22) PCT Filed: Oct. 1, 2010

(86) PCT No.: PCT/US2010/051113

§ 371 (c)(1), (2), (4) Date: Mar. 30, 2012

(87) PCT Pub. No.: WO2011/049731

PCT Pub. Date: Apr. 28, 2011

(65) Prior Publication Data

US 2012/0196845 A1 Aug. 2, 2012

Related U.S. Application Data

(60) Provisional application No. 61/253,629, filed on Oct. 21, 2009.

(51) Int. Cl.

*A61K 31/4745* (2006.01)
*A61K 31/5377* (2006.01)
*C07D 519/00* (2006.01)
*C07D 471/04* (2006.01)
*C07D 473/00* (2006.01)
*C07D 487/02* (2006.01)
*C07D 495/04* (2006.01)
*A61K 31/535* (2006.01)

(52) U.S. Cl.

CPC ............ *C07D 473/00* (2013.01); *C07D 487/02* (2013.01); *C07D 495/04* (2013.01); *A61K 31/535* (2013.01); *C07D 471/04* (2013.01)
USPC .......................................... 514/293; 546/293

(58) Field of Classification Search

CPC ... A61K 31/535; C07D 471/04; C07D 495/04
USPC ............................................ 546/82; 514/293
See application file for complete search history.

(56) References Cited

U.S. PATENT DOCUMENTS

| | | | | |
|---|---|---|---|---|
| 4,312,870 | A * | 1/1982 | Yokoyama .................... | 514/293 |
| 4,690,930 | A * | 9/1987 | Takada et al. ................. | 514/293 |
| 5,580,877 | A | 12/1996 | Macleod | |
| 6,765,011 | B2 | 7/2004 | Sui et al. | |

FOREIGN PATENT DOCUMENTS

| | | | |
|---|---|---|---|
| EP | 22078 | * | 1/1981 |
| EP | 0182165 | | 5/1986 |
| EP | 0323325 | | 7/1989 |
| EP | 0022078 | * | 1/1991 |
| EP | 0478964 | | 1/1995 |
| WO | WO9110664 | | 7/1991 |
| WO | WO2004073639 | | 9/2004 |
| WO | WO2005107463 | | 11/2005 |
| WO | WO2008154442 | | 12/2008 |

OTHER PUBLICATIONS

Crespo et al , 2000, Synthesis and Biological evaluation of 2, 5-dihydropyrazolo[4,3-c]quinolin-3-ones . . . .*

Wang et al , 1995, Computer-Aided Molecular modeling, Synthesis, and Biological Evaluation of 8-(Benzyloxy)-2-phenylpyrazozlo[4,3-c]quinoline . . . .*

Manera Clementina et al, 2007, New 1,8-naphthyridine and quinoline derivatives as CB2 selective agonists.*

Susumu Takada et al ,Tthienylpyrazoloquinolines; potent Agonists and Inverse Agonists to Benzodiazepine receptors. 1988.*

R. M. Eglen et al., "Therapeutic Opportunities from Muscarinic Receptor Research", 2001, pp. 409-414, vol. 22, No. 8, Trends in Pharmacological Sciences.

A. Fisher, Therapeutic Strategies in Alzheimer's Disease: M1 Muscarinic Agonists, 2000, pp. 101-112, vol. 84, Jpn. J. Pharmacol.

(Continued)

*Primary Examiner* — Rita Desai

(74) *Attorney, Agent, or Firm* — Sylvia A. Ayler; John C. Todaro

(57) ABSTRACT

The present invention is directed to quinolinone-pyrazolone compounds of formula (I) which are M1 receptor positive allosteric modulators and that are useful in the treatment of diseases in which the M1 receptor is involved, such as Alzheimer's disease, schizophrenia, pain or sleep disorders. The invention is also directed to pharmaceutical compositions comprising the compounds, and to the use of the compounds and compositions in the treatment of diseases mediated by the M1 receptor.

(I)

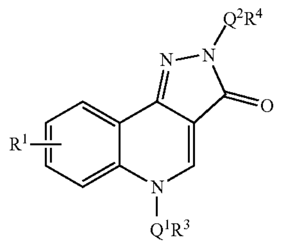

17 Claims, No Drawings

(56) References Cited

OTHER PUBLICATIONS

T. A. Spalding et al., "Discovery of an Ectopic Activation Site on the M1 Muscarinic Receptor", 2002, pp. 1297-1302, Molecular Pharmacology.
S. Lazareno et al., "Analogs of WIN 62.577 Define a Second Allosteric Site on Muscarinic Receptors", 2002, pp. 1492-1505, vol. 62, Molecular Pharmacology.
S. Lazareno et al., "Allosteric Interactions of Staurosporine and Other Indolocarbazoles with N-[methyl-3-H] Scopolamine and Acetylcholine at Muscarinic Receptor Subtypes: Identification of a Second Allosteric Site",2000, pp. 194-207, vol. 58, Molecular Pharmacology.
M. P. Caulfield, "Muscarinic Receptors-Characterization, Coupling and Function", 1993, pp. 319-379, vol. 58, Pharma. Ther.
N. J. M. Birdsall et al., "Multiple Allosteric Sites on Muscarinic Receptors", 2001, pp. 2517-2524, vol. 68, Life Sciences.
A. Christopoulos et al., "Allosteric Binding Sites on Cell-Surface Receptors: Novel Targets for Drug Discovery", 2002, pp. 198-210, Natural Reviews, Drug Discovery.
H. Brauner-Osborne et al., "Pharmacology of Muscarinic Acetylcholine Receptor Subtypes (ml-m5): High Throughput Assays in Mammalian Cells". 1996, vol. 295, pp. 93-102, E. Journal of Pharmacology.
Crespo et al., "Synthesis and Biological Evaluation of 2,5-Dihydropyrazolo[4-3-c]Quinolin-3-Ones, a Novel Series of PDE 4 Inhibitors with Low Emetic Potential and Antiasthmatic Properties", Bioorganic & Medicinal Chemistry Letters, vol. 10, No. 23, Dec. 4, 2000, pp. 2661-2664, XP004219784.
Oliveria et al., "Synthesis and Antiviral Activities of New Pyrazolo[4,3-c]Quinolin-3-Ones and Their Ribonucleoside Derivatives", Nucleosides, Nucleotides and Nucleic Acids, vol. 23, No. 5, 2004, pp. 735-748.
Manera et al., "New 1,8-Naphtyridine and Quinoline Derivatives as CB2 Selective Agonists", Bioorganic & Medicinal Chemistry Letters, vol. 17, No. 23, 2007, p. 6505-6510.
Wang et al., "Computer-Aided Molecular Modeling, Synthesis and Biological Evaluation of 8-(Benzyloxy)-2-Phenylpyrazolo not 4,3-C 3/4 Quinoline as a Novel Benzodiazepine Receptor Agonist Ligand", J. of Medicinal Chemistry, vol. 38, 1995, p. 950-957, XP001019019.

* cited by examiner

QUINOLINONE-PYRAZOLONE M1 RECEPTOR POSITIVE ALLOSTERIC MODULATORS

CROSS REFERENCE TO RELATED APPLICATIONS

This application is the National Stage of International Application No. PCT/US2010/0511131 filed on Oct. 1, 2010, which claims the benefit under 35 U.S.C. 119(e) of U.S. Provisional Application No. 61/253,629, filed Oct. 21, 2009.

FIELD OF THE INVENTION

The invention is directed to a class of quinolinone-pyrazolone compounds, their salts, pharmaceutical compositions comprising them and their use in therapy of the human body. In particular, the invention is directed to a class of quinolinone-pyrazolone compounds, which are muscarinic M1 receptor positive allosteric modulators, and hence are useful in the treatment of Alzheimer's Disease and other diseases mediated by the muscarinic M1 receptor.

BACKGROUND OF THE INVENTION

Alzheimer's Disease is a common neurodegenerative disease affecting the elderly, resulting in progressive memory impairment, loss of language and visuospatial skills, and behavior deficits. Characteristics of the disease include degeneration of cholinergic neurons in the cerebral cortex, hippocampus, basal forebrain, and other regions of the brain, neurofibrillary tangles, and accumulation of the amyloid β peptide (Aβ). Aβ is a 39-43 amino acid produced in the brain by processing of the beta-amyloid precursor protein (APP) by the beta-amyloid protein cleaving enzyme ("beta secretase" or "BACE") and gamma-secretase. The processing leads to accumulation of Aβ in the brain.

Cholinergic neurotransmission involves the binding of acetylcholine either to the nicotinic acetylcholine receptor (nAChR) or to the muscarinic acetylcholine receptor (mAChR). It has been hypothesized that cholinergic hypofunction contributes to the cognitive deficits of patients suffering from Alzheimer's Disease. Consequently, acetyl cholinesterase inhibitors, which inhibit acetylcholine hydrolysis, have been approved in the United States for use in the treatment of the cognitive impairments of Alzheimer's Disease patients. While acetyl cholinesterase inhibitors have provided some cognitive enhancement in Alzheimer's Disease patients, the therapy has not been shown to change the underlying disease pathology.

A second potential pharmacotherapeutic target to counteract cholinergic hypofunction is the activation of muscarinic receptors. Muscarinic receptors are prevalent throughout the body. Five distinct muscarinic receptors (M1-M5) have been identified in mammals. In the central nervous system, muscarinic receptors are involved in cognitive, behavior, sensory, motor and autonomic functions. The muscarinic M1 receptor, which is prevalent in the cerebral cortex, hippocampus and striatum, has been found to have a major role in cognitive processing and is believed to have a role in the pathophysiology of Alzheimer's Disease. See Eglen et al, *TRENDS in Pharmacological Sciences,* 2001, 22:8, 409-414. In addition, unlike acetyl cholinesterase inhibitors, which are known to provide only symptomatic treatment, M1 agonists also have the potential to treat the underlying disease mechanism of Alzheimer's Disease. The cholinergic hypothesis of Alzheimer's Disease is linked to both β-amyloid and hyperphosphorylated tau protein. Formation of β-amyloid may impair the coupling of the muscarinic receptor with G-proteins. Stimulation of the M1 muscarinic receptor has been shown to increase formation of the neuroprotective αAPPs fragment, thereby preventing the formation of the Aβ peptide. Thus, M1 agonists may alter APP processing and enhance αAPPs secretion. See Fisher, *Jpn J Pharmacol,* 2000, 84:101-112.

However, M1 ligands which have been developed and studied for Alzheimer's Disease have produced side effects common to other muscarinic receptor ligands, such as sweating, nausea and diarrhea. See Spalding et al, *Mol Pharmacol,* 2002, 61:6, 1297-1302.

The muscarinic receptors are known to contain one or more allosteric sites, which may alter the affinity with which muscarinic ligands bind to the primary binding or orthosteric sites. See, e.g., S. Lazareno et al, *Mol Pharmacol,* 2002, 62:6, 1491-1505; S. Lazareno et al, *Mol Pharmacol,* 2000, 58, 194-207.

Thus the compounds of the invention, which are muscarinic M1 receptor positive allosteric modulators, are believed to be useful in the treatment of Alzheimer's Disease and other diseases mediated by the muscarinic M1 receptor.

SUMMARY OF THE INVENTION

The present invention is directed to quinolinone-pyrazolone compounds of generic formula (I)

(I)

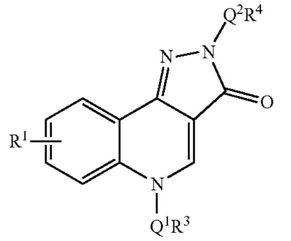

or a pharmaceutically acceptable salt thereof, which is useful as an M1 receptor positive allosteric modulator.

The invention is further directed to methods of treating a patient (preferably a human) for diseases or disorders in which the M1 receptor is involved, such as Alzheimer's disease, cognitive impairment, schizophrenia, pain disorders and sleep disorders, by administering to the patient a therapeutically effective amount of a compound of general formula (I), or a pharmaceutically acceptable salt thereof. The invention is also directed to pharmaceutical compositions which include an effective amount of a compound of formula (I), or a pharmaceutically acceptable salt thereof, and a pharmaceutically acceptable carrier, and the use of the compounds and pharmaceutical compositions of the invention in the treatment of such diseases.

DETAILED DESCRIPTION OF THE INVENTION

In one embodiment, the invention is directed to quinolinone-pyrazolone compounds of general formula (I)

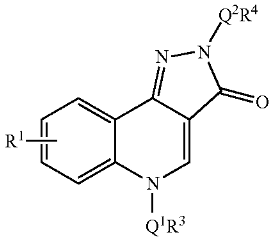
(I)

and pharmaceutically acceptable salts thereof, wherein $R^1$ is optionally present at one or more of the phenyl moiety ring carbon atoms, and each $R^1$ is selected from the group consisting of (1) halogen,
(2) —$C_{1-6}$ alkyl,
(3) —O—$C_{1-6}$ alkyl,
(4) hydroxyl,
(5) —O—C(═O)—$R^7$,
(6) —O—S(═O)$_2$—$R^7$,
(7) —NH—$C_{1-4}$alkyl-$C_{6-10}$ aryl-heteroaryl, wherein the heteroaryl is an aromatic cyclic group, having from five to twelve ring atoms, said ring atoms selected from C, O, N, N→O, C(═O) or S, at least one of which is O, N, N→O or S, and
(8) —CN;

$Q^1$ is selected from the group consisting of (1) —$(CH_2)_n$—, or
(2) —$(CH_2)_n$—C(═O)—;

$R^3$ is selected from the group consisting of (1) —$C_{6-10}$ aryl,
(2) heteroaryl, wherein the heteroaryl is an aromatic cyclic group, having from five to twelve ring atoms, said ring atoms selected from C, O, N, N→O, C(═O) or S, at least one of which is O, N, N→O or S,
(3) a heterocyclic group having 4 to 8 ring atoms selected from C, O, N, N→O, C(═O), $SO_2$ or S, at least one of which is O, N, N→O, $SO_2$ or S,
(4) —$C_{3-8}$ alkyl,
(5) —$C_{3-8}$ cycloalkyl, wherein each alkyl, aryl, heteroaryl or heterocyclic is optionally substituted with one or more $R^5$ group;

$R^5$ is selected from the group consisting of (1) halogen,
(2) —$C_{1-6}$ alkyl,
(3) —$C_{3-8}$ alkenyl,
(4) —O—$C_{1-6}$ alkyl,
(5) hydroxyl,
(6) —C(═O)—$(O)_m$—$R^7$,
(7) NH—C(═O)—$R^7$,
(8) —$C_{3-8}$ cycloalkyl,
(9) —S(═O)$_2$—$R^7$,
(10) —NH—S(═O)$_2$—$R^7$,
(11) —$NO_2$,
(12) —CN;
(13) $C_{6-10}$ aryl,
(14) heteroaryl, which is an aromatic cyclic or polycyclic group, having from five to twelve ring atoms, said ring atoms selected from C, O, N, N→O, C(═O) or S, at least one of which is O, N, N→O or S,
(15) —$NR^9R^{10}$,
(16) —$B(OH)_2$, wherein said alkyl, cycloalkyl, aryl or heteroaryl $R^5$ group is optionally substituted with one or more (a) halogen,
(b) —$C_{1-6}$ alkyl,
(c) —$C_{3-8}$ cycloalkyl,
(d) —$NR^{11}R^{12}$,
(e) —O—$C_{1-6}$ alkyl,
(f) $C_{6-10}$ aryl,
(g) CN,
(h) hydroxyl
(i) —C(═O)—O—$R^7$,
(j) —NH—C(═O)—$R^7$,
(k) —S(═O)$_2$—$R^7$,
(l) —NH—S(═O)$_2$—$R^7$, wherein said alkyl or aryl is optionally substituted with one or more (i) halogen,
(ii) hydroxyl,
(iii) —$NR^{13}R^{14}$;

$Q^2$ is selected from the group consisting of (1) —$(CH_2)_n$—,
(2) —$(CH_2)_n$—C(═O)—,
(3) —C(═O)—O—,
(4) —C(N)—, or
(5) —$(CF_{12})_p$—O—;

$R^4$ is selected from the group consisting of (1) hydrogen
(2) —$C_{6-10}$ aryl,
(3) heteroaryl, which is an aromatic cyclic or polycyclic group, having from five to twelve ring atoms, said ring atoms selected from C, O, N, N→O, C(═O) or S, at least one of which is O, or S,
(4) a heterocyclic group having 4 to 8 ring atoms selected from C, O, N, N→O, C(═O), $SO_2$ or S, at least one of which is O, N, N→O, $SO_2$ or S,
(5) —$C_{3-8}$ alkyl,
(6) —$C_{3-8}$ alkenyl,
(7) —$C_{3-8}$ cycloalkyl,
(8) —$C_{3-8}$ cycloalkenyl,
(9) —$NR^9R^{10}$ wherein each alkyl, aryl, heteroaryl or heterocyclic is optionally substituted with one or more $R^6$ group;

$R^6$ is selected from the group consisting of (1) halogen,
(2) —$C_{1-6}$ alkyl,
(3) —$C_{3-8}$ alkenyl,
(4) —O—$C_{1-6}$ alkyl,
(5) hydroxyl,
(6) —C(═O)—$(O)_m$—$R^7$,
(7) —O—C(═O)—$NR^9R^{10}$,
(8) —O—C(═O)—$R^7$,
(9) —NH—C(═O)—$R^7$,
(10) —NH—C(═O)—$OR^7$,
(11) —$C_{3-8}$ cycloalkyl,
(12) —S(═O)$_2$—$R^7$,
(13) —S(═O)$_2$—$OR^7$,
(14) —S(═O)$_2$—$NR^9R^{10}$,
(15) —NH—S(═O)$_2$—$R^7$,
(16) —$NO_2$,
(17) —CN;
(18) —$C_{6-10}$ aryl,
(19) —O—$C_{6-10}$ aryl,
(20) heteroaryl, which is an aromatic cyclic or polycyclic group, having from five to twelve ring atoms, said ring atoms selected from C, O, N, N→O, C(═O) or S, at least one of which is O, N, N→O or S,
(21) —$NR^9R^{10}$, wherein said alkyl, cycloalkyl, aryl or heteroaryl $R^5$ group is optionally substituted with one or more (a) halogen,
(b) —$C_{1-6}$ alkyl,
(c) —$NR^{11}R^{12}$,
(d) —O—$C_{1-6}$ alkyl,
(e) —$C_{6-10}$ aryl,
(f) heteroaryl, which is an aromatic cyclic or polycyclic group, having from five to twelve ring atoms, said ring atoms selected from C, O, N, N→O, C(═O), $SO_2$ or S, at least one of which is O, N, N→O, $SO_2$ or S,
(g) CN,
(h) hydroxyl wherein said alkyl, aryl or heteroaryl is optionally substituted with one or more
(i) halogen,
(ii) hydroxyl,
(iii) —$NR^{13}R^{14}$;

$R^7$ is selected from the group consisting of
(1) hydrogen,
(2) —$C_{1-6}$ alkyl;
(3) —$C_{3-8}$ cycloalkyl;
(4) —$C_{2-6}$ alkenyl;
(5) —$C_{0-2}$ alkyl-$C_{6-10}$ aryl,
(6) —$C_{0-2}$ alkyl-heteroaryl group, wherein the heteroaryl is an aromatic cyclic or polycyclic group, having from five to twelve ring atoms, said ring atoms selected from C, O, N, N→O, C(═O) or S, at least one of which is O, N, N→O, or S, wherein said alkyl, alkenyl, aryl or heteroaryl $R^7$ group is optionally substituted with one or more
(a) halogen,
(b) hydroxy,
(c) —O—$C_{1-6}$ alkyl,
(d) —$C_{1-6}$ alkyl, optionally substituted with halogen;

$R^9$ and $R^{10}$, or $R^{11}$ and $R^{12}$, or $R^{13}$ and $R^{14}$ are each independently selected from the group consisting of
(1) hydrogen,
(2) —$C_{1-6}$ alkyl,
(3) —$C_{3-8}$ cycloalkyl, or
(4) —$C_{6-10}$ aryl, wherein said alkyl, cycloalkyl or aryl is optionally substituted with one or more
(a) halogen,
(b) —$C_{1-6}$ alkyl,
(c) —$C_{3-8}$ cycloalkyl,
(d) —N(—$C_{1-6}$ alkyl$)_2$,
(e) —O—$C_{1-6}$ alkyl,
(f) —$C_{6-10}$ aryl,
(g) heteroaryl, which is an aromatic cyclic or polycyclic cyclic, having from five to twelve ring atoms, said ring atoms selected from C, O, N, N→O, C(═O), $SO_2$ or S, at least one of which is O, N, N→O, $SO_2$ or S,
(h) CN,
(i) hydroxyl
(i) —C(═O)—O—$R^7$,
(j) —NH—C(═O)—$R^7$,
(k) —S(═O$)_2$—$R^7$,
(l) —NH—S(═O$)_2$—$R^7$, or $R^9$ and $R^{10}$, or $R^{11}$ and $R^{12}$, or $R^{13}$ and $R^{14}$ are linked together with the nitrogen to which they are both attached to form a 4-8 membered carbocyclic ring, wherein one or two of the ring carbon atoms is replaced by a nitrogen, oxygen or sulfur, and the carbocyclic is optionally substituted with one or more
(a) halogen,
(b) —$C_{1-6}$ alkyl,
(c) —O—$C_{1-6}$ alkyl, or
(d) —$C_{6-10}$ aryl, m is 0 or 1;
n is 0, 1 or 2;
p is 0, 1 or 2.

In one embodiment of the compounds of formula (I), $R^1$ is absent.

In another embodiment of the compounds of formula (I), $R^1$ is present at one or two of the phenyl moiety ring carbon atoms, and are each selected from the group consisting of
(1) halogen,
(2) —$C_{1-6}$ alkyl, or
(3) —O—$C_{1-6}$ alkyl.

In another embodiment of the compounds of formula (I), $R^1$ is present at one of the phenyl moiety ring carbon atoms, and is selected from the group consisting of
(1) halogen,
(2) —$C_{1-6}$ alkyl, or
(3) —O—$C_{1-6}$ alkyl.

In one embodiment of the compounds of formula (I), $Q^1$ is —$(CH_2)_n$—, wherein n is 0 or 1.

In one embodiment of the compounds of formula (I), $R^3$ is selected from the group consisting of
(1) —$C_{6-10}$ aryl (preferably phenyl),
(2) heteroaryl, which is an aromatic cyclic or polycyclic group, having from five to twelve ring atoms, said ring atoms selected from C, O, N, N→O, C(═O) or S, at least one of which is O, N, N→O or S,
(3) a heterocyclic group having 4 to 8 ring atoms selected from C, O, N, N→O, C(═O), $SO_2$ or S, at least one of which is O, N, N→O, $SO_2$ or S,
(4) —$C_{3-8}$ alkyl,
(5) —$C_{3-8}$ cycloalkyl, wherein each alkyl, aryl, heteroaryl or heterocyclic is optionally substituted with one or more $R^5$ groups.

Exemplary $R^3$ aryl groups are phenyl, naphthyl, indanyl and dihydroindanyl.

One exemplary $R^3$ heteroaryl group is heteroaryls having five ring atoms, the ring atoms selected from C, N, N→O and S, wherein one, two, three or four of the ring atoms is N, N→O or S (for example, imidazolyl, pyrazolyl, pyrrolyl, triazolyl, oxazolyl, triazolyl, thienyl and furanyl).

Another exemplary $R^3$ heteroaryl group is heteroaryls having six ring atoms, the ring atoms selected from C, N, N→O and S, wherein one or two of the ring atoms is N, N→O or S (for example, pyridyl, pyridyl N-oxide and pyrimidine). For example, in certain embodiments $R^3$ is pyridyl.

Another exemplary $R^3$ heteroaryl group is fused heteroaryls having nine or ten ring atoms, the ring atoms selected from C, O, N, N→O and S, wherein one, two or three of the ring atoms is N, N→O, O or S (for example, indole, quinoline, isoquinoline, tetrahydronaphthyridinyl, benzothiophene, benzimidazole, purine and benzotriazole).

Suitable $R^3$ heterocyclic groups are heterocyclic moieties having from 4 to 8 ring atoms selected from the group consisting of C, C(═O), N, O, $SO_2$ and S, wherein at least one ring atom is a heteroatom selected from N, O, $SO_2$ or S. Exemplary $R^4$ heterocyclic groups are piperidine, piperazines, benzodioxan, tetrahyropyran, tetrahydrofuran, dioxin and morpholine.

In one embodiment of the compounds of formula (I), $R^5$ is present at one or more of the ring atoms, and is selected from the group consisting of
(1) halogen,
(2) —$C_{1-6}$ alkyl,
(3) —O—$C_{1-6}$ alkyl,
(4) hydroxyl,
(5) —C(═O)—$(O)_m$—$R^7$,
(6) —NH—C(═O)—$R^7$, (7) $—NH—S(=O)_2—R^7$, (8) $—NO_2$, (9) —CN;

(10) $C_{6-10}$ aryl,

(11) heteroaryl, which is an aromatic cyclic or polycyclic group, having from five to twelve ring atoms, said ring atoms selected from C, O, N, N→O, C(=O) or S, at least one of which is O, N, N→O or S,

(12) $—NR^9R^{10}$, wherein said alkyl, cycloalkyl, aryl or heteroaryl $R^5$ group is optionally substituted with one or more (a) halogen, (b) $—C_{1-6}$ alkyl, (c) $—C_{3-8}$ cycloalkyl, (d) $—NR^{11}R^{12}$, (e) $—O—C_{1-6}$ alkyl, (f) $C_{6-10}$ aryl, (g) CN, (h) hydroxyl (i) $—C(=O)—O—R^7$, (j) $—NH—C(=O)—R^7$, (k) $—S(=O)_2—R^7$, (l) $—NH—S(=O)_2—R^7$, wherein said alkyl or aryl is optionally substituted with one or more (i) halogen, (ii) hydroxyl, or (iii) $—NR^{11}R^{12}$.

In other embodiments, $R^5$ is present at one or more of the ring atoms, and is selected from the group consisting of (1) halogen, (2) $—C_{1-6}$ alkyl, (3) $—O—C_{1-6}$ alkyl, (4) $C_{6-10}$ aryl (suitably phenyl), (5) heteroaryl, which is an aromatic cyclic or polycyclic group, having from five to twelve ring atoms, said ring atoms selected from C, O, N, N→O, C(=O) or S, at least one of which is O, N, N→O or S, or (6) $—NR^9R^{10}$, wherein said alkyl, cycloalkyl, aryl or heteroaryl. $R^5$ group is optionally substituted with one or more (a) halogen, (b) $—C_{1-6}$ alkyl, (c) $—C_{3-8}$ cycloalkyl, (d) $—NR^{11}R^{12}$, (e) $—O—C_{1-6}$ alkyl, (f) $C_{6-10}$ aryl, (g) CN, (h) hydroxyl (i) $—C(=O)—O—R^7$, (j) $—NH—C(=O)—R^7$, (k) $—S(=O)_2—R^7$, (l) $—NH—S(=O)_2—R^7$, wherein said alkyl or aryl is optionally substituted with one or more (i) halogen, (ii) hydroxyl, or (iii) $—NR^{11}R^{12}$.

One exemplary $R^5$ heteroaryl group is heteroaryls having five ring atoms, the ring atoms selected from C, N, N→O and S, wherein one, two, three or four of the ring atoms is N, N→O, or S (for example, imidazolyl, triazolyl, oxadiazolyl, isothiazolyl, pyrazolyl, thiazolyl, oxazolyl, triazolyl, thienyl and furanyl).

Another exemplary $R^5$ heteroaryl group is heteroaryls having six ring atoms, the ring atoms selected from C, N, N→O and S, wherein one or two of the ring atoms is N, N→O or S (for example, pyridyl).

Another exemplary $R^5$ heteroaryl group is fused heteroaryls having nine or ten ring atoms, the ring atoms selected from C, O, N, N→O and S, wherein one, two or three of the ring atoms is N, N→O, O or S (for example, indole)

Suitable $R^5$ heterocyclic groups are heterocyclic moieties having from 4 to 8 ring atoms selected from the group consisting of C, C(=O), N, O, $SO_2$ and S, wherein at least one ring atom is a heteroatom selected from N, O, $SO_2$ or S (for example, oxazolidine).

In one embodiment of the compounds of formula (I), $Q^2$ is selected from the group consisting of (1) $—(CH_2)_n—$, (2) $—(CH_2)_n—C(=O)—$, or (3) —C(=O)—O—, wherein n is preferably 0 or 1.

In one embodiment of the compounds of formula (I), $R^4$ is selected from the group consisting of (1) hydrogen (2) $—C_{6-10}$ aryl (preferably phenyl), (3) heteroaryl, which is an aromatic cyclic or polycyclic group, having from five to twelve ring atoms, said ring atoms selected from C, O, N, N→O, C(=O) or S, at least one of which is O, N, N→O or S, (3) a heterocyclic group having 4 to 8 ring atoms, selected from C, O, N, N→O, (C=O), SO2NS, at least one of which is O, N, N→O, $SO_2$ or S, (5) $—C_{3-8}$ alkyl, (6) $—C_{3-8}$ cycloalkyl, (7) $—NR^9R^{10}$ wherein each alkyl, aryl, heteroaryl or heterocyclic is optionally substituted with one or more $R^6$ group.

An exemplary $R^4$ group is phenyl.

One exemplary $R^4$ heteroaryl group is heteroaryls having five ring atoms, the ring atoms selected from C, N, N→O and S, wherein one, two, three or four of the ring atoms is N, N→O, or S (for example, imidazolyl, pyrazolyl, thiazolyl, tetrazolyl, triazolyl and thienyl).

Another exemplary $R^4$ heteroaryl group is heteroaryls having six ring atoms, the ring atoms selected from C, N, N→O and S, wherein one or two of the ring atoms is N, N→O or S (for example, pyridyl, pyridyl N-oxide, pyrimidinyl and pyridazinyl). For example, in certain embodiments $R^4$ is pyridyl.

Another exemplary $R^4$ heteroaryl group is fused heteroaryls having nine or ten ring atoms, the ring atoms selected from C, O, N, N→O and S, wherein one, two or three of the ring atoms is N, N→O, O or S (for example, quinoxaline, quinoline, isoquinoline, indazolyl, quinazolinlyl, purinyl, benzoxazolyl and benzothiazolyl).

Suitable $R^4$ heterocyclic groups are heterocyclic moieties having from 4 to 8 ring atoms selected from the group consisting of C, C(=O), N, O, $SO_2$ and S, wherein at least one ring atom is a heteroatom selected from N, O, $SO_2$ or S. Exemplary $R^4$ heterocyclic groups are piperidine and piperazine.

In one embodiment, the invention is directed to methods of treating a patient (preferably a human) for diseases in which the M1 receptor is involved, such as Alzheimer's Disease, cognitive impairment, schizophrenia, pain disorders and sleep disorders, by administering to the patient a therapeutically effective amount of a compound of general formula (I).

The invention is also directed to the use of a compound of formula (I) for treating diseases or disorders in which the M1 receptor is involved, such as Alzheimer's disease, cognitive impairment, schizophrenia, pain disorders and sleep disorders.

The invention is also directed to medicaments or pharmaceutical compositions for treating diseases or disorders in which the M1 receptor is involved, such as Alzheimer's disease, cognitive impairment, schizophrenia, pain disorders and sleep disorders, which comprise a compound of formula (I), or a pharmaceutically acceptable salt thereof, and a pharmaceutically acceptable carrier.

The invention is further directed to a method for the manufacture of a medicament or a composition for treating diseases or disorders in which the M1 receptor is involved, such as Alzheimer's disease, cognitive impairment, schizophrenia, pain disorders and sleep disorders, comprising combining a compound of formula (I) with one or more pharmaceutically acceptable carriers.

Within the genus of compounds of formula (I), there is a sub-genus of compounds of formula (II):

(II)

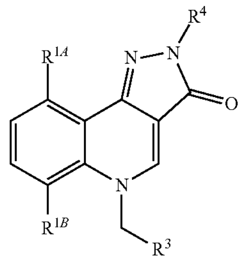

and pharmaceutically acceptable salts thereof, wherein $R^3$ and $R^4$ are as described above, and $R^{1A}$ and $R^{1B}$ are either hydrogen or from the same group as $R^1$.

In one embodiment of the compounds of formula (I), $R^{1A}$ and $R^{1B}$ are each hydrogen.

In another embodiment of the compounds of formula (I), $R^{1A}$ and $R^{1B}$ are each selected from the group consisting of (1) hydrogen, (2) halogen, (3) —$C_{1-6}$ alkyl, or (4) —O—$C_{1-6}$ alkyl.

In one embodiment of the compounds of formula (I), $R^4$ is selected from the group consisting of (1) hydrogen (2) —$C_{6-10}$ aryl (preferably phenyl), (3) heteroaryl, which is a cyclic or polycyclic group having 5 to 12 ring atoms, said ring atoms selected from C, C(═O), N, O or S, wherein at least one ring atom is a heteroatom selected from N, O or S, wherein at least one of the rings is aromatic, (4) a heterocyclic group from 4 to 8 ring atoms selected from the group consisting of C, C(═O), N, O, $SO_2$ and S, wherein at least one ring atom is a heteroatom selected from N, O, $SO_2$ or S;

(5) —$C_{3-8}$ alkyl, (6) —$C_{3-8}$ cycloalkyl, (7) —$NR^9R^{10}$ wherein each alkyl, aryl, heteroaryl or heterocyclic is optionally substituted with one or more $R^6$ group.

An exemplary $R^4$ group is phenyl.

One exemplary $R^4$ heteroaryl group is heteroaryls having five ring atoms, the ring atoms selected from C, N, N→O and S, wherein one, two, three or four of the ring atoms is N, N→O or S (for example, imidazolyl, pyrazolyl, thiazolyl, tetrazolyl, triazolyl and thienyl).

Another exemplary $R^4$ heteroaryl group is heteroaryls having six ring atoms, the ring atoms selected from C, N, N→O and S, wherein one or two of the ring atoms is N, N→O or S (for example, pyridyl, pyridyl N-oxide, pyrimidinyl and pyridazinyl,). For example, in certain embodiments $R^4$ is pyridyl.

Another exemplary $R^4$ heteroaryl group is fused heteroaryls having nine or ten ring atoms, the ring atoms selected from C, O, N, N→O and S, wherein one, two or three of the ring atoms is N, N→O, O or S (for example, quinoxaline, quinoline, isoquinoline, indazolyl, quinazolinlyl, purinyl, benzoxazolyl and benzothiazolyl).

Suitable $R^4$ heterocyclic groups are heterocyclic moieties having from 4 to 8 ring atoms selected from the group consisting of C, C(═O), N, O, $SO_2$ and S, wherein at least one ring atom is a heteroatom selected from N, O, $SO_2$ or S. Exemplary $R^4$ heterocyclic groups are piperidine and piperazine.

In one embodiment of the compounds of formula (I), $R^3$ is selected from the group consisting of (1) —$C_{6-10}$ aryl (preferably phenyl), (2) heteroaryl, which is an aromatic cyclic or polycyclic group, having from five to twelve ring atoms, said ring atoms selected from C, O, N, N→O, C(═O) or S, at least one of which is O, N, N→O or S, (3) a heterocyclic group having 4 to 8 ring atoms selected from C, O, N, N→O, C(═O), $SO_2$ or S, at least one of which is O, N, N→O, $SO_2$ or S, (4) —$C_{3-8}$ alkyl, (5) —$C_{3-8}$ cycloalkyl, wherein each alkyl, aryl, heteroaryl or heterocyclic is optionally substituted with one or more $R^5$ groups.

Exemplary $R^3$ aryl groups are phenyl, naphthyl, indanyl and dihydroindanyl.

One exemplary $R^3$ heteroaryl group is heteroaryls having five ring atoms, the ring atoms selected from C, N, N→O and S, wherein one, two, three or four of the ring atoms is N, N→O or S (for example, imidazolyl, pyrazolyl, pyrrolyl, thiazolyl, oxazolyl, triazolyl, thienyl and furanyl).

Another exemplary $R^3$ heteroaryl group is heteroaryls having six ring atoms, the ring atoms selected from C, N, N→O and S, wherein one or two of the ring atoms is N, N→O or S (for example, pyridyl, pyridyl N-oxide and pyrimidine). For example, in certain embodiments $R^3$ is pyridyl.

Another exemplary $R^3$ heteroaryl group is fused heteroaryls having nine or ten ring atoms, the ring atoms selected from C, O, N, N→O and S, wherein one, two or three of the ring atoms is N, N→O, O or S (for example, indole, quinoline, isoquinoline, tetrahydronaphthyridinyl, benzothiophene, benzimidazole, purine and benzotriazole).

Suitable $R^3$ heterocyclic groups are heterocyclic moieties having from 4 to 8 ring atoms selected from the group consisting of C, C(═O), N, O, $SO_2$ and S, wherein at least one ring atom is a heteroatom selected from N, O or S. Exemplary $R^4$ heterocyclic groups are piperidine, piperazines, benzodioxan, tetrahyropyran, tetrahydrofuran, dioxin and morpholine.

Within the genus of compounds of formula (I), there is a sub-genus of compounds of formula (III):

(III)

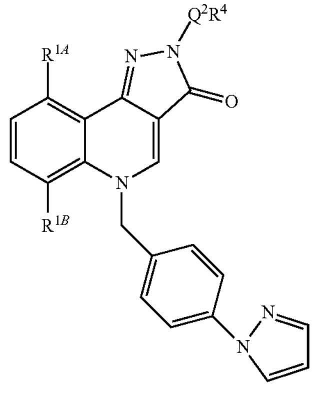

and pharmaceutically acceptable salts thereof, wherein $Q^2$ and $R^4$ are described above, and $R^{1A}$ and $R^{1B}$ are either hydrogen or from the same group as $R^1$.

In one embodiment of the compounds of formula (I), $R^{1A}$ and $R^{1B}$ are each hydrogen.

In another embodiment of the compounds of formula (I), $R^{1A}$ and $R^{1B}$ are each selected from the group consisting of (1) hydrogen, (2) halogen, (3) —$C_{1-6}$ alkyl, or (4) —O—$C_{1-6}$ alkyl.

In one embodiment of the compounds of formula (I), $Q^2$ is selected from the group consisting of (1) —$(CH_2)_n$—, (2) —$(CH_2)_n$—C(═O)—, or (3) —C(═O)—O—, wherein n is preferably 0 or 1.

An exemplary $R^4$ group is phenyl.

One exemplary $R^4$ heteroaryl group is heteroaryls having five ring atoms, the ring atoms selected from C, N, N→O and S, wherein one, two, three or four of the ring atoms is N, N→O or S (for example, imidazolyl, pyrazolyl, thiazolyl, tetrazolyl, triazolyl and thienyl).

Another exemplary $R^4$ heteroaryl group is heteroaryls having six ring atoms, the ring atoms selected from C, N and N→O, wherein one or two of the ring atoms is N or N→O (for example, pyridyl, pyridyl N-oxide, pyrimidinyl and pyridazinyl,). For example, in certain embodiments $R^4$ is pyridyl.

Another exemplary $R^4$ heteroaryl group is fused heteroaryls having nine or ten ring atoms, the ring atoms selected from C, O, N, N→O and S, wherein one, two or three of the ring atoms is N, N→O, O or S (for example, quinoxaline, quinoline, isoquinoline, indazolyl, quinazolinlyl, purinyl, benzoxazolyl and benzothiazolyl).

Suitable $R^4$ heterocyclic groups are heterocyclic moieties having from 4 to 8 ring atoms selected from the group consisting of C, C(═O), N, O, $SO_2$ and S, wherein at least one ring atom is a heteroatom selected from N, O, $SO_2$ or S. Exemplary $R^4$ heterocyclic groups are piperidine and piperazine.

Within the genus of compounds of formula (I), there is a sub-genus of compounds of formula (IV)

(IV)

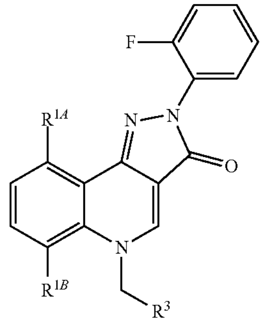

and pharmaceutically acceptable salts thereof, wherein $R^3$ is described above, and $R^{1A}$ and $R^{1B}$ are either hydrogen or from the same group as $R^1$.

In one embodiment of the compounds of formula (I), $R^{1A}$ and $R^{1B}$ are each hydrogen.

In another embodiment of the compounds of formula (I), $R^{1A}$ and $R^{1B}$ are each selected from the group consisting of (1) hydrogen, (2) halogen, (3) —$C_{1-6}$ alkyl, or (4) —O—$C_{1-6}$ alkyl.

In one embodiment of the compounds of formula (I), $R^3$ is selected from the group consisting of (1) —$C_{6-10}$ aryl (preferably phenyl), (2) heteroaryl, which is an aromatic cyclic or polycyclic group, having from five to twelve ring atoms, said ring atoms selected from C, O, N, N→O, C(═O) or S, at least one of which is O, N, N→O or S, (3) a heterocyclic group having 4 to 8 ring atoms selected from C, O, N, N→O, C(═O), $SO_2$ or S, at least one of which is O, N, N→O, $SO_2$ or S, (4) —$C_{3-8}$ alkyl, (5) —$C_{3-8}$ cycloalkyl, wherein each alkyl, aryl, heteroaryl or heterocyclic is optionally substituted with one or more $R^5$ groups.

Exemplary $R^3$ aryl groups are phenyl, naphthyl, indanyl and dihydroindanyl.

One exemplary $R^3$ heteroaryl group is heteroaryls having five ring atoms, the ring atoms selected from C, N, N→O and S, wherein one, two, three or four of the ring atoms is N, N→O or S (for example, imidazolyl, pyrazolyl, pyrrolyl, thiazolyl, oxazolyl, triazolyl, thienyl and furanyl).

Another exemplary $R^3$ heteroaryl group is heteroaryls having six ring atoms, the ring atoms selected from C, N, N→O and S, wherein one or two of the ring atoms is N, N→O or S (for example, pyridyl, pyridyl N-oxide and pyrimidine). For example, in certain embodiments $R^3$ is pyridyl.

Another exemplary $R^3$ heteroaryl group is fused heteroaryls having nine or ten ring atoms, the ring atoms selected from C, O, N, N→O and S, wherein one, two or three of the ring atoms is N, N→O, O or S (for example, indole, quinoline, isoquinoline, tetrahydronaphthyridinyl, benzothiophene, benzimidazole, purine and benzotriazole).

Suitable $R^3$ heterocyclic groups are heterocyclic moieties having from 4 to 8 ring atoms selected from the group consisting of C, C(═O), N, O, $SO_2$ and S, wherein at least one ring atom is a heteroatom selected from N, O or S. Exemplary $R^4$ heterocyclic groups are piperidine, piperazines, benzodioxan, tetrahyropyran, tetrahydrofuran, dioxin and morpholine.

Specific embodiments of formula (I) are described herein as Examples 1-792, and pharmaceutically acceptable salts thereof.

The invention is also directed to methods of treating a patient (preferably a human) for diseases or disorders in which the M1 receptor is involved, such as Alzheimer's Disease, cognitive impairment, schizophrenia, pain disorders and sleep disorders, by administering to the patient a therapeutically effective amount of a compound of formulae (II) and (III), or a pharmaceutically acceptable salt thereof.

The invention is also directed to the use of a compound of formulae (II) to (IV), for treating a disease or disorder in which the M1 receptor is involved, such as Alzheimer's Disease, cognitive impairment, schizophrenia, pain disorders and sleep disorders, by administering to the patient a compound of formulae (II) to (IV), or a pharmaceutically acceptable salt thereof.

The invention is also directed to medicaments or pharmaceutical compositions for the treatment of diseases or disorders in a patient (preferably a human) in which the M1 receptor is involved, such as Alzheimer's Disease, cognitive impairment, schizophrenia, pain disorders, and sleep disorders, which comprise a compound of formulae (II) to (IV), or a pharmaceutically acceptable salt thereof, and a pharmaceutically acceptable carrier.

The invention is also directed to a method for the manufacture of a medicament or a pharmaceutical composition for treating diseases in which M1 receptor is involved, such as Alzheimer's Disease, cognitive impairment, schizophrenia, pain disorders, and sleep disorders, comprising combining a compound of formulae (II) to (IV), or a pharmaceutically acceptable salt thereof, with a pharmaceutically acceptable carrier.

Where a variable occurs more than once in any of formulae (II) to (IV), or in a substituent thereof, the individual occurrences of that variable are independent of each other, unless otherwise specified.

As used herein, the term "alkyl," by itself or as part of another substituent, means a saturated straight or branched chain hydrocarbon radical having the number of carbon atoms designated (e.g., $C_{1-10}$ alkyl means an alkyl group having from one to ten carbon atoms). Preferred alkyl groups for use in the invention are $C_{1-6}$ alkyl groups, having from one to six atoms. Exemplary alkyl groups include methyl, ethyl, n-propyl, isopropyl, n-butyl, isobutyl, tert-butyl, pentyl, hexyl, and the like. $C_0$ alkyl means a bond.

As used herein, the term "cycloalkyl," by itself or as part of another substituent, means a saturated cyclic hydrocarbon radical having the number of carbon atoms designated (e.g., $C_{3-12}$ cycloalkyl means a cycloalkyl group having from three to twelve carbon atoms). The term cycloalkyl as used herein includes mono-, bi- and tricyclic saturated carbocycles, spirocycles, and bridged and fused ring carbocycles.

Preferred cycloalkyl groups for use in the invention are monocyclic $C_{3-8}$ cycloalkyl groups, having from three to eight carbon atoms. Exemplary monocyclic cycloalkyl groups include cyclopropyl, cyclobutyl, cyclopentyl, cyclohexyl and the like. Exemplary bridged cycloalkyl groups include adamantyl and norbornyl. Exemplary fused cycloalkyl groups include decahydronaphthalene.

As used herein, the term "aryl," by itself or as part of another substituent, means an aromatic cyclic hydrocarbon radical. Preferred aryl groups have from six to ten carbons atoms. The term "aryl" includes multiple ring systems as well as single ring systems. Preferred aryl groups for use in the invention include phenyl and naphthyl.

The term "aryl" also includes fused cyclic hydrocarbon rings which are partially aromatic (i.e., one of the fused rings is aromatic and the other is non-aromatic). An exemplary aryl group which is partially aromatic is indanyl.

As used herein, the term "heteroaryl," by itself or as part of another substituent, means a cyclic or polycyclic group having from five to twelve ring atoms selected from C, N, O and S, wherein at least one ring heteroatom is O, N or S, and wherein at least one of the constituent rings is aromatic. Exemplary heteroaryl groups for use in the invention include carbazolyl, carbolinlyl, chromenyl, cinnolinyl, furanyl, benzofuranyl, benzofurazanyl, isobenzofuranyl, imidazolyl, benzimidazolyl, benzimidazolonyl, indazolyl, indolyl, isoindolyl, indolinyl, indolazinyl, indynyl, oxadiazolyl, oxazolyl, benzoxazolyl, isoxazolyl, pyranyl, pyrazinyl, pyrazolyl, benzopyrazolyl, pyridazinyl, pyridyl, pyrimidinyl, pyrrolyl, quinolyl, isoquinolyl, tetrazolyl, thiazolyl, isothiazolyl, thiadiazolyl, thienyl, benzothioenyl, benzothiazolyl, quinoxalinyl, triazinyl and triazolyl, and N-oxides thereof.

One subgroup of heteroaryl groups have 5 ring atoms. Exemplary heteroaryl groups in this embodiment are pyrazolyl, pyridyl, thiazolyl and imidazolyl.

Another subgroup of heteroaryl groups have 6 ring atoms. Exemplary heteroaryl groups in this embodiment are pyridinyl and pyrimidinyl.

The term "heteroaryl" also includes fused cyclic heterocyclic rings which are partially aromatic (i.e., one of the fused rings is aromatic and the other is non-aromatic). An exemplary heteroaryl group which is partially aromatic is benzodioxol.

When a heteroaryl group as defined herein is substituted, the substituent may be bonded to a ring carbon atom of the heteroaryl group, or on a ring heteroatom (i.e., a nitrogen, oxygen or sulfur), which has a valence which permits substitution. Preferably, the substituent is bonded to a ring carbon atom. Similarly, when a heteroaryl group is defined as a substituent herein, the point of attachment may be at a ring carbon atom of the heteroaryl group, or on a ring heteroatom (i.e., a nitrogen, oxygen or sulfur), which has a valence which permits attachment. Preferably, the attachment is at a ring carbon atom.

As used herein, the term "halo" or "halogen" includes fluoro, chloro, bromo and iodo.

The compounds of the invention may have one or more asymmetric centers. Compounds with asymmetric centers give rise to enantiomers (optical isomers), diastereomers (configurational isomers) or both, and it is intended that all of the possible enantiomers and diastereomers in mixtures and as pure or partially purified compounds are included within the scope of this invention. The present invention is meant to encompass all such isomeric forms of the compounds of formulae (I) to (IV).

Formulae (I) to (IV) are shown above without a definite stereochemistry. The present invention includes all stereoisomers of formulae (I) to (IV), and pharmaceutically acceptable salts thereof.

The independent syntheses of the enantiomerically or diastereomerically enriched compounds, or their chromatographic separations, may be achieved as known in the art by appropriate modification of the methodology disclosed herein. Their absolute stereochemistry may be determined by the x-ray crystallography of crystalline products or crystalline intermediates that are derivatized, if necessary, with a reagent containing an asymmetric center of known absolute configuration.

If desired, racemic mixtures of the compounds may be separated so that the individual enantiomers or diastereomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diastereomeric derivatives may then be converted to the pure enantiomers by cleavage of the added chiral residue. The racemic mixture of the compounds can also be separated directly by chromatographic methods using chiral stationary phases, which methods are well known in the art.

Alternatively, any enantiomer or diastereomer of a compound may be obtained by stereoselective synthesis using optically pure starting materials or reagents of known configuration by methods well known in the art.

The compounds of the invention may be prepared according to the following reaction Schemes, in which variables are as defined before or are derived, using readily available starting materials, from reagents and conventional synthetic procedures. It is also possible to use variants which are themselves known to those of ordinary skill in organic synthesis art, but are not mentioned in greater detail.

The present invention also provides a method for the synthesis of compounds useful as intermediates in the preparation of compounds of the invention.

During any of the above synthetic sequences it may be necessary or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973, and T. W. Greene & P/G. M. Wuts, *Protective Groups in Organic Synthesis*, John Wiley & Sons, 1999. The protecting groups may be removed at a convenient sequent stage using methods known from the art.

Specific embodiments of the compounds of the invention, and methods of making them, are described in the Examples herein.

The term "substantially pure" means that the isolated material is at least 90% pure, and preferably 95% pure, and even more preferably 99% pure as assayed by analytical techniques known in the art.

As used herein, the term "muscarinic M1 receptor" refers to one of the five subtypes of the muscarinic acetylcholine receptor, which is from the superfamily of G-protein coupled receptors. The family of muscarinic receptors is described, for example, in *Pharmacol Ther,* 1993, 58:319-379*; Eur J Pharmacol,* 1996, 295:93-102, and *Mol Pharmacol,* 2002, 61:1297-1302. The muscarinic receptors are known to contain one or more allosteric sites, which may alter the affinity with which muscarinic ligands bind to the primary binding or orthosteric sites. See, e.g., S. Lazareno et al, *Mol Pharmacol,* 2002, 62:6, 1491-1505.

As used herein, the terms "positive allosteric modulator" and "allosteric potentiator" are used interchangeably, and refer to a ligand which interacts with an allosteric site of a receptor to activate the primary binding site. The compounds of the invention are positive allosteric modulators of the muscarinic M1 receptor. For example, a modulator or potentiator may directly or indirectly augment the response produced by the endogenous ligand (such as acetylcholine or xanomeline) at the orthosteric site of the muscarinic M1 receptor in an animal, in particular, a human.

The actions of ligands at allosteric receptor sites may also be understood according to the "allosteric ternary complex model," as known by those skilled in the art. The allosteric ternary complex model is described with respect to the family of muscarinic receptors in Birdsall et al, *Life Sciences,* 2001, 68:2517-2524. For a general description of the role of allosteric binding sites, see Christopoulos, *Nature Reviews: Drug Discovery,* 2002, 1:198-210.

It is believed that the compounds of the invention bind to an allosteric binding site that is distinct from the orthosteric acetylcholine site of the muscarinic M1 receptor, thereby augmenting the response produced by the endogenous ligand acetylcholine at the orthosteric site of the M1 receptor. It is also believed that the compounds of the invention bind to an allosteric site which is distinct from the xanomeline site of the muscarinic M1 receptor, thereby augmenting the response produced by the endogenous ligand xanomeline at the orthosteric site of the M1 receptor.

The term "pharmaceutically acceptable salts" refers to salts prepared from pharmaceutically acceptable non-toxic bases or acids including inorganic or organic bases and inorganic or organic acids. The compounds of the invention may be mono, di or tris salts, depending on the number of acid functionalities present in the free base form of the compound. Free bases and salts derived from inorganic bases include aluminum, ammonium, calcium, copper, ferric, ferrous, lithium, magnesium, manganic salts, manganous, potassium, sodium, zinc, and the like.

Salts in the solid form may exist in more than one crystal structure, and may also be in the form of hydrates. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, trifluoroacetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, para-toluenesulfonic acid, and the like.

The present invention is directed to the use of the compounds of formulae (I) to (III) disclosed herein as M1 allosteric modulators in a patient or subject such as a mammal in need of such activity, comprising the administration of an effective amount of the compound. In addition to humans, a variety of other mammals can be treated according to the method of the present invention.

The compounds of the present invention have utility in treating or ameliorating Alzheimer's disease. The compounds may also be useful in treating or ameliorating other diseases mediated by the muscarinic M1 receptor, such as schizophrenia, sleep disorders, pain disorders (including acute pain, inflammatory pain and neuropathic pain) and cognitive disorders (including mild cognitive impairment). Other conditions that may be treated by the compounds of the invention include Parkinson's Disease, pulmonary hypertension, chronic obstructive pulmonary disease (COPD), asthma, urinary incontinence, glaucoma, schizophrenia, Trisomy 21 (Down Syndrome), cerebral amyloid angiopathy, degenerative dementia, Hereditary Cerebral Hemorrhage with Amyloidosis of the Dutch-Type (HCHWA-D), Creutzfeld-Jakob disease, prion disorders, amyotrophic lateral sclerosis, progressive supranuclear palsy, head trauma, stroke, pancreatitis, inclusion body myositis, other peripheral amyloidoses, diabetes, autism and atherosclerosis.

In preferred embodiments, the compounds of the invention are useful in treating Alzheimer's Disease, cognitive disorders, schizophrenia, pain disorders and sleep disorders. For example, the compounds may be useful for the prevention of dementia of the Alzheimer's type, as well as for the treatment of early stage, intermediate stage or late stage dementia of the Alzheimer's type.

Potential schizophrenia conditions or disorders for which the compounds of the invention may be useful include one or more of the following conditions or diseases: schizophrenia or psychosis including schizophrenia (paranoid, disorganized, catatonic or undifferentiated), schizophreniform disorder, schizoaffective disorder, delusional disorder, brief psychotic disorder, shared psychotic disorder, psychotic disorder due to a general medical condition and substance-induced or drug-induced (phencyclidine, ketanine and other dissociative anaesthetics, amphetamine and other psychostimulants and cocaine) psychosispsychotic disorder, psychosis associated with affective disorders, brief reactive psychosis, schizoaffective psychosis, "schizophrenia-spectrum" disorders such as schizoid or schizotypal personality disorders, or illness associated with psychosis (such as major depression, manic depressive (bipolar) disorder, Alzheimer's disease and post-traumatic stress syndrome), including both the positive and the negative symptoms of schizophrenia and other psychoses; cognitive disorders including dementia (associated with Alzheimer's disease, ischemia, multi-infarct dementia, trauma, vascular problems or stroke, HIV disease, Parkinson's disease, Huntington's disease, Pick's disease, Creutzfeldt-Jacob disease, perinatal hypoxia, other general medical conditions or substance abuse); delirium, amnestic disorders or age related cognitive decline.

In another specific embodiment, the present invention provides a method for treating schizophrenia or psychosis comprising administering to a patient in need thereof an effective amount of a compound of the present invention. Particular schizophrenia or psychosis pathologies are paranoid, disorganized, catatonic or undifferentiated schizophrenia and substance-induced psychotic disorder. At present, the text revision of the fourth edition of the Diagnostic and Statistical Manual of Mental Disorders (DSM-IV-TR) (2000, American Psychiatric Association, Washington D.C.) provides a diagnostic tool that includes paranoid, disorganized, catatonic or undifferentiated schizophrenia and substance-induced psychotic disorder. As used herein, the term "schizophrenia or psychosis" includes treatment of those mental disorders as described in DSM-IV-TR. The skilled artisan will recognize that there are alternative nomenclatures, nosologies and classification systems for mental disorders, and that these systems evolve with medical and scientific progress. Thus the term "schizophrenia or psychosis" is intended to include like disorders that are described in other diagnostic sources.

Examples of combinations of the compounds include combinations with agents for the treatment of schizophrenia, for example in combination with sedatives, hypnotics, anxiolytics, antipsychotics, antianxiety agents, cyclopyrrolones, imidazopyridines, pyrazolopyrimidines, minor tranquilizers, melatonin agonists and antagonists, melatonergic agents, benzodiazepines, barbiturates, 5HT-2 antagonists, and the like, such as: adinazolam, allobarbital, alonimid, aiprazolam, amisulpride, amitriptyline, amobarbital, amoxapine, aripiprazole, bentazepam, benzoctamine, brotizolam, bupropion, busprione, butabarbital, butalbital, capuride, carbocloral, chloral betaine, chloral hydrate, clomipramine, clonazepam, cloperidone, clorazepate, chlordiazepoxide, clorethate, chlorpromazine, clozapine, cyprazepam, desipramine, dexclamol, diazepam, dichloralphenazone, divalproex, diphenhydramine, doxepin, estazolam, ethchlorvynol, etomidate, fenobam, flunitrazepam, flupentixol, fluphenazine, flurazepam, fluvoxamine, fluoxetine, fosazepam, glutethimide, halazepam, haloperidol, hydroxyzine, imipramine, lorazepam, lormetazepam, maprotiline, mecloqualone, melatonin, mephobarbital, meprobamate, methaqualone, midaflur, midazolam, nefazodone, nisobamate, nitrazepam, nortriptyline, olanzapine, oxazepam, paraldehyde, paroxetine, pentobarbital, perlapine, perphenazine, phenelzine, phenobarbital, prazepam, promethazine, propofol, protriptyline, quazepam, quetiapine, reclazepam, risperidone, raletamide, secobarbital, sertraline, suproelone, temazepam, thioridazine, thiothixene, tracazolate, tranylcypromaine, trazodone, triazolam, trepipam, tricetamide, triclofos, trifluoperazine, trimetozine, trimipramine, uldazepam, venlafaxine, zaleplon, ziprasidone, zolazepam, zolpidem, and salts thereof, and combinations thereof, and the like, or the subject compound may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists, NMDA receptor antagonists, serotonin receptor antagonists and dopamine receptor agonists such as alentemol, bromocriptine, fenoldopam, lisuride, naxagolide, pergolide and pramipexole. It will be appreciated that the dopamine agonist may be in the form of a pharmaceutically acceptable salt, for example, alentemol hydrobromide, bromocriptine mesylate, fenoldopam mesylate, naxagolide hydrochloride and pergolide mesylate.

In another embodiment, the subject compound may be employed in combination with a compound from the phenothiazine, thioxanthene, heterocyclic dibenzazepine, butyrophenone, diphenylbutylpiperidine and indolone classes of neuroleptic agent. Suitable examples of phenothiazines include chlorpromazine, mesoridazine, thioridazine, acetophenazine, fluphenazine, perphenazine and trifluoperazine. Suitable examples of thioxanthenes include chlorprothixene and thiothixene. An example of a dibenzazepine is clozapine. An example of a butyrophenone is haloperidol. An example of a diphenylbutylpiperidine is pimozide. An example of an indolone is molindolone. Other neuroleptic agents include loxapine, sulpiride and risperidone. It will be appreciated that the neuroleptic agents when used in combination with the subject compound may be in the form of a pharmaceutically acceptable salt, for example, chlorpromazine hydrochloride, mesoridazine besylate, thioridazine hydrochloride, acetophenazine maleate, fluphenazine hydrochloride, flurphenazine enathate, fluphenazine decanoate, trifluoperazine hydrochloride, thiothixene hydrochloride, haloperidol decanoate, loxapine succinate and molindone hydrochloride. Perphenazine, chlorprothixene, clozapine, haloperidol, pimozide and risperidone are commonly used in a non-salt form. Thus, the subject compound may be employed in combination with acetophenazine, alentemol, aripiprazole, amisuipride, benzhexol, bromocriptine, biperiden, chlorpromazine, chlorprothixene, clozapine, diazepam, fenoldopam, fluphenazine, haloperidol, levodopa, levodopa with benserazide, levodopa with carbidopa, lisuride, loxapine, mesoridazine, molindolone, naxagolide, olanzapine, pergolide, perphenazine, pimozide, pramipexole, quetiapine, risperidone, sulpiride, tetrabenazine, frihexyphenidyl, thioridazine, thiothixene, trifluoperazine or ziprasidone.

Potential sleep conditions or disorders for which the compounds of the invention may be useful include enhancing sleep quality; improving sleep quality; augmenting sleep maintenance; increasing the value which is calculated from the time that a subject sleeps divided by the time that a subject is attempting to sleep; decreasing sleep latency or onset (the time it takes to fall asleep); decreasing difficulties in falling asleep; increasing sleep continuity; decreasing the number of awakenings during sleep; decreasing nocturnal arousals; decreasing the time spent awake following the initial onset of sleep; increasing the total amount of sleep; reducing the fragmentation of sleep; altering the timing, frequency or duration of REM sleep bouts; altering the timing, frequency or duration of slow wave (i.e. stages 3 or 4) sleep bouts; increasing the amount and percentage of stage 2 sleep; promoting slow wave sleep; enhancing EEG-delta activity during sleep; increasing daytime alertness; reducing daytime drowsiness; treating or reducing excessive daytime sleepiness; insomnia; hypersomnia; narcolepsy; interrupted sleep; sleep apnea; wakefulness; nocturnal myoclonus; REM sleep interruptions; jet-lag; shift workers' sleep disturbances; dyssomnias; night terror; insomnias associated with depression, emotional/mood disorders, as well as sleep walking and enuresis, and sleep disorders which accompany aging; Alzheimer's sundowning; conditions associated with circadian rhythmicity as well as mental and physical disorders associated with travel across time zones and with rotating shift-work schedules; conditions due to drugs which cause reductions in REM sleep as a side effect; syndromes which are manifested by non-restorative sleep and muscle pain or sleep apnea which is associated with respiratory disturbances during sleep; and conditions which result from a diminished quality of sleep.

Pain disorders for which the compounds of the invention may be useful include neuropathic pain (such as postherpetic neuralgia, nerve injury, the "dynias", e.g., vulvodynia, phantom limb pain, root avulsions, painful diabetic neuropathy, painful traumatic mononeuropathy, painful polyneuropathy); central pain syndromes (potentially caused by virtually any lesion at any level of the nervous system); postsurgical pain syndromes (eg, postmastectomy syndrome, postthoracotomy syndrome, stump pain); bone and joint pain (osteoarthritis), repetitive motion pain, dental pain, cancer pain, myofascial pain (muscular injury, fibromyalgia); perioperative pain (general surgery, gynecological), chronic pain, dysmennorhea, as well as pain associated with angina, and inflammatory pain of varied origins (e.g. osteoarthritis, rheumatoid arthritis, rheumatic disease, teno-synovitis and gout), headache, migraine and cluster headache, headache, primary hyperalgesia, secondary hyperalgesia, primary allodynia, secondary allodynia, or other pain caused by central sensitization.

Compounds of the invention may also be used to treat or prevent dyskinesias. Furthermore, compounds of the invention may be used to decrease tolerance and/or dependence to opioid treatment of pain, and for treatment of withdrawal syndrome of e.g., alcohol, opioids, and cocaine.

The subject or patient to whom the compounds of the present invention is administered is generally a human being, male or female, in whom M1 allosteric modulation is desired, but may also encompass other mammals, such as dogs, cats, mice, rats, cattle, horses, sheep, rabbits, monkeys, chimpanzees or other apes or primates, for which treatment of the above noted disorders is desired.

The compounds of the present invention may be used in combination with one or more other drugs in the treatment of diseases or conditions for which the compounds of the present invention have utility, where the combination of the drugs together are safer or more effective than either drug alone. Additionally, the compounds of the present invention may be used in combination with one or more other drugs that treat, prevent, control, ameliorate, or reduce the risk of side effects or toxicity of the compounds of the present invention. Such other drugs may be administered, by a route and in an amount commonly used therefor, contemporaneously or sequentially with the compounds of the present invention. Accordingly, the pharmaceutical compositions of the present invention include those that contain one or more other active ingredients, in addition to the compounds of the present invention. The combinations may be administered as part of a unit dosage form combination product, or as a kit or treatment protocol wherein one or more additional drugs are administered in separate dosage forms as part of a treatment regimen.

Examples of combinations of the compounds of the present invention include combinations with anti-Alzheimer's Disease agents, for example beta-secretase inhibitors; alpha 7 nicotinic agonists; ADAM 10 ligands or activators; gamma-secretase inhibitors; gamma secretase modulators; tau phosphorylation inhibitors; glycine transport inhibitors; LXR β agonists; ApoE4 conformational modulators; NR2B antagonists; androgen receptor modulators; blockers of Aβ oligomer formation; 5-HT4 agonists; 5-HT6 antagonists; 5-HT1a antagonists, such as lecozotan; p25/CDK5 inhibitors; NK1/NK3 receptor antagonists; COX-2 inhibitors; HMG-CoA reductase inhibitors; NSAIDs including ibuprofen; vitamin E; anti-amyloid antibodies (including anti-amyloid humanized monoclonal antibodies), such as bapineuzumab; anti-inflammatory compounds such as (R)-flurbiprofen, nitroflurbiprofen; PPAR gamma agonists, such as pioglitazone and rosiglitazone; CB-1 receptor antagonists or CB-1 receptor inverse agonists; antibiotics such as doxycycline and rifampin; N-methyl-D-aspartate (NMDA) receptor antagonists, such as memantine and neramexane; cholinesterase inhibitors such as galantamine, rivastigmine, donepezil, tacrine, phenserine and ladostigil; growth hormone secretagogues such as ibutamoren, ibutamoren mesylate, and capromorelin; histamine $H_3$ receptor antagonists; AMPA agonists or AMPA modulators; PDE IV inhibitors; PDE10A inhibitors; $GABA_A$ inverse agonists; GSK3β inhibitors; neuronal nicotinic agonists; selective M1 agonists; HDAC inhibitors; and microtubule affinity regulating kinase (MARK) ligands; or other drugs that affect receptors or enzymes that either increase the efficacy, safety, convenience, or reduce unwanted side effects or toxicity of the compounds of the present invention.

Examples of combinations of the compounds include combinations with agents for the treatment of pain, for example non-steroidal anti-inflammatory agents, such as aspirin, diclofenac, duflunisal, fenoprofen, flurbiprofen, ibuprofen, indomethacin, ketoprofen, ketorolac, naproxen, oxaprozin, piroxicam, sulindac and tolmetin; COX-2 inhibitors, such as celecoxib, rofecoxib and valdecoxib; CB-2 agonists; VR-1 antagonists; bradykinin B1 receptor antagonists; sodium channel blockers and antagonists; nitric oxide synthase (NOS) inhibitors (including iNOS and nNOS inhibitors); glycine site antagonists, including lacosamide; neuronal nicotinic agonists; NMDA antagonists; potassium channel openers; AMPA/kainate receptor antagonists; calcium channel blockers, such as ziconotide; GABA-A receptor IO modulators (e.g., a GABA-A receptor agonist); matrix metalloprotease (MMP) inhibitors; thrombolytic agents; opioid analgesics such as codeine, fentanyl, hydromorphone, levorphanol, meperidine, methadone, morphine, oxycodone, oxymorphone, pentazocine, propoxyphene; neutrophil inhibitory factor (NIF); pramipexole, ropinirole; anticholinergics; amantadine; monoamine oxidase B15 ("MAO-B") inhibitors; 5HT receptor agonists or antagonists; mGlu5 antagonists; alpha agonists; neuronal nicotinic agonists; NMDA receptor agonists or antagonists; NKI antagonists; selective serotonin reuptake inhibitors ("SSRI") and/or selective serotonin and norepinephrine reuptake inhibitors ("SSNRI"), such as duloxetine; tricyclic antidepressant drugs, norepinephrine modulators; lithium; valproate; gabapentin; pregabalin; rizatriptan; zolmitriptan; naratriptan and sumatriptan.

The compounds of the present invention may be administered in combination with compounds useful for enhancing sleep quality and preventing and treating sleep disorders and sleep disturbances, including e.g., sedatives, hypnotics, anxiolytics, antipsychotics, antianxiety agents, antihistamines, benzodiazepines, barbiturates, cyclopyrrolones, orexin antagonists, alpha-1 antagonists, GABA agonists, 5HT-2 antagonists including 5HT-2A antagonists and 5HT-2A/2C antagonists, histamine antagonists including histamine H3 antagonists, histamine H3 inverse agonists, imidazopyridines, minor tranquilizers, melatonin agonists and antagonists, melatonergic agents, other orexin antagonists, orexin agonists, prokineticin agonists and antagonists, pyrazolopyrimidines, T-type calcium channel antagonists, triazolopyridines, and the like, such as: adinazolam, allobarbital, alonimid, alprazolam, amitriptyline, amobarbital, amoxapine, armodafinil, APD-125, bentazepam, benzoctamine, brotizolam, bupropion, busprione, butabarbital, butalbital, capromorelin, capuride, carbocloral, chloral betaine, chloral hydrate, chlordiazepoxide, clomipramine, clonazepam, cloperidone, clorazepate, clorethate, clozapine, conazepam, cyprazepam, desipramine, dexclamol, diazepam, dichloralphenazone, divalproex, diphenhydramine, doxepin, EMD-281014, eplivanserin, estazolam, eszopiclone, ethchlorynol, etomidate, fenobam, flunitrazepam, flurazepam, fluvoxamine, fluoxetine, fosazepam, gaboxadol, glutethimide, halazepam, hydroxyzine, ibutamoren, imipramine, indiplon, lithium, lorazepam, lormetazepam, LY-156735, maprotiline, MDL-100907, mecloqualone, melatonin, mephobarbital, meprobamate, methaqualone, methyprylon, midaflur, midazolam, modafinil, nefazodone, NGD-2-73, nisobamate, nitrazepam, nortriptyline, oxazepam, paraldehyde, paroxetine, pentobarbital, perlapine, perphenazine, phenelzine, phenobarbital, prazepam, promethazine, propofol, protriptyline, quazepam, ramelteon, reclazepam, roletamide, secobarbital, sertraline, suproclone, TAK-375, temazepam, thioridazine, tiagabine, tracazolate, tranylcypromaine, trazodone, triazolam, trepipam, tricetamide, triclofos, trifluoperazine, trimetozine, trimipramine, uldazepam, venlafaxine, zaleplon, zolazepam, zopiclone, zolpidem, and salts thereof, and combinations thereof, and the like, or the compound of the present invention may be administered in conjunction with the use of physical methods such as with light therapy or electrical stimulation.

In another embodiment, the subject compound may be employed in combination with levodopa (with or without a selective extracerebral decarboxylase inhibitor such as carbidopa or benserazide), anticholinergics such as biperiden (optionally as its hydrochloride or lactate salt) and trihexyphenidyl (benzhexyl)hydrochloride, COMT inhibitors such as entacapone, MOA-B inhibitors, antioxidants, A2a adenosine receptor antagonists, cholinergic agonists and dopamine receptor agonists such as alentemol, bromocriptine, fenoldopam, lisuride, naxagolide, pergolide and pramipexole.

The term "composition" as used herein is intended to encompass a product comprising specified ingredients in predetermined amounts or proportions, as well as any product which results, directly or indirectly, from combination of the specified ingredients in the specified amounts. This term in relation to pharmaceutical compositions is intended to encompass a product comprising one or more active ingredients, and an optional carrier comprising inert ingredients, as well as any product which results, directly or indirectly, from combination, complexation or aggregation of any two or more of the ingredients, or from dissociation of one or more of the ingredients, or from other types of reactions or interactions of one or more of the ingredients.

In general, pharmaceutical compositions are prepared by uniformly and intimately bringing the active ingredient into association with a liquid carrier or a finely divided solid carrier or both, and then, if necessary, shaping the product into the desired formulation. In the pharmaceutical composition the active compound, which is a compound of formulae (I) to (VIII), is included in an amount sufficient to produce the desired effect upon the process or condition of diseases. Accordingly, the pharmaceutical compositions of the present invention encompass any composition made by admixing a compound of the present invention and a pharmaceutically acceptable carrier.

The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion or as a water-in-oil liquid emulsion. In addition to the common dosage forms set out above, the compounds of the invention, or pharmaceutically acceptable salts thereof, may also be administered by controlled release means and/or delivery devices.

Pharmaceutical compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be, for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example magnesium stearate, stearic acid or talc. The tablets may be uncoated or they may be coated by known techniques to delay disintegration and absorption in the gastrointestinal tract and thereby provide a sustained action over a longer period.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.1 mg to about 500 mg of the active ingredient and each cachet or capsule preferably containing from about 0.1 mg to about 500 mg of the active ingredient.

Compositions for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Other pharmaceutical compositions include aqueous suspensions, which contain the active materials in admixture with excipients suitable for the manufacture of aqueous suspensions. In addition, oily suspensions may be formulated by suspending the active ingredient in a vegetable oil, for example arachis oil, olive oil, sesame oil or coconut oil, or in a mineral oil such as liquid paraffin. Oily suspensions may also contain various excipients. The pharmaceutical compositions of the invention may also be in the form of oil-in-water emulsions, which may also contain excipients such as sweetening and flavoring agents.

The pharmaceutical compositions may be in the form of a sterile injectable aqueous or oleaginous suspension, or in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi.

Pharmaceutical compositions of the present invention can be in a fault suitable for topical use such as, for example, an aerosol, cream, ointment, lotion, dusting powder, or the like. Further, the compositions can be in a form suitable for use in transdermal devices. These formulations may be prepared via conventional processing methods. As an example, a cream or ointment is prepared by mixing hydrophilic material and water, together with about 5 wt % to about 10 wt % of the compound, to produce a cream or ointment having a desired consistency.

Pharmaceutical compositions of this invention can also be in a form suitable for rectal administration wherein the carrier is a solid. It is preferable that the mixture forms unit dose suppositories. Suitable carriers include cocoa butter and other materials commonly used in the art.

By "pharmaceutically acceptable" it is meant the carrier, diluent or excipient must be compatible with the other ingredients of the formulation and not deleterious to the recipient thereof.

The terms "administration of" or "administering a" compound should be understood to mean providing a compound of the invention to the individual in need of treatment in a form that can be introduced into that individual's body in a therapeutically useful form and therapeutically useful amount, including, but not limited to: oral dosage forms, such as tablets, capsules, syrups, suspensions, and the like; injectable dosage forms, such as IV, IM, or IP, and the like; transdermal dosage forms, including creams, jellies, powders, or patches; buccal dosage forms; inhalation powders, sprays, suspensions, and the like; and rectal suppositories.

The terms "effective amount" or "therapeutically effective amount" means the amount of the subject compound that will elicit the biological or medical response of a tissue, system, animal or human that is being sought by the researcher, veterinarian, medical doctor or other clinician.

As used herein, the term "treatment" or "treating" means any administration of a compound of the present invention and includes (I) inhibiting the disease in an animal that is experiencing or displaying the pathology or symptomatology of the diseased (i.e., arresting further development of the pathology and/or symptomatology), or (2) ameliorating the disease in an animal that is experiencing or displaying the pathology or symptomatology of the diseased (i.e., reversing the pathology and/or symptomatology).

The compositions containing compounds of the present invention may conveniently be presented in unit dosage form and may be prepared by any of the methods well known in the art of pharmacy. The term "unit dosage form" is taken to mean a single dose wherein all active and inactive ingredients are combined in a suitable system, such that the patient or person administering the drug to the patient can open a single container or package with the entire dose contained therein, and does not have to mix any components together from two or more containers or packages. Typical examples of unit dosage forms are tablets or capsules for oral administration, single dose vials for injection, or suppositories for rectal administration. This list of unit dosage forms is not intended to be limiting in any way, but merely to represent typical examples of unit dosage forms.

The compositions containing compounds of the present invention may conveniently be presented as a kit, whereby two or more components, which may be active or inactive ingredients, carriers, diluents, and the like, are provided with instructions for preparation of the actual dosage form by the patient or person administering the drug to the patient. Such kits may be provided with all necessary materials and ingredients contained therein, or they may contain instructions for using or making materials or components that must be obtained independently by the patient or person administering the drug to the patient.

When treating or ameliorating a disorder or disease for which compounds of the present invention are indicated, generally satisfactory results are obtained when the compounds of the present invention are administered at a daily dosage of from about 0.1 mg to about 100 mg per kg of animal body weight, preferably given as a single daily dose or in divided doses two to six times a day, or in sustained release form. The total daily dosage is from about 1.0 mg to about 2000 mg, preferably from about 0.1 mg to about 20 mg per kg of body weight. In the case of a 70 kg adult human, the total daily dose will generally be from about 7 mg to about 1,400 mg. This dosage regimen may be adjusted to provide the optimal therapeutic response. The compounds may be administered on a regimen of 1 to 4 times per day, preferably once or twice per day.

The amount of active ingredient that may be combined with the carrier materials to produce a single dosage form will vary depending upon the host treated and the particular mode of administration. For example, a formulation intended for the oral administration to humans may conveniently contain from about 0.005 mg to about 2.5 g of active agent, compounded with an appropriate and convenient amount of carrier material. Unit dosage forms will generally contain between from about 0.005 mg to about 1000 mg of the active ingredient, typically 0.005, 0.01 mg, 0.05 mg, 0.25 mg, 1 mg, 5 mg, 25 mg, 50 mg, 100 mg, 200 mg, 300 mg, 400 mg, 500 mg, 600 mg, 800 mg or 1000 mg, administered once, twice or three times a day.

It will be understood, however, that the specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the host undergoing therapy.

Several methods for preparing the compounds of this invention are illustrated in the schemes and examples herein. Starting materials are made according to procedures known in the art or as illustrated herein. The following examples are provided so that the invention might be more fully understood.

potassium carbonate. Conversion to the thioketone 4 may be performed with an agent such as phosphorus pentasulfide at elevated temperatures. Conversion to 5 may be performed in the presence of a suitably substituted hydrazine 7 in the presence of a base, such as potassium carbonate, at elevated temperature. Conversion to 6 can be effected, by treatment of 4 with hydrazine in the presence of a base, such as potassium carbonate, at elevated temperature. Alkylation of 6 can be performed in the presence of a suitably substituted halide ($R^2X$), in the presence of a base, such as sodium hydride, to afford 5. Alternatively, N-arylation of a suitably substituted halide ($R^2X$) can be performed in the presence of a catalyst, such as copper(I) iodide, in the presence of a suitable ligand, such as (±)-trans-N,N'-bismethyl-1,2-cyclohexane diamine, and in the presence of a suitable base, such as potassium phosphate, at elevated temperature. Additionally, 3 may be treated with a chlorinating reagent, such as phosphorus oxy- Generic Scheme 1:

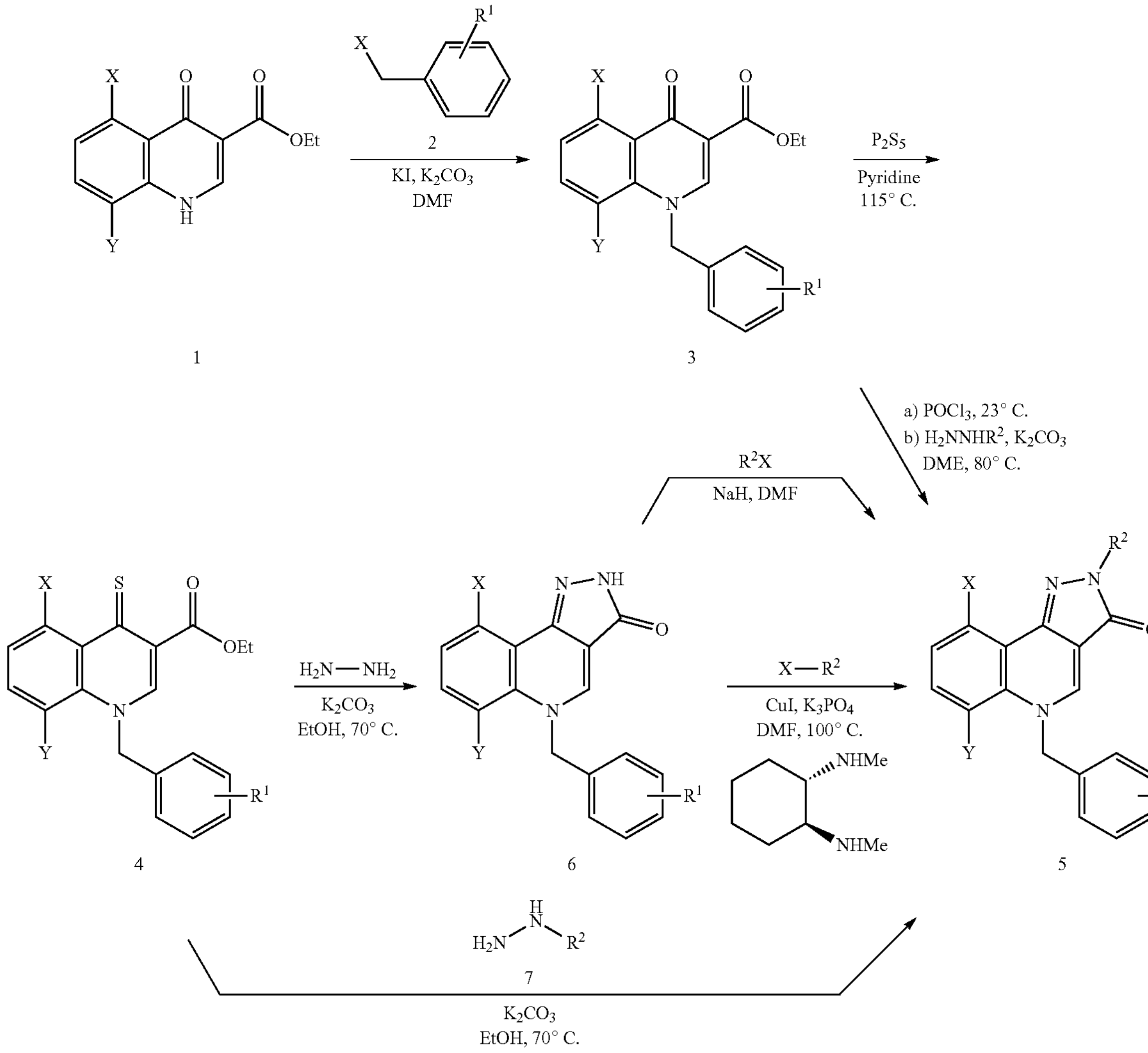

1 3 4 6 5

X = H or F
Y = H or F

Commercially available substituted quinolinone esters, such as 1 (Scheme 1), may be alkylated with benzylic halides (2) to afford 3 in the presence of a suitable base, such as chloride, and converted to the quinolinium salt in situ, which upon treatment with a substituted hydrazine in the presence of a base, such as potassium carbonate, may be converted directly to 5. Depending on the substitution of $R^2$, further chemistries may be carried out, but are not limited to the following: reductive amination, N-arylation and reduction. Depending on the substitution of $R^1$, further chemistry can be carried out, but are not limited to the following: N-arylation, Suzuki-Miyaura and Stille cross-coupling.

Generic Scheme 2:

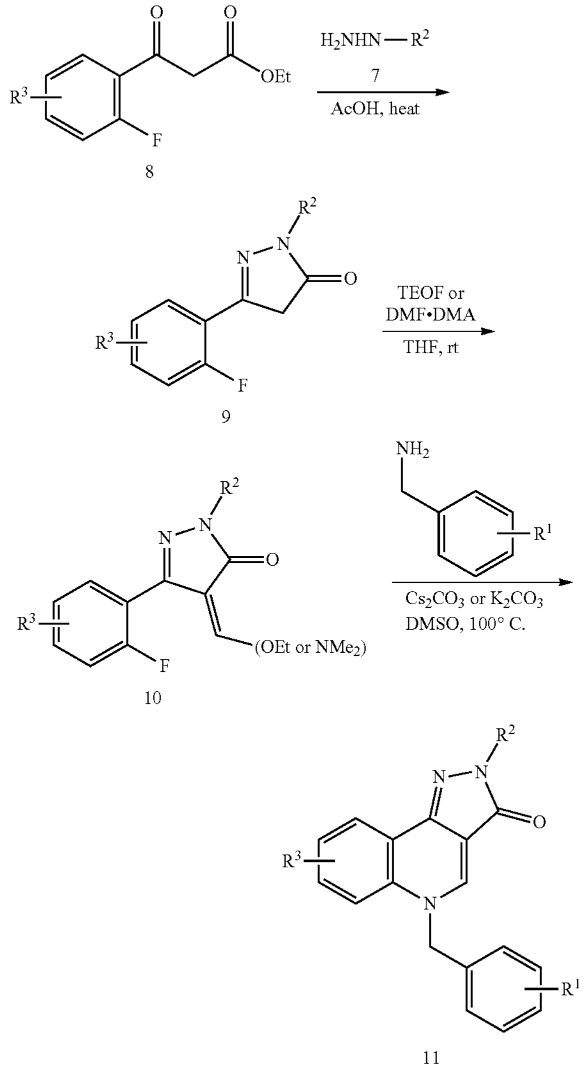

A suitably substituted β-ketoester (8, Scheme 2) can be treated with a substituted hydrazine (7) in a solvent such as acetic acid at elevated temperature to provide 9. Treatment with triethylorthoformate or N,N-dimethylformamide dimethylacetal in a solvent such as tetrahydrofuran can afford 10 as the enamine or enolether, respectively. Treatment of 10 with a suitable substituted amine in the presence of a base, such as cesium or potassium carbonate, in a solvent such as dimethylsulfoxide at elevated temperature can afford 11.

Generic Scheme 3:

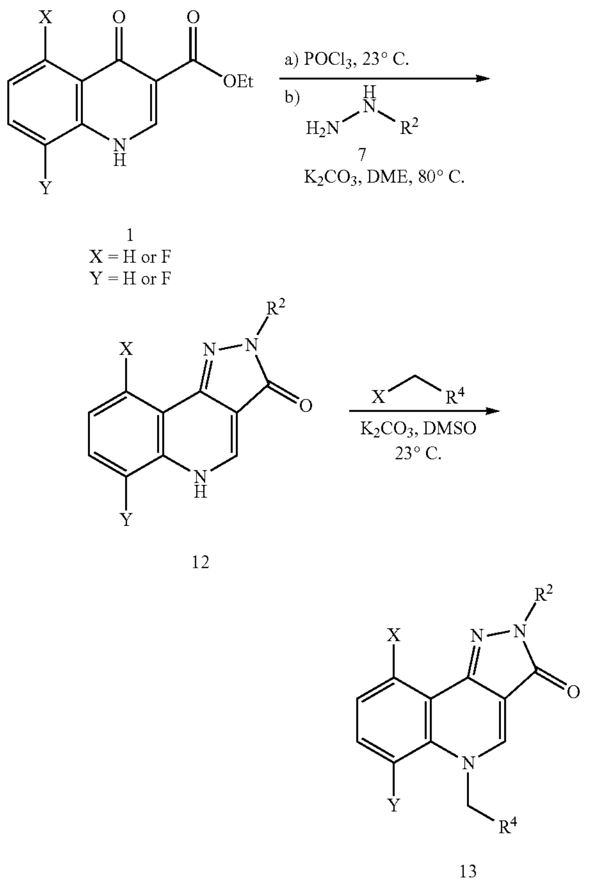

Commercially available substituted quinolinone esters, such as 1 (Scheme 3), may be treated with a chlorinating agent, such as phosphorus oxychloride, to afford the 4-chloroquinoline in situ, which upon treatment with a suitably substituted hydrazine (7) in the presence of a base, such as potassium carbonate at elevated temperature can afford 12. Alkylation of 12 can be performed in the presence of a suitable halide ($R^4CH_2X$) in the presence of a base, such as potassium carbonate, in a solvent such as dimethylsulfoxide to afford 13.

Generic Scheme 4:

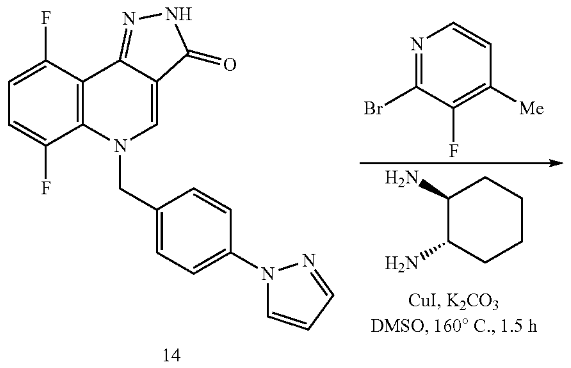

-continued

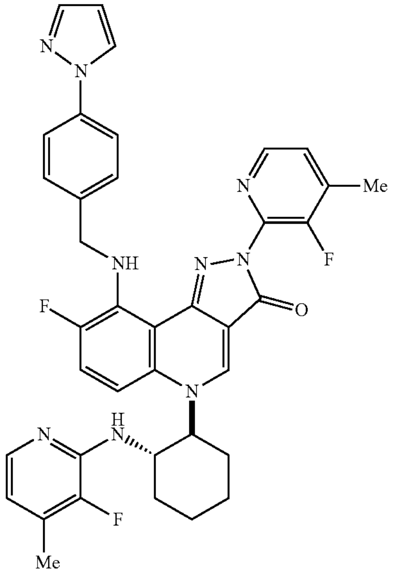

15

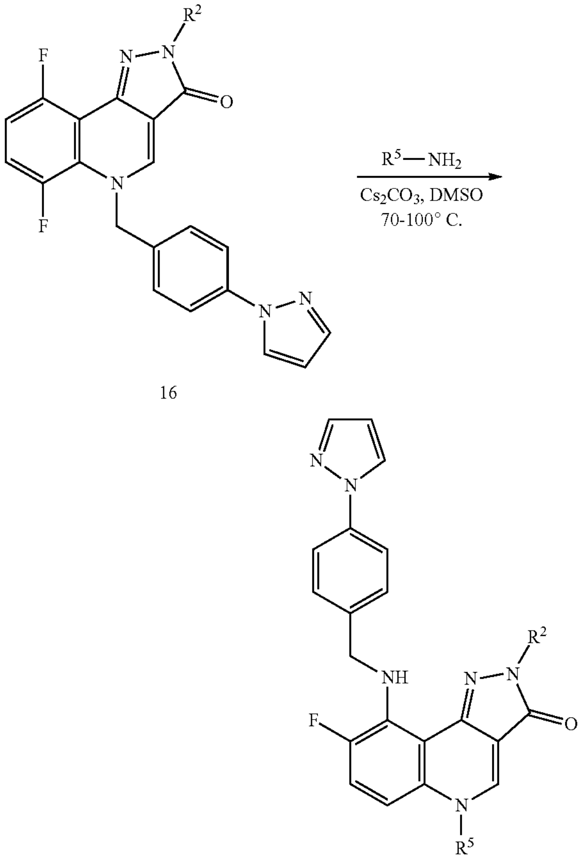

16

17

A compound like 14 (Scheme 4) can be treated with a suitable halide, in the presence of a catalyst, such as copper(I) iodide, in the presence of a base, such as potassium carbonate, in a solvent like dimethylsulfoxide at elevated temperature to afford a rearrangement product like 15. Furthermore, compounds such as 16, can be treated with an amine ($H_2NR^5$) in the presence of a base, such as cesium carbonate, in a solvent such as dimethylsulfoxide at elevated temperature to afford the rearrangement product 17.

The following examples are provided to illustrate the invention and are not to be construed as limiting the scope of the invention in any manner.

Example 1

2-(2-Fluorophenyl)-5-{[4-(methoxy)phenyl]methyl}-2,5-dihydro-3H-pyrazolo[4,3-c]quinolin-3-one

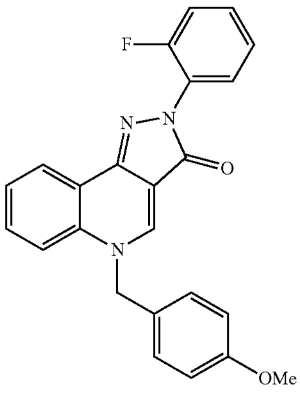 [SMILES: COc1ccc(Cn2cc3c(=O)n(-c4ccccc4F)nc-3c3ccccc32)cc1]

Step 1: Preparation of ethyl {[4-(methoxy)phenyl] methyl}-4-oxo-1,4-dihydroquinoline-3-carboxylate Ethyl 4-oxo-1,4-dihydroquinoline-3-carboxylate (3.17 g, 14.6 mmol) and 4-methoxybenzylchloride (2.18 mL, 16.0 mmol, 1.1 equiv) were combined in N,N-dimethylformamide (50 mL) and stirred at ambient temperature for 72 hours. The mixture was poured into water (500 mL) and extracted with dichloromethane (2×250 mL). The combined organic extracts were dried with sodium sulfate, filtered and concentrated in vacuo. The residue was treated with water (500 mL), hexanes (500 mL) and ethyl acetate (500 mL) and aged for 30 minutes. The mixture was filtered and the solid was dissolved in dichloromethane (500 mL) and combined with the filtrate. The filtrate was partitioned and the aqueous layer was discarded. The organic layer was dried with sodium sulfate, filtered and concentrated in vacuo, providing the titled compound.

Step 2: Preparation of ethyl {[4-(methoxy)phenyl] methyl}-4-thioxo-1,4-dihydroquinoline-3-carboxylate Ethyl {[4-(methoxy)phenyl]methyl}-4-oxo-1,4-dihydroquinoline-3-carboxylate (1.15 g, 3.41 mmol) and phosphorous pentasulfide (758 mg, 3.41 mmol, 1 equiv) were combined in pyridine (10 mL) and placed into an oil bath preheated at 115° C. for 1 hour. The mixture was cooled to ambient temperature, poured into water and extracted with dichloromethane (2×300 mL). The combined organic extracts were washed with sodium thiosulfate (50 mL, aqueous saturated), dried with sodium sulfate, filtered and concentrated in vacuo, providing the titled compound.

Step 3: Preparation of 2-(2-fluorophenyl)-5-{[4-(methoxy)phenyl]methyl}-2,5-dihydro-3H-pyrazolo [4,3-c]quinolin-3-one Ethyl {[4-(methoxy)phenyl]methyl}-4-thioxo-1,4-dihydroquinoline-3-carboxylate (128 mg, 0.362 mmol), 2-fluorophenylhydrazine hydrochloride (88. mg, 0.543 mmol, 1.5 equiv) and potassium carbonate (250 mg, 1.81 mmol, 5 equiv) were combined in absolute ethanol (5 mL) and placed into an oil bath preheated at 70° C. for 14 hours. Additional hydrazine (120 mg, 1.09 mmol, 3 equiv) was added and the mixture was heated for an additional 24 hours at 70° C. The mixture was cooled to ambient temperature, poured into sodium bicarbonate (20 mL, aqueous saturated) and extracted with ethyl acetate (1×75 mL). The organic extract was dried with sodium sulfate, filtered and concentrated in vacuo. The residue was purified by silica gel gradient chromatography (100:0 to 95:5; dichloromethane:methanol), providing the titled compound: $^{1}$H-NMR (500 MHz, d$^{6}$-DMSO) δ 9.10 (1H, s), 8.19 (1H, dd, J=8.0, 1.3 Hz), 7.81 (1H, d, J=8.7 Hz), 7.64-7.58 (2H, m), 7.53 (1H, t, J=7.6 Hz), 7.47-7.43 (1H, m), 7.40 (1H, ddd, J=10.2, 8.3, 1.3 Hz), 7.35-7.31 (1H, m), 7.30 (2H, d, J=8.6 Hz), 6.92 (2H, d, J=8.6 Hz), 5.66 (2H, s), 3.71 (3H, s) ppm; high resolution mass spectrometry (ES+) m/z 400.1461 [(M+H)$^{+}$; calculated for $C_{24}H_{18}FN_3O_2$: 400.1456].

The following compounds were prepared according to the general procedure described in Example 1, substituting the appropriately substituted hydrazine for 2-fluorophenylhydrazine hydrochloride (Step 3). The starting materials are either commercially available, known in the literature or may be prepared from commercially available reagents using conventional reactions well known in the art.

(IA)

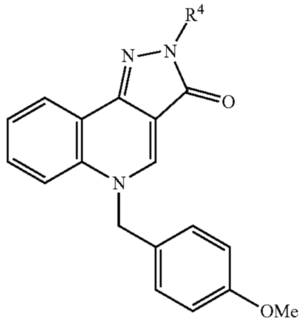

| Ex. | $R^4$ | HRMS/LRMS |
|---|---|---|
| 2 | H | $C_{18}H_{15}N_3O_2$; [M + H]; calc. 306.1237; obs. 306.1241 |
| 3 | Me | $C_{19}H_{18}N_3O_2$; [M + H]; calc. 320.1394 obs. 320.1390 |
| 4 | Ph | $C_{24}H_{20}N_3O_2$; [M + H]; calc. 382.1 obs. 382.1 |
| 5 | Et | $C_{20}H_{20}N_3O_2$; [M + H]; calc. 334.1550 obs. 334.1551 |
| 6 | 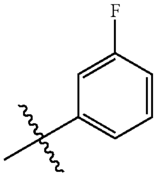 [SMILES: *c1cccc(F)c1] | $C_{24}H_{19}FN_3O_2$; [M + H]; calc. 400.1456; obs. 400.1456 |
| 7 | 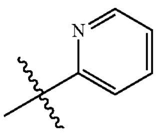 [SMILES: *c1ccccn1] | $C_{23}H_{19}N_4O_2$; [M + H]; calc. 383.1503 obs. 383.1502 |

Example 8

2-(2-Fluorophenyl)-5-(biphenyl-4-ylmethyl)-2,5-dihydro-3H-pyrazolo[4,3-c]quinolin-3-one

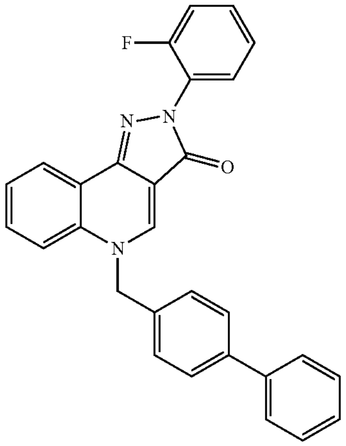 [SMILES: O=c1c2cn(Cc3ccc(-c4ccccc4)cc3)c3ccccc3c-2nn1-c1ccccc1F]

Step 1: Preparation of ethyl 1-(biphenyl-4-ylmethyl)-4-oxo-1,4-dihydroquinoline-3-carboxylate Ethyl 4-oxo-1,4-dihydroquinoline-3-carboxylate (6.11 g, 28.1 mmol), 4-(bromomethyl)biphenyl (9.04 g, 36.6 mmol, 1.3 equiv), potassium iodide (467 mg, 2.81 mmol, 0.1 equiv) and potassium carbonate (9.72 g, 70.3 mmol, 2.5 equiv) were combined in N,N-dimethylformamide (10 mL) and stirred at ambient temperature for 18 hours. The mixture was poured into water (100 mL) and ethyl acetate (100 mL) and aged for 2 hours. The mixture was filtered, the filtrate discarded and the solid was dissolved in dichloromethane (100 mL), dried with sodium sulfate, filtered and concentrated in vacuo, providing the titled compound.

Step 2: Preparation of ethyl 1-(biphenyl-4-ylmethyl)-4-thioxo-1,4-dihydroquinoline-3-carboxylate Ethyl 1-(biphenyl-4-ylmethyl)-4-oxo-1,4-dihydroquinoline-3-carboxylate (474 mg, 1.24 mmol) and phosphorous pentasulfide (275 mg, 1.24 mmol, 1 equiv) were combined in pyridine (10 mL) and placed into an oil bath preheated at 115° C. for 45 minutes. The mixture was cooled to ambient temperature, poured into a 1:1 mixture of sodium bicarbonate (aqueous saturated):sodium thiosulfate (aqueous saturated) and extracted with ethyl acetate (2×100 mL). The combined organic extracts were dried with sodium sulfate, filtered and concentrated in vacuo, providing the titled compound.

Step 3: Preparation of 5-(biphenyl-4-ylmethyl)-2,5-dihydro-3H-pyrazolo[4,3-c]quinolin-3-one Ethyl 1-(biphenyl-4-ylmethyl)-4-thioxo-1,4-dihydroquinoline-3-carboxylate (0.43 g, 1.1 mmol) and hydrazine (38 μL, 1.1 mmol, 1 equiv) were combined in absolute ethanol (10 mL) and placed into a preheated oil bath at 75° C. for 1 hour. The mixture was cooled to ambient temperature and concentrated in vacuo. The residue was purified by silica gel gradient chromatography (100:0 to 90:10; dichloromethane:methanol), providing the titled compound.

Step 4: Preparation of 2-(2-fluorophenyl)-5-(biphenyl-4-ylmethyl)-2,5-dihydro-3H-pyrazolo[4,3-c]quinolin-3-one 5-Biphenyl-4-ylmethyl)-2,5-dihydro-3H-pyrazolo[4,3-c]quinolin-3-one (51 mg, 0.14 mmol), potassium phosphate (77 mg, 0.36 mmol, 2.5 equiv), (±)-trans-N,N'-bismethyl-1,2-cyclohexane diamine (4.1 mg, 0.029 mmol, 0.2 equiv), copper(I) iodide (2.8 mg, 0.015 mmol, 0.1 equiv) and 2-fluoroiodobenzene (17 µL, 0.14 mmol, 1 equiv) were combined in a sealed tube containing N,N-dimethylformamide (2 mL). The mixture was sparged under a nitrogen atmosphere, the vessel was sealed and placed into an preheated oil bath at 110° C. for 15 hours. The mixture was cooled to ambient temperature, poured into sodium bicarbonate (20 mL, aqueous saturated) and extracted with ethyl acetate (2×75 mL). The combined organic extracts were dried with sodium sulfate, filtered and concentrated in vacuo. The residue was purified by silica gel gradient chromatography (100:0 to 95:5; dichloromethane:methanol), providing the titled compound: $^1$H-NMR (500 MHz, d$^6$-DMSO) δ 9.17 (1H, s), 8.21 (1H, dd, J=8.0, 1.4 Hz), 7.80 (1H, d, J=8.6 Hz), 7.66 (2H, d, J=8.2 Hz), 7.64-7.59 (4H, m), 7.54 (1H, t, J=7.4 Hz), 7.46-7.32 (8H, m), 5.79 (2H, s) ppm; high resolution mass spectrometry (ES+) m/z 446.1668 [(M+H)$^+$; calculated for $C_{29}H_{21}FN_3O$: 446.1663].

The following compounds were prepared according to the general procedure described in Example 8, substituting the appropriately substituted iodide or bromide for 2-fluoroiodobenzene (Step 4). The starting materials are either commercially available, known in the literature or may be prepared from commercially available reagents using conventional reactions well known in the art.

(IB)

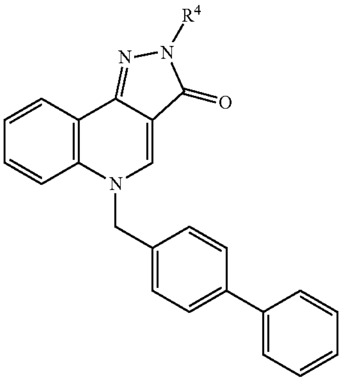

| Ex. | $R^4$ | HRMS/LRMS |
|---|---|---|
| 9 | 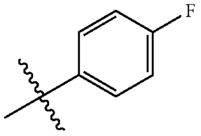 [SMILES: *c1ccc(F)cc1] | $C_{29}H_{21}FN_3O$; [M + H]; calc. 446.1663; obs. 446.1661 |
| 10 | 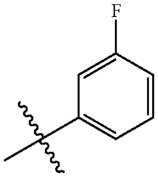 [SMILES: *c1cccc(F)c1] | $C_{29}H_{21}FN_3O$; [M + H]; calc. 446.1663; obs. 446.1662 |

-continued (IB)

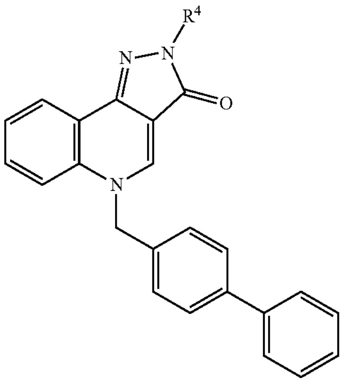

| Ex. | $R^4$ | HRMS/LRMS |
|---|---|---|
| 11 | 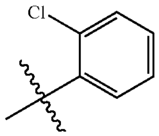 [SMILES: *c1ccccc1Cl] | $C_{29}H_{21}ClN_3O$; [M + H]; calc. 461.1368; obs. 461.1374 |
| 12 | 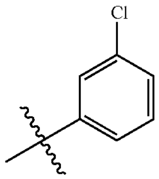 | $C_{29}H_{21}ClN_3O$; [M + H]' calc. 461.1368; obs. 461.1371 |
| 13 | 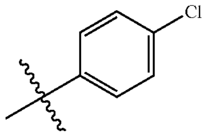 [SMILES: *c1ccc(Cl)cc1] | $C_{29}H_{21}ClN_3O$; [M + H]; calc. 461.1368; obs. 461.1371 |
| 14 | 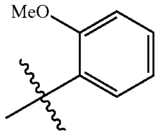 [SMILES: *c1ccccc1OC] | $C_{30}H_{24}N_3O_2$; [M + H]; calc. 458.1863; obs. 458.1876 |
| 15 | 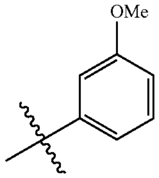 [SMILES: *c1cccc(OC)c1] | $C_{30}H_{24}N_3O_2$; [M + H]; calc. 458.1863; obs. 458.1868 |
| 16 | 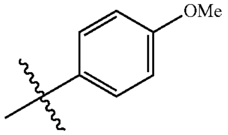 [SMILES: *c1ccc(OC)cc1] | $C_{30}H_{24}N_3O_2$; [M + H]; calc. 458.1863; obs. 458.1870 |
| 17 | 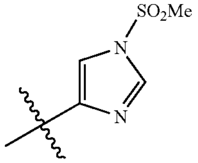 [SMILES: *c1cn(S(C)(=O)=O)cn1] | $C_{28}H_{25}N_6O_3S$; [M + H]; calc. 525.1704; obs. 525.1712 |

-continued (IB)

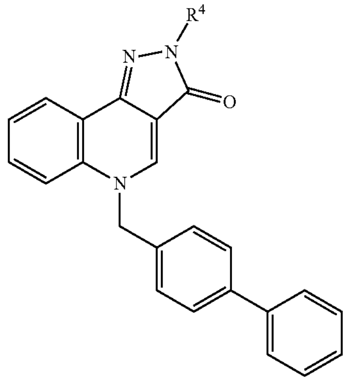

| Ex. | $R^4$ | HRMS/LRMS |
|---|---|---|
| 18 | 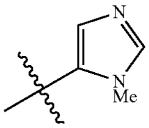 [SMILES: *c1cncn1C] | $C_{27}H_{22}N_5O'$; [M + H]; calc. 432.1819; obs. 432.1834 |
| 19 | 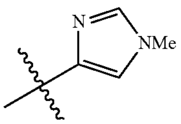 [SMILES: *c1cn(C)cn1] | $C_{27}H_{22}N_5O$; [M + H]; calc. 432.1819; obs. 432.1833 |
| 20 | 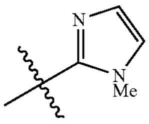 [SMILES: *c1nccn1C] | $C_{27}H_{22}N_5O$; [M + H]; calc. 432.1819; obs. 432.1831 |
| 21 | 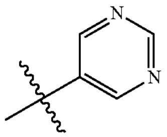 [SMILES: *c1cncnc1] | $C_{27}H_{20}N_5O$; [M + H]; calc. 430.1662; obs. 430.1647 |

Example 22

5-(Biphenyl-4-ylmethyl)-2-phenyl-2,5-dihydro-3H-pyrazolo[4,3-c]quinolin-3-one

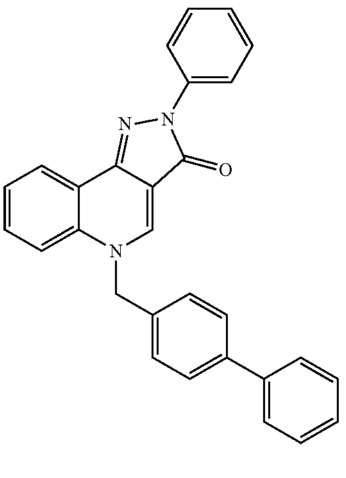 [SMILES: O=c1c2cn(Cc3ccc(-c4ccccc4)cc3)c3ccccc3c-2nn1-c1ccccc1]

Ethyl 1-(biphenyl-4-ylmethyl)-4-thioxo-1,4-dihydroquinoline-3-carboxylate [(Example 8, Step 2), 72 mg, 0.18 mmol] and phenylhydrazine (0.19 g, 1.8 mmol, 10 equiv) were combined in absolute ethanol (5 mL) and placed into a preheated oil bath at 75° C. for 18 hours. The mixture was cooled to ambient temperature and concentrated in vacuo. The residue was dissolved in dichloromethane (10 mL) and treated with di-tert-butyldicarbonate (0.30 g, 1.4 mmol, 7.8 equiv). After stirring for 5 hours at ambient temperature, the mixture was concentrated in vacuo and the residue was purified by silica gel gradient chromatography (100:0 to 95:5; dichloromethane:methanol), providing the titled compound: $^1$H-NMR (500 MHz, $d^6$-DMSO) δ 9.17 (1H, s), 8.31 (1H, dd, J=7.8, 1.4 Hz), 8.22 (2H, d, J=7.6 Hz), 7.81 (1H, d, J=8.8 Hz), 7.67-7.62 (5H, m), 7.57 (1H, t, J=7.8 Hz), 7.48-7.40 (6H, m), 7.35 (1H, t, J=7.4 Hz), 7.20 (1H, t, J=7.4 Hz), 5.80 (2H, s) ppm; high resolution mass spectrometry (ES+) m/z 428.1757 $[(M+H)^+$; calculated for $C_{29}H_{22}N_3O$: 428.1758].

Example 23

5-(Biphenyl-4-ylmethyl)-2-(phenylmethyl)-2,5-dihydro-3H-pyrazolo[4,3-c]quinolin-3-one

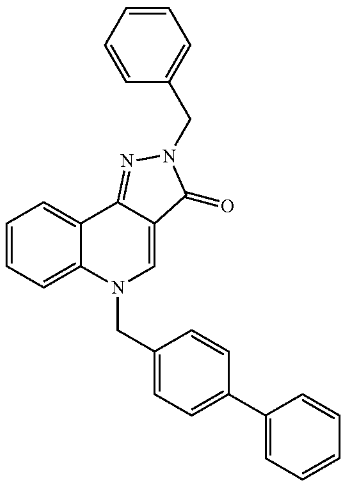 [SMILES: O=c1c2cn(Cc3ccc(-c4ccccc4)cc3)c3ccccc3c-2nn1Cc1ccccc1]

5-Biphenyl-4-ylmethyl)-2,5-dihydro-3H-pyrazolo[4,3-c]quinolin-3-one [(Example 8, Step 3), 110 mg, 0.313 mmol] was dissolved in N,N-dimethylformamide (5 mL), cooled to 0° C. and treated with sodium hydride (37.6 mg, 0.939 mmol, 3 equiv). After stirring for 15 minutes, the mixture was warmed to ambient temperature and stirred for an additional 15 minutes. The mixture was cooled to 0° C., treated with benzyl bromide (0.112 mL, 0.939 mmol, 3 equiv) and after 5 minutes, was warmed to ambient temperature over 2 hours and stirred for an additional 14 hours at ambient temperature. The mixture was poured into water (40 mL) and extracted with ethyl acetate (2×50 mL). The combined organic extracts were dried with sodium sulfate, filtered and concentrated in vacuo. The residue was purified by silica gel gradient chromatography (100:0 to 95:5; dichloromethane:methanol), providing the titled compound: high resolution mass spectrometry (ES+) m/z 442.1922 $[(M+H)^+$; calculated for $C_{30}H_{24}N_3O$: 442.1914].

Example 24

6,9-Difluoro-2-(1-methyl-1H-imidazol-4-yl)-5-{[4-(1H-pyrazol-1-yl)phenyl]methyl}-2,5-dihydro-3H-pyrazolo[4,3-c]quinolin-3-one

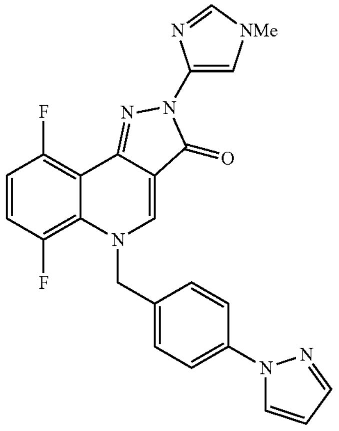 [SMILES: Cn1cnc(-n2nc3c4c(F)ccc(F)c4n(Cc4ccc(-n5cccn5)cc4)cc-3c2=O)c1]

Using the procedures described in Example 8, substituting ethyl 5,8-difluoro-4-oxo-1,4-dihydroquinoline-3-carboxylate for ethyl 4-oxo-1,4-dihydroquinoline-3-carboxylate (Step 1), and, substituting 1-[4-(bromomethyl)phenyl]-1H-pyrazole for 4-(bromomethyl)biphenyl (Step 1), and, substituting 4-iodo-1-methyl-1H-imidazole for 2-fluoroiodobenzene (Step 4), the titled compound was obtained: $^{1}$H-NMR (500 MHz, $d^6$-DMSO) δ 9.01 (1H, s), 8.45 (1H, d, J=2.5 Hz), 7.79 (2H, d, J=8.4 Hz), 7.72 (1H, s), 7.57 (1H, s), 7.52-7.45 (2H, m), 7.42 (1H, td, J=9.0, 3.4 Hz), 7.31 (2H, d, J=8.5 Hz), 6.52 (1H, dd, J=2.5, 1.6 Hz), 5.77 (2H, s), 3.72 (3H, s) ppm; high resolution mass spectrometry (ES+) m/z 458.1530 [(M+H)$^+$; calculated for $C_{24}H_{19}F_2N_7O$: 458.1536].

The following compounds were prepared according to the general procedure described in Example 24, substituting the appropriately substituted iodide or bromide for 4-iodo-1-methyl-1H-imidazole. The starting materials are either commercially available, known in the literature or may be prepared from commercially available reagents using conventional reactions well known in the art.

(IC)

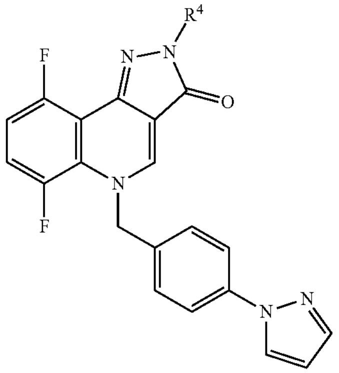

| Ex. | $R^4$ | HRMS/LRMS |
|---|---|---|
| 25 | 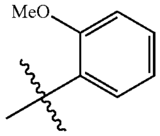 [SMILES: *c1ccccc1OC] | $C_{27}H_{20}F_2N_5O_2$ [M + H] calc. 484.1580 obs. 484.1568 |

-continued (IC)

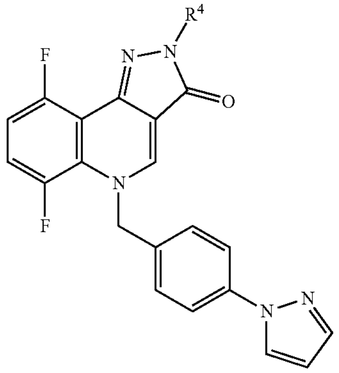

| Ex. | $R^4$ | HRMS/LRMS |
|---|---|---|
| 26 | 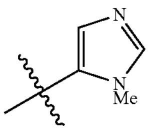 [SMILES: *c1cncn1C] | $C_{24}H_{18}F_2N_7O$ [M + H] calc. 458.1536 obs. 458.1530 |
| 27 | 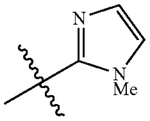 [SMILES: *c1nccn1C] | $C_{24}H_{18}F_2N_7O$ [M + H] calc. 458.1536 obs. 458.1530 |
| 28 | 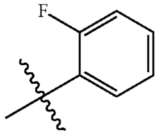 [SMILES: *c1ccccc1F] | $C_{26}H_{17}F_3N_5O$ [M + H] calc. 472.1380 obs. 472.1371 |
| 29 | 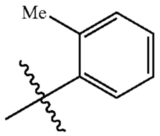 [SMILES: *c1ccccc1C] | $C_{27}H_{20}F_2N_5O$ [M + H] calc. 468.1631 obs. 468.1637 |
| 30 | 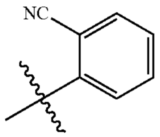 [SMILES: *c1ccccc1C#N] | $C_{27}H_{17}F_2N_6O$ [M + H] calc. 479.1427 obs. 479.1435 |
| 31 | 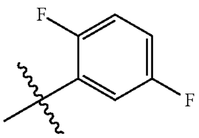 [SMILES: *c1cc(F)ccc1F] | $C_{26}H_{16}F_4N_5O$ [M + H] calc. 490.1286 obs. 490.1300 |
| 32 | 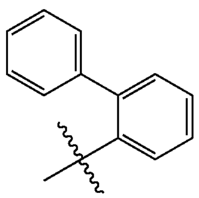 [SMILES: *c1ccccc1-c1ccccc1] | $C_{32}H_{22}F_2N_5O$ [M + H] calc. 530.1787 obs. 530.1796 |

-continued
(IC)
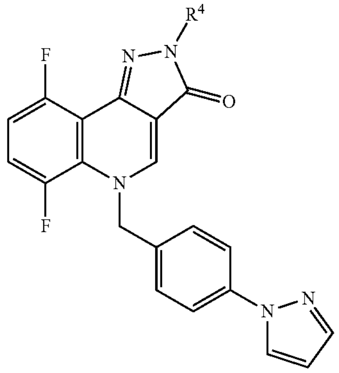
| Ex. | $R^4$ | HRMS/LRMS |
|---|---|---|
| 33 | 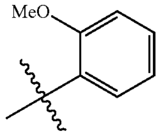 [SMILES: *c1ccccc1OC] | $C_{27}H_{17}F_5N_5O_2$ [M + H] calc. 538.1297 obs. 538.1298 |
| 34 | 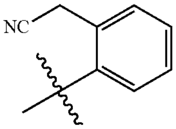 [SMILES: *c1ccccc1CC#N] | $C_{28}H_{19}F_2N_6O$ [M + H] calc. 493.1583 obs. 493.1594 |
| 35 | 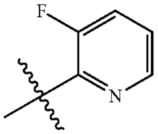 [SMILES: *c1ncccc1F] | $C_{25}H_{16}F_3N_6O$ [M + H] calc. 473.1332 obs. 473.1337 |
| 36 | 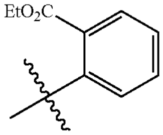 | $C_{29}H_{22}F_2N_5O_3$ [M + H] calc. 526.1685 obs. 526.1695 |
| 37 | 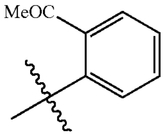 | $C_{28}H_{20}F_2N_5O_2$ [M + H] calc. 496.1580 obs. 496.1591 |
| 38 | 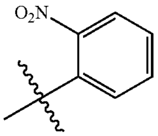 [SMILES: *c1ccccc1[N+](=O)[O-]] | $C_{26}H_{17}F_2N_6O_3$ [M + H] calc. 499.1325 obs. 499.1334 |
| 39 | 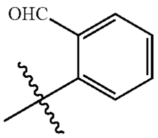 [SMILES: *c1ccccc1C=O] | $C_{27}H_{18}F_2N_5O_2$ [M + H] calc. 482.1423 obs. 482.1406 |
-continued
(IC)
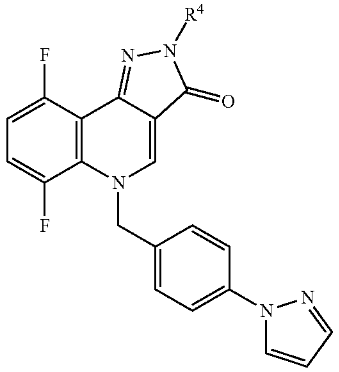
| Ex. | $R^4$ | HRMS/LRMS |
|---|---|---|
| 40 | 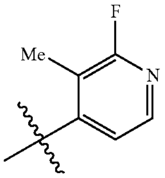 [SMILES: *c1ccnc(F)c1C] | $C_{26}H_{18}F_3N_6O$ [M + H] calc. 487.1489 obs. 487.1484 |
| 41 | 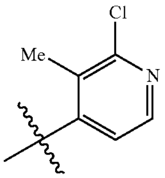 | $C_{26}H_{18}ClF_3N_6O$ [M + H] calc. 503.1193 obs. 503.1194 |
| 42 | 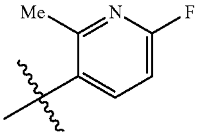 [SMILES: *c1ccc(F)nc1C] | $C_{26}H_{18}F_3N_6O$ [M + H] calc. 487.1489 obs. 487.1503 |
| 43 | 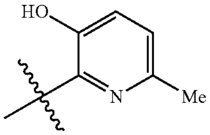 [SMILES: *c1nc(C)ccc1O] | $C_{26}H_{19}F_2N_6O_2$ [M + H] calc. 485.1532 obs. 485.1529 |
| 44 | 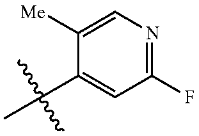 [SMILES: *c1cc(F)ncc1C] | $C_{26}H_{18}F_3N_6O$ [M + H] calc. 487.1489 obs. 487.1480 |
| 45 | 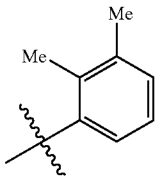 [SMILES: *c1cccc(C)c1C] | $C_{28}H_{22}F_2N_5O$ [M + H] calc. 482.1787 obs. 482.1788 |

-continued (IC)

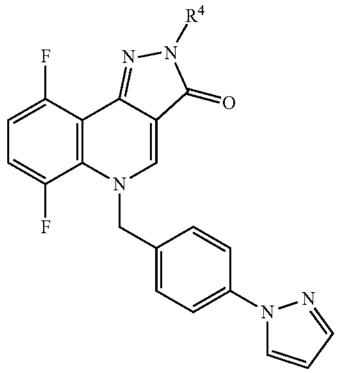

| Ex. | $R^4$ | HRMS/LRMS |
|---|---|---|
| 46 | 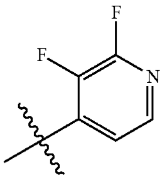 [SMILES: *c1ccnc(F)c1F] | $C_{25}H_{15}F_4N_6O$ [M + H] calc. 491.1238 obs. 491.1230 |
| 47 | 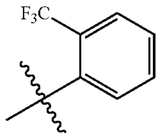 [SMILES: *c1ccccc1C(F)(F)F] | $C_{27}H_{17}F_5N_5O$ [M + H] calc. 522.1348 obs. 522.1349 |
| 48 | 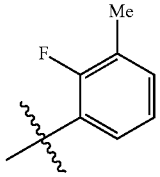 [SMILES: *c1cccc(C)c1F] | $C_{27}H_{19}F_3N_5O$ [M + H] calc. 486.1536 obs. 486.1539 |
| 49 | 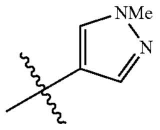 [SMILES: *c1cnn(C)c1] | $C_{24}H_{18}F_2N_7O$ [M + H] calc. 458.1535 obs. 458.1535 |
| 50 | 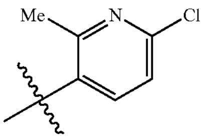 [SMILES: *c1ccc(Cl)nc1C] | $C_{26}H_{18}ClF_2N_6O$ [M + H] calc. 503.1193 obs. 503.1202 |
| 51 | 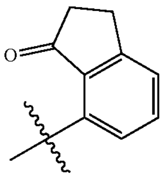 [SMILES: *c1cccc2c1C(=O)CC2] | $C_{29}H_{20}F_2N_5O_2$ [M + H] calc. 508.1580 obs. 508.1586 |

-continued (IC)

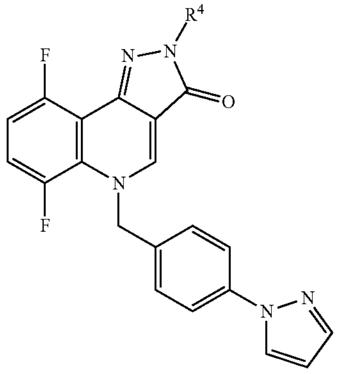

| Ex. | $R^4$ | HRMS/LRMS |
|---|---|---|
| 52 | 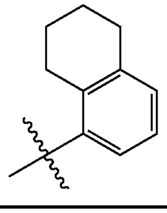 | $C_{30}H_{24}F_2N_5O$ [M + H] calc. 508.1943 obs. 508.1955 |

Example 53

6,9-Difluoro-2-(1-iodophenyl)-5-{[4-(1H-pyrazol-1-yl)phenyl]methyl}-2,5-dihydro-3H-pyrazolo[4,3-c]quinolin-3-one

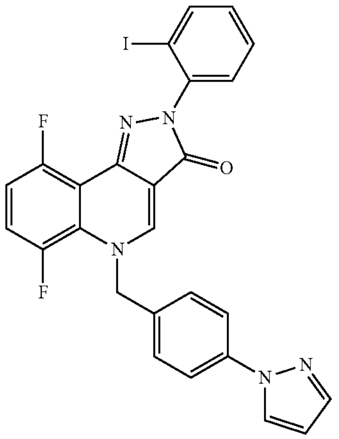 [SMILES: O=c1c2cn(Cc3ccc(-n4cccn4)cc3)c3c(F)ccc(F)c3c-2nn1-c1ccccc1I]

Step 1: Preparation of 5,8-difluoro-4-thioxo-1{[4-(1H-pyrazol-1-yl)phenyl]methyl}-1,4-dihydroquinolinone-3-carboxylate Using the procedures described in Example 8, substituting ethyl 5,8-difluoro-4-oxo-1,4-dihydroquinoline-3-carboxylate for ethyl 4-oxo-1,4-dihydroquinoline-3-carboxylate (Step 1), and, substituting 1-[4-(bromomethyl)phenyl]-1H-pyrazole for 4-(bromomethyl)biphenyl (Step 1), the titled compound was obtained.

Step 2: Preparation of 6,9-difluoro-2-(1-iodophenyl)-5-{[4-(1H-pyrazol-1-yl)phenyl]methyl}-2,5-dihydro-3H-pyrazolo[4,3-c]quinolin-3-one 5,8-Difluoro-4-thioxo-1{[4-(1H-pyrazol-1-yl)phenyl]methyl}-1,4-dihydroquinolinone-3-carboxylate (73 mg, 0.17 mmol) was dissolved in absolute ethanol (8 mL), treated with potassium carbonate (0.14 g, 1.0 mmol, 6 equiv) and 2-iodophenylhydrazine oxylate (72 mg, 0.22 mmol, 1.3 equiv) and placed into an oil bath preheated at 85° C. for 24 hours. The mixture was cooled to ambient temperature, poured into sodium bicarbonate (50 mL, aqueous saturated) and extracted with ethyl acetate (3×100 mL). The combined organic extracts were dried with sodium sulfate, filtered and concentrated in vacuo. The residue was purified by silca gel gradient chromatography (100:0 to 0:100; hexanes:ethyl acetate; then 95:5 ethyl acetate:methanol), providing the titled compound: $^1$H-NMR (400 MHz, d$^6$-DMSO) δ 9.06 (1H, s), 8.46 (1H, d, J=2.4 Hz), 8.03 (1H, J=7.9, 1.2 Hz), 7.82 (2H, d, J=8.6 Hz), 7.73 (1H, d, J=1.6 Hz), 7.58-7.39 (3H, m), 7.33 (2H, d, J=8.7 Hz), 7.25 (1H, td, J=7.6, 1.7 Hz), 6.53 (1H, dd, J=2.4, 1.8 Hz), 5.78 (2H, d, J=3.4 Hz) ppm; high resolution mass spectrometry (ES+) m/z 580.0420 [(M+H)$^+$; calculated for $C_{26}H_{16}F_2IN_5O$: 580.0441].

Example 54

6,9-Difluoro-2-[2-(1H-pyrazol-1-yl)phenyl]-5-{[4-(1H-pyrazol-1-yl)phenyl]methyl}-2,5-dihydro-3H-pyrazolo[4,3-c]quinolin-3-one

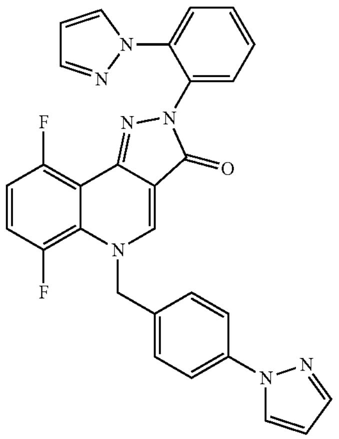 [SMILES: O=c1c2cn(Cc3ccc(-n4cccn4)cc3)c3c(F)ccc(F)c3c-2nn1-c1ccccc1-n1cccn1]

6,9-Difluoro-2-(1-iodophenyl)-5-{[4-(1H-pyrazol-1-yl)phenyl]methyl}-2,5-dihydro-3H-pyrazolo[4,3-c]quinolin-3-one [(Example 53), 36 mg, 0.062 mmol], potassium phosphate (40 mg, 0.19 mmol, 3 equiv), (±)-trans-N,N'-bismethyl-1,2-cyclohexane diamine (7.1 mg, 0.050 mmol, 0.8 equiv), copper(I) iodide (4.7 mg, 0.025 mmol, 0.4 equiv) and pyrazole (8.5 mg, 0.12 mmol, 2 equiv) were combined in dimethylsulfoxide (0.9 mL) and water (0.1 mL). The mixture was sparged under a nitrogen atmosphere, the vessel was sealed and placed into an preheated oil bath at 130° C. for 3 hours. The mixture was cooled to ambient temperature, poured into water (10 mL) and extracted with ethyl acetate (2×50 mL). The combined organic extracts were dried with sodium sulfate, filtered and concentrated in vacuo. The residue was purified by preparative reverse phase HPLC (20:80 to 95:5; water containing 0.1% trifluoroacetic acid:acetonitrile containing 0.1% trifluoroacetic acid). The appropriate fractions were poured into sodium bicarbonate (50 mL, aqueous saturated) and extracted with ethyl acetate (2×50 mL). The combined organic extracts were dried with sodium sulfate, filtered and concentrated in vacuo, providing the titled compound: $^1$H-NMR (400 MHz, d$^6$-DMSO) δ 8.96 (1H, s), 8.46 (1H, d, J=2.6 Hz), 7.81 (2H, d, J=8.7 Hz), 7.76-7.68 (3H, m), 7.64-7.47 (5H, m), 7.40 (1H, td, J=8.9, 3.5 Hz), 7.30 (2H, d, J=8.6 Hz), 6.53 (1H, dd, J=2.4, 2.0 Hz), 6.34 (1H, dd, J=2.4, 1.9 Hz), 5.75 (2H, d, J=3.1 Hz) ppm; high resolution mass spectrometry (ES+) m/z 520.1697 [(M+H)$^+$; calculated for $C_{29}H_{19}F_2N_7O$: 520.1692].

Example 55

6,9-Difluoro-2-[2-(hydroxymethyl)phenyl]-5-{[4-(1H-pyrazol-1-yl)phenyl]methyl}-2,5-dihydro-3H-pyrazolo[4,3-c]quinolin-3-one

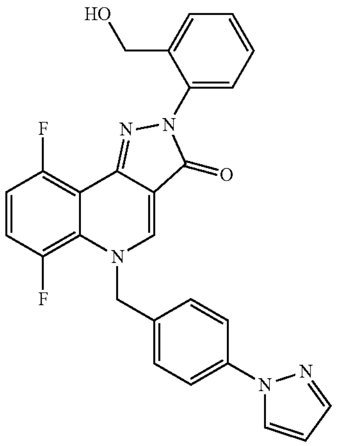 [SMILES: O=c1c2cn(Cc3ccc(-n4cccn4)cc3)c3c(F)ccc(F)c3c-2nn1-c1ccccc1CO]

2-(6,9-Difluoro-3-oxo-5-{[4-(1H-pyrazol-1-yl)phenyl]methyl}-3,5-dihydro-2H-pyrazolo[4,3-c]quinolin-2-yl)benzaldehyde [(Example 39) 15 mg, 0.31 mmol] was dissolved in methanol (3 mL), treated with sodium borohydride (4 mg, 0.62 mmol, 2 equiv) and stirred at ambient temperature for 2 hours. The mixture was concentrated in vacuo and the residue was purified by silica gel gradient chromatography (100:0 to 80:20; dichloromethane:methanol), providing the titled compound: $^1$H-NMR (400 MHz, $CDCl_3$) δ 8.46 (1H, s), 7.91 (1H, d, J=2.5 Hz), 7.75-7.70 (3H, m), 7.56 (1H, dd, J=7.3, 1.3 Hz), 7.45 (1H, td, J=7.6, 1.5 Hz), 7.38 (1H, td, J=7.4, 1.4 Hz), 7.30-7.17 (5H, m), 6.48 (1H, dd, J=2.4, 1.7 Hz), 5.66 (1H, d, J=2.4 Hz), 4.52 (2H, br s) ppm; high resolution mass spectrometry (ES+) m/z 484.1567 [$(M+H)^+$; calculated for $C_{27}H_{20}F_2N_5O_2$: 484.1580].

Example 56

2-{2-[(Ethylamino)methyl]phenyl-6,9-difluoro-5-{[4-(1H-pyrazol-1-yl)phenyl]methyl}-2,5-dihydro-3H-pyrazolo[4,3-c]quinolin-3-one

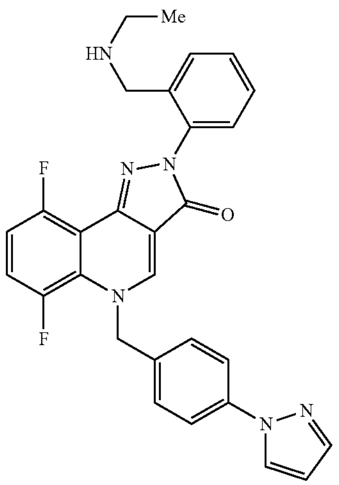 [SMILES: CCNCc1ccccc1-n1nc2c3c(F)ccc(F)c3n(Cc3ccc(-n4cccn4)cc3)cc-2c1=O]

2-(6,9-Difluoro-3-oxo-5-{[4-(1H-pyrazol-1-yl)phenyl]methyl}-3,5-dihydro-2H-pyrazolo[4,3-c]quinolin-2-yl)benzaldehyde [(Example 39) 15 mg, 0.031 mmol] was suspended in acetonitrile (1.5 mL), treated with ethylamine (0.15 mL, 0.15 mmol, 1.0 M tetrahydrofuran solution, 5 equiv), acetic acid (10 μL, 0.17 mmol, 5.6 equiv) and powdered 4 Å molecular sieves (15 mg, 1 wt equiv) and stirred for 30 minutes at ambient temperature. Sodium triacetoxyborohydride (6.6 mg, 0.031 mmol, 1 equiv) was added and the mixture was stirred for 3 hours at ambient temperature. The mixture was diluted with dichloromethane (5 mL), filtered and concentrated in vacuo. The residue was diluted with dimethylsulfoxide (1 mL) and water (0.1 mL) and treated with 2,3-dichloro-5,6-dicyanobenzoquinone (DDQ, 7.0 mg, 0.031 mmol, 1 equiv). After stirring for 30 minutes, the mixture was filtered and purified by preparative reverse phase HPLC (5:95 to 95:5; water containing 0.1% trifluoroacetic acid:acetonitrile containing 0.1% trifluoroacetic acid:acetonitrile), providing the titled compound: $^1$H-NMR (400 MHz, $d^6$-DMSO) δ 9.24 (1H, s), 8.80 (2H, br s), 8.47 (1H, d, J=2.5 Hz), 7.82 (2H, d, J=8.7 Hz), 7.73-7.68 (3H, m), 7.64-7.58 (2H, m), 7.55-7.50 (2H, m), 7.35 (2H, d, J=8.6 Hz), 6.54 (1H, dd, J=2.4, 1.9 Hz), 5.86 (2H, d, J=3.2 Hz), 4.16 (2H, br m), 2.97-2.92 (2H, m), 0.91 (3H, t, J=7.5 Hz) ppm; high resolution mass spectrometry (ES+) m/z 511.2035 [$(M+H)^+$; calculated for $C_{29}H_{25}F_2N_6O$: 511.2053].

The following compounds were prepared according to the general procedure described in Example 56, substituting the appropriately substituted amine for ethylamine. The starting materials are either commercially available, known in the literature or may be prepared from commercially available reagents using conventional reactions well known in the art.

(ID)

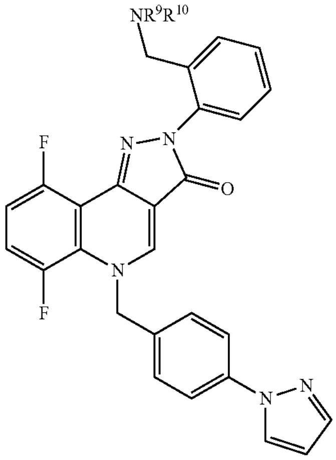

| Ex. | $R^9R^{10}N$ | HRMS/LRMS |
|---|---|---|
| 57 | 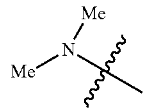 [SMILES: *N(C)C] | $C_{29}H_{25}F_2N_6O$ [M + H] calc. 511.2 obs. 511.0 |
| 58 | 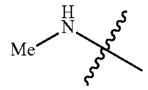 | $C_{28}H_{23}F_2N_6O$ [M + H] calc. 497.1896 obs. 497.1878 |
| 59 | 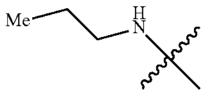 | $C_{30}H_{27}F_2N_6O$ [M + H] calc. 525.2209 obs. 525.2196 |
| 60 | 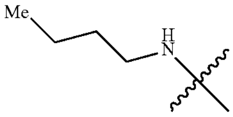 [SMILES: *NCCCC] | $C_{31}H_{29}F_2N_6O$ [M + H] calc. 539.2366 obs. 539.2355 |
| 61 | 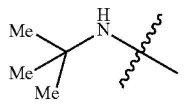 | $C_{31}H_{29}F_2N_6O$ [M + H] calc. 539.2366 obs. 539.2351 |
| 62 | 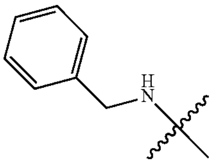 [SMILES: *NCc1ccccc1] | $C_{34}H_{27}F_2N_6O$ [M + H] calc. 573.2209 obs. 573.2196 |
| 63 | 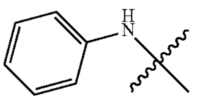 [SMILES: *Nc1ccccc1] | $C_{33}H_{25}F_2N_6O$ [M + H] calc. 559.2053 obs. 559.2048 |
| 64 | 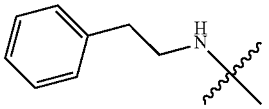 [SMILES: *NCCc1ccccc1] | $C_{35}H_{29}F_2N_6O$ [M + H] calc. 587.2366 obs. 587.2360 |

-continued
(ID)
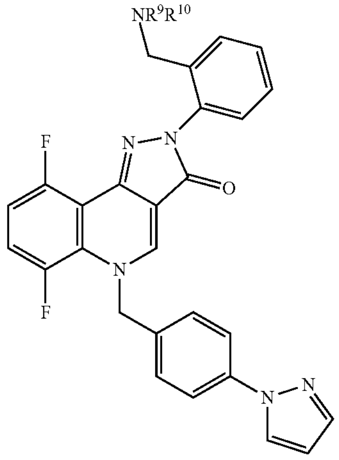
| Ex. | $R^9R^{10}N$ | HRMS/LRMS |
|---|---|---|
| 65 | 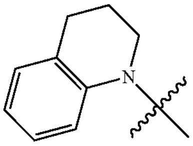 [SMILES: *N1CCCc2ccccc21] | $C_{36}H_{28}F_2N_6O$ [M + H] calc. 599.2366 obs. 599.2347 |
| 66 | 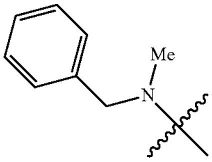 [SMILES: *N(C)Cc1ccccc1] | $C_{35}H_{29}F_2N_6O$ [M + H] calc. 587.2366 obs. 587.2345 |
| 67 | 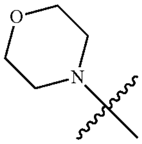 [SMILES: *N1CCOCC1] | $C_{31}H_{27}F_2N_6O_2$ [M + H] calc. 553.2158 obs. 553.2141 |
| 68 | 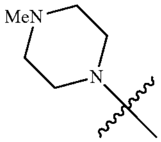 | $C_{32}H_{30}F_2N_7O$ [M + H] calc. 566.2 obs. 566.1 |
| 69 | 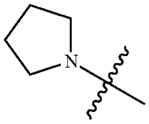 [SMILES: *N1CCCC1] | $C_{31}H_{27}F_2N_7O$ [M + H] calc. 537.2209 obs. 537.2197 |
| 70 | 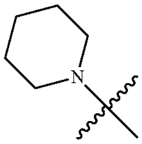 [SMILES: *N1CCCCC1] | $C_{32}H_{29}F_2N_7O$ [M + H] calc. 551.2366 obs. 551.2353 |
| 71 | 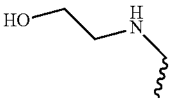 | $C_{29}H_{26}F_2N_6O_2$ [M + H] calc. 527.2002 obs. 527.1987 |
-continued
(ID)
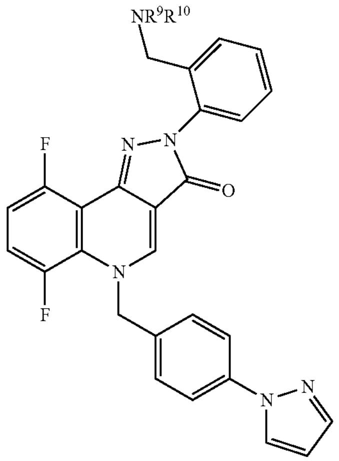
| Ex. | $R^9R^{10}N$ | HRMS/LRMS |
|---|---|---|
| 72 | 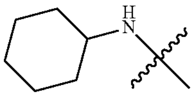 [SMILES: *NC1CCCCC1] | $C_{33}H_{31}F_2N_6O$ [M + H] calc. 565.2522 obs. 565.2511 |
| 73 | 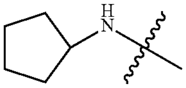 [SMILES: *NC1CCCC1] | $C_{32}H_{29}F_2N_6O$ [M + H] calc. 551.2366 obs. 551.2356 |
| 74 | 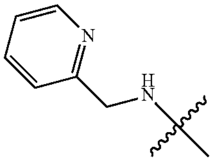 [SMILES: *NCc1ccccn1] | $C_{33}H_{26}F_2N_7O$ [M + H] calc. 574.2162 obs. 574.2154 |
| 75 | 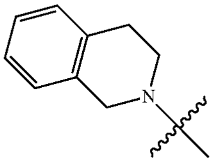 [SMILES: *N1CCc2ccccc2C1] | $C_{36}H_{29}F_2N_6O$ [M + H] calc. 599.2366 obs. 599.2343 |
| 76 | 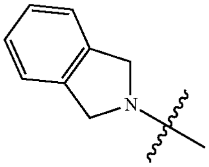 [SMILES: *N1Cc2ccccc2C1] | $C_{35}H_{27}F_2N_6O$ [M + H] calc. 585.2209 obs. 585.2191 |

Example 77

6,9-Difluoro-5-{[4-(1H-pyrazol-1-yl)phenyl]methyl}-2-[3-(trifluoromethyl)pyridin-2-yl]-2,5-dihydro-3H-pyrazolo[4,3-c]quinolin-3 one

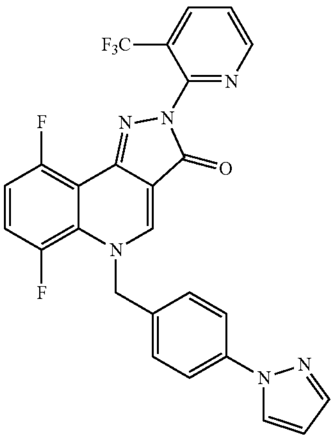 [SMILES: O=c1c2cn(Cc3ccc(-n4cccn4)cc3)c3c(F)ccc(F)c3c-2nn1-c1ncccc1C(F)(F)F]

5,8-Difluoro-4-thioxo-1{[4-(1H-pyrazol-1-yl)phenyl]methyl}-1,4-dihydroquinolinone-3-carboxylate [(Example 53, Step 1), 50 mg, 0.12 mmol] was suspended in 1,2-dimethoxyethane (2 mL), treated with potassium carbonate (0.13 g, 0.94 mmol, 8 equiv) and 2-hydrazino-3-(trifluoromethyl)pyridine (31 mg, 0.18 mmol, 1.5 equiv). The mixture was placed into a preheated oil bath at 80° C. for 1 hour, cooled to ambient temperature, poured into water (20 mL) and extracted once with dichloromethane (50 mL). The organic extract was dried with sodium sulfate, filtered and concentrated in vacuo. The residue was purified by silica gel gradient chromatography (100:0 to 95:5; dichloromethane:methanol), providing the titled compound: $^1$H-NMR (400 MHz, $CDCl_3$) δ 8.84 (1H, dd, J=4.7, 1.3 Hz), 8.34 (1H, s), 8.17 (1H, dd, J=7.9, 1.6 Hz), 7.91 (1H, d, J=2.5 Hz), 7.72 (1H, m), 7.71 (2H, d, J=8.8 Hz), 7.52 (1H, dd, J=8.0, 4.8 Hz), 7.28-7.12 (4H, m), 6.47 (1H, m), 5.61 (1H, d, 2.9 Hz) ppm; high resolution mass spectrometry (ES+) m/z 523.1314 [$(M+H)^+$; calculated for $C_{26}H_{16}F_5N_6O$: 523.1300].

The following compounds were prepared according to the general procedure described in Example 77, substituting the appropriately substituted hydrazine for 2-hydrazino-3-(trifluoromethyl)pyridine. The starting materials are either commercially available, known in the literature or may be prepared from commercially available reagents using conventional reactions well known in the art.

(IE)

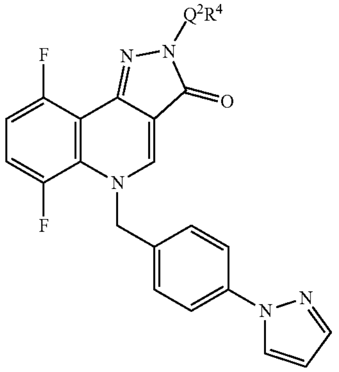

| Ex. | $Q^2R^4$ | HRMS/LRMS |
|---|---|---|
| 78 | 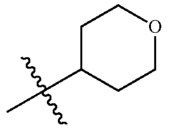 [SMILES: *C1CCOCC1] | $C_{25}H_{22}F_2N_5O_2$; [M + H]; calc. 462.1736; obs. 462.1737 |
| 79 | 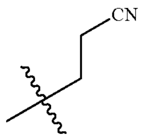 [SMILES: *CCC#N] | $C_{23}H_{17}F_2N_6O$; [M + H]; calc. 431.1426; obs. 431.1411 |
| 80 | 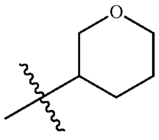 [SMILES: *C1CCCOC1] | $C_{25}H_{22}F_2N_5O_2$; [M + H]' calc. 462.2; obs. 462.3 |

Example 81

5-[(4-Bromo-2-fluorophenyl)methyl-6,9-difluoro-2-(2-fluorophenyl)-2,5-dihydro-3H-pyrazolo[4,3-c]quinolin-3-one

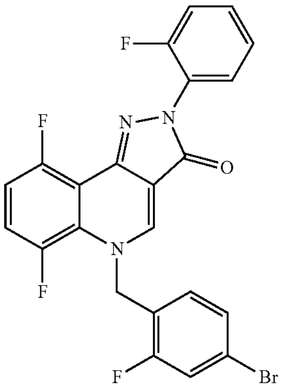 [SMILES: O=c1c2cn(Cc3ccc(Br)cc3F)c3c(F)ccc(F)c3c-2nn1-c1ccccc1F]

Using the procedures described in Example 53, substituting 4-bromo-2-fluorobenzyl bromide for 1-[4-(bromomethyl)phenyl]-1H-pyrazole (Step 1), and, substituting 2-fluorophenylhydrazine hydrochloride for 2-iodophenylhydrazine oxylate (Step 2), the titled compound was obtained: high resolution mass spectrometry (ES+) m/z 502.0145 [$(M+H)^+$; calculated for $C_{23}H_{11}BrF_4N_3O$: 502.0172].

Example 82

6,9-Difluoro-2-(2-fluorophenyl)-5-{[2-fluoro-4-(1H-pyrazol-1-yl)phenyl]methyl}-2,5-dihydro-3H-pyrazolo[4,3-c]quinolin-3-one

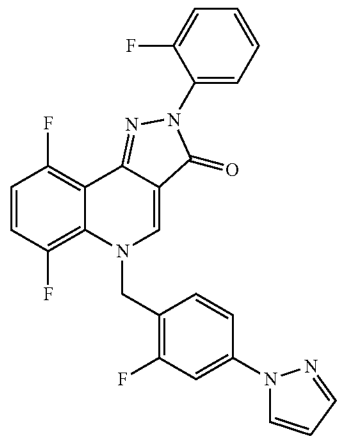 [SMILES: O=c1c2cn(Cc3ccc(-n4cccn4)cc3F)c3c(F)ccc(F)c3c-2nn1-c1ccccc1F]

5-[(4-Bromo-2-fluorophenyl)methyl-6,9-difluoro-2-(2-fluorophenyl)-2,5-dihydro-3H-pyrazolo[4,3-c]quinolin-3-one (Example 78, 50 mg, 0.10 mmol), potassium carbonate (35 mg, 0.25 mmol, 2.5 equiv), copper(I) iodide (1.9 mg, 0.001 mmol, 0.1 equiv), pyrazole (10 mg, 0.15 mmol, 1.5 equiv) and (±)-trans-N,N'-bismethyl-1,2-cyclohexane diamine (2.0 mg, 0.002 mmol, 0.2 equiv) were combined in a sealed tube containing degassed N,N-dimethylformamide (0.6 mL). The mixture was sparged under a nitrogen atmosphere, the vessel was sealed and placed into an preheated oil bath at 110° C. for 15 hours. The mixture was cooled to ambient temperature, poured into water (20 mL) and extracted with ethyl acetate (2×75 mL). The combined organic extracts were dried with sodium sulfate, filtered and concentrated in vacuo. The residue was purified by silica gel gradient chromatography (100:0 to 95:5; chloroform:methanol), providing the titled compound; low resolution mass spectrometry (ES+) m/z 490.1 [$(M+H)^+$; calculated for $C_{26}H_{16}F_4N_5O$: 490.1].

Example 83

5-[(4-Iodo-2-fluorophenyl)methyl-6,9-difluoro-2-(2-fluorophenyl)-2,5-dihydro-3H-pyrazolo[4,3-c]quinolin-3-one

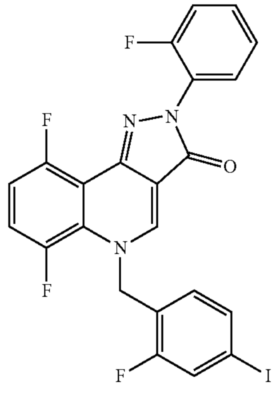 [SMILES: O=c1c2cn(Cc3ccc(I)cc3F)c3c(F)ccc(F)c3c-2nn1-c1ccccc1F]

Step 1: Preparation of 1-(bromomethyl)-2-fluoro-4-iodobenzene

2-Fluoro-4-iodo-1-methylbenzene (2.0 g, 8.6 mmol) was dissovled in carbon tetrachloride (10 mL), treated with N-bromosuccinimide (1.5 g, 8.6 mmol, 1 equiv) and benzoyl peroxide (9.0 mg, 0.004 equiv) and placed into an oil bath preheated to 80° C. for 3 hours. The mixture was cooled to ambient temperature, filtered and the filtrate was concentrated in vacuo, providing the titled compound.

Step 2: Preparation of 5-[(4-iodo-2-fluorophenyl) methyl-6,9-difluoro-2-(2-fluorophenyl)-2,5-dihydro-3H-pyrazolo[4,3-c]quinolin-3-one Using the procedures described in Example 53, substituting 1-(bromomethyl)-2-fluoro-4-iododbenzene for 1-[4-(bromomethyl)phenyl]-1H-pyrazole for 4-(bromomethyl)biphenyl (Step 1), and, substituting 2-fluorophenylhydrazine hydrochloride for 2-iodophenylhydrazine oxalate (Step 2), the titled compound was obtained: $^1$H-NMR (500 MHz, $d^6$-DMSO) δ 8.98 (1H, s), 7.73 (1H, dd, J=9.9, 1.4 Hz), 7.58 (1H, td, J=7.9, 1.5 Hz), 7.55-7.40 (5H, m), 7.35 (1H, td, J=7.6, 1.3 Hz), 6.89 (1H, t, J=8.2 Hz), 5.74 (2H, d, J=4.3 Hz) ppm; high resolution mass spectrometry (ES+) m/z 550.0024 [$(M+H)^+$; calculated for $C_{23}H_{13}F_4IN_3O$: 550.0034].

Example 84

6,9-Difluoro-2-(2-fluorophenyl)-5-{[2-fluoro-4-(1H-1,2,4-triazol-1-yl)phenyl]methyl}-2,5-dihydro-3H-pyrazolo[4,3-c]quinolin-3-one

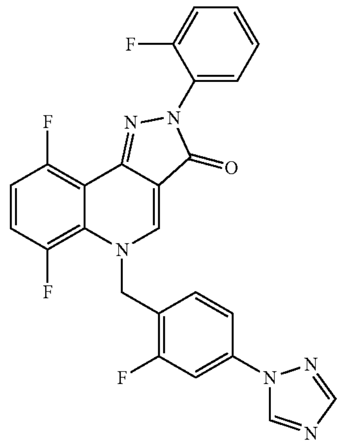 [SMILES: O=c1c2cn(Cc3ccc(-n4cncn4)cc3F)c3c(F)ccc(F)c3c-2nn1-c1ccccc1F]

5-[(4-Iodo-2-fluorophenyl)methyl-6,9-difluoro-2-(2-fluorophenyl)-2,5-dihydro-3H-pyrazolo[4,3-c]quinolin-3-one (Example 83, 26 mg, 0.047 mmol), potassium phosphate (20 mg, 0.095 mmol, 2 equiv), copper(I) iodide (0.90 mg, 4.3 μmol, 0.1 equiv), 1,2,4-triazole (3.9 mg, 0.057 mmol, 1.2 equiv) and (±)-trans-N,N'-bismethyl-1,2-cyclohexane diamine (0.60 mg, 4.3 μmol, 0.1 equiv) were combined in a sealed tube containing dimethylsulfoxide (0.5 mL) and water (0.1 mL). The mixture was sparged under a nitrogen atmosphere, the vessel was sealed and placed into an preheated oil bath at 100° C. for 4 hours. The mixture was cooled to ambient temperature, filtered and purified by preparative reverse phase HPLC (25:75 to 80:20; water containing 0.1% trifluoroacetic acid:acetonitrile containing 0.1% trifluoroacetic acid), providing the titled compound; high resolution mass spectrometry (ES+) m/z 491.1225 [(M+H)$^+$; calculated for $C_{25}H_{15}F_4N_6O$: 491.1238].

The following compounds were prepared according to the general procedure described in Example 84, substituting the appropriately substituted heterocycle for 1,2,4-triazole. The starting materials are either commercially available, known in the literature or may be prepared from commercially available reagents using conventional reactions well known in the art.

(IF)

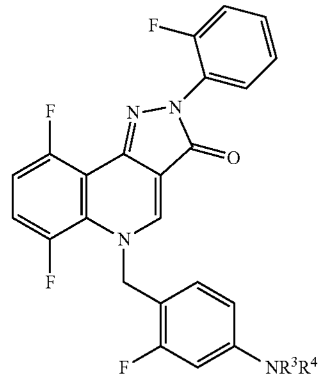

| Ex. | $R^3R^4N$ | HRMS/LRMS |
|---|---|---|
| 85 | 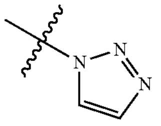 [SMILES: *n1ccnn1] | $C_{25}H_{15}F_4N_6O$<br>[M + H]<br>calc. 491.1<br>obs. 491.0 |
| 86 | 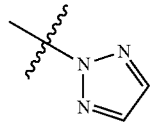 [SMILES: *n1nccn1] | $C_{25}H_{15}F_4N_6O$<br>[M + H]<br>calc. 491.1<br>obs. 491.0 |
| 87 | 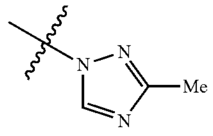 [SMILES: *n1cnc(C)n1] | $C_{25}H_{15}F_4N_6O$<br>[M + H]<br>calc. 505.1394<br>obs. 505.1402 |
| 88 | 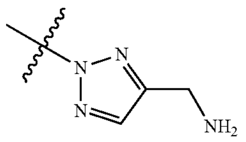 [SMILES: *n1ncc(CN)n1] | $C_{26}H_{18}F_4N_7O$<br>[M + H]<br>calc. 520.2<br>obs. 520.0 |
| 89 | 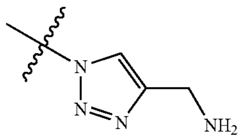 [SMILES: *n1cc(CN)nn1] | $C_{26}H_{18}F_4N_7O$<br>[M + H]<br>calc. 520.1504<br>obs. 520.1526 |

-continued (IF)

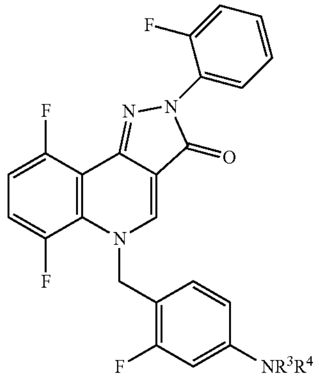

| Ex. | $R^3R^4N$ | HRMS/LRMS |
|---|---|---|
| 90 | 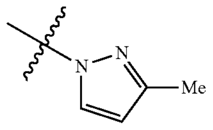 [SMILES: *n1ccc(C)n1] | $C_{27}H_{18}F_4N_5O$<br>[M + H]<br>calc. 504.1442<br>obs. 504.1433 |
| 91 | 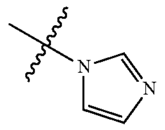 [SMILES: *n1ccnc1] | $C_{26}H_{16}F_4N_5O$<br>[M + H]<br>calc. 490.1286<br>obs. 490.1292 |
| 92 | 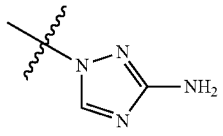 [SMILES: *n1cnc(N)n1] | $C_{25}H_{16}F_4N_7O$<br>[M + H]<br>calc. 505.2<br>obs. 505.9 |
| 93 | 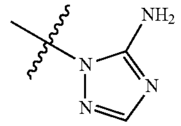 [SMILES: *n1ncnc1N] | $C_{25}H_{16}F_4N_7O$<br>[M + H]<br>calc. 505.2<br>obs. 505.9 |
| 94 | 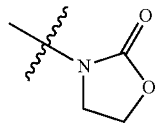 [SMILES: *N1CCOC1=O] | $C_{26}H_{17}F_4N_4O_3$<br>[M + H]<br>calc. 509.1232<br>obs. 509.1230 |

Example 95

6,9-Difluoro-5-({2-fluoro-4-[1-(2-methylpropyl)-1H-pyrazol-4-yl]phenyl}methyl)-2-(2-fluorophenyl)-2,5-dihydro-3H-pyrazolo[4,3-c]quinolin-3-one

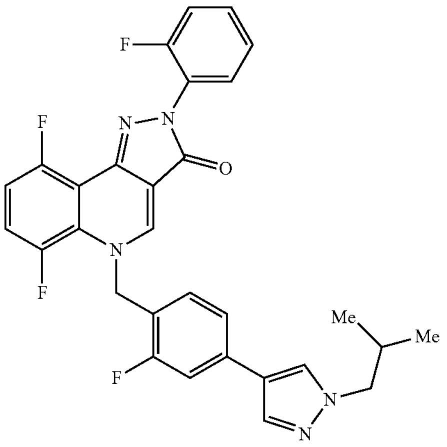 [SMILES: CC(C)Cn1cc(-c2ccc(Cn3cc4c(=O)n(-c5ccccc5F)nc-4c4c(F)ccc(F)c43)c(F)c2)cn1]

5-[(4-Bromo-2-fluorophenyl)methyl-6,9-difluoro-2-(2-fluorophenyl)-2,5-dihydro-3H-pyrazolo[4,3-c]quinolin-3-one (Example 78, 25 mg, 0.050 mmol), 1-iso-butyl-4-(4,4,5,5-tetramethyl-1,3,2-dioxaborolan-2-yl)-1H-pyrazole (22 mg, 0.087 mmol, 1.75 equiv) and potassium carbonate (17 mg, 0.12 mmol, 2.5 equiv) were combined in dimethylsulfoxide (1.5 mL) and the mixture was sparged under an atmosphere of nitrogen. Palladium(II) acetate (1.1 mg, 5.0 μmol, 0.1 equiv) and 2-dicyclohexylphosphino-2',4',6'-tri-iso-propyl-1,1'-biphenyl (7.1 mg, 0.015 mmol) were added and the mixture was placed into an oil bath preheated to 90° C. for 16 hours. The mixture was cooled to ambient temperature, poured into sodium bicarbonate (20 mL, aqueous saturated) and extracted with ethyl acetate (2×50 mL). The combined organic extracts were dried with sodium sulfate, filtered and concentrated in vacuo. The residue was purified by preparative reverse phase HLPC (20:80 to 95:5; water containing 0.1% trifluoroacetic acid:acetonitrile containing 0.1% trifluoroacetic acid), providing the titled compound: $^1$H-NMR (400 MHz, $CDCl_3$) δ 8.82 (1H, s), 7.85 (1H, s), 7.64 (1H, s), 7.60 (1H, t, J=7.6 Hz), 7.43-7.39 (1H, m), 7.35-7.22 (6H, m), 7.11 (1H, t, J=7.9 Hz), 5.74 (2H, d, J=2.2 Hz), 4.00 (21-1, d, J=7.3 Hz), 2.25-2.17 (1H, m), 0.93 (611, d, J=6.6 Hz) ppm; high resolution mass spectrometry (ES+) m/z 546.1918 [(M+H)$^+$; calculated for $C_{30}H_{24}F_4N_5O$: 546.1912].

The following compounds were prepared according to the general procedure described in Example 95, substituting the appropriately substituted boronic acid or ester for 1-iso-butyl-4-(4,4,5,5-tetramethyl-1,3,2-dioxaborolan-2-yl)-1H-pyrazole. The starting materials are either commercially available, known in the literature or may be prepared from commercially available reagents using conventional reactions well known in the art.

(IG)

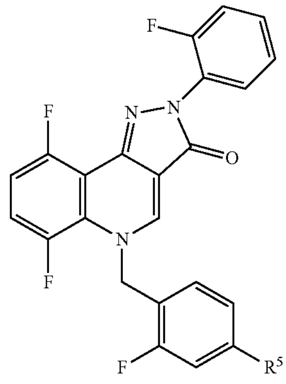

| Ex. | $R^5$ | HRMS/LRMS |
|---|---|---|
| 96 | 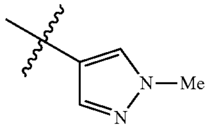 [SMILES: *c1cnn(C)c1] | $C_{27}H_{18}F_4N_5O$ [M + H] calc. 504.1442 obs. 504.1448 |
| 97 | 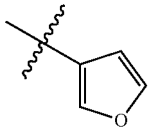 | $C_{27}H_{16}F_4N_3O_2$ [M + H] calc. 490.1173 obs. 490.1178 |
| 98 | 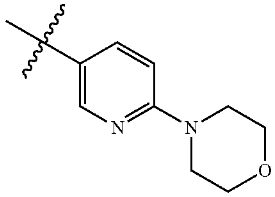 [SMILES: *c1ccc(N2CCOCC2)nc1] | $C_{32}H_{24}F_4N_5O_2$ [M + H] calc. 586.1861 obs. 586.1873 |
| 99 | 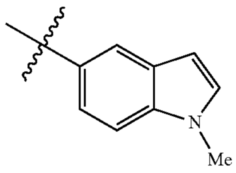 [SMILES: *c1ccc2c(ccn2C)c1] | $C_{32}H_{21}F_4N_4O$ [M + H] calc. 553.2 obs. 553.0 |
| 100 | 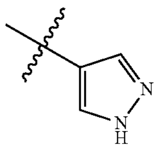 [SMILES: *c1cn[nH]c1] | $C_{26}H_{16}F_4N_5O$ [M + H] calc. 490.1286 obs. 490.1295 |
| 101 | 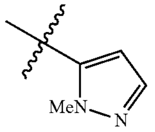 [SMILES: *c1ccnn1C] | $C_{27}H_{18}F_4N_5O$ [M + H] calc. 504.1 obs. 503.9 |
| 102 | 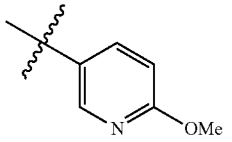 [SMILES: *c1ccc(OC)nc1] | $C_{29}H_{19}F_4N_4O_2$ [M + H] calc. 531.1439 obs. 531.1438 |

Example 103

5-[(5-Bromo-3-fluoropyridin-2-yl)methyl]-6,9-difluoro-2-(2-fluorophenyl)-2,5-dihydro-3H-pyrazolo[4,3-c]quinolin-3-one

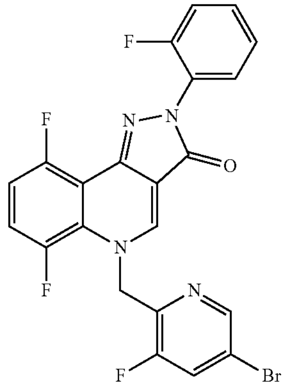 [SMILES: O=c1c2cn(Cc3ncc(Br)cc3F)c3c(F)ccc(F)c3c-2nn1-c1ccccc1F]

Step 1: Preparation of 5-bromo-3-fluoropyridine-2-carboxylic acid

5-Bromo-3-fluoropyridine-2-carbonitrile (1.0 g, 5.0 mmol) was treated with hydrochloric acid (6 mL, 12 N aqueous) and placed into a preheated oil bath at 120° C. for 3 hours. The mixture was cooled to 0° C., treated with sodium hydroxide (40% aqueous) until pH 4. The mixture was filtered and the resulting solid was collected and dried in vacuo, providing the titled compound.

Step 2: Preparation of 5-bromo-3-fluoropyridine-2-carbonyl chloride

5-Bromo-3-fluoropyridine-2-carboxylic acid (0.40 g, 1.8 mmol) was dissolved in dichloromethane (8 mL), treated with thionyl chloride (0.80 mL, 11 mmol, 6 equiv) and the mixture was placed into a preheated oil bath at 45° C. for 3 hours. The mixture was concentrated in vacuo, providing the titled compound.

Step 3: Preparation of (5-bromo-3-fluoropyridin-2-yl)methanol

5-Bromo-3-fluoropyridine-2-carbonyl chloride (0.50 g, 2.1 mmol) was dissolved in tetrahydrofuran (10 mL), cooled to 0° C. and treated with lithium borohydride (1.0 mL, 2 M tetrahydrofuran solution, 2.1 mmol, 1 equiv). After stirring for 30 minutes at 0° C., the mixture was treated with methanol (2 mL) and concentrated in vacuo. The residue was purified by silica gel gradient chromatography (100:0 to 0:100; hexanes:ethyl acetate), providing the titled compound.

Step 4: Preparation of (5-bromo-3-fluoropyridin-2-yl)methyl methanesulfonate (5-Bromo-3-fluoropyridin-2-yl)methanol (0.20 g, 0.99 mmol) was dissolved in dichloromethane (5 mL), cooled to 0° C. and treated with triethylamine (0.15 mL, 1.1 mmol, 1.1 equiv) and methanesulfonyl chloride (0.085 mL, 1.1 mmol, 1.1 equiv). After 15 minutes, the mixture was diluted with dichloromethane (100 mL) and washed once with sodium bicarbonate (20 mL, aqueous saturated) and brine (50 mL), dried with sodium sulfate, filtered and concentrated in vacuo, providing the titled compound.

Step 5: Preparation of 5-[(5-bromo-3-fluoropyridin-2-yl)methyl]-6,9-difluoro-2-(2-fluorophenyl)-2,5-dihydro-3H-pyrazolo[4,3-c]quinolin-3-one Using the procedures described in Example 53, substituting (5-bromo-3-fluoropyridin-2-yl)methyl methanesulfonate for 1-[4-(bromomethyl)phenyl]-1H-pyrazole (Step 1), and, substituting 2-fluorophenylhydrazine hydrochloride for 2-iodophenylhydrazine oxylate (Step 2), the titled compound was obtained: $^1$H-NMR (500 MHz, $d^6$-DMSO) δ 8.92 (1H, s), 8.47 (1H, s), 8.33 (1H, d, J=9.6 Hz), 7.60 (1H, t, J=7.7 Hz), 7.54-7.47 (2H, m), 7.45-7.40 (2H, m), 7.35 (1H, t, J=7.6 Hz), 5.93 (2H, d, J=4.6 Hz) ppm; high resolution mass spectrometry (ES+) m/z 503.0151 [$(M+H)^+$; calculated for $C_{22}H_{12}BrF_4N_4O$: 503.0125].

Example 104

6,9-Difluoro-5-{[3-fluoro-5-(1-methyl-1H-pyrazol-4-yl)pyridin-2-yl]methyl}-2-(2-fluorophenyl)-2,5-dihydro-3H-pyrazolo[4,3-c]quinolin-3-one

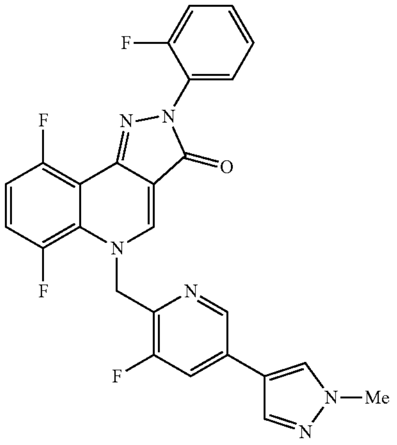 [SMILES: Cn1cc(-c2cnc(Cn3cc4c(=O)n(-c5ccccc5F)nc-4c4c(F)ccc(F)c43)c(F)c2)cn1]

5-[(5-Bromo-3-fluoropyridin-2-yl)methyl]-6,9-difluoro-2-(2-fluorophenyl)-2,5-dihydro-3H-pyrazolo[4,3-c]quinolin-3-one (Example 103, 63 mg, 0.13 mmol), 1-methyl-4-(4,4,5,5-tetramethyl-1,3,2-dioxaborolan-2-yl)-1H-pyrazole (45 mg, 0.21 mmol, 1.7 equiv), potassium carbonate (52 mg, 0.38 mmol, 3 equiv), palladium(II) acetate (5.7 mg, 0.025 mmol, 0.2 equiv) and 2-dicyclohexylphosphino-2',4',6'-tri-iso-propyl-1,1'-biphenyl (28 mg, 0.058 mmol, 0.46 equiv) were combined in dimethylsulfoxide (0.9 mL) and water (0.2 mL). The mixture was sparged under an atmosphere of nitrogen, the vessel was sealed and placed into a preheated oil bath at 88° C. for 4 hours. The mixture was cooled to ambient temperature, poured into water (25 mL) and extracted with ethyl acetate (2×50 mL). The combined organic extracts were washed once with water (10 mL) and brine (10 mL), dried with sodium sulfate, filtered and concentrated in vacuo. The residue was purified by silica gel chromatography (eluting with 98:2; chloroform:methanol), providing the titled compound: high resolution mass spectrometry (ES+) m/z 505.1385 [$(M+H)^+$; calculated for $C_{26}H_{17}F_4N_6O$: 505.1395].

Example 105

6,9-Difluoro-5-[(5-fluoro-6'-morpholin-4-yl-3,3'-bipyridin-6-yl)methyl]-2-(2-fluorophenyl)-2,5-dihydro-3H-pyrazolo[4,3-c]quinolin-3-one

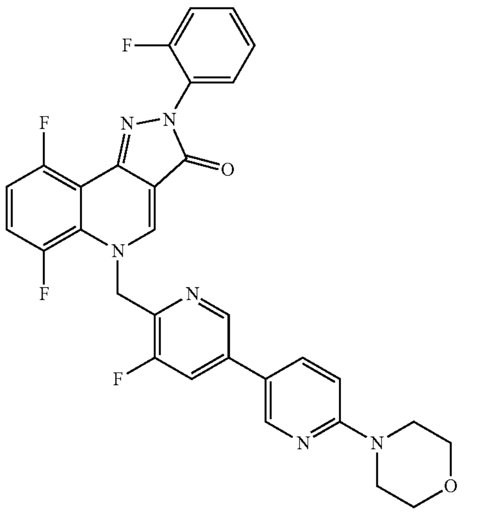 [SMILES: O=c1c2cn(Cc3ncc(-c4ccc(N5CCOCC5)nc4)cc3F)c3c(F)ccc(F)c3c-2nn1-c1ccccc1F]

Using the procedures described in Example 104, substituting 4-[5-4,4,5,5-tetramethyl-1,3,2-dioxaborolan-2-yl]pyridin-2-yl]morpholine for 1-methyl-4-(4,4,5,5-tetramethyl-1,3,2-dioxaborolan-2-yl)-1H-pyrazole, the titled compound was obtained: high resolution mass spectrometry (ES+) m/z 587.1808 $[(M+H)^+$; calculated for $C_{31}H_{23}F_4N_6O_2$: 587.1813].

Example 106

6,9-Difluoro-2-(2-fluorophenyl)-5-{3-fluoro-5-(1H-pyrazol-1-yl)pyridin-2-yl}methyl}-2,5-dihydro-3H-pyrazolo[4,3-c]quinolin-3-one

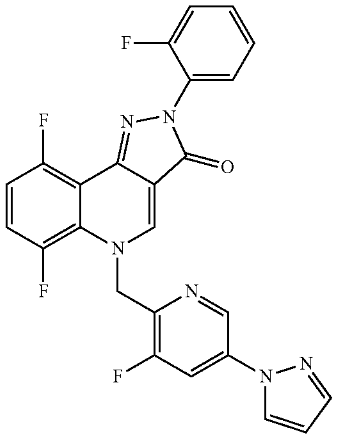 [SMILES: O=c1c2cn(Cc3ncc(-n4cccn4)cc3F)c3c(F)ccc(F)c3c-2nn1-c1ccccc1F]

Using the procedures described in Example 84, substituting pyrazole for 1,2,4-triazole, and, substituting 5-[(5-bromo-3-fluoropyridin-2-yl)methyl]-6,9-difluoro-2-(2-fluorophenyl)-2,5-dihydro-3H-pyrazolo[4,3-c]quinolin-3-one (Example 103) for 5-[(4-iodo-2-fluorophenyl)methyl-6,9-difluoro-2-(2-fluorophenyl)-2,5-dihydro-3H-pyrazolo[4,3-c]quinolin-3-one (Example 83), the titled compound was obtained: $^1H$-NMR (500 MHz, $d^6$-DMSO) δ 8.97 (1H, s), 8.85 (1H, s), 8.56 (1H, d, J=1.9 Hz), 8.34 (1H, d, J=11.1 Hz), 7.83 (1H, s), 7.61 (1H, t, J=7.5 Hz), 7.54-7.47 (2H, m), 7.44-7.40 (2H, m), 7.36 (1H, t, J=7.8 Hz), 6.62 (1H, s), 5.99 (2H, d, J=4.3 Hz) ppm; high resolution mass spectrometry (ES+) m/z 491.1234 $[(M+H)^+$; calculated for $C_{25}H_{15}F_4N_6O$: 491.1238].

Example 107

2-Fluorophenyl-5-{[4-(1H-pyrazol-1-yl)phenyl]methyl}-2,5-dihydro-3H-pyrazolo[4,3-c]quinolin-3-one

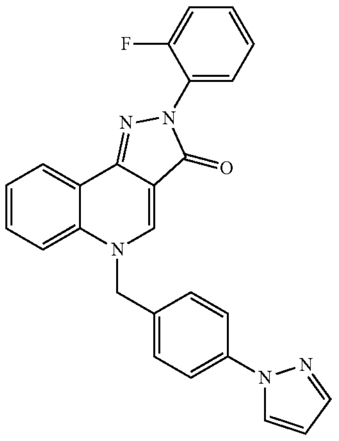 [SMILES: O=c1c2cn(Cc3ccc(-n4cccn4)cc3)c3ccccc3c-2nn1-c1ccccc1F]

Step 1: Preparation of 2,5-bis(2-fluorophenyl)-2,4-dihydro-3H-pyrazol-3-one

2-Fluorophenyl hydrazine (1.26 g, 9.99 mmol) and ethyl 3-(2-fluorophenyl)-3-oxopropanoate (2.10 g, 9.99 mmol, 1 equiv) were combined in acetic acid (20 mL) and placed into an oil bath preheated at 120° C. for 3 hours. The mixture was cooled of ambient temperature and concentrated in vacuo. The residue was concentrated from toluene (3×50 mL), providing the titled compound.

Step 2: Preparation of (4Z)-4-[(dimethylamino)methylidene]-2,5-bis(2-fluorophenyl)-2,4-dihydro-3H-pyrazol-3-one 2,5-Bis(2-fluorophenyl)-2,4-dihydro-3H-pyrazol-3-one (2.5 g, 8.1 mmol) was dissolved in methanol (3 mL), treated with N,N-dimethylformamide dimethylacetal (1.2 g, 9.7 mmol, 1.2 equiv) and placed into a preheated oil bath at 60° C. for 1 hour. The mixture was cooled to ambient temperature and concentrated in vacuo, providing the titled compound.

Step 3: Preparation of 2-fluorophenyl-5-{[4-(1H-pyrazol-1-yl)phenyl]methyl}-2,5-dihydro-3H-pyrazolo[4,3-c]quinolin-3-one (4Z)-4-[(Dimethylamino)methylidene]-2,5-bis(2-fluorophenyl)-2,4-dihydro-3H-pyrazol-3-one (241 mg, 0.735 mmol) and 1-[4-(1H-pyrazol-1-yl)phenyl]methanamine (127 mg, 0.735 mmol, 1 equiv) were combined in dimethylsulfoxide (10 mL) and placed into a preheated oil bath at 100° C. for 1.5 hours. To the mixture was added potassium carbonate (102 mg, 0.735 mmol, 1 equiv) and the mixture was heated for an additional 1 hour at 140° C. Additional 1-[4-(1H-pyrazol-1-yl)phenyl]methanamine (127 mg, 0.735 mmol, 1 equiv) and potassium carbonate (102 mg, 0.735 mmol, 1 equiv) were added and the mixture was heated for an additional 1 hour at 140° C. The mixture was cooled to ambient temperature, poured into water (75 mL) and extracted with ethyl acetate (2×75 mL). The combined organic extracts were dried with sodium sulfate, filtered and concentrated in vacuo. The residue was purified by silica gel gradient chromatography (100:0 to 95:5; dichloromethane:methanol; then 100:0 to 0:100; hexanes:ethyl acetate), providing the titled compound: $^1$H-NMR (500 MHz, d$^6$-DMSO) δ 9.16 (1H, s), 8.46 (1H, d, J=2.4 Hz), 8.20 (1H, dd, J=7.8, 1.4 Hz), 7.82 (2H, d, J=8.7 Hz), 7.77 (1H, d, J=8.7 Hz), 7.72 (1H, d, J=14.6 Hz), 7.64-7.59 (2H, m), 7.55-7.52 (1H, m), 7.47 (2H, d, J=8.4 Hz), 7.47-7.38 (2H, m), 7.36-7.32 (1H, m), 6.53 (1H, dd, J=2.4, 1.7 Hz), 5.78 (2H, s) ppm; high resolution mass spectrometry (ES+) m/z 436.1560 [(M+H)$^+$; calculated for $C_{26}H_{19}FN_5O$: 436.1568].

Example 108

5-{[4-(3-Methyl-1H-pyrazol-1-yl)phenyl]methyl}-2-phenyl-2,5-dihydro-3H-pyrazolo[4,3-c]quinolin-3-one

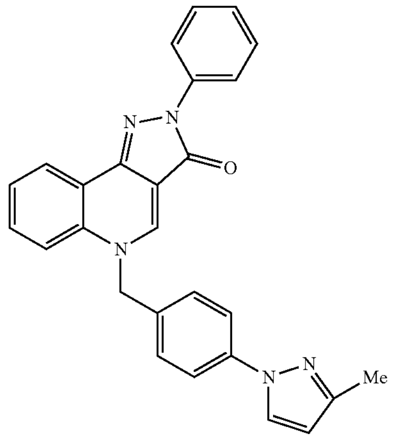 [SMILES: Cc1ccn(-c2ccc(Cn3cc4c(=O)n(-c5ccccc5)nc-4c4ccccc43)cc2)n1]

Step 1: Preparation of 5-(2-fluorophenyl)-2-phenyl-2,4-dihydro-3H-pyrazol-3-one

Using the procedures described in Example 107, substituting phenylhydrazine for 2-fluorophenyl hydrazine (Step 1), the titled compound was obtained.

Step 2: Preparation of (4Z)-4-[(dimethylamino)methylidene]-5-(2-fluorophenyl)-2-phenyl-2,4-dihydro-3H-pyrazol-3-one 5-(2-Fluorophenyl)-2-phenyl-2,4-dihydro-3H-pyrazol-3-one (2.5 g, 8.1 mmol) and N,N-dimethylformamide dimethylacetal (1.2 g, 9.7 mmol, 1.2 equiv) were combined in methanol (3 mL) and placed into a preheated oil bath at 60° C. for 1 hour. The mixture was cooled to ambient and concentrated in vacuo, providing the titled compound.

Step 3: Preparation of 5-{[4-(3-methyl-1H-pyrazol-1-yl)phenyl]methyl}-2-phenyl-2,5-dihydro-3H-pyrazolo[4,3-c]quinolin-3-one Using the procedures described in Example 107, substituting (4Z)-4-[(dimethylamino)methylidene]-5-(2-fluorophenyl)-2-phenyl-2,4-dihydro-3H-pyrazol-3-one for (4Z)-4-[(dimethylamino)methylidene]-2,5-bis(2-fluorophenyl)-2,4-dihydro-3H-pyrazol-3-one (Step 3), and, substituting 1-[4-(3-methyl-1H-pyrazol-1-yl)phenyl]methanamine for 1-[4-(1H-pyrazol-1-yl)phenyl]methanamine (Step 3), the titled compound was obtained: $^1$H-NMR (500 MHz, d$^6$-DMSO) δ 9.15 (1H, s), 8.32-8.30 (2H, m), 8.22 (1H, dd, J=8.6, 1.2 Hz), 7.78 (1H, d, J=7.8 Hz), 7.76 (2H, d, J=7.6 Hz), 7.64 (1H, ddd, J=8.4, 7.4, 1.8 Hz), 7.56 (1H, t, J=7.9 Hz), 7.48-7.45 (2H, m), 7.43 (2H, d, J=8.8 Hz), 7.20 (1H, t, J=7.4 Hz), 6.31 (1H, d, J=2.5 Hz), 5.76 (2H, s), 2.24 (3H, s) ppm; low resolution mass spectrometry (ES+) m/z 432.17 [(M+H)$^+$; calculated for $C_{27}H_{22}N_5O$: 432.16].

Example 109

2-(2-Fluorophenyl)-5-(1H-indol-5-ylmethyl)-2,5-dihydro-3H-pyrazolo[4,3-c]quinolin-3-one

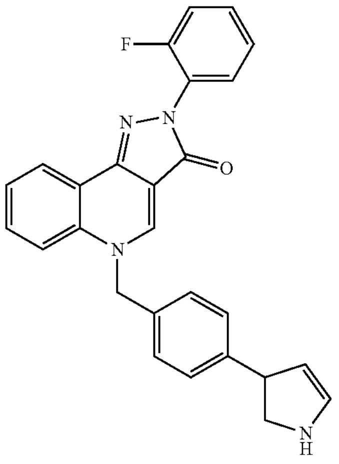 [SMILES: O=c1c2cn(Cc3ccc(C4C=CNC4)cc3)c3ccccc3c-2nn1-c1ccccc1F]

Step 1: Preparation of (4Z)-4-[(ethoxy)methylidene]-2,5-bis(2-fluorophenyl)-2,4-dihydro-3H-pyrazol-3-one 2,5-Bis(2-fluorophenyl)-2,4-dihydro-3H-pyrazol-3-one [(Example 107, Step 1), 85 mg, 0.31 mmol] and triethylorthoformate (0.057 mL, 0.34 mmol, 1.1 equiv) were combined and placed into a preheated oil bath at 100° C. for 1 hour. The mixture was cooled to ambient temperature and concentrated in vacuo, providing the titled compound.

Step 2: Preparation of 2-(2-fluorophenyl)-5-(1H-indol-5-ylmethyl)-2,5-dihydro-3H-pyrazolo[4,3-c]quinolin-3-one (4Z)-4-[(Ethoxy)methylidene]-2,5-bis(2-fluorophenyl)-2,4-dihydro-3H-pyrazol-3-one (236 mg, 0.720 mmol), potassium carbonate (100 mg, 0.720 mmol, 1 equiv) and 1-(1H-indol-5-yl)methanamine (105 mg, 0.720 mmol, 1 equiv) were combined and placed into a preheated oil bath at 100° C. open to the air for 2.5 hours. The mixture was cooled to ambient temperature, poured into water (50 mL) and extracted with ethyl acetate (3×100 mL). The combined organic extracts were dried with sodium sulfate, filtered and concentrated in vacuo. The residue was purified by silica gel gradient chromatography (100:0 to 90:10; dichloromethane:methanol), providing the titled compound: $^1$H-NMR (500 MHz, $d^6$-DMSO) δ 11.14 (1H, s), 9.12 (1H, s), 8.18 (1H, d, J=8.0 Hz), 7.89 (1H, d, J=9.0 Hz), 7.62-7.58 (2H, m), 7.53 (1H, s), 7.51 (1H, t, J=7.7 Hz), 7.48-7.38 (3H, m), 7.36-7.32 (2H, m), 7.09 (1H, d, J=8.6 Hz), 6.40 (1H, br m), 5.78 (2H, m) ppm; low resolution mass spectrometry (ES+) m/z 409.1449 [(M+H)$^+$; calculated for $C_{25}H_{18}FN_4O$: 409.1459].

The following compounds were prepared according to the general procedure described in Example 109, substituting the appropriately substituted amine for 1-(1H-indol-5-yl)methanamine (Step 2), or, substituting cesium carbonate for potassium carbonate (Step 2). The starting materials are either commercially available, known in the literature or may be prepared from commercially available reagents using conventional reactions well known in the art.

(IH)

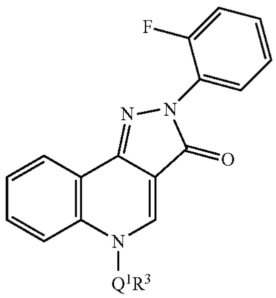

| Ex. | $Q^1R^3$ | HRMS/LRMS |
|---|---|---|
| 110 | 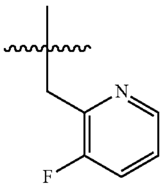 [SMILES: *Cc1ncccc1F] | $C_{22}H_{15}F_2N_4O$ [M + H] calc. 389.1209 obs. 389.1195 |
| 111 | 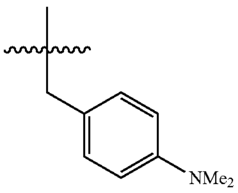 [SMILES: *Cc1ccc(N(C)C)cc1] | $C_{25}H_{22}FN_4O$ [M + H] calc. 413.1772 obs. 413.1758 |
| 112 | 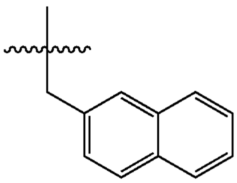 [SMILES: *Cc1ccc2ccccc2c1] | $C_{27}H_{19}FN_3O$ [M + H] calc. 420.1507 obs. 420.1494 |

-continued (IH)

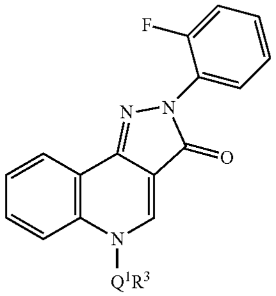

| Ex. | $Q^1R^3$ | HRMS/LRMS |
|---|---|---|
| 113 | 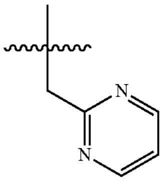 | $C_{21}H_{15}FN_5O$ [M + H] calc. 372.1255 obs. 372.1252 |
| 114 | 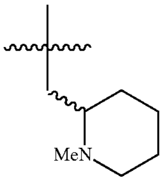 [SMILES: *CC1CCCCN1C] | $C_{23}H_{24}FN_4O$ [M + H] calc. 391.1929 obs. 391.1924 |
| 115 | 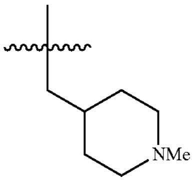 [SMILES: *CC1CCN(C)CC1] | $C_{23}H_{24}FN_4O$ [M + H] calc. 391.1929 obs. 391.1938 |
| 116 | 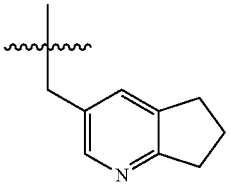 [SMILES: *Cc1cnc2c(c1)CCC2] | $C_{25}H_{20}FN_4O$ [M + H] calc. 411.1616 obs. 411.1626 |
| 117 | 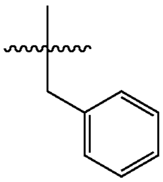 [SMILES: *Cc1ccccc1] | $C_{23}H_{17}FN_3O$ [M + H] calc. 370.1350 obs. 370.1350 |
| 118 | 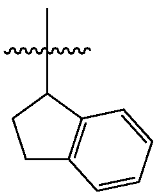 [SMILES: *C1CCc2ccccc21] | $C_{25}H_{19}FN_3O$ [M + H] calc. 396.1507 obs. 396.1505 |

-continued (IH)

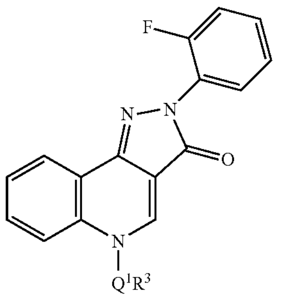

| Ex. | $Q^1R^3$ | HRMS/LRMS |
|---|---|---|
| 119 | 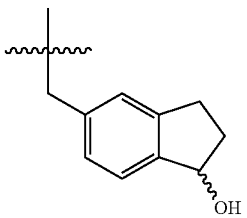 [SMILES: *Cc1ccc2c(c1)CCC2O] | $C_{26}H_{21}FN_3O_2$ [M + H] calc. 426.1613 obs. 426.1617 |
| 120 | 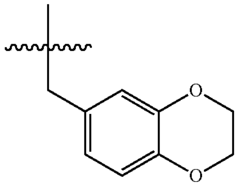 [SMILES: *Cc1ccc2c(c1)OCCO2] | $C_{25}H_{19}FN_3O_3$ [M + H] calc. 428.1405 obs. 428.1407 |

Example 121

2-(2-Fluorophenyl)-5-[(2-oxo-1-phenylpiperidin-4-yl)methyl]-2,5-dihydro-3H-pyrazolo[4,3-c]quinolin-3-one

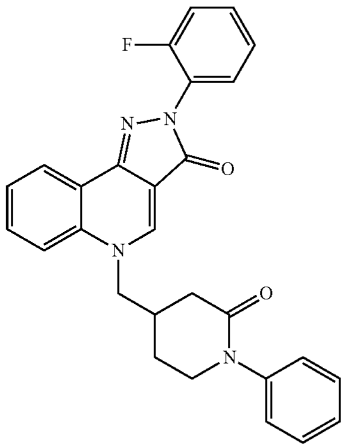 [SMILES: O=C1CC(Cn2cc3c(=O)n(-c4ccccc4F)nc-3c3ccccc32)CCN1c1ccccc1]

Step 1: Preparation of ethyl 2-oxo-1-phenylpiperidine-4-carboxylate

Ethyl 2-oxopiperidine-4-carboxylate (0.50 g, 2.9 mmol), iodobenzene (0.77 g, 3.8 mmol, 1.3 equiv), copper(I) iodide (56 mg, 0.29 mmol, 0.1 equiv), 4,7-bis(methoxy)-1,10-phenanthroline (70 mg, 0109 mmol, 0.1 equiv) and potassium carbonate (0.40 g, 3.8 mmol, 1 equiv) were combined in dimethylsulfoxide (10 mL) and placed into a preheated oil bath at 100° C. for 120 hours. The mixture was cooled to ambient temperature, diluted with ethyl acetate (50 mL) and washed with water (2×25 mL) and once with brine (25 mL). The organic extract was dried with sodium sulfate, filtered and concentrated in vacuo, providing the titled compound.

Step 2: Preparation of 4-(hydroxymethyl)-1-phenylpiperidin-2-one

Ethyl 2-oxo-1-phenylpiperidine-4-carboxylate (0.31 g, 1.3 mmol) was dissolved in tetrahydrofuran (10 mL), cooled to −78° C. and treated with lithium aluminum hydride (0.16 mL, 2 M tetrahydrofuran solution, 3.8 mmol, 3 equiv). The mixture was warmed to −40° C., stirred for 1 hour and treated with ammonium chloride (50 mL, aqueous saturated). The aqueous layer was extracted with ethyl acetate (2×50 mL) and the combined organic extracts were dried with sodium sulfate, filtered and concentrated in vacuo, providing the titled compound.

Step 3: Preparation of (2-oxo-1-phenylpiperidin-4-yl)methyl methanesulfonate 4-(Hydroxymethyl)-1-phenylpiperidin-2-one (0.27 g, 1.3 mmol) was dissolved in dichloromethane (15 mL), cooled to 0° C. and treated with triethylamine (1.0 mL, 7.2 mmol, 5.5 equiv). To the mixture was added methanesulfonyl chloride (0.10 mL, 1.3 mmol, 1 equiv), the mixture was warmed to ambient temperature and stirred for an additional 15 hours. The mixture was poured into water (25 mL) and extracted with dichloromethane (2×20 mL). The combined organic extracts were dried with sodium sulfate, filtered and concentrated in vacuo, providing the titled compound.

Step 4: Preparation of 4-(azidomethyl)-1-phenylpiperidin-2-one (2-oxo-1-phenylpiperidin-4yl)methyl methanesulfonate (0.37 g, 1.3 mmol) was dissolved in dimethylsulfoxide (6 mL), treated with sodium azide (0.18 g, 2.8 mmol, 2.1 equiv) and placed into a preheated oil bath at 60° C. for 18 hours. The mixture was cooled to ambient temperature, diluted with ethyl acetate (50 mL) and washed twice with water (50 mL) and brine (50 mL). The organic extract was dried with sodium sulfate, filtered and concentrated in vacuo, providing the titled compound.

Step 5: Preparation of 4-(aminomethyl)-1-phenylpiperidin-2-one 4-(Azidomethyl)-1-phenylpiperidin-2-one (0.37 g, 1.3 mmol) was dissolved in tetrahydrofuran (10 mL) and treated with triphenylphosphine (0.36 g, 1.4 mmol, 1.05 equiv). After stirring for 1 hour, the mixture was treated with water (1 mL) and stirred for 14 hours. The mixture was dried with sodium sulfate, filtered and concentrated in vacuo, providing the titled compound.

Step 6: Preparation of (4Z)-4-[(dimethylamino)methylidene]-2,5-bis(2-fluorophenyl)-2,4-dihydro-3H-pyrazol-3-one 2,5-Bis(2-fluorophenyl)-2,4-dihydro-3H-pyrazol-3-one [(Example 107, Step 1), 0.20 g, 0.73 mmol] and N,N-dimethylformamide dimethylacetal (0.12 mL, 0.88 mmol, 1.2 equiv) were combined in tetrahydrofuran (5 mL) and placed into a preheated oil bath at 65° C. for 1 hour. The mixture was cooled to ambient temperature and concentrated in vacuo, providing the titled compound.

Step 7: Preparation of 2-(2-fluorophenyl)-5-[(2-oxo-1-phenylpiperidin-4-yl)methyl]-2,5-dihydro-3H-pyrazolo[4,3-c]quinolin-3-one (4Z)-4-[(Dimethylamino)methylidene]-2,5-bis(2-fluorophenyl)-2,4-dihydro-3H-pyrazol-3-one (0.12 g, 0.37 mmol), 4-(aminomethyl)-1-phenylpiperidin-2-one (76 mg, 0.37 mmol, 1 equiv) and potassium carbonate (0.15 g, 1.1 mmol, 3 equiv) were combined in degassed dimethylsulfoxide (5 mL) and placed into a preheated oil bath at 100° C. open to the air for 1 hour. Additional 4-(aminomethyl)-1-phenylpiperidin-2-one (0.15 g, 0.74 mmol, 2 equiv) and potassium carbonate (0.15 g, 1.1 mmol, 3 equiv) were added and the mixture was heated at 100° C. for an additional 2 hours. The mixture was cooled to ambient temperature, poured into sodium bicarbonate (40 mL, aqueous saturated) and extracted with ethyl acetate (2×75 mL). The combined organic extracts were dried with sodium sulfate, filtered and concentrated in vacuo. The residue was purified by silica gel gradient chromatography (100:0 to 0:100 hexanes:ethyl acetate containing 5% methanol; then eluted with chloroform containing 15% methanol), providing the titled compound: $^1$H-NMR (400 MHz, $d^6$-DMSO) δ 8.93 (1H, s), 8.23 (1H, dd, 7.8, 1.4 Hz), 8.06 (1H, d, J=8.7 Hz), 7.79-7.75 (1H, m), 7.63-7.57 (2H, m), 7.47-7.30 (5H, m), 7.27-7.21 (3H, m), 4.49 (2H, d, J=7.1 Hz), 3.66-3.53 (2H, m), 2.68-2.58 (1H, m), 2.47-2.30 (2H, m), 1.89 (1H, br d, J=12.5 Hz), 1.85-1.73 (1H, m) ppm; low resolution mass spectrometry (ES+) m/z 466.97 [(M+H)$^+$]; calculated for $C_{28}H_{24}FN_4O_2$: 467.18].

The following compounds were prepared according to the general procedure described in Example 121, substituting the appropriately substituted amine for 4-(aminomethyl)-1-phenylpiperidin-2-one (Step 7), or, substituting cesium carbonate for potassium carbonate (Step 7). The starting materials are either commercially available, known in the literature or may be prepared from commercially available reagents using conventional reactions well known in the art.

(IJ)

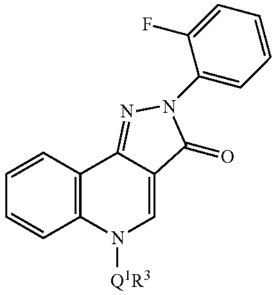

| Ex. | $Q^1R^3$ | HRMS/LRMS |
|---|---|---|
| 122 | 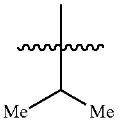 | $C_{19}H_{17}FN_3O$ [M + H] calc. 322.1350 obs. 322.1352 |

-continued (IJ)

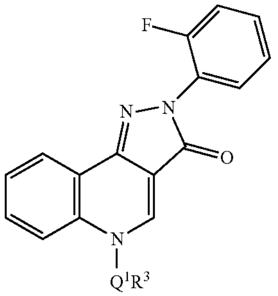

| Ex. | $Q^1R^3$ | HRMS/LRMS |
|---|---|---|
| 123 | 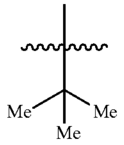 [SMILES: *C(C)(C)C] | $C_{20}H_{19}FN_3O$ [M + H] calc. 336.1507 obs. 336.1509 |
| 124 | 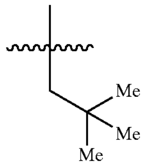 [SMILES: *CC(C)(C)C] | $C_{21}H_{21}FN_3O$ [M + H] calc. 350.1663 obs. 350.1650 |
| 125 | 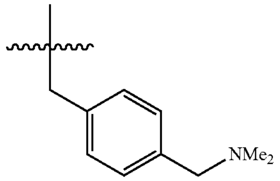 [SMILES: *Cc1ccc(CN(C)C)cc1] | $C_{26}H_{24}FN_4O$ [M + H] calc. 427.1929 obs. 427.1947 |
| 126 | 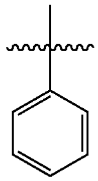 [SMILES: *c1ccccc1] | $C_{22}H_{15}FN_3O$ [M + H] calc. 356.1194 obs. 356.1191 |
| 127 | 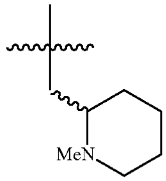 [SMILES: *CC1CCCCN1C] | $C_{23}H_{24}FN_4O$ [M + H] calc. 391.1929 obs. 391.1934 |
| 128 | 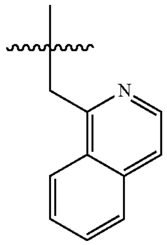 [SMILES: *Cc1nccc2ccccc12] | $C_{26}H_{17}FN_4O$ [M + H] calc. 421.1 obs. 421.0 |

(IJ)
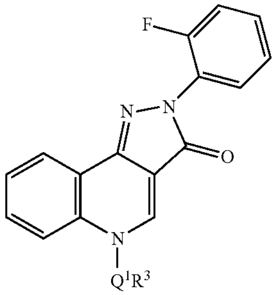
| Ex. | $Q^1R^3$ | HRMS/LRMS |
|---|---|---|
| 129 | 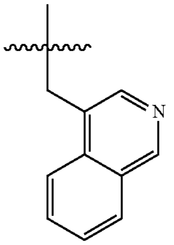 | $C_{26}H_{17}FN_4O$ [M + H] calc. 421.1459 obs. 421.1461 |
| 130 | 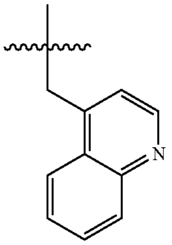 [SMILES: *Cc1ccnc2ccccc12] | $C_{26}H_{17}FN_4O$ [M + H] calc. 421.1459 obs. 421.1465 |
| 131 | 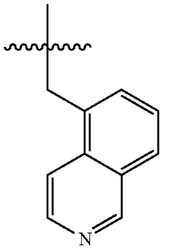 [SMILES: *Cc1cccc2cnccc12] | $C_{26}H_{17}FN_4O$ [M + H] calc. 421.1459 obs. 421.1454 |
| 132 | 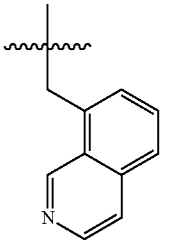 [SMILES: *Cc1cccc2ccncc12] | $C_{26}H_{17}FN_4O$ [M + H] calc. 421.1459 obs. 421.1458 |
| 133 | 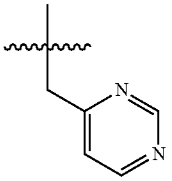 [SMILES: *Cc1ccncn1] | $C_{21}H_{14}FN_5O$ [M + H] calc. 372.1255 obs. 372.1250 |
(IJ)
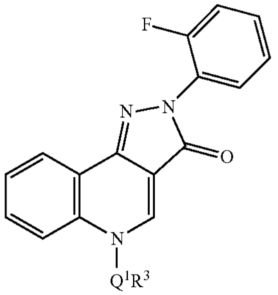
| Ex. | $Q^1R^3$ | HRMS/LRMS |
|---|---|---|
| 134 | 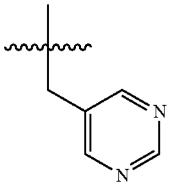 [SMILES: *Cc1cncnc1] | $C_{21}H_{14}FN_5O$ [M + H] calc. 372.1255 obs. 372.1254 |
| 135 | 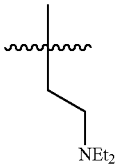 | $C_{22}H_{23}FN_4O$ [M + H] calc. 379.1929 obs. 379.1926 |
| 136 | 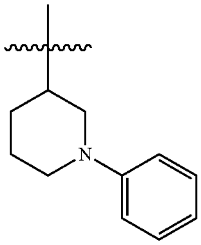 [SMILES: *C1CCCN(c2ccccc2)C1] | $C_{27}H_{23}FN_4O$ [M + H] calc. 439.1929 obs. 439.1931 |
| 137 | 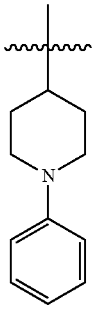 [SMILES: *C1CCN(c2ccccc2)CC1] | $C_{27}H_{23}FN_4O$ [M + H] calc. 439.1929 obs. 439.1921 |
| 138 | 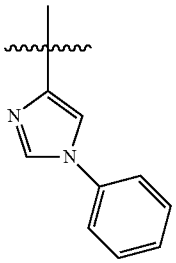 [SMILES: *c1cn(-c2ccccc2)cn1] | $C_{25}H_{16}FN_5O$ [M + H] calc. 422.1412 obs. 422.1415 |

-continued
(IJ)
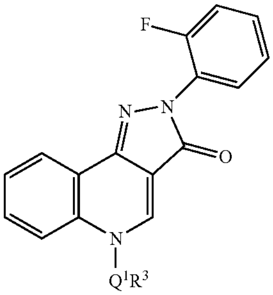
| Ex. | $Q^1R^3$ | HRMS/LRMS |
|---|---|---|
| 139 | 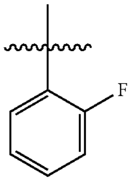 [SMILES: *c1ccccc1F] | $C_{22}H_{13}F_2N_3O$ [M + H] calc. 374.1099 obs. 374.1103 |
| 140 | 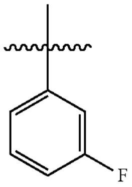 [SMILES: *c1cccc(F)c1] | $C_{22}H_{13}F_2N_3O$ [M + H] calc. 374.1099 obs. 374.1100 |
| 141 | 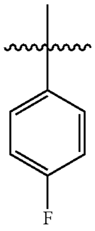 [SMILES: *c1ccc(F)cc1] | $C_{22}H_{13}F_2N_3O$ [M + H] calc. 374.1099 obs. 374.1096 |
| 142 | 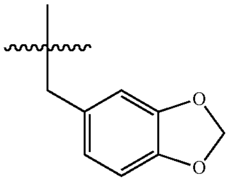 [SMILES: *Cc1ccc2c(c1)OCO2] | $C_{24}H_{17}F_2N_3O_3$ [M + H] calc. 414.1248 obs. 414.1242 |
| 143 | 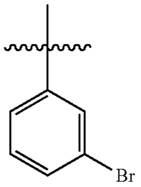 [SMILES: *c1cccc(Br)c1] | $C_{22}H_{13}BrFN_3O$ [M + H] calc. 434.0299 obs. 434.0297 |
| 144 | 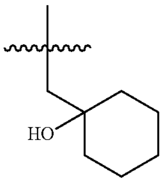 [SMILES: *CC1(O)CCCCC1] | $C_{23}H_{22}FN_3O_2$ [M + H] calc. 392.1769 obs. 392.1762 |
-continued
(IJ)
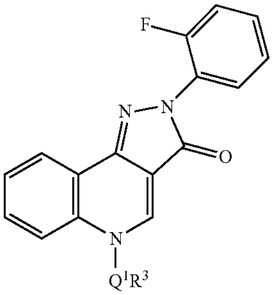
| Ex. | $Q^1R^3$ | HRMS/LRMS |
|---|---|---|
| 145 | 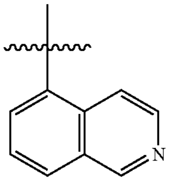 [SMILES: *c1cccc2cnccc12] | $C_{25}H_{15}FN_4O$ [M + H] calc. 407.1303 obs. 407.1300 |
| 146 | 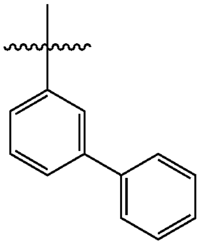 [SMILES: *c1cccc(-c2ccccc2)c1] | $C_{28}H_{18}FN_3O$ [M + H] calc. 432.1507 obs. 432.1507 |
| 147 | 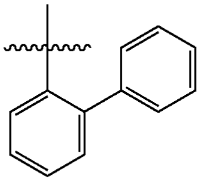 [SMILES: *c1ccccc1-c1ccccc1] | $C_{28}H_{18}FN_3O$ [M + H] calc. 432.1507 obs. 432.1506 |
| 148 | 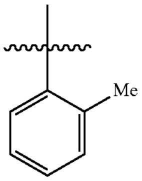 [SMILES: *c1ccccc1C] | $C_{23}H_{16}FN_3O$ [M + H] calc. 370.1350 obs. 370.1351 |
| 149 | 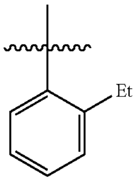 [SMILES: *c1ccccc1CC] | $C_{24}H_{18}FN_3O$ [M + H] calc. 384.1507 obs. 384.1506 |
| 150 | 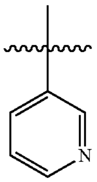 [SMILES: *c1cccnc1] | $C_{21}H_{13}FN_4O$ [M + H] calc. 357.1146 obs. 357.1143 |

-continued
(IJ)
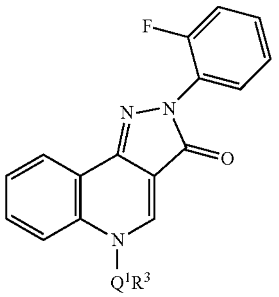
| Ex. | $Q^1R^3$ | HRMS/LRMS |
| --- | --- | --- |
| 151 | 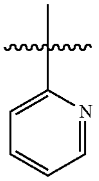 [SMILES: *c1ccccn1] | $C_{21}H_{13}FN_4O$ [M + H] calc. 357.1146 obs. 357.1143 |
| 152 | 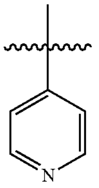 | $C_{21}H_{13}FN_4O$ [M + H] calc. 357.1146 obs. 357.1144 |
| 153 | 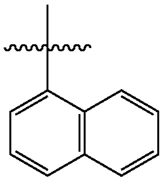 [SMILES: *c1cccc2ccccc12] | $C_{26}H_{16}FN_3O$ [M + H] calc. 446.1663 obs. 446.1660 |
| 154 | 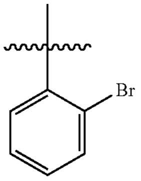 [SMILES: *c1ccccc1Br] | $C_{22}H_{13}BrFN_3O$ [M + H] calc. 434.0299 obs. 434.0297 |
| 155 | 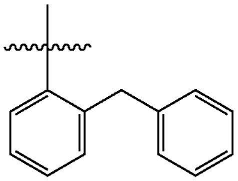 [SMILES: *c1ccccc1Cc1ccccc1] | $C_{29}H_{20}FN_3O$ [M + H] calc. 446.1663 obs. 446.1660 |
| 156 | 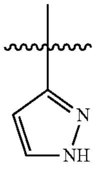 [SMILES: *c1cc[nH]n1] | $C_{19}H_{12}FN_5O$ [M + H] calc. 346.1099 obs. 346.1096 |
-continued
(IJ)
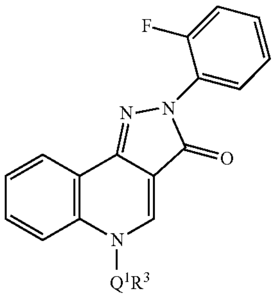
| Ex. | $Q^1R^3$ | HRMS/LRMS |
| --- | --- | --- |
| 157 | 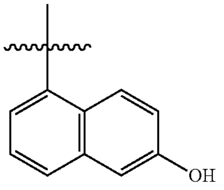 [SMILES: *c1cccc2cc(O)ccc12] | $C_{26}H_{16}FN_3O_2$ [M + H] calc. 422.1299 obs. 422.1296 |
| 158 | 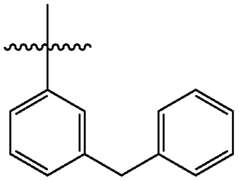 [SMILES: *c1cccc(Cc2ccccc2)c1] | $C_{29}H_{20}FN_3O$ [M + H] calc. 446.1663 obs. 446.1657 |
| 159 | 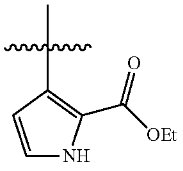 [SMILES: *c1cc[nH]c1C(=O)OCC] | $C_{23}H_{17}FN_4O_3$ [M + H] calc. 417.1357 obs. 417.1352 |
| 160 | 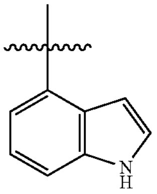 [SMILES: *c1cccc2[nH]ccc12] | $C_{24}H_{15}FN_4O$ [M + H] calc. 395.1303 obs. 395.1299 |
| 161 | 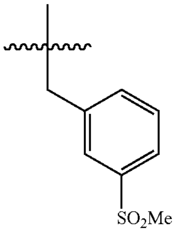 | $C_{24}H_{19}FN_3O_3S$ [M + H] calc. 448.1126 obs. 448.1123 |
| 162 | 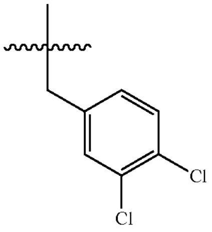 [SMILES: *Cc1ccc(Cl)c(Cl)c1] | $C_{23}H_{14}Cl_2FN_3O$ [M + H] calc. 438.0571 obs. 438.0571 |

-continued
(IJ)
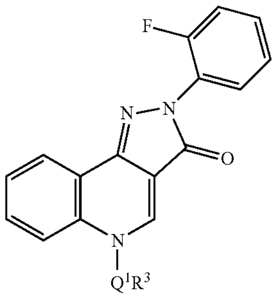
| Ex. | $Q^1R^3$ | HRMS/LRMS |
|---|---|---|
| 163 | 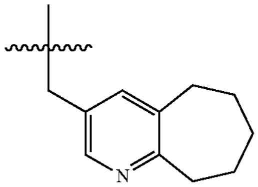 [SMILES: *Cc1cnc2c(c1)CCCCC2] | $C_{27}H_{24}FN_4O$ [M + H] calc. 439.1929 obs. 439.1938 |
| 164 | 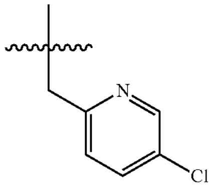 [SMILES: *Cc1ccc(Cl)cn1] | $C_{22}H_{15}ClFN_4O$ [M + H] calc. 405.0913 obs. 405.0923 |
| 165 | 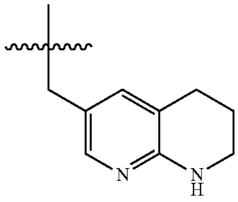 [SMILES: *Cc1cnc2c(c1)CCCN2] | $C_{25}H_{21}FN_5O$ [M + H] calc. 426.1725 obs. 426.1731 |
| 166 | 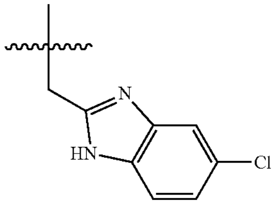 [SMILES: *Cc1nc2cc(Cl)ccc2[nH]1] | $C_{24}H_{16}ClFN_5O$ [M + H] calc. 444.1022 obs. 444.1028 |
| 167 | 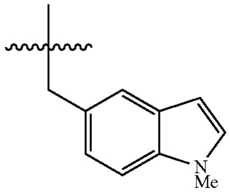 [SMILES: *Cc1ccc2c(ccn2C)c1] | $C_{26}H_{20}FN_4O$ [M + H] calc. 423.1616 obs. 423.1624 |
| 168 | 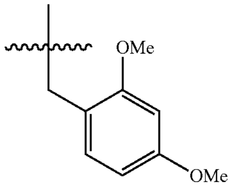 [SMILES: *Cc1ccc(OC)cc1OC] | $C_{25}H_{21}FN_3O_3$ [M + H] calc. 430.1561 obs. 430.1572 |
-continued
(IJ)
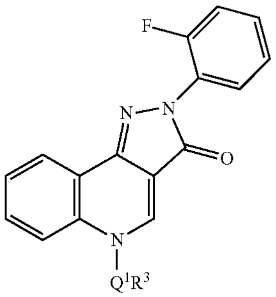
| Ex. | $Q^1R^3$ | HRMS/LRMS |
|---|---|---|
| 169 | 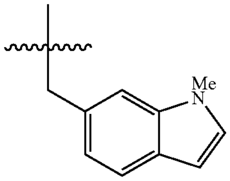 [SMILES: *Cc1ccc2ccn(C)c2c1] | $C_{26}H_{20}FN_4O$ [M + H] calc. 423.1616 obs. 423.1625 |
| 170 | 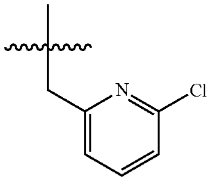 [SMILES: *Cc1cccc(Cl)n1] | $C_{22}H_{15}ClFN_4O$ [M + H] calc. 405.0913 obs. 405.0917 |
| 171 | 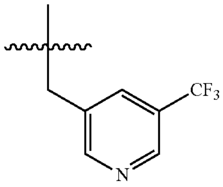 [SMILES: *Cc1cncc(C(F)(F)F)c1] | $C_{23}H_{15}F_4N_4O$ [M + H] calc. 439.1177 obs. 439.1184 |
| 172 | 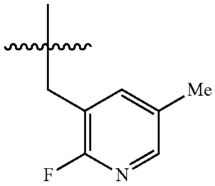 [SMILES: *Cc1cc(C)cnc1F] | $C_{23}H_{17}F_2N_4O$ [M + H] calc. 403.1365 obs. 403.1366 |
| 173 | 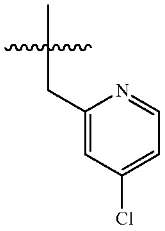 [SMILES: *Cc1cc(Cl)ccn1] | $C_{22}H_{15}ClFN_4O$ [M + H] calc. 405.0913 obs. 405.0913 |
| 174 | 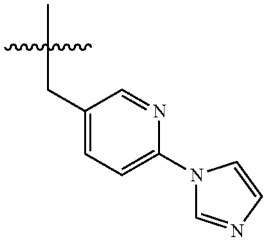 [SMILES: *Cc1ccc(-n2ccnc2)nc1] | $C_{25}H_{18}FN_6O$ [M + H] calc. 437.1521 obs. 437.1518 |

-continued
(IJ)
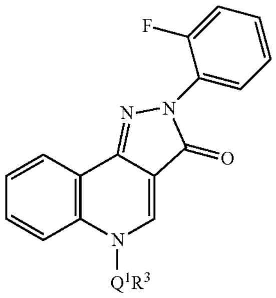
| Ex. | $Q^1R^3$ | HRMS/LRMS |
|---|---|---|
| 175 | 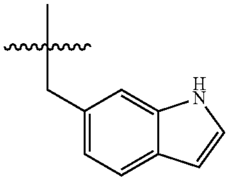 [SMILES: *Cc1ccc2cc[nH]c2c1] | $C_{25}H_{18}FN_4O$ [M + H] calc. 409.1459 obs. 409.1465 |
| 176 | 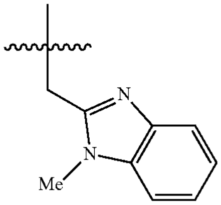 [SMILES: *Cc1nc2ccccc2n1C] | $C_{25}H_{19}FN_5O$ [M + H] calc. 424.1568 obs. 424.1568 |
| 177 | 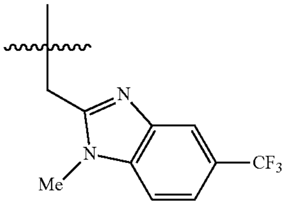 [SMILES: *Cc1nc2cc(C(F)(F)F)ccc2n1C] | $C_{26}H_{18}F_4N_5O$ [M + H] calc. 492.1442 obs. 492.1439 |
| 178 | 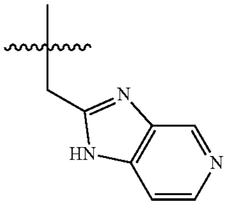 [SMILES: *Cc1nc2cnccc2[nH]1] | $C_{23}H_{16}FN_6O$ [M + H] calc. 411.1364 obs. 411.1362 |
| 179 | 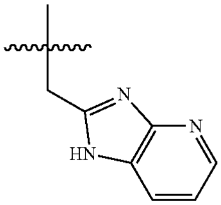 [SMILES: *Cc1nc2ncccc2[nH]1] | $C_{23}H_{16}FN_6O$ [M + H] calc. 411.1364 obs. 411.1364 |
| 180 | 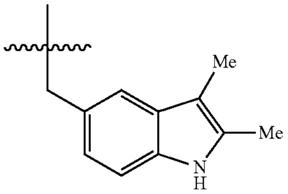 [SMILES: *Cc1ccc2[nH]c(C)c(C)c2c1] | $C_{27}H_{22}FN_4O$ [M + H] calc. 437.1772 obs. 437.1769 |
-continued
(IJ)
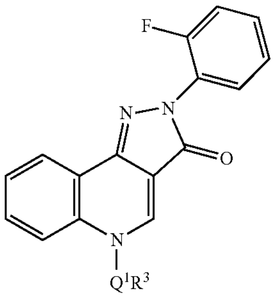
| Ex. | $Q^1R^3$ | HRMS/LRMS |
|---|---|---|
| 181 | 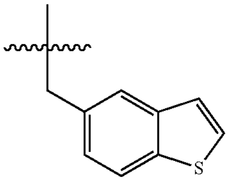 [SMILES: *Cc1ccc2sccc2c1] | $C_{25}H_{17}FN_3OS$ [M + H] calc. 426.1071 obs. 426.1070 |
| 182 | 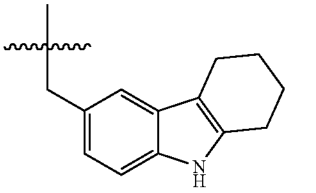 [SMILES: *Cc1ccc2[nH]c3c(c2c1)CCCC3] | $C_{29}H_{24}FN_4O$ [M + H] calc. 463.1929 obs. 463.1928 |
| 183 | 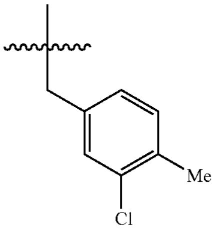 [SMILES: *Cc1ccc(C)c(Cl)c1] | $C_{24}H_{18}ClFN_3O$ [M + H] calc. 418.1117 obs. 418.1117 |
| 184 | 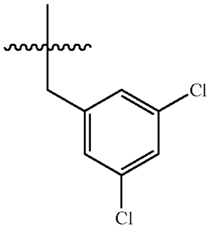 [SMILES: *Cc1cc(Cl)cc(Cl)c1] | $C_{23}H_{15}Cl_2FN_3O$ [M + H] calc. 438.0571 obs. 438.0575 |
| 185 | 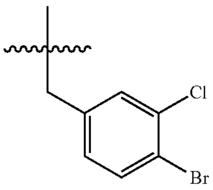 [SMILES: *Cc1ccc(Br)c(Cl)c1] | $C_{23}H_{15}BrClFN_3O$ [M + H] calc. 482.0066 obs. 482.0076 |
| 186 | 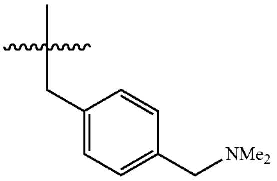 [SMILES: *Cc1ccc(CN(C)C)cc1] | $C_{26}H_{24}FN_4O$ [M + H] calc. 427.1929 obs. 427.1947 |

Example 187

5{[2-Fluoro-4-(1H-indol-5-yl)phenyl]methyl}-2-(2-fluorophenyl)-2,5-dihydro-3H-pyrazolo[4,3-c]quinolin-3-one

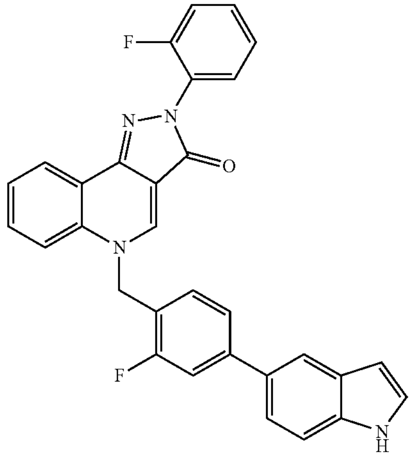 [SMILES: O=c1c2cn(Cc3ccc(-c4ccc5[nH]ccc5c4)cc3F)c3ccccc3c-2nn1-c1ccccc1F]

Step 1: Preparation of ethyl 1-[(2-fluoro-4-iodophenyl)methyl]-4-oxo-1,4-dihydroquinoline-3-carboxylate Using the procedures described in Example 8, substituting 1-(bromomethyl)-2-fluoro-4-iododbenzene (Example 83, Step 1) for 4-(bromomethyl)biphenyl (Step 1), the titled compound was obtained.

Step 2: Preparation of 5-[(2-fluoro-4-iodophenyl)methyl]-2-(2-fluorophenyl)-2,5-dihydro-3H-pyrazol[4,3-c]quinolin-3-one Ethyl 1-[(2-fluoro-4-iodophenyl)methyl]-4-oxo-1,4-dihydroquinoline-3-carboxylate (1.4 g, 3.1 mmol) was dissovled in phosphorus oxychloride (6.0 mL, 64 mmol, 21 equiv) and stirred for 2.5 hours at ambient temperature. The mixture was diluted with toluene (10 mL) and concentrated in vacuo. The residue was dissolved in dioxane (17 mL), treated with 2-fluorophenylhydrazine (0.87 g, 6.8 mmol, 2.2 equiv) and potassium carbonate (1.3 g, 9.4 mmol, 3 equiv) and stirred at ambient temperature for 5 minutes. The mixture was placed into a preheated oil bath at 80° C. for 1 hour, cooled to ambient temperature and diluted with chloroform (150 mL). The organic mixture was washed once with water (50 mL) and brine (50 mL), dried with sodium sulfate, filtered and concentrated in vacuo. The residue was triturated with a chloroform:methanol (95:5) solution (30 mL). The solid was filtered and dried in vacuo, providing the titled compound.

Step 3: Preparation of 5{[2-fluoro-4-(1H-indol-5-yl)phenyl]methyl}-2-(2-fluorophenyl)-2,5-dihydro-3H-pyrazolo[4,3-c]quinolin-3-one 5-[(2-Fluoro-4-iodophenyl)methyl]-2-(2-fluorophenyl)-2,5-dihydro-3H-pyrazol[4,3-c]quinolin-3-one (51 mg, 0.10 mmol), 1H-indol-5-ylboronic acid (27 mg, 0.17 mmol, 1.7 equiv), potassium carbonate (34 mg, 0.25 mmol, 2.5 equiv), palladium(II) acetate (12 mg, 0.0010 mmol, 0.1 equiv) and 2-dicyclohexylphosphino-2',4',6'-tri-iso-propyl-1,1'-biphenyl (14 mg, 0.030 mmol, 0.3 equiv) were combined in water (0.1 mL) and dimethylsulfoxide (0.5 mL) and placed into a preheated oil bath at 85° C. for 90 minutes. The mixture was cooled to ambient temperature, filtered and purified by reverse phase HPLC (80:20 to 5:95; water containing 0.1% trifluoroacetic acid:acetonitrile containing 0.1% trifluoroacetic acid), providing the titled compound: $^1$H-NMR (400 MHz, d$^6$-DMSO) δ 11.18 (1H, s), 9.11 (1H, s), 8.22 (1H, dd, J=7.9, 1.5 Hz), 7.85 (1H, s), 7.79 (1H, d, J=8.7 Hz), 7.68 (1H, ddd, J=8.5, 7.3, 1.6 Hz), 7.62 (1H, dd, J=7.9, 1.7 Hz), 7.60 (1H, br s), 7.57 (1H, s), 7.55 (1H, d, J=7.4 Hz), 7.49 (1H, dd, J=8.1, 1.8 Hz), 7.47-7.37 (4H, m), 7.34 (1H, td, J=7.5, 1.4 Hz), 7.28 (1H, t, J=8.2 Hz), 6.48-6.47 (1H, m), 5.83 (2H, s) ppm; low resolution mass spectrometry (ES+) m/z 503.1667 [(M+H)$^+$; calculated for $C_{31}H_{21}F_2N_4O$: 503.1678].

The following compounds were prepared according to the general procedure described in Example 187, substituting the appropriately substituted boronic acid or ester for 1H-indol-5-ylboronic acid (Step 3). The starting materials are either commercially available, known in the literature or may be prepared from commercially available reagents using conventional reactions well known in the art.

(IK)

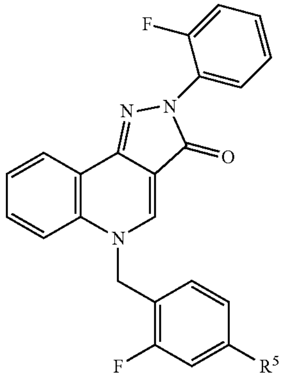

| Ex. | $R^5$ | HRMS/LRMS |
|---|---|---|
| 188 | 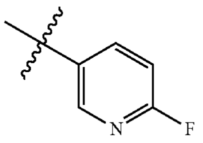 [SMILES: *c1ccc(F)nc1] | $C_{28}H_{18}F_3N_4O$ [M + H] calc. 483.1427 obs. 483.1420 |
| 189 | 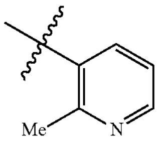 [SMILES: *c1cccnc1C] | $C_{29}H_{21}F_2N_4O$ [M + H] calc. 479.1678 obs. 479.1663 |
| 190 | 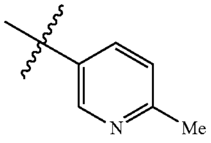 [SMILES: *c1ccc(C)nc1] | $C_{29}H_{21}F_2N_4O$ [M + H] calc. 479.1678 obs. 479.1672 |
| 191 | 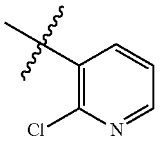 [SMILES: *c1cccnc1Cl] | $C_{28}H_{18}ClF_2N_4O$ [M + H] calc. 499.1132 obs. 499.1116 |

-continued (IK)

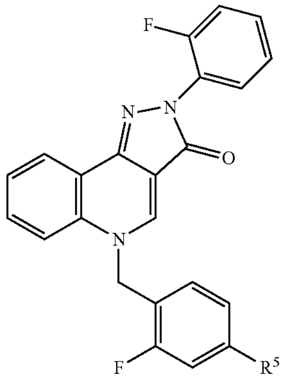

| Ex. | $R^5$ | HRMS/LRMS |
|---|---|---|
| 192 | 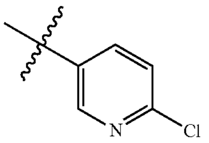 [SMILES: *c1ccc(Cl)nc1] | $C_{28}H_{18}ClF_2N_4O$<br>[M + H]<br>calc. 499.1132<br>obs. 499.1122 |
| 193 | 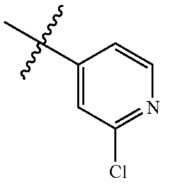 [SMILES: *c1ccnc(Cl)c1] | $C_{28}H_{18}ClF_2N_4O$<br>[M + H]<br>calc. 499.1132<br>obs. 499.1123 |
| 194 | 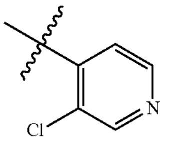 [SMILES: *c1ccncc1Cl] | $C_{28}H_{18}ClF_2N_4O$<br>[M + H]<br>calc. 499.1132<br>obs. 499.1124 |
| 195 | 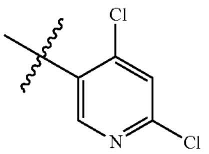 | $C_{28}H_{17}Cl_2F_2N_4O$<br>[M + H]<br>calc. 533.0742<br>obs. 533.0735 |
| 196 | 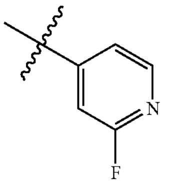 [SMILES: *c1ccnc(F)c1] | $C_{28}H_{18}F_3N_4O$<br>[M + H]<br>calc. 483.1427<br>obs. 483.1418 |
| 197 | 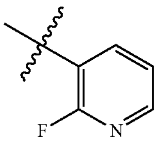 | $C_{28}H_{18}F_3N_4O$<br>[M + H]<br>calc. 483.1427<br>obs. 483.1421 |

-continued (IK)

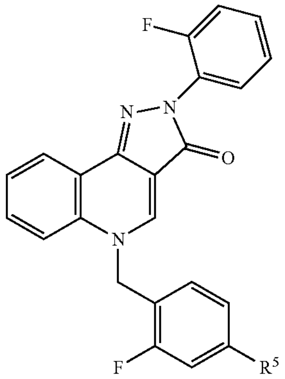

| Ex. | $R^5$ | HRMS/LRMS |
|---|---|---|
| 198 | 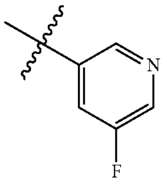 [SMILES: *c1cncc(F)c1] | $C_{28}H_{18}F_3N_4O$<br>[M + H]<br>calc. 483.1427<br>obs. 483.1421 |
| 199 | 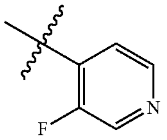 [SMILES: *c1ccncc1F] | $C_{28}H_{18}F_3N_4O$<br>[M + H]<br>calc. 483.1427<br>obs. 483.1416 |
| 200 | 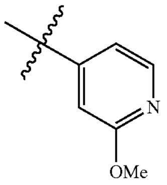 [SMILES: *c1ccnc(OC)c1] | $C_{28}H_{21}F_2N_4O_2$<br>[M + H]<br>calc. 495.1627<br>obs. 495.1626 |
| 201 | 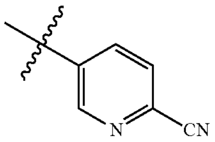 | $C_{28}H_{18}F_2N_5O$<br>[M + H]<br>calc. 490.1474<br>obs. 490.1461 |
| 202 | 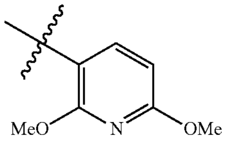 [SMILES: *c1ccc(OC)nc1OC] | $C_{30}H_{23}F_2N_4O_3$<br>[M + H]<br>calc. 525.1733<br>obs. 525.1720 |
| 203 | 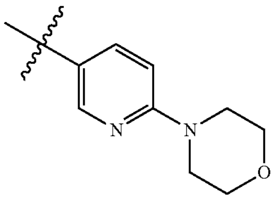 [SMILES: *c1ccc(N2CCOCC2)nc1] | $C_{32}H_{26}F_2N_5O_2$<br>[M + H]<br>calc. 550.2049<br>obs. 550.2045 |
| 204 | 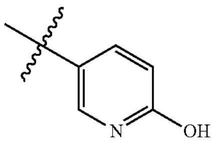 [SMILES: *c1ccc(O)nc1] | $C_{28}H_{19}F_2N_4O_2$<br>[M + H]<br>calc. 481.1471<br>obs. 481.1459 |

-continued
(IK)
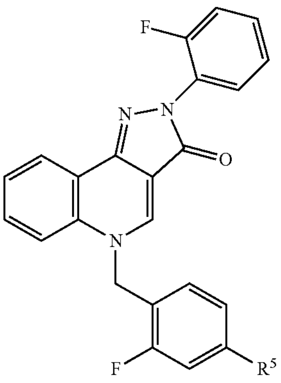
| Ex. | $R^5$ | HRMS/LRMS |
|---|---|---|
| 205 | 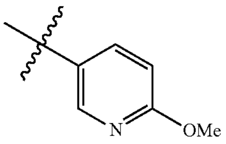 | $C_{29}H_{21}F_2N_4O_2$ [M + H] calc. 495.1627 obs. 495.1621 |
| 206 | 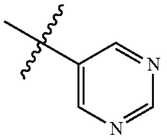 [SMILES: *c1cncnc1] | $C_{27}H_{18}F_2N_5O$ [M + H] calc. 466.1474 obs. 466.1463 |
| 207 | 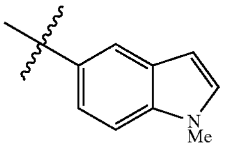 [SMILES: *c1ccc2c(ccn2C)c1] | $C_{32}H_{23}F_2N_4O$ [M + H] calc. 517.1835 obs. 517.1825 |
| 208 | 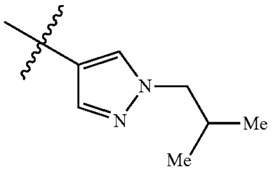 [SMILES: *c1cnn(CC(C)C)c1] | $C_{30}H_{26}F_2N_5O$ [M + H] calc. 510.2100 obs. 510.2108 |
| 209 | 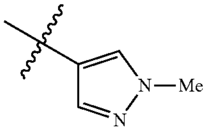 [SMILES: *c1cnn(C)c1] | $C_{27}H_{20}F_2N_5O$ [M + H] calc. 468.1631 obs. 468.1631 |
| 210 | 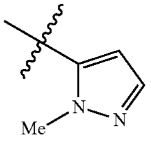 [SMILES: *c1ccnn1C] | $C_{27}H_{20}F_2N_5O$ [M + H] calc. 468.1631 obs. 468.1620 |
| 211 | 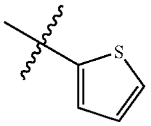 [SMILES: *c1cccs1] | $C_{27}H_{18}F_2N_3OS$ [M + H] calc. 470.1133 obs. 470.1129 |
-continued
(IK)
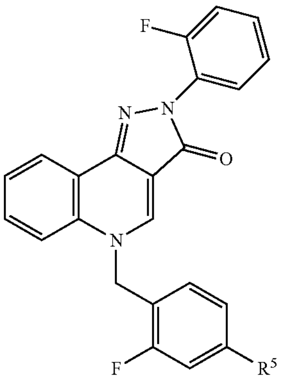
| Ex. | $R^5$ | HRMS/LRMS |
|---|---|---|
| 212 | 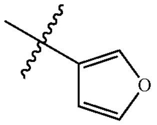 [SMILES: *c1ccoc1] | $C_{27}H_{18}F_2N_3O_2$ [M + H] calc. 454.1362 obs. 454.1358 |
| 213 | 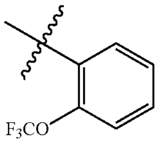 | $C_{30}H_{19}F_5N_3O_2$ [M + H] calc. 548.1392 obs. 548.1388 |
| 214 | 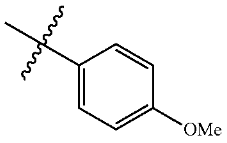 [SMILES: *c1ccc(OC)cc1] | $C_{30}H_{22}F_2N_3O_2$ [M + H] calc. 494.1675 obs. 494.1669 |
| 215 | 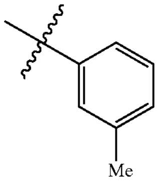 [SMILES: *c1cccc(C)c1] | $C_{30}H_{22}F_2N_3O$ [M + H] calc. 478.1726 obs. 478.1721 |
| 216 | 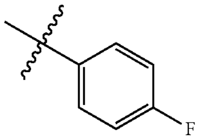 [SMILES: *c1ccc(F)cc1] | $C_{29}H_{19}F_3N_3O$ [M + H] calc. 482.1475 obs. 482.1467 |
| 217 | 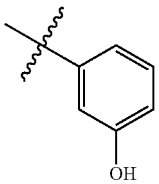 [SMILES: *c1cccc(O)c1] | $C_{29}H_{20}F_2N_3O_2$ [M + H] calc. 480.1518 obs. 480.1501 |
| 218 | 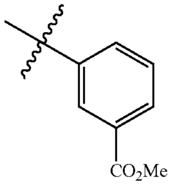 [SMILES: *c1cccc(C(=O)OC)c1] | $C_{31}H_{22}F_2N_3O_3$ [M + H] calc. 522.1624 obs. 522.1620 |

-continued (IK)

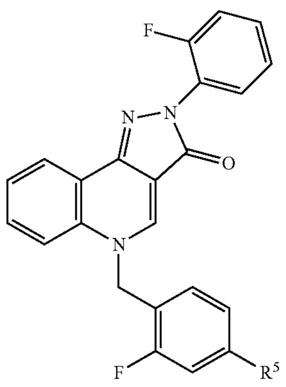

| Ex. | $R^5$ | HRMS/LRMS |
|---|---|---|
| 219 | 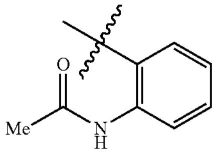 [SMILES: *c1ccccc1NC(C)=O] | $C_{31}H_{23}F_2N_4O_2$ [M + H] calc. 521.1784 obs. 521.1790 |
| 220 | 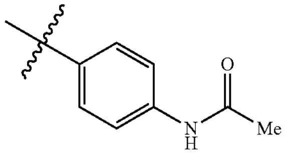 [SMILES: *c1ccc(NC(C)=O)cc1] | $C_{31}H_{23}F_2N_4O_2$ [M + H] calc. 521.1784 obs. 521.1777 |
| 221 | 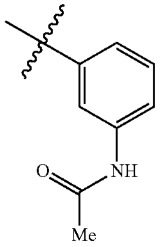 [SMILES: *c1cccc(NC(C)=O)c1] | $C_{31}H_{23}F_2N_4O_2$ [M + H] calc. 521.1784 obs. 521.1777 |
| 222 | 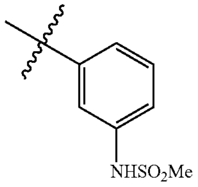 | $C_{30}H_{23}F_2N_4O_3S$ [M + H] calc. 557.1454 obs. 557.1445 |
| 223 | 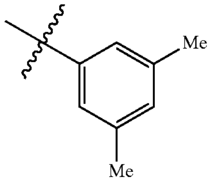 [SMILES: *c1cc(C)cc(C)c1] | $C_{31}H_{24}F_2N_3O$ [M + H] calc. 492.1882 obs. 492.1883 |
| 224 | 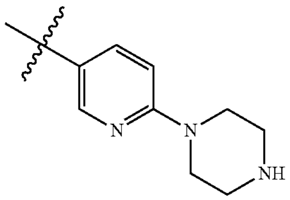 [SMILES: *c1ccc(N2CCNCC2)nc1] | $C_{32}H_{27}F_2N_6O$ [M + H] calc. 549.2209 obs. 549.2225 |

Example 225

5-[(6-Chloropyridin-3-yl)methyl]-2-(2-fluorophenyl)-2,5-dihydro-3H-pyrazolo[4,3-c]quinolin-3-one

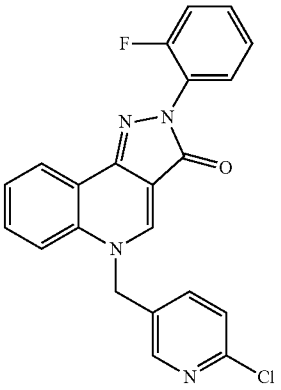 [SMILES: O=c1c2cn(Cc3ccc(Cl)nc3)c3ccccc3c-2nn1-c1ccccc1F]

Using the procedures described in Example 187, substituting 2-chloro-5-methylpyridine for 1-(bromomethyl)-2-fluoro-4-iodobenzene (Step 1), the titled compound was obtained: $^1$H-NMR (400 MHz, $d^6$-DMSO) δ 9.13 (1H, s), 8.55 (1H, d, J=2.4 Hz), 8.20 (1H, dd, J=7.9, 1.5 Hz), 7.78-7.74 (2H, m), 7.66-7.52 (3H, m), 7.49-7.37 (3H, m), 7.34 (1H, td, J=7.6, 1.6 Hz), 5.78 (2H, s) ppm; low resolution mass spectrometry (ES+) m/z 404.9 $[(M+H)^+]$; calculated for $C_{22}H_{15}ClFN_4O$: 405.1].

Example 226

2-(2-Fluorophenyl)-5-{[6-(1-methyl-1H-pyrazol-4-yl)pyridin-4-yl]methyl}-2,5-dihydro-3H-pyrazolo[4,3-c]quinolin-3-one

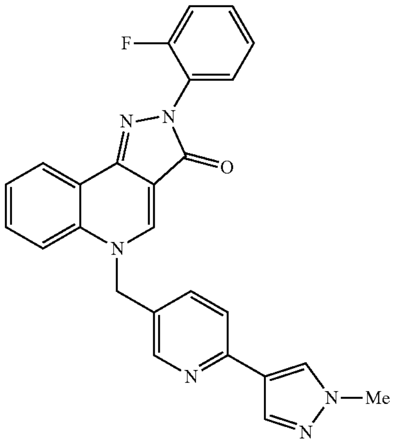 [SMILES: Cn1cc(-c2ccc(Cn3cc4c(=O)n(-c5ccccc5F)nc-4c4ccccc43)cn2)cn1]

5-[(6-Chloropyridin-3-yl)methyl]-2-(2-fluorophenyl)-2,5-dihydro-3H-pyrazolo[4,3-c]quinolin-3-one (Example 225, 40 mg, 0.10 mmol), bis(tri-tert-butylphosphine)palladium(0) (5.0 mg, 0.010 mmol, 0.1 equiv), cesium carbonate (0.20 mL, 1 M aqueous, 0.20 mmol, 2 equiv) and 1-methyl-4-(4,4,5,5-tetramethyl-1,3,2-dioxaborolan-2-yl)-1H-pyrazole (35 mg, 0.17 mmol, 1.7 equiv) were suspended in tetrahydrofuran (1 mL) and the mixture was irradiated (high setting) for 10 minutes at 140° C. The mixture was cooled to ambient temperature, the organic layer removed, stirred with Quadrapure® (40 mg, 1 wt equiv) for 1 hour, filtered and purified by reverse phase HPLC (80:20 to 5:95; water containing 0.1% trifluoroacetic acid:acetonitrile containing 0.1% trifluoroacetic acid), providing the titled compound: $^1$H-NMR (400 MHz, d$^6$-DMSO) δ 9.16 (1H, s), 8.65 (1H, d, J=2.2 Hz), 829 (1H, s), 8.20 (1H, dd, J=7.8, 1.4 Hz), 7.99 (1H, s), 7.83 (1H, d, J=8.7 Hz), 7.76 (1H, dd, J=8.2, 2.0 Hz), 7.66-7.58 (3H, m), 7.54 (1H, t, J=7.5 Hz), 7.48-7.37 (2H, m), 7.34 (1H, td, J=7.7, 1.5 Hz), 5.76 (2H, s), 3.87 (3H, s) ppm; low resolution mass spectrometry (ES+) m/z 451.0 [(M+H)$^+$; calculated for $C_{26}H_{20}FN_6O$: 451.2].

The following compounds were prepared according to the general procedure described in Example 226, substituting the appropriately substituted boronic acid or ester for 1-methyl-4-(4,4,5,5-tetramethyl-1,3,2-dioxaborolan-2-yl)-1H-pyrazole. The starting materials are either commercially available, known in the literature or may be prepared from commercially available reagents using conventional reactions well known in the art.

(IL)

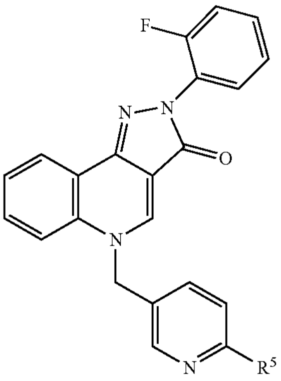

| Ex. | $R^5$ | HRMS/LRMS |
|---|---|---|
| 227 | 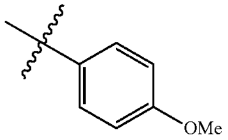 [SMILES: *c1ccc(OC)cc1] | $C_{29}H_{22}FN_4O_2$ [M + H] calc. 477.1 obs. 477.0 |
| 228 | 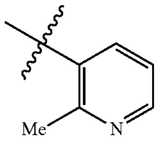 [SMILES: *c1cccnc1C] | $C_{28}H_{21}FN_5O$ [M + H] calc. 462.1 obs. 462.1 |
| 229 | 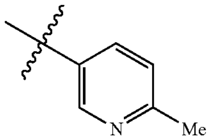 [SMILES: *c1ccc(C)nc1] | $C_{28}H_{21}FN_5O$ [M + H] calc. 462.1 obs. 462.1 |
| 230 | 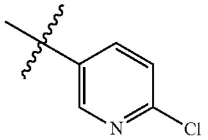 [SMILES: *c1ccc(Cl)nc1] | $C_{27}H_{18}ClFN_5O$ [M + H] calc. 482.1 obs. 482.1 |

-continued (IL)

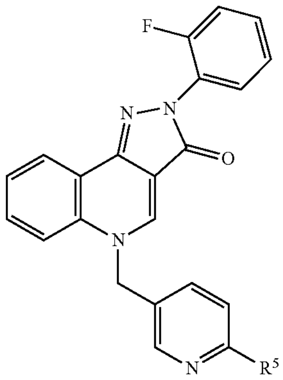

| Ex. | $R^5$ | HRMS/LRMS |
|---|---|---|
| 231 | 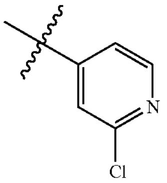 [SMILES: *c1ccnc(Cl)c1] | $C_{27}H_{18}ClFN_5O$ [M + H] calc. 482.1 obs. 482.1 |
| 232 | 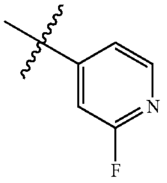 [SMILES: *c1ccnc(F)c1] | $C_{27}H_{18}F_2N_5O$ [M + H] calc. 466.1 obs. 466.1 |
| 233 | 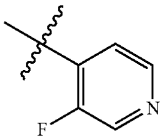 [SMILES: *c1ccncc1F] | $C_{27}H_{18}F_2N_5O$ [M + H] calc. 466.1 obs. 466.1 |
| 234 | 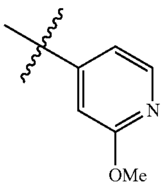 [SMILES: *c1ccnc(OC)c1] | $C_{28}H_{21}FN_5O_2$ [M + H] calc. 478.2 obs. 478.1 |
| 235 | 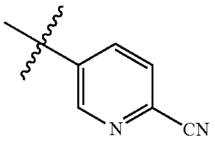 [SMILES: *c1ccc(C#N)nc1] | $C_{28}H_{18}FN_6O$ [M + H] calc. 473.1 obs. 473.1 |
| 236 | 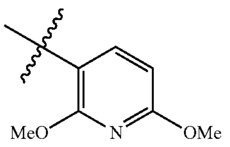 [SMILES: *c1ccc(OC)nc1OC] | $C_{29}H_{23}FN_5O_3$ [M + H] calc. 508.2 obs. 508.2 |

-continued
(IL)
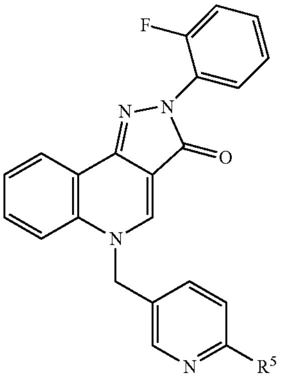
| Ex. | $R^5$ | HRMS/LRMS |
|---|---|---|
| 237 | 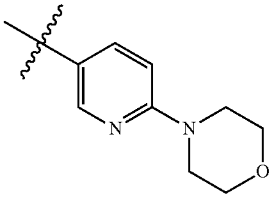 [SMILES: *c1ccc(N2CCOCC2)nc1] | $C_{31}H_{26}FN_6O_2$ [M + H] calc. 533.2 obs. 533.2 |
| 238 | 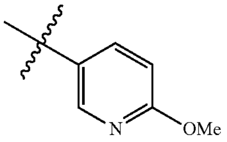 | $C_{28}H_{21}FN_5O_2$ [M + H] calc. 478.2 obs. 478.1 |
| 239 | 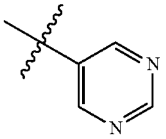 [SMILES: *c1cncnc1] | $C_{26}H_{18}FN_6O$ [M + H] calc. 449.2 obs. 449.1 |
| 240 | 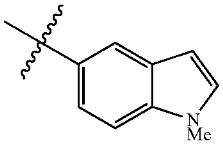 [SMILES: *c1ccc2c(ccn2C)c1] | $C_{31}H_{23}FN_5O$ [M + H] calc. 500.2 obs. 500.2 |
| 241 | 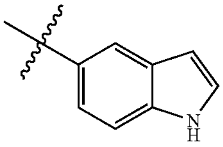 [SMILES: *c1ccc2[nH]ccc2c1] | $C_{30}H_{21}FN_5O$ [M + H] calc. 486.2 obs. 486.2 |
| 242 | 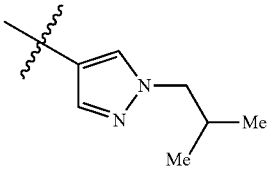 [SMILES: *c1cnn(CC(C)C)c1] | $C_{29}H_{26}FN_6O$ [M + H] calc. 493.2 obs. 493.2 |
| 243 | 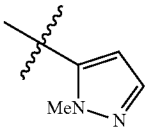 [SMILES: *c1ccnn1C] | $C_{26}H_{20}FN_6O$ [M + H] calc. 451.2 obs. 451.2 |
-continued
(IL)
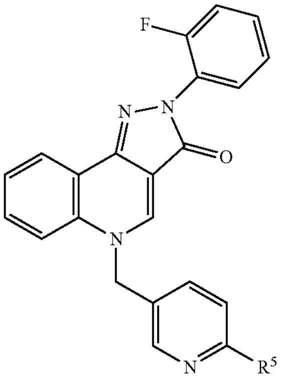
| Ex. | $R^5$ | HRMS/LRMS |
|---|---|---|
| 244 | 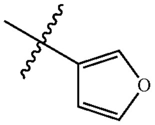 [SMILES: *c1ccoc1] | $C_{26}H_{18}FN_4O_2$ [M + H] calc. 437.1 obs. 437.1 |
| 245 | 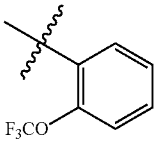 | $C_{29}H_{19}F_4N_4O_2$ [M + H] calc. 531.1 obs. 531.1 |
| 246 | 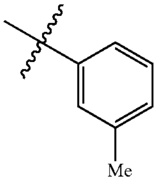 [SMILES: *c1cccc(C)c1] | $C_{29}H_{22}FN_4O$ [M + H] calc. 461.2 obs. 461.2 |
| 247 | 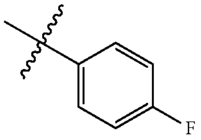 [SMILES: *c1ccc(F)cc1] | $C_{28}H_{19}F_2N_4O$ [M + H] calc. 465.2 obs. 465.1 |
| 248 | 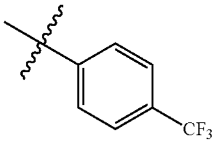 | $C_{29}H_{19}F_4N_4O$ [M + H] calc. 515.1 obs. 515.1 |
| 249 | 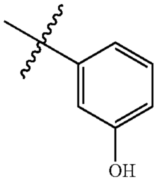 [SMILES: *c1cccc(O)c1] | $C_{28}H_{20}FN_4O_2$ [M + H] calc. 463.2 obs. 463.2 |
| 250 | 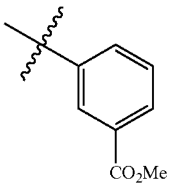 [SMILES: *c1cccc(C(=O)OC)c1] | $C_{30}H_{22}FN_4O_3$ [M + H] calc. 505.2 obs. 505.2 |

-continued (IL)

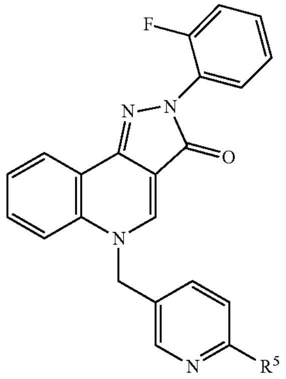

| Ex. | $R^5$ | HRMS/LRMS |
|---|---|---|
| 251 | 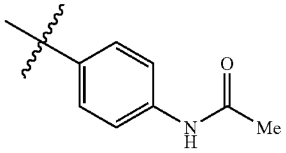 [SMILES: *c1ccc(NC(C)=O)cc1] | $C_{30}H_{23}FN_5O_2$ [M + H] calc. 504.2 obs. 504.2 |
| 252 | 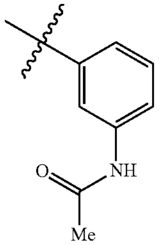 [SMILES: *c1cccc(NC(C)=O)c1] | $C_{30}H_{23}FN_5O_2$ [M + H] calc. 504.2 obs. 504.2 |
| 253 | 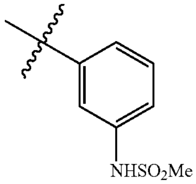 | $C_{29}H_{23}FN_5O_3S$ [M + H] calc. 540.2 obs. 540.1 |
| 254 | 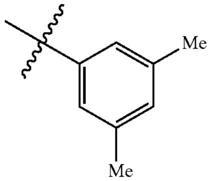 [SMILES: *c1cc(C)cc(C)c1] | $C_{30}H_{24}FN_4O$ [M + H] calc. 475.2 obs. 475.2 |
| 255 | 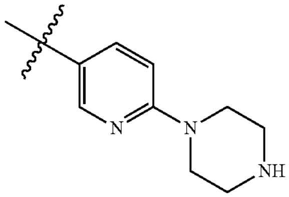 [SMILES: *c1ccc(N2CCNCC2)nc1] | $C_{31}H_{27}FN_7O$ [M + H] calc. 532.2 obs. 532.2 |
| 256 | 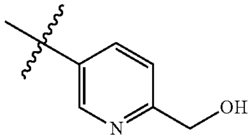 | $C_{28}H_{21}FN_5O_2$ [M + H] calc. 478.5 obs. 477.9 |

Example 257

2-(2-Fluorophenyl)-5-[(2'-methyl-3,3'-bipyridin-6-yl)methyl]-2,5-dihydro-3H-pyrazolo[4,3-c]quinolin-3-one

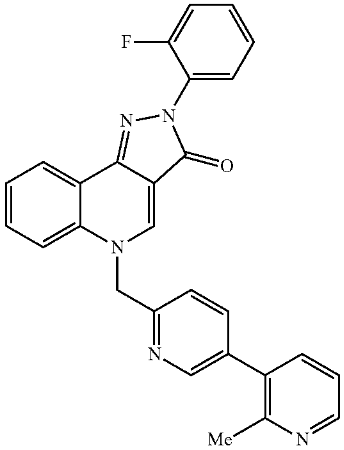 [SMILES: Cc1ncccc1-c1ccc(Cn2cc3c(=O)n(-c4ccccc4F)nc-3c3ccccc32)nc1]

Step 1: Preparation of 5-[(5-bromopyridin-2-yl)methyl]-2-(2-fluorophenyl)-2,5-dihydro-3H-pyrazolo[4,3-c]quinolin-3-one Using the procedures described in Example 187, substituting (5-bromopyridin-2-yl)methyl methanesulfonate for 1-(bromomethyl)-2-fluoro-4-iodobenzene, the titled compound was obtained.

Step 2: Preparation of 2-(2-fluorophenyl)-5-[(2'-methyl-3,3'-bipyridin-6-yl)methyl]-2,5-dihydro-3H-pyrazolo[4,3-c]quinolin-3-one 5-[(5-Bromopyridin-2-yl)methyl]-2-(2-fluorophenyl)-2,5-dihydro-3H-pyrazolo[4,3-c]quinolin-3-one (51 mg, 0.11 mmol), 2-dicyclohexylphosphino-2',4',6'-tri-iso-propyl-1,1'-biphenyl (16 mg, 0.034 mmol, 0.3 equiv), (2-methylpyridin-3-yl)boronic acid (26 mg, 0.19 mmol, 1.7 equiv), palladium (II) acetate (2.6 mg, 0.011 mmol, 0.1 equiv) and an aqueous solution (0.1 mL) of potassium carbonate (39 mg, 0.28 mmol, 2.5 equiv) were combined in dimethylsulfoxide (0.5 mL) and placed into a preheated oil bath at 85° C. for 90 minutes. The mixture was cooled to ambient temperature, stirred with Quadrapure® (50 mg, 1 wt equiv) for 1 hour, filtered and purified by reverse phase HPLC (80:20 to 5:95; water containing 0.1% trifluoroacetic acid:acetonitrile containing 0.1% trifluoroacetic acid), providing the titled compound: $^1$H-NMR (500 MHz, $d^6$-DMSO) δ 9.10 (1H, s), 8.57 (1H, d, J=2.1 Hz), 8.55 (1H, d, J=4.6 Hz), 8.21 (1H, dd, J=7.9, 1.4 Hz), 7.96 (1H, dd, J=8.1, 2.4 Hz), 7.84 (1H, d, J=8.7 Hz), 7.80 (1H, br s), 7.72 (1H, d, J=8.3 Hz), 7.65 (1H, ddd, J=8.6, 7.3, 1.5 Hz), 7.61 (1H, td, J=7.8, 1.6 Hz), 7.54 (1H, br t, J=7.6 Hz), 7.48-7.38 (3H, m), 7.34 (1H, td, J=7.6, 1.5 Hz), 5.92 (2H, s), 2.44 (3H, s) ppm; low resolution mass spectrometry (ES+) m/z 462.1709 $[(M+H)^+$; calculated for $C_{28}H_{21}FN_5O$: 462.1725].

The following compounds were prepared according to the general procedure described in Example 257, substituting the appropriately substituted boronic acid or ester for (2-methylpyridin-3-yl)boronic acid. The starting materials are either commercially available, known in the literature or may be prepared from commercially available reagents using conventional reactions well known in the art.

(IM)

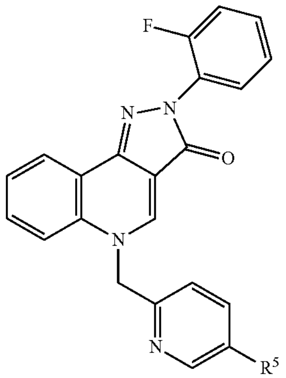

| Ex. | $R^5$ | HRMS/LRMS |
|---|---|---|
| 258 | 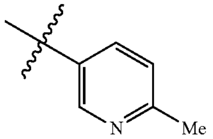 [SMILES: *c1ccc(C)nc1] | $C_{28}H_{21}FN_5O$ [M + H] calc. 462.1725 obs. 462.1709 |
| 259 | 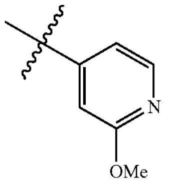 [SMILES: *c1ccnc(OC)c1] | $C_{29}H_{21}FN_5O_2$ [M + H] calc. 478.1674 obs. 478.1657 |
| 260 | 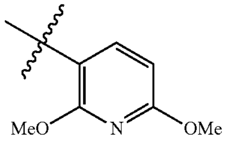 [SMILES: *c1ccc(OC)nc1OC] | $C_{29}H_{23}FN_5O_3$ [M + H] calc. 508.1780 obs. 508.1759 |
| 261 | 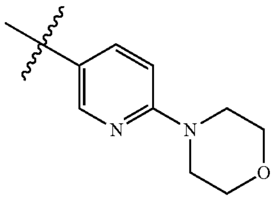 [SMILES: *c1ccc(N2CCOCC2)nc1] | $C_{31}H_{26}FN_6O_2$ [M + H] calc. 533.2096 obs. 533.2075 |
| 262 | 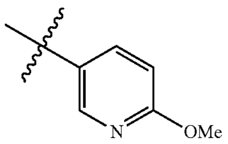 [SMILES: *c1ccc(OC)nc1] | $C_{28}H_{21}FN_5O_2$ [M + H] calc. 478.1674 obs. 478.1659 |
| 263 | 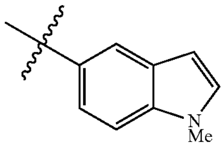 [SMILES: *c1ccc2c(ccn2C)c1] | $C_{31}H_{23}FN_5O$ [M + H] calc. 500.1881 obs. 500.1865 |

-continued (IM)

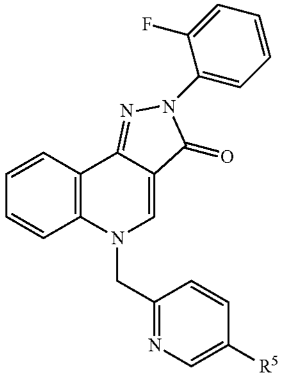

| Ex. | $R^5$ | HRMS/LRMS |
|---|---|---|
| 264 | 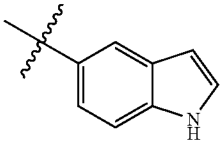 [SMILES: *c1ccc2[nH]ccc2c1] | $C_{30}H_{21}FN_5O$ [M + H] calc. 486.1725 obs. 486.1712 |
| 265 | 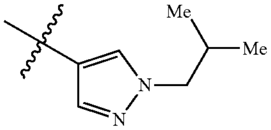 [SMILES: *c1cnn(CC(C)C)c1] | $C_{29}H_{26}FN_6O$ [M + H] calc. 493.2147 obs. 493.2137 |
| 266 | 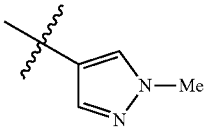 [SMILES: *c1cnn(C)c1] | $C_{26}H_{20}FN_6O$ [M + H] calc. 451.1677 obs. 451.1668 |
| 267 | 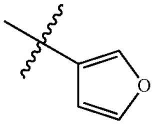 [SMILES: *c1ccoc1] | $C_{26}H_{18}FN_4O_2$ [M + H] calc. 437.1409 obs. 437.1398 |
| 268 | 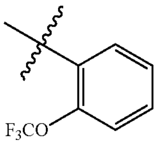 | $C_{29}H_{19}F_4N_4O_2$ [M + H] calc. 531.1439 obs. 531.1425 |
| 269 | 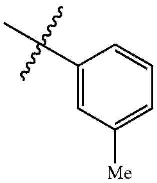 [SMILES: *c1cccc(C)c1] | $C_{29}H_{22}FN_4O$ [M + H] calc. 461.1772 obs. 461.1760 |
| 270 | 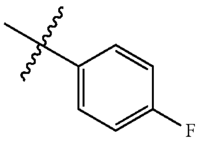 [SMILES: *c1ccc(F)cc1] | $C_{28}H_{19}F_2N_4O$ [M + H] calc. 465.1522 obs. 465.1511 |

-continued
(IM)
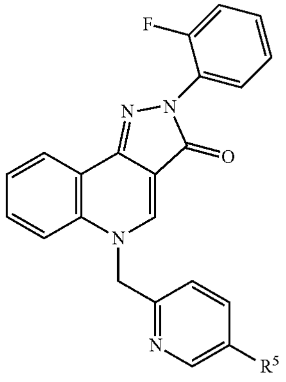
| Ex. | $R^5$ | HRMS/LRMS |
|---|---|---|
| 271 | 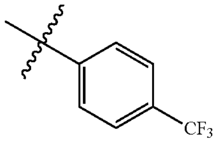 [SMILES: *c1ccc(C(F)(F)F)cc1] | $C_{29}H_{19}F_4N_4O$ [M + H] calc. 515.1490 obs. 515.1468 |
| 272 | 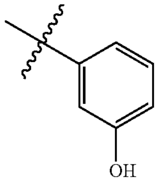 [SMILES: *c1cccc(O)c1] | $C_{28}H_{20}FN_4O_2$ [M + H] calc. 463.1565 obs. 463.1551 |
| 273 | 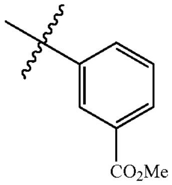 [SMILES: *c1cccc(C(=O)OC)c1] | $C_{30}H_{22}FN_4O_3$ [M + H] calc. 505.1671 obs. 505.1655 |
| 274 | 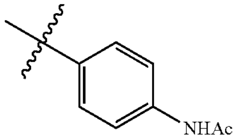 [SMILES: *c1ccc(NC(C)=O)cc1] | $C_{30}H_{23}FN_5O_2$ [M + H] calc. 504.1831 obs. 504.1819 |
| 275 | 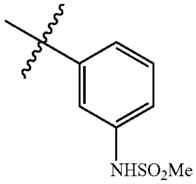 | $C_{29}H_{23}FN_5O_3S$ [M + H] calc. 540.1500 obs. 540.1482 |
| 276 | 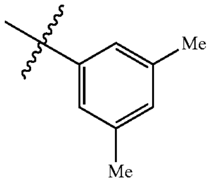 [SMILES: *c1cc(C)cc(C)c1] | $C_{30}H_{24}FN_4O$ [M + H] calc. 475.1929 obs. 475.1915 |
-continued
(IM)
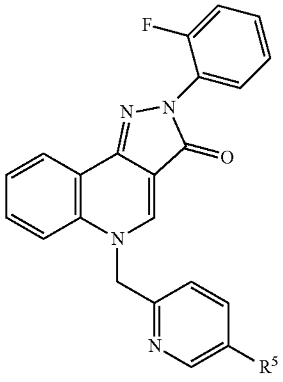
| Ex. | $R^5$ | HRMS/LRMS |
|---|---|---|
| 277 | 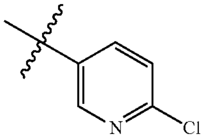 [SMILES: *c1ccc(Cl)nc1] | $C_{27}H_{18}ClFN_5O$ [M + H] calc. 482.1 obs. 481.8 |
| 278 | 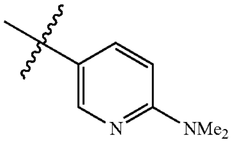 [SMILES: *c1ccc(N(C)C)nc1] | $C_{29}H_{24}FN_6O$ [M + H] calc. 491.1990 obs. 491.1994 |
| 279 | 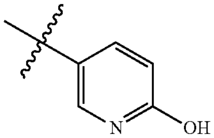 [SMILES: *c1ccc(O)nc1] | $C_{27}H_{19}FN_5O_2$ [M + H] calc. 464.1517 obs. 464.1511 |
| 280 | 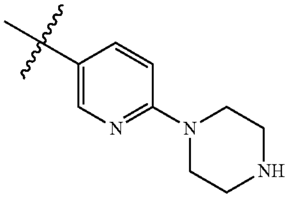 [SMILES: *c1ccc(N2CCNCC2)nc1] | $C_{31}H_{27}FN_7O$ [M + H] calc. 532.2256 obs. 532.2254 |
| 281 | 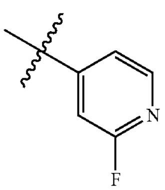 [SMILES: *c1ccnc(F)c1] | $C_{27}H_{18}F_2N_5O$ [M + H] calc. 466.1474 obs. 466.1467 |
| 282 | 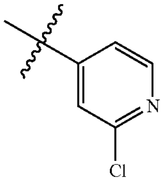 [SMILES: *c1ccnc(Cl)c1] | $C_{27}H_{18}ClFN_5O$ [M + H] calc. 482.1178 obs. 482.1172 |

-continued (IM)

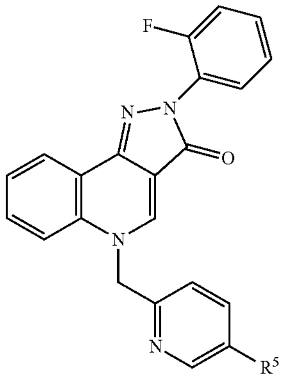

| Ex. | $R^5$ | HRMS/LRMS |
|---|---|---|
| 283 | 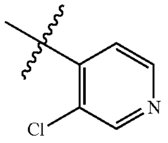 [SMILES: *c1ccncc1Cl] | $C_{27}H_{18}ClFN_5O$ [M + H] calc. 482.1178 obs. 482.1195 |
| 284 | 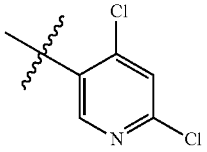 [SMILES: *c1cnc(Cl)cc1Cl] | $C_{27}H_{17}Cl_2FN_5O$ [M + H] calc. 516.0789 obs. 516.0792 |
| 285 | 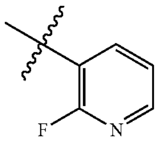 [SMILES: *c1cccnc1F] | $C_{27}H_{18}F_2N_5O$ [M + H] calc. 466.1474 obs. 466.1478 |
| 286 | 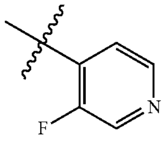 [SMILES: *c1ccncc1F] | $C_{27}H_{18}F_2N_5O$ [M + H] calc. 466.1474 obs. 466.1476 |
| 287 | 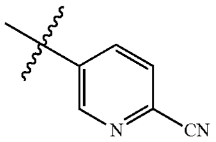 | $C_{28}H_{18}FN_6O$ [M + H] calc. 473.1521 obs. 473.1509 |
| 288 | 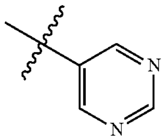 [SMILES: *c1cncnc1] | $C_{26}H_{18}FN_6O$ [M + H] calc. 449.1521 obs. 449.1520 |
| 289 | 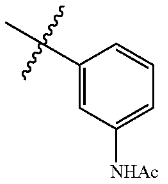 [SMILES: *c1cccc(NC(C)=O)c1] | $C_{30}H_{23}FN_5O_2$ [M + H] calc. 504.1830 obs. 504.1840 |

-continued (IM)

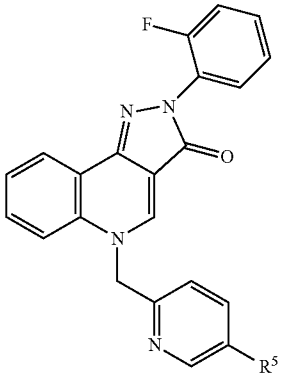

| Ex. | $R^5$ | HRMS/LRMS |
|---|---|---|
| 290 | 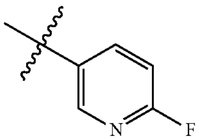 [SMILES: *c1ccc(F)nc1] | $C_{27}H_{18}F_2N_5O$ [M + H] calc. 466.1474 obs. 466.1479 |
| 291 | 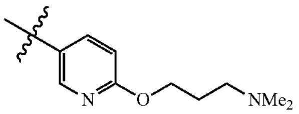 [SMILES: *c1ccc(OCCCN(C)C)nc1] | $C_{32}H_{30}FN_6O_2$ [M + H] calc. 549.2409 obs. 549.2406 |

Example 292

2-(2-Fluorophenyl)-5-{[5-(4-methyl-1H-imidazol-1-yl)pyridin-2-yl]methyl}-2,5-dihydro-3H-pyrazolo[4,3-c]quinolin-3-one

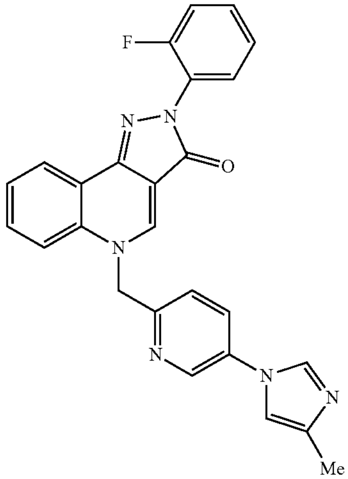 [SMILES: Cc1cn(-c2ccc(Cn3cc4c(=O)n(-c5ccccc5F)nc-4c4ccccc43)nc2)cn1]

5-[(5-Bromopyridin-2-yl)methyl]-2-(2-fluorophenyl)-2,5-dihydro-3H-pyrazolo[4,3-c]quinolin-3-one [(Example 257, Step 1), 0.13 g, 030 mmol], 4-methyl-1H-imidazole (99 mg, 1.2 mmol, 4 equiv), copper(I) iodide (23 mg, 0.12 mmol, 0.4 equiv), (±)-trans-N,N'-dimethylcyclohexane-1,2-diamine (34 mg, 0.24 mmol, 0.8 equiv) and potassium phosphate (0.19 g, 0.90 mmol, 3 equiv) were combined in water (0.2 mL) and dimethylsulfoxide (1 mL). The mixture was sparged under an atmosphere of nitrogen, the vessel was sealed and placed into a preheated oil bath at 100° C. for 9 hours. The mixture was cooled to ambient temperature, poured into water (25 mL) and extracted with chloroform (2×25 mL). The combined organic extracts were washed with water (20 mL) and brine (20 mL), dried with sodium sulfate, filtered and concentrated in vacuo. The residue was purified by silica gel gradient chromatography (100:0 to 96:4; chloroform:methanol), providing the titled compound: $^{1}$H-NMR (400 MHz, $CDCl_3$) δ 8.70 (1H, d, J=2.7 Hz), 8.55 (1H, s), 8.42 (1H, d, J=7.2 Hz), 7.76 (1H, s), 7.67-7.63 (2H, m), 7.56-7.47 (3H, m), 7.39-7.31 (2H, m), 7.29-7.23 (2H, m), 7.00 (1H, s), 5.59 (2H, s), 2.30 (3H, s) ppm; high resolution mass spectrometry (ES+) m/z 451.1653 [$(M+H)^+$; calculated for $C_{26}H_{20}FN_6O$: 451.1677].

Example 293

5-Ethyl-2-(2-fluorophenyl)-2,5-dihydro-3H-pyrazolo[4,3-c]quinolin-3-one

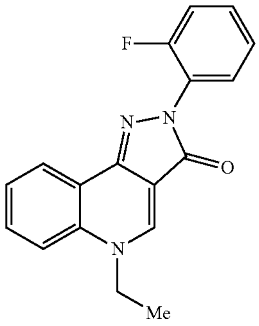 [SMILES: CCn1cc2c(=O)n(-c3ccccc3F)nc-2c2ccccc21]

Step 1: Preparation of 2-(2-fluorophenyl)-2,5-dihydro-3H-pyrazolo[4,3-c]quinolin-3-one Ethyl 4-oxo-1,4-dihydroquinoline-3-carboxylate (3.8 g, 17 mmol) was dissolved in phosphorus oxychloride (25 mL, 0.26 mol, 15 equiv) and stirred at ambient temperature for 14 hours. The mixture was concentrated in vacuo and the residue was concentrated from toluene (3×25 mL). The resulting residue was dissolved in 1,2-dimethoxyethane (60 mL) and degassed N,N-dimethylformamide (10 mL) and treated with 2-fluorophenylhydrazine (4.4 g, 35 mmol, 2 equiv) and potassium carbonate (12 g, 87 mmol, 5 equiv). The mixture was placed into a preheated oil bath at 80° C. for 14 hours. The mixture was cooled to ambient temperature, diluted with water (100 mL) and ethyl acetate (100 mL) and filtered. The solid was collected and dried in vacuo, providing the titled compound as a yellow solid.

Step 2: Preparation of 5-ethyl-2-(2-fluorophenyl)-2,5-dihydro-3H-pyrazolo[4,3-c]quinolin-3-one 2-(2-Fluorophenyl)-2,5-dihydro-3H-pyrazolo[4,3-c]quinolin-3-one (51 mg, 0.18 mmol) was dissolved in dimethylsulfoxide (1 mL) and treated with iodoethane (0.018 mL, 0.22 mmol, 1.2 equiv) and potassium carbonate (30 mg, 0.22 mmol, 1.2 equiv). The mixture was stirred at ambient temperature for 14 hours, filtered and purified by preparative reverse phase HPLC (82:20 to 5:95; water containing 0.1% trifluoroacetic acid:acetonitrile containing 0.1% trifluoroacetic acid), providing the titled compound: $^{1}$H-NMR (400 MHz, $CDCl_3$) δ 8.78 (1H, s), 8.48 (1H, dd, J=8.0, 1.5 Hz), 7.74-7.58 (4H, m), 7.42-7.36 (1H, m), 7.29-7.23 (2H, m), 4.44 (1H, q, J=7.4 Hz), 1.64 (3H, t, J=7.2 Hz) ppm; low resolution mass spectrometry (ES+) m/z 308.0 [$(M+H)^+$; calculated for $C_{18}H_{15}FN_3O$: 308.1].

The following compounds were prepared according to the general procedure described in Example 293, substituting the appropriately substituted halide for iodoethane, or, substituting sodium hydride for potassium carbonate. The starting materials are either commercially available, known in the literature or may be prepared from commercially available reagents using conventional reactions well known in the art.

(IN)

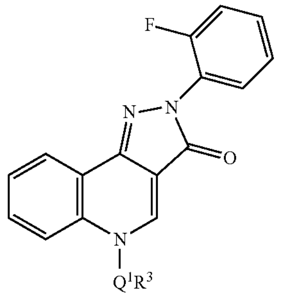

| Ex. | $Q^1R^3$ | HRMS/LRMS |
|---|---|---|
| 294 | 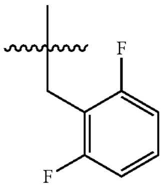 [SMILES: *Cc1c(F)cccc1F] | $C_{23}H_{15}F_3N_3O$ [M + H] calc. 406.1162 obs. 406.1165 |
| 295 | 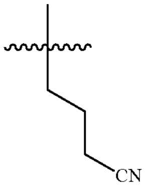 [SMILES: *CCCC#N] | $C_{20}H_{16}FN_4O$ [M + H] calc. 347.1303 obs. 347.1288 |
| 296 | 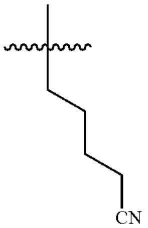 [SMILES: *CCCCC#N] | $C_{21}H_{18}FN_4O$ [M + H] calc. 361.1459 obs. 361.1465 |
| 297 | 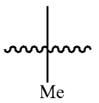 | $C_{17}H_{13}FN_3O$ [M + H] calc. 294.1037 obs. 294.1035 |
| 298 | 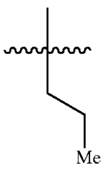 [SMILES: *CCC] | $C_{19}H_{17}FN_3O$ [M + H] calc. 322.1350 obs. 322.1348 |

-continued
(IN)
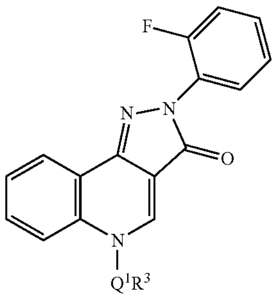
| Ex. | $Q^1R^3$ | HRMS/LRMS |
|---|---|---|
| 299 | 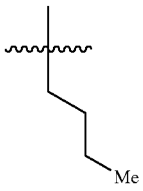 [SMILES: *CCCC] | $C_{20}H_{19}FN_3O$ [M + H] calc. 336.1507 obs. 336.1510 |
| 300 | 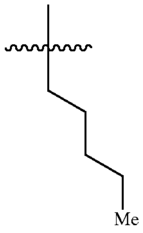 [SMILES: *CCCCC] | $C_{21}H_{21}FN_3O$ [M + H] calc. 350.1663 obs. 350.1668 |
| 301 | 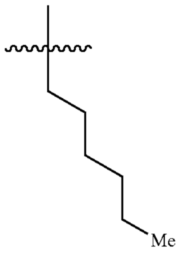 [SMILES: *CCCCCC] | $C_{22}H_{23}FN_3O$ [M + H] calc. 364.1820 obs. 364.1824 |
| 302 | 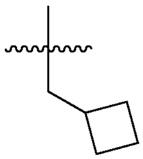 [SMILES: *CC1CCC1] | $C_{21}H_{19}FN_3O$ [M + H] calc. 348.1507 obs. 348.1510 |
| 303 | 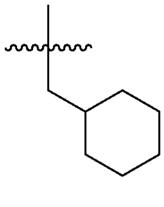 [SMILES: *CC1CCCCC1] | $C_{23}H_{23}FN_3O$ [M + H] calc. 376.1820 obs. 376.1820 |
-continued
(IN)
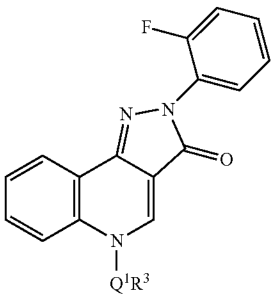
| Ex. | $Q^1R^3$ | HRMS/LRMS |
|---|---|---|
| 304 | 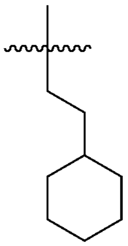 [SMILES: *CCC1CCCCC1] | $C_{24}H_{25}FN_3O$ [M + H] calc. 390.1976 obs. 390.1974 |
| 305 | 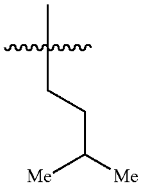 [SMILES: *CCC(C)C] | $C_{21}H_{21}FN_3O$ [M + H] calc. 350.1663 obs. 350.1671 |
| 306 | 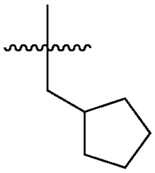 [SMILES: *CC1CCCC1] | $C_{22}H_{21}FN_3O$ [M + H] calc. 362.2 obs. 362.0 |
| 307 | 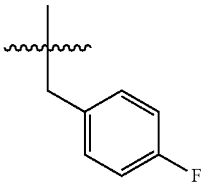 [SMILES: *Cc1ccc(F)cc1] | $C_{23}H_{16}F_2N_3O$ [M + H] calc. 388.1256 obs. 388.1277 |
| 308 | 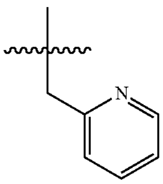 [SMILES: *Cc1ccccn1] | $C_{22}H_{16}FN_4O$ [M + H] calc. 371.1303 obs. 371.1318 |
| 309 | 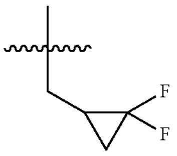 [SMILES: *CC1CC1(F)F] | $C_{20}H_{15}F_3N_3O$ [M + H] calc. 370.1162 obs. 370.1165 |

-continued
(IN)
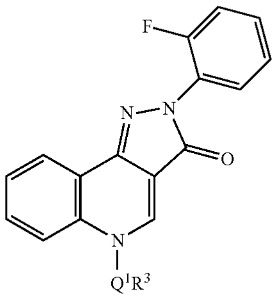
| Ex. | $Q^1R^3$ | HRMS/LRMS |
|---|---|---|
| 310 | 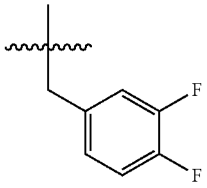 [SMILES: *Cc1ccc(F)c(F)c1] | $C_{23}H_{15}F_3N_3O$ [M + H] calc. 406.1162 obs. 406.1172 |
| 311 | 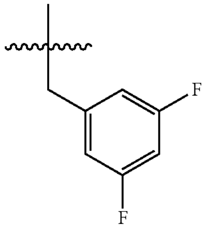 [SMILES: *Cc1cc(F)cc(F)c1] | $C_{23}H_{15}F_3N_3O$ [M + H] calc. 406.1162 obs. 406.1171 |
| 312 | 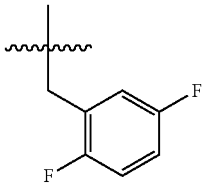 [SMILES: *Cc1cc(F)ccc1F] | $C_{23}H_{15}F_3N_3O$ [M + H] calc. 406.1162 obs. 406.1165 |
| 313 | 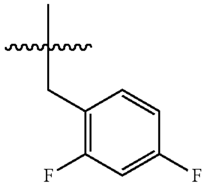 | $C_{23}H_{15}F_3N_3O$ [M + H] calc. 406.1162 obs. 406.1162 |
| 314 | 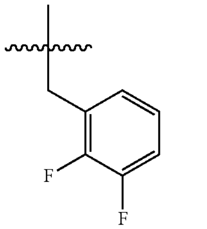 [SMILES: *Cc1cccc(F)c1F] | $C_{23}H_{15}F_3N_3O$ [M + H] calc. 406.1162 obs. 406.1160 |
| 315 | 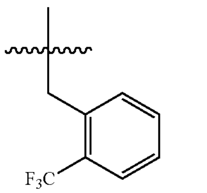 [SMILES: *Cc1ccccc1C(F)(F)F] | $C_{24}H_{15}F_4N_3O$ [M + H] calc. 438.1224 obs. 438.1234 |
-continued
(IN)
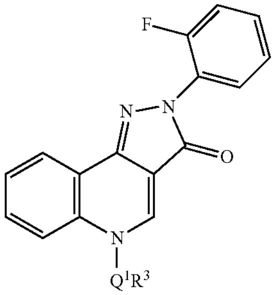
| Ex. | $Q^1R^3$ | HRMS/LRMS |
|---|---|---|
| 316 | 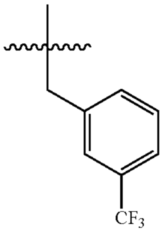 [SMILES: *Cc1cccc(C(F)(F)F)c1] | $C_{24}H_{15}F_4N_3O$ [M + H] calc. 438.1224 obs. 438.1243 |
| 317 | 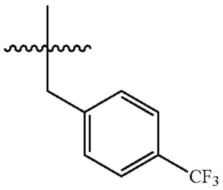 [SMILES: *Cc1ccc(C(F)(F)F)cc1] | $C_{24}H_{15}F_4N_3O$ [M + H] calc. 438.1224 obs. 438.1234 |
| 318 | 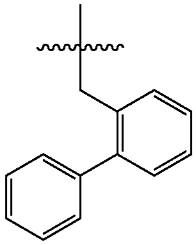 [SMILES: *Cc1ccccc1-c1ccccc1] | $C_{29}H_{20}FN_3O$ [M + H] calc. 446.1663 obs. 446.1669 |
| 319 | 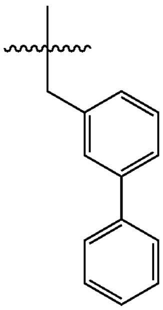 [SMILES: *Cc1cccc(-c2ccccc2)c1] | $C_{29}H_{20}FN_3O$ [M + H] calc. 446.1663 obs. 446.1673 |
| 320 | 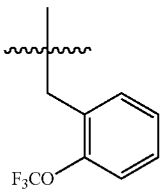 [SMILES: *Cc1ccccc1OC(F)(F)F] | $C_{24}H_{15}F_4N_3O_2$ [M + H] calc. 454.1173 obs. 454.1185 |

-continued
(IN)
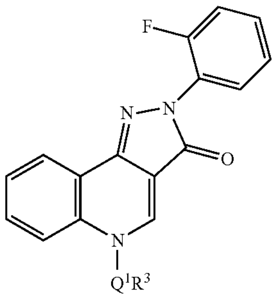
| Ex. | $Q^1R^3$ | HRMS/LRMS |
|---|---|---|
| 321 | 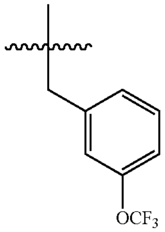 [SMILES: *Cc1cccc(OC(F)(F)F)c1] | $C_{24}H_{15}F_4N_3O_2$ [M + H] calc. 454.1173 obs. 454.1185 |
| 322 | 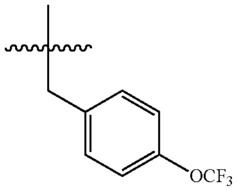 [SMILES: *Cc1ccc(OC(F)(F)F)cc1] | $C_{24}H_{15}F_4N_3O_2$ [M + H] calc. 454.1173 obs. 454.1184 |
| 323 | 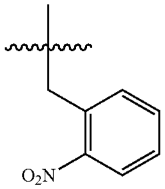 | $C_{23}H_{15}FN_4O_3$ [M + H] calc. 415.1201 obs. 415.1197 |
| 324 | 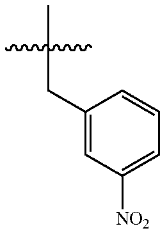 [SMILES: *Cc1cccc([N+](=O)[O-])c1] | $C_{23}H_{15}FN_4O_3$ [M + H] calc. 415.1201 obs. 415.1206 |
| 325 | 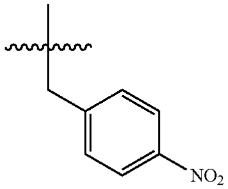 [SMILES: *Cc1ccc([N+](=O)[O-])cc1] | $C_{23}H_{15}FN_4O_3$ [M + H] calc. 415.1201 obs. 415.1200 |
| 326 | 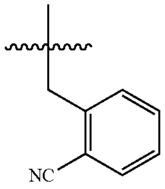 [SMILES: *Cc1ccccc1C#N] | $C_{24}H_{15}FN_4O$ [M + H] calc. 395.1303 obs. 395.1301 |
-continued
(IN)
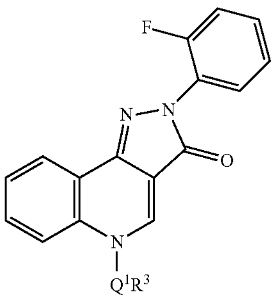
| Ex. | $Q^1R^3$ | HRMS/LRMS |
|---|---|---|
| 327 | 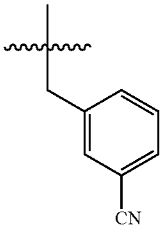 [SMILES: *Cc1cccc(C#N)c1] | $C_{24}H_{15}FN_4O$ [M + H] calc. 395.1303 obs. 395.1318 |
| 328 | 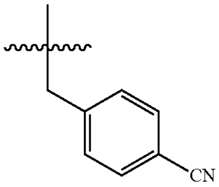 [SMILES: *Cc1ccc(C#N)cc1] | $C_{24}H_{15}FN_4O$ [M + H] calc. 395.1303 obs. 395.1302 |
| 329 | 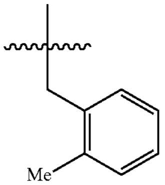 [SMILES: *Cc1ccccc1C] | $C_{24}H_{18}FN_3O$ [M + H] calc. 384.1507 obs. 384.1508 |
| 330 | 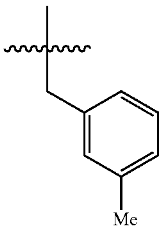 [SMILES: *Cc1cccc(C)c1] | $C_{24}H_{18}FN_3O$ [M + H] calc. 384.1507 obs. 384.1508 |
| 331 | 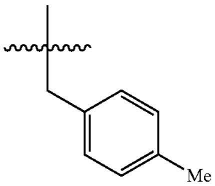 [SMILES: *Cc1ccc(C)cc1] | $C_{24}H_{18}FN_3O$ [M + H] calc. 384.1507 obs. 384.1512 |

-continued
(IN)
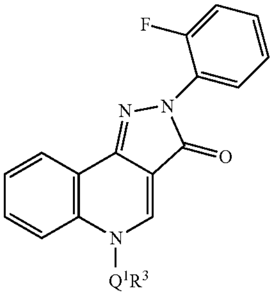
| Ex. | $Q^1R^3$ | HRMS/LRMS |
|---|---|---|
| 332 | 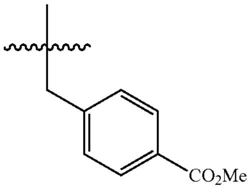 | $C_{25}H_{18}FN_3O_3$ [M + H] calc. 428.1405 obs. 428.1407 |
| 333 | 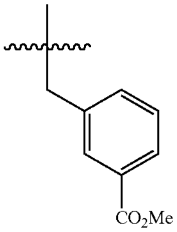 | $C_{25}H_{18}FN_3O_3$ [M + H] calc. 428.1405 obs. 428.1407 |
| 334 | 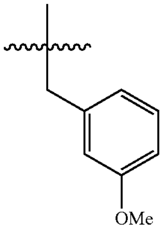 [SMILES: *Cc1cccc(OC)c1] | $C_{24}H_{18}FN_3O_2$ [M + H] calc. 400.1456 obs. 400.1460 |
| 335 | 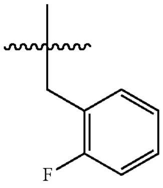 [SMILES: *Cc1ccccc1F] | $C_{23}H_{15}F_2N_3O$ [M + H] calc. 388.1256 obs. 388.1258 |
| 336 | 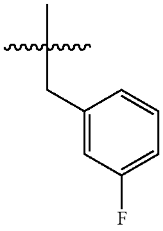 [SMILES: *Cc1cccc(F)c1] | $C_{23}H_{15}F_2N_3O$ [M + H] calc. 388.1256 obs. 388.1259 |
-continued
(IN)
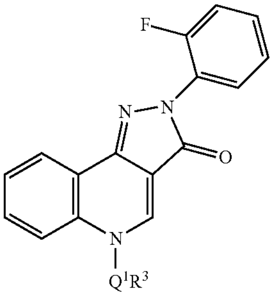
| Ex. | $Q^1R^3$ | HRMS/LRMS |
|---|---|---|
| 337 | 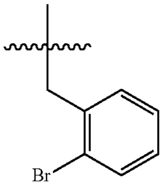 | $C_{23}H_{15}BrFN_3O$ [M + H] calc. 448.0455 obs. 448.0447 |
| 338 | 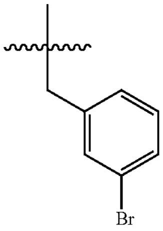 [SMILES: *Cc1cccc(Br)c1] | $C_{23}H_{15}BrFN_3O$ [M + H] calc. 448.0455 obs. 448.0468 |
| 339 | 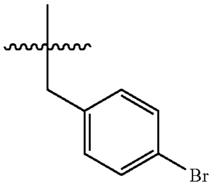 [SMILES: *Cc1ccc(Br)cc1] | $C_{23}H_{15}BrFN_3O$ [M + H] calc. 448.0455 obs. 448.0468 |
| 340 | 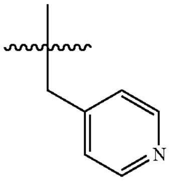 [SMILES: *Cc1ccncc1] | $C_{22}H_{16}FN_4O$ [M + H] calc. 371.1303 obs. 371.1308 |
| 341 | 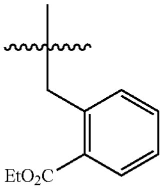 | $C_{26}H_{21}FN_3O_3$ [M + H] calc. 442.1561 obs. 442.1570 |
| 342 | 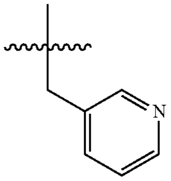 [SMILES: *Cc1cccnc1] | $C_{22}H_{16}FN_4O$ [M + H] calc. 371.1303 obs. 371.1302 |

-continued
(IN)
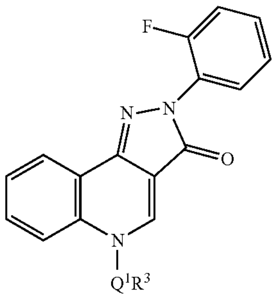
| Ex. | $Q^1R^3$ | HRMS/LRMS |
|---|---|---|
| 343 | 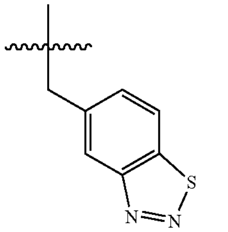 [SMILES: *Cc1ccc2snnc2c1] | $C_{23}H_{15}FN_5OS$ [M + H] calc. 428.1 obs. 428.1 |
| 344 | 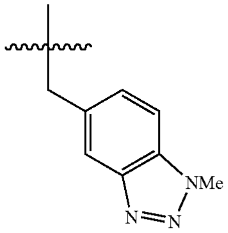 [SMILES: *Cc1ccc2c(c1)nnn2C] | $C_{24}H_{17}FN_6O$ [M + H] calc. 425.1521 obs. 425.1524 |
| 345 | 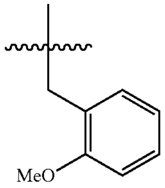 [SMILES: *Cc1ccccc1OC] | $C_{24}H_{18}FN_3O_2$ [M + H] calc. 400.1456 obs. 400.1459 |
| 346 | 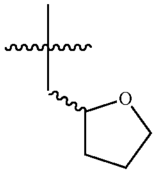 [SMILES: *CC1CCCO1] | $C_{21}H_{18}FN_3O_2$ [M + H] calc. 364.1456 obs. 364.1477 |
| 347 | 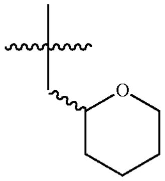 [SMILES: *CC1CCCCO1] | $C_{22}H_{20}FN_3O_2$ [M + H] calc. 378.1612 obs. 378.1621 |
| 348 | 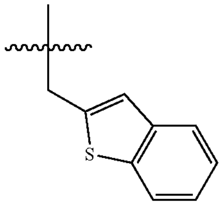 [SMILES: *Cc1cc2ccccc2s1] | $C_{25}H_{16}FN_3OS$ [M + H] calc. 426.1071 obs. 426.1085 |
-continued
(IN)
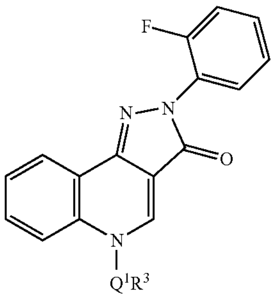
| Ex. | $Q^1R^3$ | HRMS/LRMS |
|---|---|---|
| 349 | 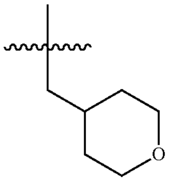 [SMILES: *CC1CCOCC1] | $C_{22}H_{20}FN_3O_2$ [M + H] calc. 378.1612 obs. 378.1628 |
| 350 | 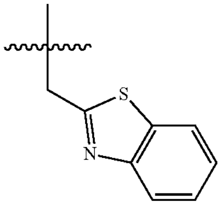 [SMILES: *Cc1nc2ccccc2s1] | $C_{24}H_{15}FN_4OS$ [M + H] calc. 427.1023 obs. 427.1026 |
| 351 | 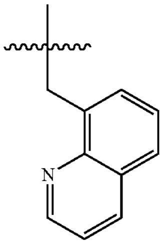 | $C_{26}H_{17}FN_4O$ [M + H] calc. 421.1459 obs. 421.1463 |
| 352 | 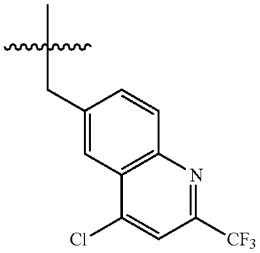 [SMILES: *Cc1ccc2nc(C(F)(F)F)cc(Cl)c2c1] | $C_{27}H_{15}ClF_4N_4O$ [M + H] calc. 523.0943 obs. 523.0939 |
| 353 | 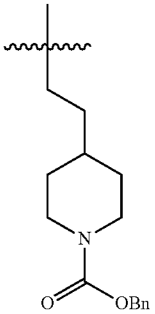 [SMILES: *CCC1CCN(C(=O)OCc2ccccc2)CC1] | $C_{31}H_{29}FN_4O_3$ [M + H] calc. 525.2296 obs. 525.2289 |

-continued
(IN)
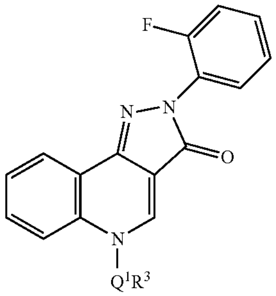
| Ex. | $Q^1R^3$ | HRMS/LRMS |
|---|---|---|
| 354 | 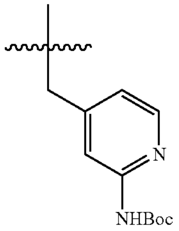 [SMILES: *Cc1ccnc(NC(=O)OC(C)(C)C)c1] | $C_{27}H_{24}FN_5O_3$ [M + H] calc. 486.1936 obs. 486.1949 |
| 355 | 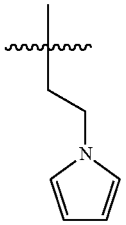 [SMILES: *CCn1cccc1] | $C_{22}H_{17}FN_4O$ [M + H] calc. 373.1459 obs. 373.1471 |
| 356 | 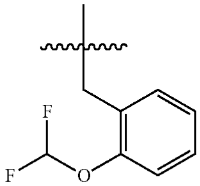 [SMILES: *Cc1ccccc1OC(F)F] | $C_{24}H_{16}F_3N_3O_2$ [M + H] calc. 436.1267 obs. 436.1265 |
| 357 | 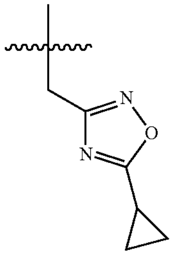 [SMILES: *Cc1noc(C2CC2)n1] | $C_{22}H_{16}FN_5O_2$ [M + H] calc. 402.1361 obs. 402.1368 |
| 358 | 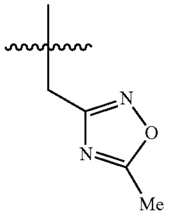 | $C_{20}H_{14}FN_5O_2$ [M + H] calc. 376.1204 obs. 376.1213 |
-continued
(IN)
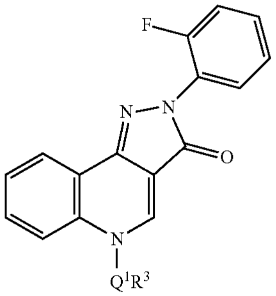
| Ex. | $Q^1R^3$ | HRMS/LRMS |
|---|---|---|
| 359 | 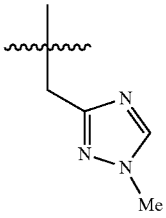 [SMILES: *Cc1ncn(C)n1] | $C_{20}H_{15}FN_6O$ [M + H] calc. 375.1364 obs. 375.1375 |
| 360 | 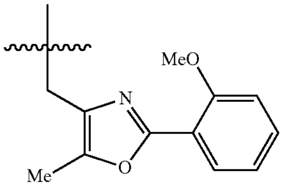 [SMILES: *Cc1nc(-c2ccccc2OC)oc1C] | $C_{28}H_{21}FN_4O_3$ [M + H] calc. 481.1670 obs. 481.1666 |
| 361 | 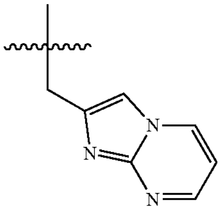 [SMILES: *Cc1cn2cccnc2n1] | $C_{23}H_{15}FN_6O$ [M + H] calc. 411.1364 obs. 411.1367 |
| 362 | 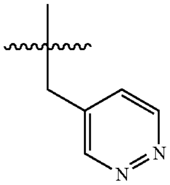 [SMILES: *Cc1ccnnc1] | $C_{21}H_{14}FN_5O$ [M + H] calc. 372.1255 obs. 372.1262 |
| 363 | 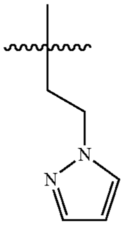 | $C_{21}H_{16}FN_5O$ [M + H] calc. 374.1412 obs. 374.1426 |

-continued
(IN)
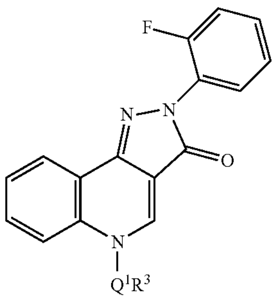
| Ex. | $Q^1R^3$ | HRMS/LRMS |
|---|---|---|
| 364 | 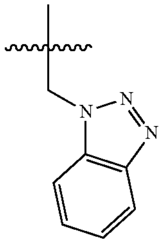 [SMILES: *Cn1nnc2ccccc21] | $C_{23}H_{15}FN_6O$ [M + H] calc. 411.1364 obs. 411.1374 |
| 365 | 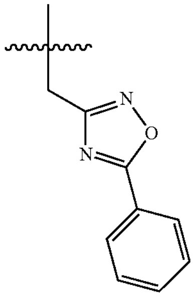 [SMILES: *Cc1noc(-c2ccccc2)n1] | $C_{25}H_{16}FN_5O_2$ [M + H] calc. 438.1361 obs. 438.1358 |
| 366 | 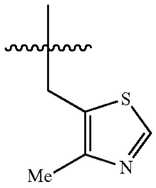 | $C_{21}H_{15}FN_4OS$ [M + H] calc. 391.1023 obs. 391.1028 |
| 367 | 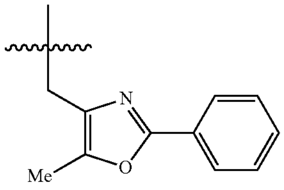 [SMILES: *Cc1nc(-c2ccccc2)oc1C] | $C_{27}H_{19}FN_4O_2$ [M + H] calc. 451.1565 obs. 451.1561 |
| 368 | 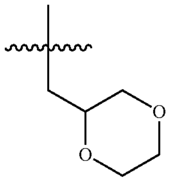 [SMILES: *CC1COCCO1] | $C_{21}H_{18}FN_3O_3$ [M + H] calc. 380.1405 obs. 380.1414 |
-continued
(IN)
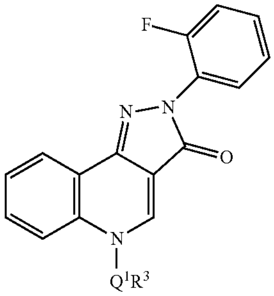
| Ex. | $Q^1R^3$ | HRMS/LRMS |
|---|---|---|
| 369 | 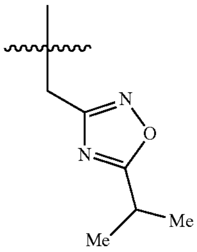 [SMILES: *Cc1noc(C(C)C)n1] | $C_{22}H_{18}FN_5O_2$ [M + H] calc. 404.1517 obs. 404.1521 |
| 370 | 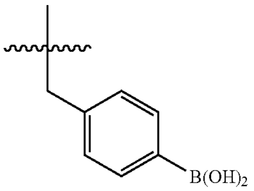 [SMILES: *Cc1ccc(B(O)O)cc1] | $C_{23}H_{18}BFN_3O_3$ [M + H] calc. 414.1420 obs. 414.1432 |
| 371 | 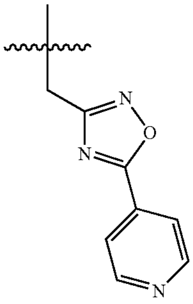 [SMILES: *Cc1noc(-c2ccncc2)n1] | $C_{24}H_{15}FN_6O_2$ [M + H] calc. 439.1313 obs. 439.1330 |
| 372 | 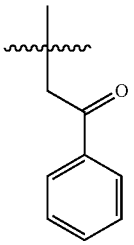 [SMILES: *CC(=O)c1ccccc1] | $C_{24}H_{17}FN_3O_2$ [M + H] calc. 398.1299 obs. 398.1314 |
| 373 | 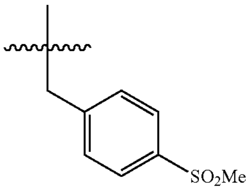 | $C_{24}H_{19}FN_3O_3S$ [M + H] calc. 448.1126 obs. 448.1122 |

-continued (IN)

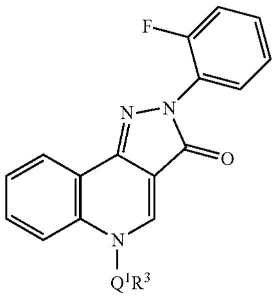

| Ex. | $Q^1R^3$ | HRMS/LRMS |
|---|---|---|
| 374 | 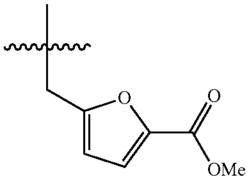 [SMILES: *Cc1ccc(C(=O)OC)o1] | $C_{23}H_{17}FN_3O_4$ [M + H] calc. 418.1 obs. 418.1 |
| 375 | 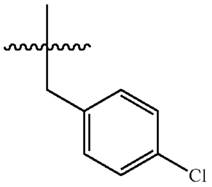 [SMILES: *Cc1ccc(Cl)cc1] | $C_{23}H_{15}ClFN_3O$ [M + H] calc. 404.0960 obs. 404.0959 |
| 376 | 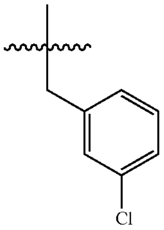 [SMILES: *Cc1cccc(Cl)c1] | $C_{23}H_{15}ClFN_3O$ [M + H] calc. 404.0960 obs. 404.0957 |
| 377 | 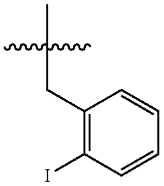 | $C_{23}H_{15}FIN_3O$ [M + H] calc. 496.0317 obs. 496.0311 |
| 378 | 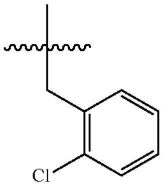 [SMILES: *Cc1ccccc1Cl] | $C_{23}H_{15}ClFN_3O$ [M + H] calc. 404.0960 obs. 404.0956 |
| 379 | 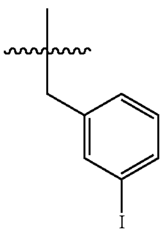 [SMILES: *Cc1cccc(I)c1] | $C_{23}H_{15}FIN_3O$ [M + H] calc. 496.0317 obs. 496.0311 |

-continued (IN)

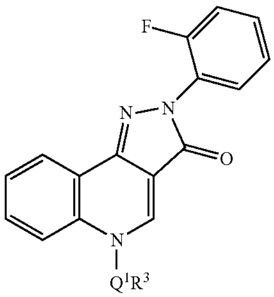

| Ex. | $Q^1R^3$ | HRMS/LRMS |
|---|---|---|
| 380 | 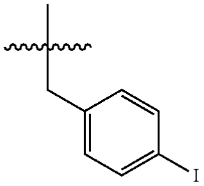 [SMILES: *Cc1ccc(I)cc1] | $C_{23}H_{15}FIN_3O$ [M + H] calc. 496.0317 obs. 496.0311 |

Example 381

2-(2-Fluorophenyl)-5-{[4-(1,3-oxadiazol-2-yl)phenyl]methyl}-2,5-dihydro-3H-pyrazolo[4,3-c]quinolin-3-one

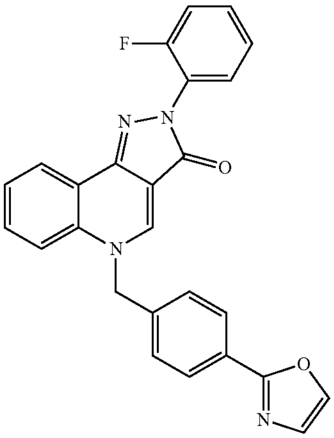 [SMILES: O=c1c2cn(Cc3ccc(-c4ncco4)cc3)c3ccccc3c-2nn1-c1ccccc1F]

2-(2-Fluorophenyl)-5-[(4-iodophenyl)methyl]-2,5-dihydro-3H-pyrazolo[4,3-c]quinolin-3-one (Example 380, 65 mg, 0.13 mmol) was dissolved in degassed N,N-dimethylformamide (1 mL) and treated with 2-(tributylstannanyl)-1,3-oxazole (70 mg, 0.20 mmol, 1.5 equiv), cesium fluoride (40 mg, 0.26 mmol, 2 equiv), copper(I) iodide (10 mg, 0.052 mmol, 0.5 equiv) and tetrakis(triphenylphosphine)palladium (0) (30 mg, 0.026 mmol, 0.2 equiv). After stirring for 1 hour, the mixture was filtered and purified by preparative reverse phase HPLC (80:20 to 5:95; water containing 0.1% trifluoroacetic acid:acetonitrile containing 0.1% trifluoroacetic acid), providing the titled compound: $^1$H-NMR (400 MHz, $d^6$ DMSO) δ 9.15 (1H, s), 8.21 (1H, dd, J=7.9, 1.5 Hz), 8.21 (1H, d, J=0.6 Hz), 7.97 (2H, d, J=8.4 Hz), 7.71 (1H, d, J=8.6 Hz), 7.65-7.59 (3H, m), 7.57-7.53 (3H, m), 7.47 (2H, d, J=8.4 Hz), 7.37 (1H, 0.6 Hz), 5.82 (2H, s) ppm; high resolution mass spectrometry (ES+) m/z 437.1417 [(M+H)$^+$; calculated for $C_{26}H_{18}FN_4O_2$: 437.1408].

The following compounds were prepared according to the general procedure described in Example 381, substituting the appropriately substituted stannane for 2-(tributylstannanyl)-1,3-oxazole. The starting materials are either commercially available, known in the literature or may be prepared from commercially available reagents using conventional reactions well known in the art.

(IO)

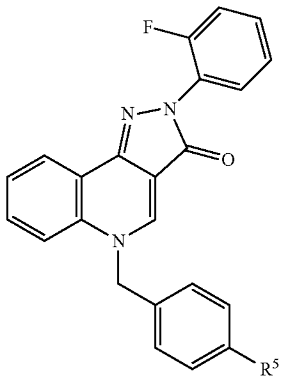

| Ex. | $R^5$ | HRMS/LRMS |
|---|---|---|
| 382 | 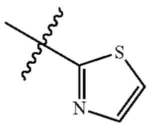 [SMILES: *c1nccs1] | $C_{26}H_{18}FN_4OS$ [M + H] calc. 453.1180 obs. 453.1188 |
| 383 | 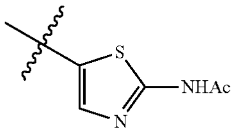 [SMILES: *c1cnc(NC(C)=O)s1] | $C_{28}H_{21}FN_5O_2S$ [M + H] calc. 510.1395 obs. 510.1386 |
| 384 | 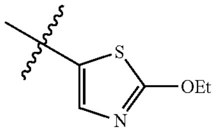 [SMILES: *c1cnc(OCC)s1] | $C_{28}H_{22}FN_4O_2S$ [M + H] calc. 497.1442 obs. 497.1447 |
| 385 | 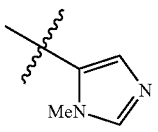 [SMILES: *c1cncn1C] | $C_{27}H_{21}FN_5O$ [M + H] calc. 450.1725 obs. 450.1728 |
| 386 | 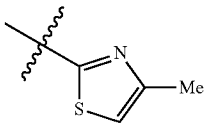 [SMILES: *c1nc(C)cs1] | $C_{27}H_{20}FN_4OS$ [M + H] calc. 467.1336 obs. 467.1344 |
| 387 | 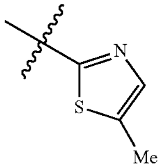 [SMILES: *c1ncc(C)s1] | $C_{27}H_{20}FN_4OS$ [M + H] calc. 467.1336 obs. 467.1340 |

-continued (IO)

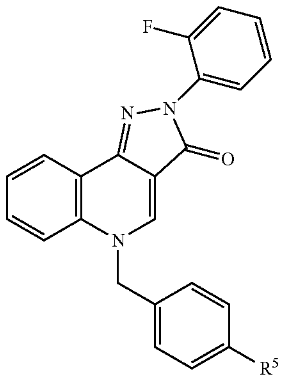

| Ex. | $R^5$ | HRMS/LRMS |
|---|---|---|
| 388 | 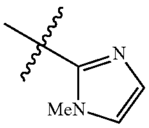 | $C_{27}H_{21}FN_5O$ [M + H] calc. 450.1725 obs. 450.1734 |
| 389 | 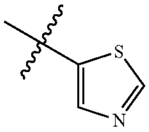 [SMILES: *c1cncs1] | $C_{26}H_{18}FN_4OS$ [M + H] calc. 453.1180 obs. 453.1190 |
| 390 | 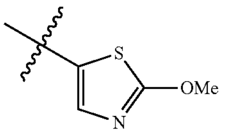 [SMILES: *c1cnc(OC)s1] | $C_{27}H_{20}FN_4O_2S$ [M + H] calc. 483.1286 obs. 483.1302 |

Example 391

2-(2-Fluorophenyl)-5-{[4-(1-methyl-1H-pyrazol-4-yl)phenyl]methyl}-2,5-dihydro-3H-pyrazolo[4,3-c]quinolin-3-one

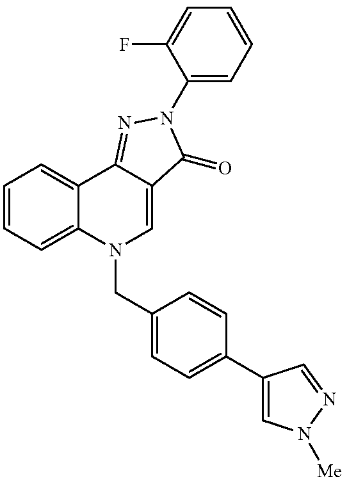 [SMILES: Cn1cc(-c2ccc(Cn3cc4c(=O)n(-c5ccccc5F)nc-4c4ccccc43)cc2)cn1]

(4-{[2-(2-Fluorophenyl)-3-oxo-2,3-dihydro-5H-pyrazolo[4,3-c]quinolin-5-yl]methyl}phenyl)boronic acid (Example 370, 60 mg, 0.14 mmol) was dissolved in degassed dimethylsulfoxide (1 mL), treated with 2-dicyclohexylphosphino-2',4',6'-tri-iso-propyl-1,1'-biphenyl (10 mg, 0.022 mmol, 0.15 equiv), 4-iodo-1-methyl-1H-pyrazole (33 mg, 0.16 mmol, 1.1 equiv), an aqueous solution (0.2 mL) of potassium carbonate (50 mg, 0.36 mmol, 2.5 equiv) and palladium(II) acetate (1.6 mg, 0.0073 mmol, 0.05 equiv) and placed into a preheated oil bath at 80° C. for 1 hour. The mixture was cooled to ambient temperature, poured into water (25 mL) and extracted with ethyl acetate (2×50 mL). The combined organic extracts were washed once with water (10 mL) and brine (10 mL), dried with sodium sulfate, filtered and concentrated in vacuo. The residue was purified by silica gel chromatography (100:0 to 95:5; chloroform:methanol), providing the titled compound: $^1$H-NMR (400 MHz, $CDCl_3$) δ 8.45 (1H, s), 8.42 (1H, br d, 7.1 Hz), 7.74 (1H, s), 7.65 (1H, td, J=7.7, 2.0 Hz), 7.60 (1H, s), 7.54-7.46 (5H, m), 7.38-7.33 (1H, m), 7.29-7.23 (2H, m), 7.20 (2H, d, J=8.2 Hz), 5.46 (2H, s), 3.94 (3H, s) ppm; high resolution mass spectrometry (ES+) m/z 450.1739 [$(M+H)^+$; calculated for $C_{27}H_{21}FN_5O$: 450.1725].

The following compounds were prepared according to the general procedure described in Example 391, substituting the appropriately substituted aryl iodide or bromide for 4-iodo-1-methyl-1H-pyrazole. The starting materials are either commercially available, known in the literature or may be prepared from commercially available reagents using conventional reactions well known in the art.

(IP)

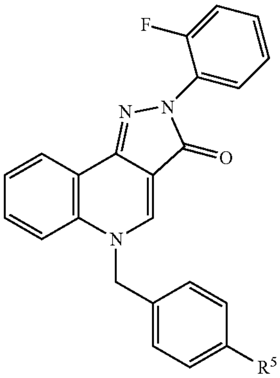

| Ex. | $R^5$ | HRMS/LRMS |
|---|---|---|
| 392 | 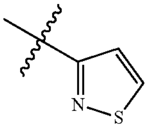 [SMILES: *c1ccsn1] | $C_{26}H_{18}FN_4OS$ [M + H] calc. 453.1180 obs. 453.1174 |
| 393 | 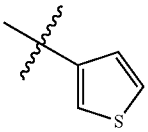 [SMILES: *c1ccsc1] | $C_{26}H_{19}FN_4OS$ [M + H] calc. 452.1227 obs. 452.1217 |
| 394 | 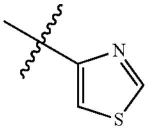 | $C_{25}H_{18}FN_5OS$ [M + H] calc. 453.1180 obs. 453.1169 |

-continued (IP)

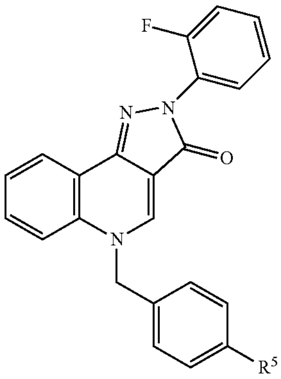

| Ex. | $R^5$ | HRMS/LRMS |
|---|---|---|
| 395 | 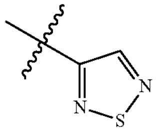 [SMILES: *c1cnsn1] | $C_{24}H_{17}FN_6OS$ [M + H] calc. 454.1132 obs. 454.1123 |
| 396 | 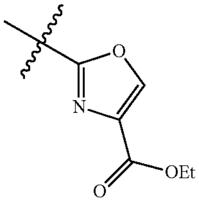 [SMILES: *c1nc(C(=O)OCC)co1] | $C_{29}H_{22}FN_4O_4$ [M + H] calc. 509.1620 obs. 509.1602 |
| 397 | 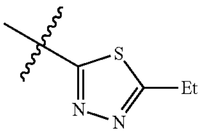 [SMILES: *c1nnc(CC)s1] | $C_{27}H_{21}FN_5OS$ [M + H] calc. 482.1445 obs. 482.1440 |
| 398 | 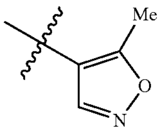 [SMILES: *c1cnoc1C] | $C_{27}H_{20}FN_4O_2$ [M + H] calc. 451.1565 obs. 451.1560 |
| 399 | 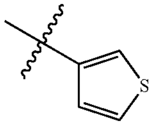 [SMILES: *c1ccsc1] | $C_{27}H_{19}FN_3OS$ [M + H] calc. 452.1227 obs. 452.1219 |
| 400 | 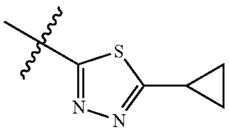 [SMILES: *c1nnc(C2CC2)s1] | $C_{28}H_{21}FN_5OS$ [M + H] calc. 494.1445 obs. 494.1430 |
| 401 | 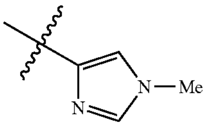 [SMILES: *c1cn(C)cn1] | $C_{27}H_{21}FN_5O$[M + H] calc. 450.1725 obs. 450.1714 |

-continued (IP)

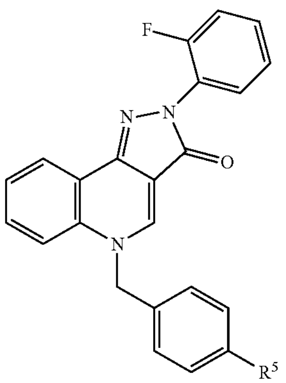

| Ex. | $R^5$ | HRMS/LRMS |
|---|---|---|
| 402 | 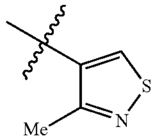 [SMILES: *c1csnc1C] | $C_{27}H_{20}FN_4OS$ [M + H] calc. 467.1336 obs. 467.1321 |

Example 403

2-(2,6-Difluorophenyl)-5-{[4-(1H-pyrazol-1-yl)phenyl]methyl}-2,5-dihydro-3H-pyrazolo[4,3-c]quinolin-3-one

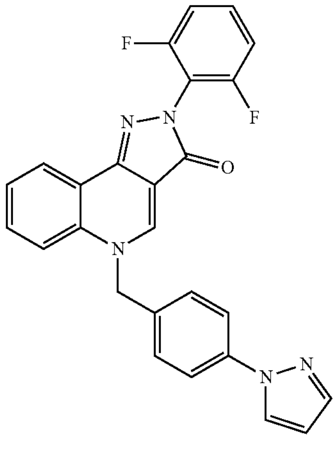 [SMILES: O=c1c2cn(Cc3ccc(-n4cccn4)cc3)c3ccccc3c-2nn1-c1c(F)cccc1F]

Step 1: Preparation of ethyl 4-oxo-1-{[4-(1H-pyrazol-1-yl)phenyl]methyl}-1,4-dihydroquinoline-3-carboxylate Using the procedures described in Example 1, substituting 1-[4-(bromomethyl)phenyl]-1H-pyrazole for 4-methoxybenzylchloride (Step 1), the titled compound was obtained.

Step 2: Preparation of 2-(2,6-difluorophenyl)-5-{[4-(1H-pyrazol-1-yl)phenyl]methyl}-2,5-dihydro-3H-pyrazolo[4,3-c]quinolin-3-one Ethyl 4-oxo-1-{[4-(1H-pyrazol-1-yl)phenyl]methyl}-1,4-dihydroquinoline-3-carboxylate (0.10 g, 0.27 mmol) was dissolved in phosphorus oxychloride (0.75 mL, 8.0 mmol, 30 equiv) and stirred vigorously for 1 hour at ambient temperature. The mixture was concentrated in vacuo and the residue was concentrated from toluene (3×10 mL). The resulting 4-chloro-3-[(ethyloxy)carbonyl]-1-{[4-(1H-pyrazol-1-yl)phenyl]methyl}quinolinium salt was dissolved in N,N-dimethylformamide (3 mL) and treated with (2,6-difluorophenyl)hydrazine (92 mg, 0.64 mmol, 2.5 equiv) and potassium carbonate (0.18 g, 1.3 mmol, 5 equiv). The mixture was placed into an oil bath preheated to 80° C. for 1 hour, cooled to ambient temperature and concentrated in vacuo. The residue was purified by preparative reverse phase HPLC (82:20 to 5:95; water containing 0.05% trifluoroacetic acid:acetonitrile containing 0.05% trifluoroacetic acid), providing the titled compound: $^1$H-NMR (400 MHz, $d^6$-DMSO) δ 9.18 (1H, s), 8.46 (1H, d, J=2.5 Hz), 8.18 (1H, dd, J=7.9, 1.3 Hz), 7.83 (2H, d, J=8.7 Hz), 7.78 (1H, d, J=9.0 Hz), 7.72 (1H, d, J=1.6 Hz), 7.66-7.57 (2H, m), 7.53 (1H, t, J=7.4 Hz), 7.48 (2H, d, J=8.5 Hz), 7.34 (2H, t, J=8.3 Hz), 6.53 (1H, dd, J=2.4, 1.8 Hz), 5.78 (2H, s) ppm; low resolution mass spectrometry (ES+) m/z 453.9 [$(M+H)^+$; calculated for $C_{26}H_{18}F_2N_5O$: 454.1].

The following compounds were prepared according to the general procedure described in Example 403, substituting the appropriately substituted hydrazine for (2,6-difluorophenyl)hydrazine. The starting materials are either commercially available, known in the literature or may be prepared from commercially available reagents using conventional reactions well known in the art.

(IQ)

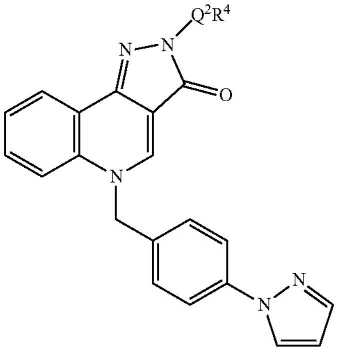

| Ex. | $Q^2R^4$ | HRMS/LRMS |
|---|---|---|
| 404 | 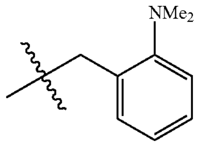 [SMILES: *Cc1ccccc1N(C)C] | $C_{29}H_{27}N_6O$ [M + H] calc. 475.2 obs. 475.0 |
| 405 | 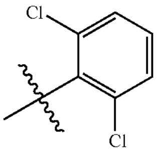 [SMILES: *c1c(Cl)cccc1Cl] | $C_{26}H_{18}Cl_2N_5O$ [M + H] calc. 486.1 obs. 485.9 |
| 406 | H | $C_{20}H_{16}N_5O$ [M + H] calc. 342.1350 obs. 342.1349 |

-continued (IQ)

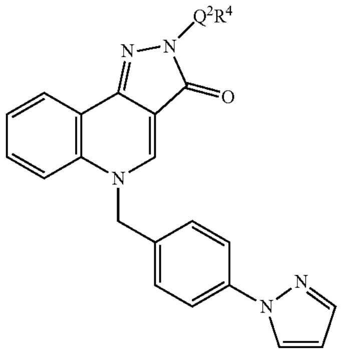

| Ex. | $Q^2R^4$ | HRMS/LRMS |
|---|---|---|
| 407 | 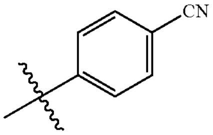 [SMILES: *c1ccc(C#N)cc1] | $C_{27}H_{19}N_6O$<br>[M + H]<br>calc. 443.1615<br>obs. 443.1615 |
| 408 | 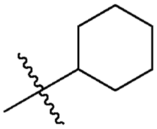 [SMILES: *C1CCCCC1] | $C_{26}H_{26}N_5O$<br>[M + H]<br>calc. 424.2132<br>obs. 424.2126 |
| 409 | 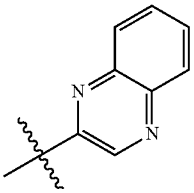 [SMILES: *c1cnc2ccccc2n1] | $C_{28}H_{20}N_7O$<br>[M + H]<br>calc. 470.1724<br>obs. 470.1727 |
| 410 | 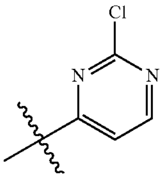 [SMILES: *c1ccnc(Cl)n1] | $C_{24}H_{17}ClN_7O$<br>[M + H]<br>calc. 454.1178<br>obs. 454.1165 |
| 411 | 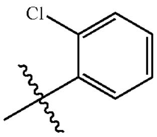 [SMILES: *c1ccccc1Cl] | $C_{26}H_{19}ClN_5O$<br>[M + H]<br>calc. 452.1273<br>obs. 452.1291 |
| 412 | 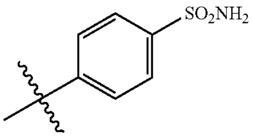 [SMILES: *c1ccc(S(N)(=O)=O)cc1] | $C_{26}H_{21}N_6O_3S$<br>[M + H]<br>calc. 497.1391<br>obs. 497.1379 |
| 413 | 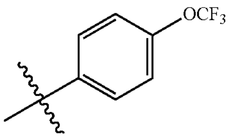 [SMILES: *c1ccc(OC(F)(F)F)cc1] | $C_{27}H_{19}F_3N_5O_2$<br>[M + H]<br>calc. 502.1486<br>obs. 502.1497 |

-continued (IQ)

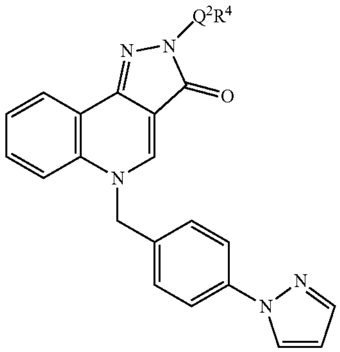

| Ex. | $Q^2R^4$ | HRMS/LRMS |
|---|---|---|
| 414 | 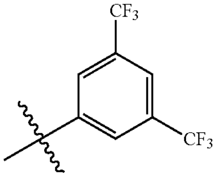 [SMILES: *c1cc(C(F)(F)F)cc(C(F)(F)F)c1] | $C_{28}H_{18}F_6N_5O$<br>[M + H]<br>calc. 554.1410<br>obs. 554.1410 |
| 415 | 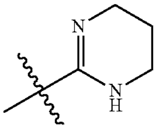 [SMILES: *C1=NCCCN1] | $C_{24}H_{22}N_7O$<br>[M + H]<br>calc. 424.1881<br>obs. 424.1881 |
| 416 | 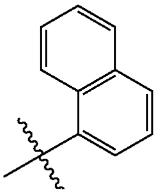 [SMILES: *c1cccc2ccccc12] | $C_{30}H_{22}N_5O$<br>[M + H]<br>calc. 468.1819<br>obs. 468.1832 |
| 417 | 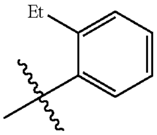 [SMILES: *c1ccccc1CC] | $C_{28}H_{24}N_5O$<br>[M + H]<br>calc. 446.1976<br>obs. 446.1989 |
| 418 | 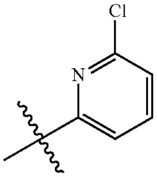 [SMILES: *c1cccc(Cl)n1] | $C_{25}H_{18}ClN_6O$<br>[M + H]<br>calc. 453.1225<br>obs. 453.1230 |
| 419 | 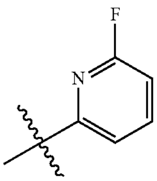 [SMILES: *c1cccc(F)n1] | $C_{25}H_{18}FN_6O$<br>[M + H]<br>calc. 437.1521<br>obs. 437.1520 |
| 420 | 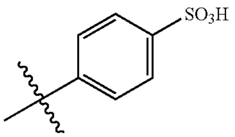 [SMILES: *c1ccc(S(=O)(=O)O)cc1] | $C_{26}H_{20}N_5O_4S$<br>[M + H]<br>calc. 498.1231<br>obs. 498.1222 |

-continued (IQ)

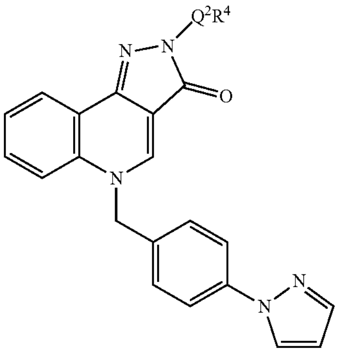

| Ex. | $Q^2R^4$ | HRMS/LRMS |
|---|---|---|
| 421 | 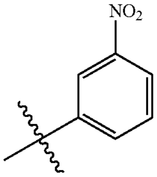 [SMILES: *c1cccc([N+](=O)[O-])c1] | $C_{26}H_{19}N_6O_3$ [M + H] calc. 463.1513 obs. 443.1502 |
| 422 | 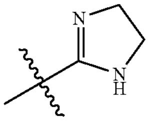 [SMILES: *C1=NCCN1] | $C_{23}H_{20}N_7O$ [M + H] calc. 410.1724 obs. 410.1729 |
| 423 | 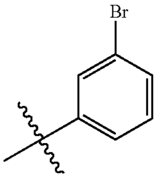 [SMILES: *c1cccc(Br)c1] | $C_{26}H_{19}BrN_5O$ [M + H] calc. 496.0768 obs. 496.0767 |
| 424 | 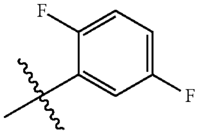 [SMILES: *c1cc(F)ccc1F] | $C_{26}H_{18}F_2N_5O$[M + H] calc. 454.1474 obs. 454.1488 |
| 425 | 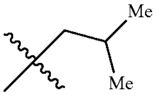 [SMILES: *CC(C)C] | $C_{24}H_{24}N_5O$[M + H] calc. 398.1976 obs. 398.1989 |
| 426 | 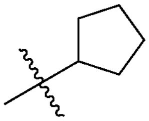 [SMILES: *C1CCCC1] | $C_{25}H_{24}N_5O$[M + H] calc. 410.1976 obs. 410.1985 |
| 427 | 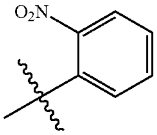 [SMILES: *c1ccccc1[N+](=O)[O-]] | $C_{26}H_{19}N_6O_3$ [M + H] calc. 463.1 obs. 463.0 |
| 428 | 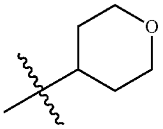 [SMILES: *C1CCOCC1] | $C_{25}H_{24}N_5O_2$ [M + H] calc. 426.2 obs. 426.0 |

-continued (IQ)

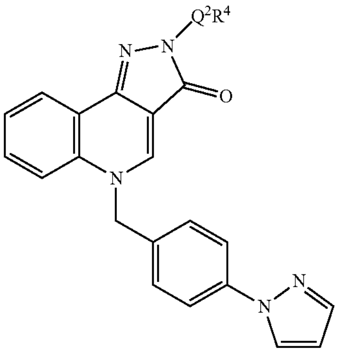

| Ex. | $Q^2R^4$ | HRMS/LRMS |
|---|---|---|
| 429 | 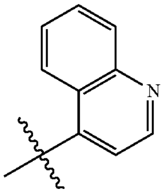 [SMILES: *c1ccnc2ccccc12] | $C_{29}H_{21}N_6O$ [M + H] calc. 469.2 obs. 469.0 |
| 430 | 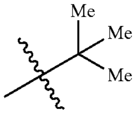 [SMILES: *C(C)(C)C] | $C_{24}H_{24}N_5O$ [M + H] calc. 398.1975 obs. 398.1968 |
| 431 | 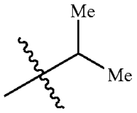 [SMILES: *C(C)C] | $C_{23}H_{22}N_5O$ [M + H] calc. 384.1819 obs. 384.1810 |
| 432 | 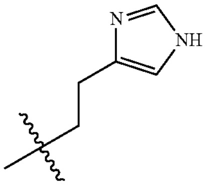 [SMILES: *CCc1c[nH]cn1] | $C_{25}H_{22}N_7O$ [M + H] calc. 436.1880 obs. 436.1864 |
| 433 | 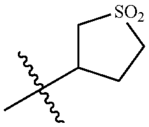 [SMILES: *C1CCS(=O)(=O)C1] | $C_{24}H_{22}N_5O_3S$[M + H] calc. 460.1438 obs. 460.1439 |
| 434 | 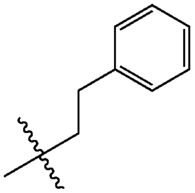 [SMILES: *CCc1ccccc1] | $C_{28}H_{24}N_5O$[M + H] calc. 446.1975 obs. 446.1985 |
| 435 | 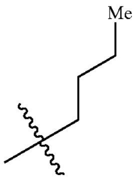 [SMILES: *CCCC] | $C_{24}H_{24}N_5O$ [M + H] calc. 398.1975 obs. 398.1965 |

-continued
(IQ)
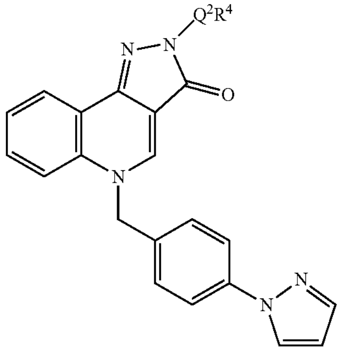
| Ex. | $Q^2R^4$ | HRMS/LRMS |
|---|---|---|
| 436 | 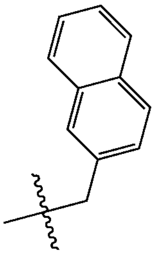 [SMILES: *Cc1ccc2ccccc2c1] | $C_{31}H_{24}N_5O$ [M + H] calc. 482.1975 obs. 482.1973 |
| 437 | 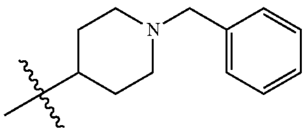 [SMILES: *C1CCN(Cc2ccccc2)CC1] | $C_{32}H_{31}N_6O$ [M + H] calc. 515.2554 obs. 515.2538 |
| 438 | 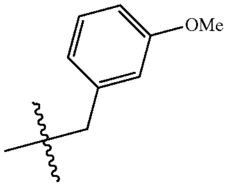 [SMILES: *Cc1cccc(OC)c1] | $C_{28}H_{24}N_6O_2$ [M + H] calc. 462.1925 obs. 462.1926 |
| 439 | Me | $C_{21}H_{18}N_5O$ [M + H] calc. 356.1506 obs. 356.1494 |
| 440 | 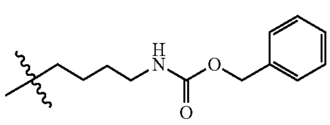 [SMILES: *CCCCNC(=O)OCc1ccccc1] | $C_{32}H_{31}N_6O_3$ [M + H] calc. 547.2452 obs. 547.2457 |
| 441 | 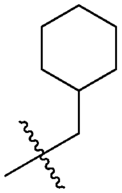 [SMILES: *CC1CCCCC1] | $C_{27}H_{28}N_5O$ [M + H] calc. 438.2288 obs. 438.2282 |
-continued
(IQ)
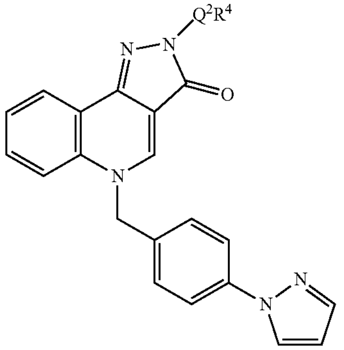
| Ex. | $Q^2R^4$ | HRMS/LRMS |
|---|---|---|
| 442 | 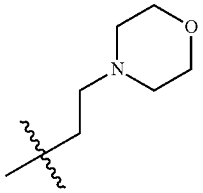 [SMILES: *CCN1CCOCC1] | $C_{26}H_{27}N_6O_2$ [M + H] calc. 455.2190 obs. 455.2174 |
| 443 | 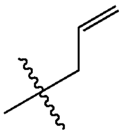 [SMILES: *CC=C] | $C_{23}H_{20}N_5O$[M + H] calc. 382.1662 obs. 382.1656 |
| 444 | 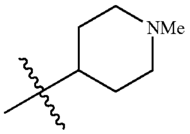 [SMILES: *C1CCN(C)CC1] | $C_{26}H_{27}N_6O$[M + H] calc. 439.2241 obs. 439.2227 |
| 445 | 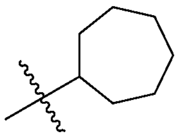 [SMILES: *C1CCCCCC1] | $C_{27}H_{28}N_5O$ [M + H] calc. 438.2288 obs. 438.2279 |
| 446 | 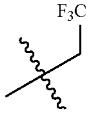 [SMILES: *CC(F)(F)F] | $C_{22}H_{17}F_3N_5O$ [M + H] calc. 424.1380 obs. 424.1369 |
| 447 | 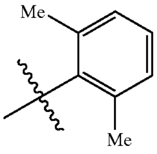 [SMILES: *c1c(C)cccc1C] | $C_{28}H_{24}N_5O$ [M + H] calc. 446.1975 obs. 446.1979 |
| 448 | 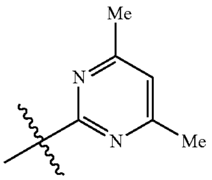 [SMILES: *c1nc(C)cc(C)n1] | $C_{26}H_{22}N_7O$ [M + H] calc. 448.1880 obs. 448.1880 |

-continued
(IQ)
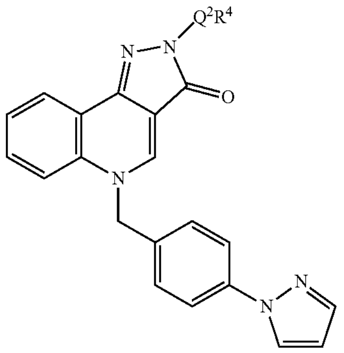
| Ex. | $Q^2R^4$ | HRMS/LRMS |
|---|---|---|
| 449 | 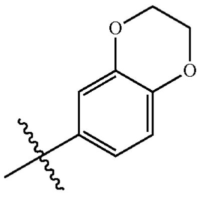 [SMILES: *c1ccc2c(c1)OCCO2] | $C_{28}H_{22}N_5O_3$ [M + H] calc. 476.1717 obs. 476.1728 |
| 450 | 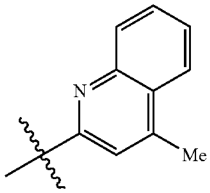 [SMILES: *c1cc(C)c2ccccc2n1] | $C_{30}H_{23}N_6O$ [M + H] calc. 483.1928 obs. 483.1936 |
| 451 | 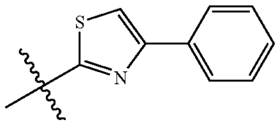 [SMILES: *c1nc(-c2ccccc2)cs1] | $C_{29}H_{21}N_6OS$ [M + H] calc. 501.1492 obs. 501.1477 |
| 452 | 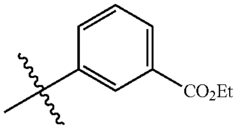 [SMILES: *c1cccc(C(=O)OCC)c1] | $C_{29}H_{24}N_5O_3$[M + H] calc. 490.1874 obs. 490.1883 |
| 453 | 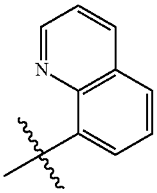 [SMILES: *c1cccc2cccnc12] | $C_{29}H_{21}N_6O$[M + H] calc. 469.1771 obs. 469.1768 |
| 454 | 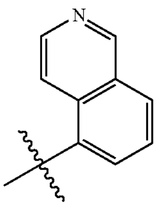 [SMILES: *c1cccc2cnccc12] | $C_{29}H_{21}N_6O$ [M + H] calc. 469.1771 obs. 469.1760 |
-continued
(IQ)
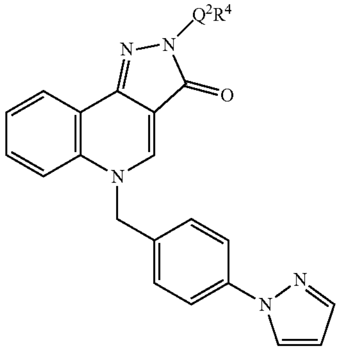
| Ex. | $Q^2R^4$ | HRMS/LRMS |
|---|---|---|
| 455 | 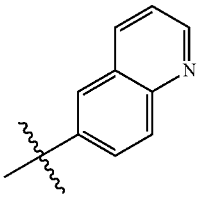 [SMILES: *c1ccc2ncccc2c1] | $C_{29}H_{21}N_6O$ [M + H] calc. 469.1771 obs. 469.1762 |
| 456 | 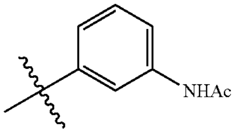 [SMILES: *c1cccc(NC(C)=O)c1] | $C_{28}H_{23}N_6O_2$ [M + H] calc. 475.1877 obs. 475.1876 |
| 457 | 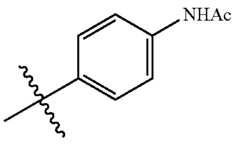 [SMILES: *c1ccc(NC(C)=O)cc1] | $C_{28}H_{23}N_6O_2$ [M + H] calc. 475.1877 obs. 475.1874 |
| 458 | 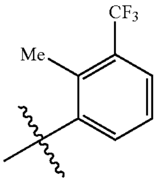 [SMILES: *c1cccc(C(F)(F)F)c1C] | $C_{28}H_{21}F_3N_5O$ [M + H] calc. 500.1693 obs. 500.1688 |
| 459 | 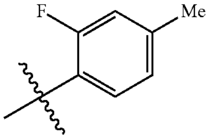 [SMILES: *c1ccc(C)cc1F] | $C_{27}H_{21}FN_5O$ [M + H] calc. 450.1725 obs. 450.1734 |
| 460 | 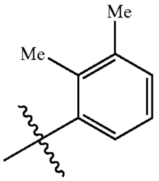 [SMILES: *c1cccc(C)c1C] | $C_{28}H_{24}N_5O$ [M + H] calc. 446.1975 obs. 446.1978 |

-continued
(IQ)
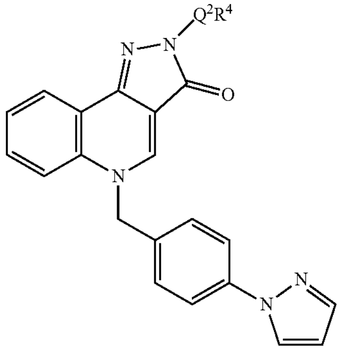
| Ex. | $Q^2R^4$ | HRMS/LRMS |
|---|---|---|
| 461 | 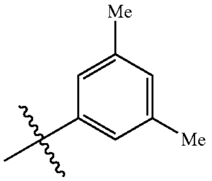 [SMILES: *c1cc(C)cc(C)c1] | $C_{28}H_{24}N_5O$[M + H] calc. 446.1975 obs. 446.1982 |
| 462 | 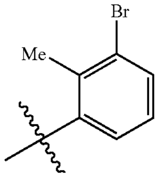 [SMILES: *c1cccc(Br)c1C] | $C_{27}H_{21}BrN_5O$[M + H] calc. 510.0924 obs. 510.0932 |
| 463 | 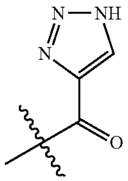 [SMILES: *C(=O)c1c[nH]nn1] | $C_{23}H_{17}N_8O_2$ [M + H] calc. 437.1469 obs. 437.1460 |
| 464 | 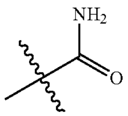 [SMILES: *C(N)=O] | $C_{21}H_{17}N_6O_2$ [M + H] calc. 385.1408 obs. 385.1400 |
| 465 | 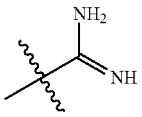 [SMILES: *C(=N)N] | $C_{21}H_{18}N_7O$ [M + H] calc. 384.1567 obs. 384.1564 |
| 466 | 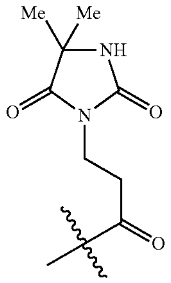 [SMILES: *C(=O)CCN1C(=O)NC(C)(C)C1=O] | $C_{28}H_{26}N_7O_4$ [M + H] calc. 524.2041 obs. 524.2054 |
-continued
(IQ)
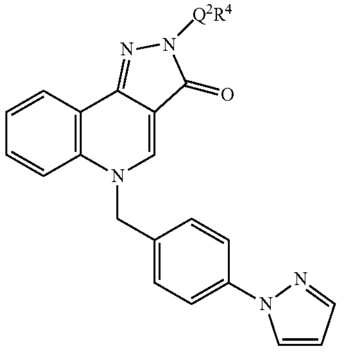
| Ex. | $Q^2R^4$ | HRMS/LRMS |
|---|---|---|
| 467 | 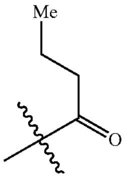 [SMILES: *C(=O)CCC] | $C_{24}H_{22}N_5O_2$ [M + H] calc. 412.1768 obs. 412.1769 |
| 468 | 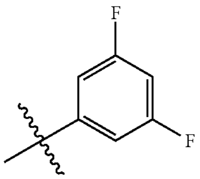 [SMILES: *c1cc(F)cc(F)c1] | $C_{26}H_{18}F_2N_5O$ [M + H] calc. 454.1474 obs. 454.1468 |
| 469 | 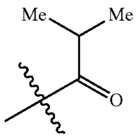 [SMILES: *C(=O)C(C)C] | $C_{24}H_{22}N_5O_2$ [M + H] calc. 412.1768 obs. 412.1773 |
| 470 | 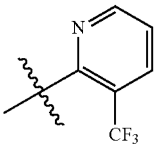 [SMILES: *c1ncccc1C(F)(F)F] | $C_{26}H_{18}F_3N_6O$ [M + H] calc. 487.1489 obs. 487.1495 |
| 471 | 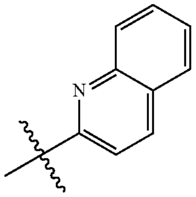 [SMILES: *c1ccc2ccccc2n1] | $C_{29}H_{21}N_6O$ [M + H] calc. 469.1771 obs. 469.1787 |
| 472 | 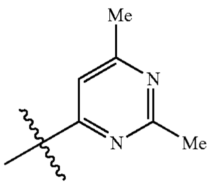 [SMILES: *c1cc(C)nc(C)n1] | $C_{26}H_{22}N_7O$ [M + H] calc. 448.1880 obs. 448.1881 |

-continued
(IQ)
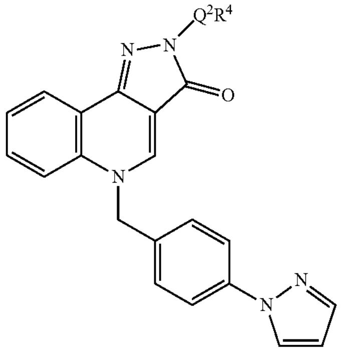
| Ex. | $Q^2R^4$ | HRMS/LRMS |
|---|---|---|
| 473 | 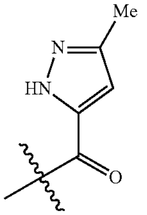 [SMILES: *C(=O)c1cc(C)n[nH]1] | $C_{25}H_{20}N_7O_2$ [M + H] calc. 450.1673 obs. 450.1668 |
| 474 | 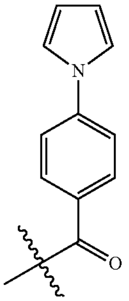 [SMILES: *C(=O)c1ccc(-n2cccc2)cc1] | $C_{31}H_{23}N_6O_2$ [M + H] calc. 511.1877 obs. 511.1866 |
| 475 | 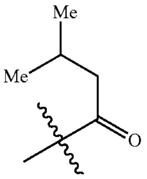 | $C_{25}H_{20}N_7O_2$ [M + H] calc. 450.1673 obs. 450.1668 |
| 476 | 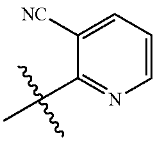 [SMILES: *c1ncccc1C#N] | $C_{26}H_{18}N_7O$ [M + H] calc. 444.1567 obs. 444.1572 |
| 477 | 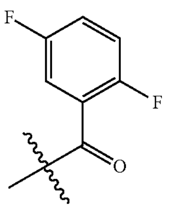 [SMILES: *C(=O)c1cc(F)ccc1F] | $C_{27}H_{18}F_2N_5O_2$ [M + H] calc. 482.1423 obs. 482.1415 |
-continued
(IQ)
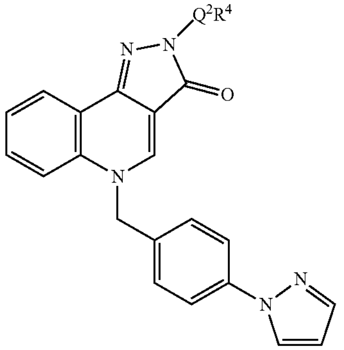
| Ex. | $Q^2R^4$ | HRMS/LRMS |
|---|---|---|
| 478 | 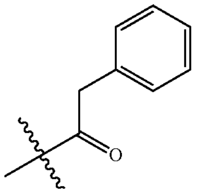 [SMILES: *C(=O)Cc1ccccc1] | $C_{28}H_{22}N_5O_2$[M + H] calc. 460.1768 obs. 460.1777 |
| 479 | 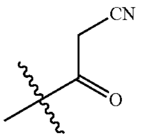 [SMILES: *C(=O)CC#N] | $C_{23}H_{17}N_6O_2$[M + H] calc. 409.1408 obs. 409.1400 |
| 480 | 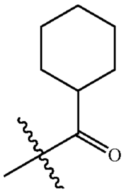 [SMILES: *C(=O)C1CCCCC1] | $C_{27}H_{26}N_5O_2$[M + H] calc. 452.2081 obs. 452.2079 |
| 481 | 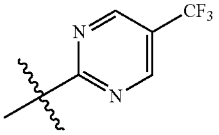 [SMILES: *c1ncc(C(F)(F)F)cn1] | $C_{26}H_{18}F_3N_6O$[M + H] calc. 487.1489 obs. 487.1488 |
| 482 | 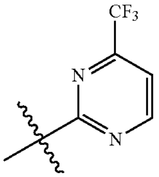 [SMILES: *c1nccc(C(F)(F)F)n1] | $C_{25}H_{17}F_3N_7O$[M + H] calc. 488.1441 obs. 488.1450 |
| 483 | 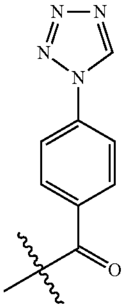 [SMILES: *C(=O)c1ccc(-n2cnnn2)cc1] | $C_{28}H_{20}N_9O_2$[M + H] calc. 514.1734 obs. 514.1732 |

-continued
(IQ)
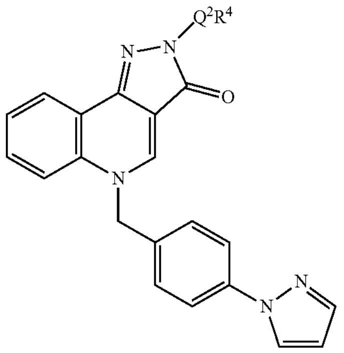
| Ex. | $Q^2R^4$ | HRMS/LRMS |
|---|---|---|
| 484 | 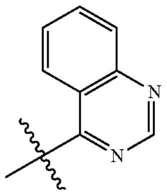 [SMILES: *c1ncnc2ccccc12] | $C_{28}H_{20}N_7O$[M + H] calc. 470.1724 obs. 470.1721 |
| 485 | 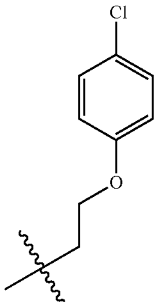 [SMILES: *CCOc1ccc(Cl)cc1] | $C_{28}H_{23}ClN_6O_2$[M + H] calc. 496.1535 obs. 496.1545 |
| 486 | 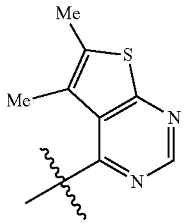 | $C_{28}H_{22}N_7OS$ [M + H] calc. 504.1601 obs. 504.1591 |
| 487 | 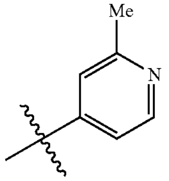 [SMILES: *c1ccnc(C)c1] | $C_{26}H_{21}N_6O$ [M + H] calc. 433.1771 obs. 433.1767 |
| 488 | 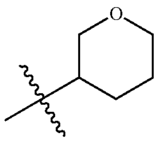 [SMILES: *C1CCCOC1] | $C_{25}H_{24}N_5O_2$ [M + H] calc. 426.1925 obs. 426.1934 |
-continued
(IQ)
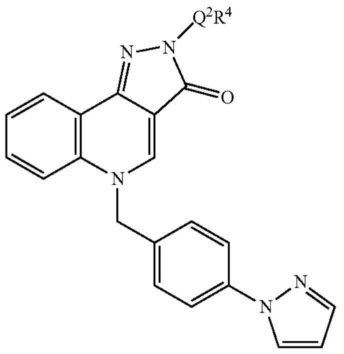
| Ex. | $Q^2R^4$ | HRMS/LRMS |
|---|---|---|
| 489 | 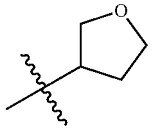 [SMILES: *C1CCOC1] | $C_{24}H_{22}N_5O_2$ [M + H] calc. 412.1768 obs. 412.1777 |
| 490 | 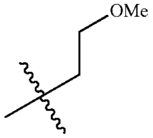 [SMILES: *CCOC] | $C_{23}H_{22}N_5O_2$[M + H] calc. 400.2 obs. 400.0 |
| 491 | 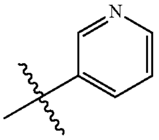 [SMILES: *c1cccnc1] | $C_{25}H_{19}N_6O$[M + H] calc. 419.1615 obs. 419.1609 |
| 492 | 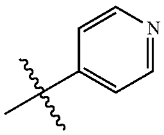 | $C_{25}H_{19}N_6O$[M + H] calc. 419.1615 obs. 419.1594 |
| 493 | 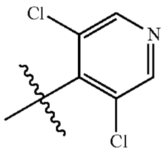 [SMILES: *c1c(Cl)cncc1Cl] | $C_{25}H_{16}Cl_2N_6O$ [M + H] calc. 487.1 obs. 487.2 |
| 494 | 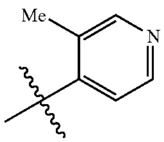 [SMILES: *c1ccncc1C] | $C_{26}H_{21}N_6O$ [M + H] calc. 433.2 obs. 433.3 |
| 495 | 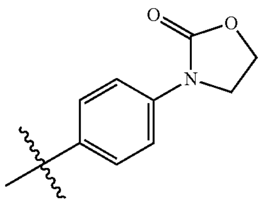 [SMILES: *c1ccc(N2CCOC2=O)cc1] | $C_{29}H_{23}N_6O_3$ [M + H] calc. 503.2 obs. 503.3 |

-continued
(IQ)
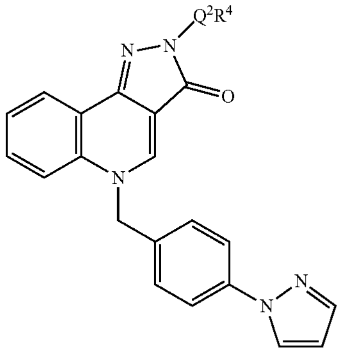
| Ex. | $Q^2R^4$ | HRMS/LRMS |
|---|---|---|
| 496 | 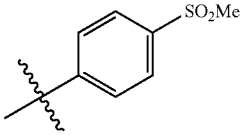 [SMILES: *c1ccc(S(C)(=O)=O)cc1] | $C_{27}H_{22}N_5O_3S$ [M + H] calc. 496.1 obs. 496.2 |
| 497 | 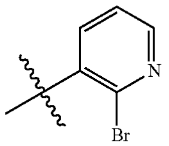 [SMILES: *c1cccnc1Br] | $C_{25}H_{18}BrN_6O$ [M + H] calc. 497.0720 obs. 497.0708 |
| 498 | 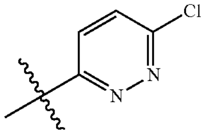 [SMILES: *c1ccc(Cl)nn1] | $C_{24}H_{17}ClN_7O$ [M + H] calc. 454.1178 obs. 454.1197 |
| 499 | 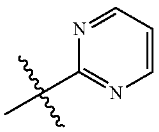 [SMILES: *c1ncccn1] | $C_{24}H_{18}N_7O$ [M + H] calc. 420.1567 obs. 420.1561 |
| 500 | 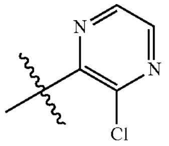 [SMILES: *c1nccnc1Cl] | $C_{24}H_{17}ClN_7O$ [M + H] calc. 454.1178 obs. 454.1176 |
| 501 | 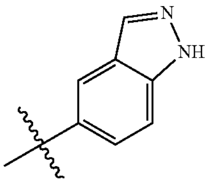 [SMILES: *c1ccc2[nH]ncc2c1] | $C_{27}H_{20}N_7O$[M + H] calc. 458.1724 obs. 458.1726 |
| 502 | 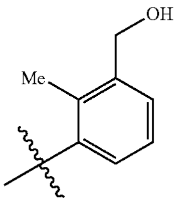 [SMILES: *c1cccc(CO)c1C] | $C_{28}H_{24}N_5O_2$[M + H] calc. 462.1925 obs. 462.1915 |
-continued
(IQ)
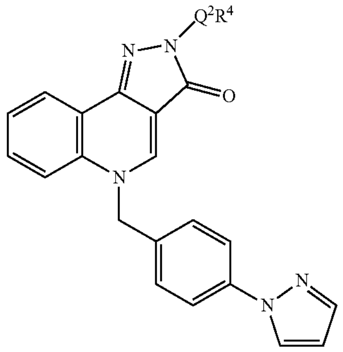
| Ex. | $Q^2R^4$ | HRMS/LRMS |
|---|---|---|
| 503 | 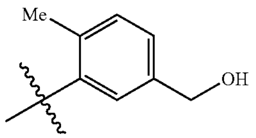 [SMILES: *c1cc(CO)ccc1C] | $C_{28}H_{24}N_5O_2$[M + H] calc. 462.1925 obs. 462.1915 |
| 504 | 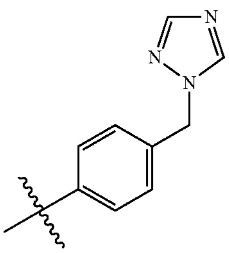 [SMILES: *c1ccc(Cn2cncn2)cc1] | $C_{29}H_{23}N_8O$ [M + H] calc. 499.1989 obs. 499.1987 |
| 505 | 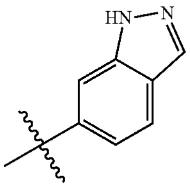 [SMILES: *c1ccc2cn[nH]c2c1] | $C_{27}H_{20}N_7O$ [M + H] calc. 458.1724 obs. 458.1720 |
| 506 | 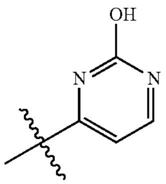 [SMILES: *c1ccnc(O)n1] | $C_{24}H_{18}N_7O_2$ [M + H] calc. 436.1516 obs. 436.1535 |
| 507 | 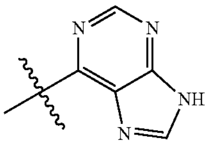 [SMILES: *c1ncnc2[nH]cnc12] | $C_{25}H_{18}N_9O$ [M + H] calc. 460.1629 obs. 460.1647 |
| 508 | 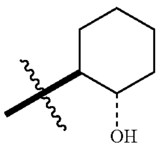 [SMILES: *[C@H]1CCCC[C@@H]1O] | $C_{26}H_{26}N_5O_2$ [M + H] calc. 440.2081 obs. 440.2096 |

-continued
(IQ)
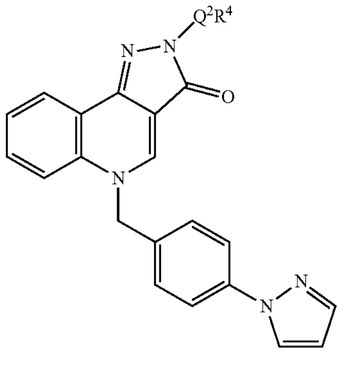
| Ex. | $Q^2R^4$ | HRMS/LRMS |
|---|---|---|
| 509 | 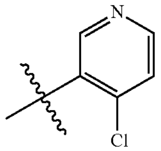 [SMILES: *c1cnccc1Cl] | $C_{25}H_{18}ClN_6O$ [M + H] calc. 453.1225 obs. 453.1233 |
| 510 | 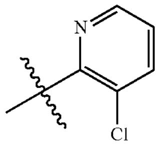 [SMILES: *c1ncccc1Cl] | $C_{25}H_{18}ClN_6O$ [M + H] calc. 453.1225 obs. 453.1240 |
| 511 | 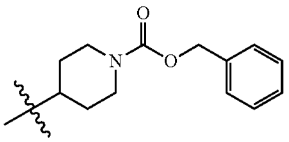 [SMILES: *C1CCN(C(=O)OCc2ccccc2)CC1] | $C_{33}H_{31}N_6O_3$ [M + H] calc. 559.2 obs. 559.3 |
| 512 | 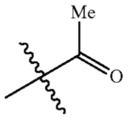 [SMILES: *C(C)=O] | $C_{22}H_{18}N_5O_2$ [M + H] calc. 384.3 obs. 383.9 |
| 513 | 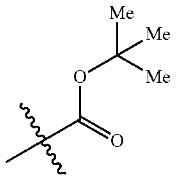 [SMILES: *C(=O)OC(C)(C)C] | $C_{25}H_{24}N_5O_3$ [M + H] calc. 442.1874 obs. 442.1903 |
| 514 | 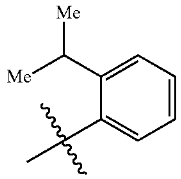 | $C_{29}H_{26}N_5O$ [M + H] calc. 460.2132 obs. 460.2146 |
| 515 | 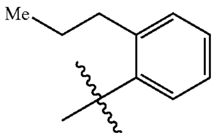 [SMILES: *c1ccccc1CCC] | $C_{29}H_{26}N_5O$ [M + H] calc. 460.2132 obs. 460.2144 |
-continued
(IQ)
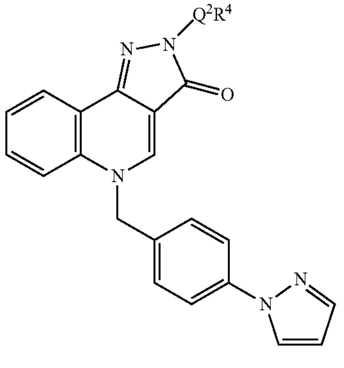
| Ex. | $Q^2R^4$ | HRMS/LRMS |
|---|---|---|
| 516 | 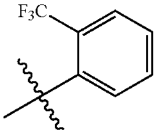 [SMILES: *c1ccccc1C(F)(F)F] | $C_{27}H_{19}F_3N_5O$ [M + H] calc. 486.1536 obs. 486.1571 |
| 517 | 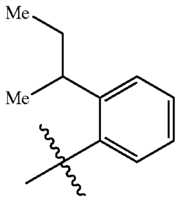 [SMILES: *c1ccccc1C(C)CC] | $C_{30}H_{28}N_5O$ [M + H] calc. 474.2289 obs. 474.2306 |
| 518 | 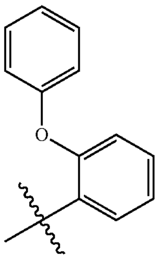 [SMILES: *c1ccccc1Oc1ccccc1] | $C_{32}H_{24}N_5O_2$ [M + H] calc. 510.1925 obs. 510.1955 |
| 519 | 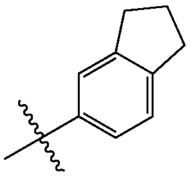 [SMILES: *c1ccc2c(c1)CCC2] | $C_{29}H_{24}N_5O$ [M + H] calc. 458.1976 obs. 458.1996 |
| 520 | 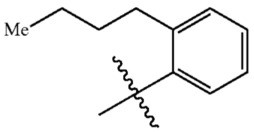 [SMILES: *c1ccccc1CCCC] | $C_{30}H_{28}N_5O$ [M + H] calc. 474.2289 obs. 474.2308 |
| 521 | 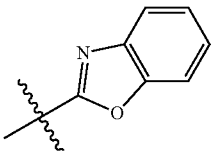 | $C_{27}H_{19}N_6O_2$ [M + H] calc. 459.1564 obs. 459.1563 |

-continued (IQ)

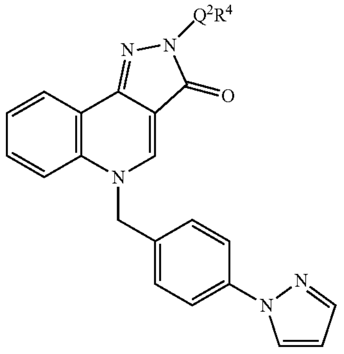

| Ex. | $Q^2R^4$ | HRMS/LRMS |
|---|---|---|
| 522 | 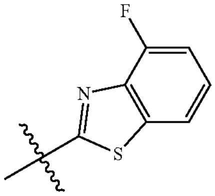 | $C_{27}H_{18}FN_6OS$ [M + H] calc. 493.1242 obs. 493.1234 |
| 523 | 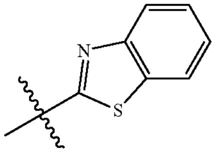 [SMILES: *c1nc2ccccc2o1] | $C_{27}H_{19}N_6OS$ [M + H] calc. 475.1336 obs. 475.1339 |
| 524 | 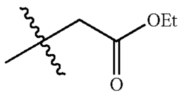 [SMILES: *CC(=O)OCC] | $C_{24}H_{22}N_5O_3$ [M + H] calc. 428.1717 obs. 428.1723 |
| 525 | 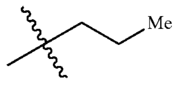 [SMILES: *CCC] | $C_{23}H_{22}N_5O$ [M + H] calc. 384.1819 obs. 384.1821 |
| 526 | 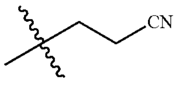 [SMILES: *CCC#N] | $C_{23}H_{19}N_6O$ [M + H] calc. 395.1615 obs. 395.1619 |
| 527 | 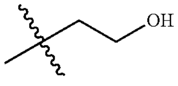 [SMILES: *CCO] | $C_{22}H_{20}N_5O_2$ [M + H] calc. 386.1612 obs. 386.1615 |

Example 528

2-(3-oxo-5-{[4-(1H-pyrazol-1-yl)phenyl]methyl}-3,5-dihydro-2H-pyrazolo[4,3c]quinolin-2-yl)benzonitrile

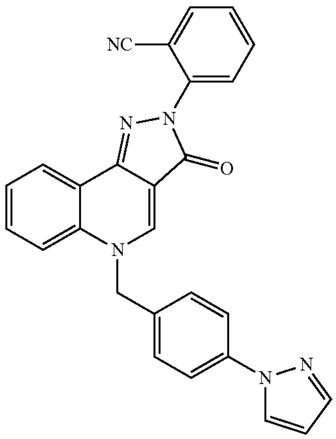 [SMILES: N#Cc1ccccc1-n1nc2c3ccccc3n(Cc3ccc(-n4cccn4)cc3)cc-2c1=O]

5-{[4-(1H-Pyrazol-1-yl)phenyl]methyl}-2,5-dihydro-3H-pyrazolo[4,3-c]quinolin-3-one (Example 406, 66 mg, 0.19 mmol), potassium phosphate (0.11 g, 0.48 mmol, 2.5 equiv), copper(I) iodide (3.7 mg, 0.019 mmol, 0.1 equiv), (±)-trans-N,N'-bismethyl-1,2-cyclohexane diamine (8.2 mg, 0.058 mmol, 0.3 equiv) and 2-iodobenzonitrile (89 mg, 0.39 mmol, 2 equiv) were combined in N,N-dimethylformamide (4 mL), the mixture was degassed, the vessel was sealed and placed into an oil bath preheated to 115° C. for 3 hours. The mixture was cooled to ambient temperature, poured into water (25 mL) and extracted with ethyl acetate (3×50 mL). The combined organic extracts were dried with sodium sulfate, filtered and concentrated in vacuo. The residue was purified by silica gel gradient chromatography (100:0 to 0:100; hexanes:ethyl acetate), providing the titled compound: $^1$H-NMR (400 MHz, $d^6$-DMSO) δ 9.24 (1H, s), 8.46 (1H, d, J=2.5 Hz), 8.24 (1H, dd, J=7.9, 1.6 Hz), 7.97 (1H, br d, J=8.2 Hz), 7.96 (1H, dd, J=7.7, 1.4 Hz), 7.85-7.79 (4H, m), 7.72 (1H, d, 1.5 Hz), 7.66 (1H, ddd, J=8.5, 7.1, 1.5 Hz), 7.58 (1H, ap t, J=7.5 Hz), 7.52 (1H, dd, J=7.7, 1.0 Hz), 7.48 (2H, d, J=8.9 Hz), 6.53 (1H, dd, J=2.3, 1.9 Hz), 5.79 (2H, s) ppm; high resolution mass spectrometry (ES+) m/z 443.1609 [$(M+H)^+$; calculated for $C_{27}H_{19}N_6O$: 443.1615].

The following compounds were prepared according to the general procedure described in Example 528, substituting the appropriately substituted iodide or bromide for 2-iodobenzonitrile, or, substituting (±)-trans-1,2-cyclohexane diamine for (±)-trans-N,N'-bismethyl-1,2-cyclohexane diamine, or, substituting potassium carbonate for potassium phosphate, or, substituting dimethylsulfoxide for N,N-dimethylformamide. The starting materials are either commercially available, known in the literature or may be prepared from commercially available reagents using conventional reactions well known in the art.

(IR)
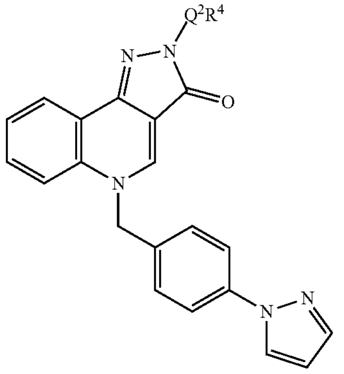
| Ex. | $Q^2R^4$ | HRMS/LRMS |
| --- | --- | --- |
| 529 | 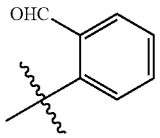 [SMILES: *c1ccccc1C=O] | $C_{27}H_{20}N_5O_2$ [M + H] calc. 446.1612 obs. 446.1633 |
| 530 | 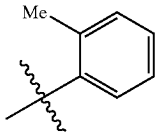 [SMILES: *c1ccccc1C] | $C_{22}H_{20}N_5O_2$ [M + H] calc. 432.1819 obs. 432.1846 |
| 531 | 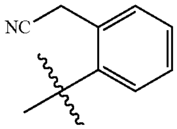 [SMILES: *c1ccccc1CC#N] | $C_{28}H_{21}N_6O$ [M + H] calc. 457.1772 obs. 457.1792 |
| 532 | 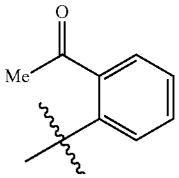 | $C_{28}H_{22}N_5O_2$ [M + H] calc. 460.1768 obs. 460.1759 |
| 533 | 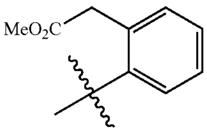 | $C_{29}H_{24}N_5O_3$ [M + H] calc. 490.1874 obs. 490.1880 |
| 534 | 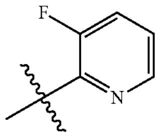 [SMILES: *c1ncccc1F] | $C_{25}H_{18}FN_6O$ [M + H] calc. 437.1521 obs. 437.1517 |
| 535 | 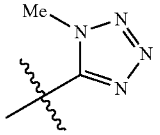 [SMILES: *c1nnnn1C] | $C_{22}H_{18}N_9O$ [M + H] calc. 424.1629 obs. 424.1640 |
| 536 | 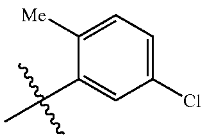 [SMILES: *c1cc(Cl)ccc1C] | $C_{27}H_{21}ClN_5O$ [M + H] calc. 466.1426 obs. 466.1434 |
-continued
(IR)
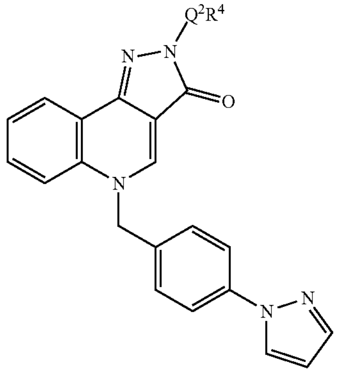
| Ex. | $Q^2R^4$ | HRMS/LRMS |
| --- | --- | --- |
| 537 | 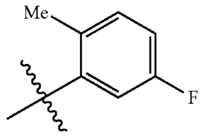 [SMILES: *c1cc(F)ccc1C] | $C_{27}H_{21}FN_5O$ [M + H] calc. 450.1725 obs. 450.1721 |
| 538 | 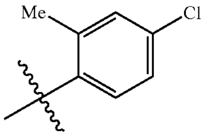 [SMILES: *c1ccc(Cl)cc1C] | $C_{27}H_{21}ClN_5O$ [M + H] calc. 466.1429 obs. 466.1442 |
| 539 | 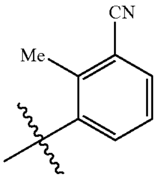 [SMILES: *c1cccc(C#N)c1C] | $C_{28}H_{21}N_6O$ [M + H] calc. 457.1771 obs. 457.1774 |
| 540 | 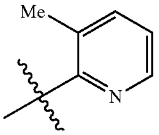 [SMILES: *c1ncccc1C] | $C_{26}H_{18}N_9O$ [M + H] calc. 433.1771 obs. 433.1777 |
| 541 | 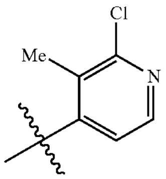 | $C_{26}H_{20}ClN_6O$ [M + H] calc. 467.1382 obs. 467.1382 |
| 542 | 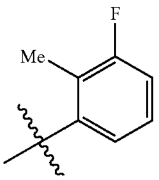 [SMILES: *c1cccc(F)c1C] | $C_{27}H_{21}FN_5O$ [M + H] calc. 450.1725 obs. 450.1733 |
| 543 | 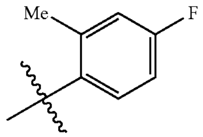 [SMILES: *c1ccc(F)cc1C] | $C_{27}H_{21}FN_5O$ [M + H] calc. 450.1725 obs. 450.1729 |

-continued
(IR)
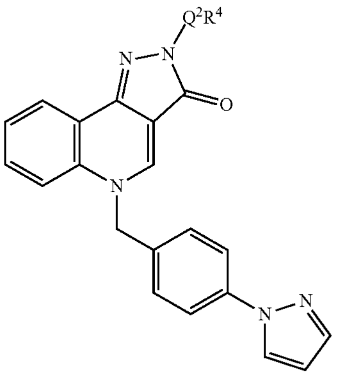
| Ex. | $Q^2R^4$ | HRMS/LRMS |
|---|---|---|
| 544 | 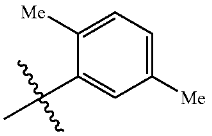 [SMILES: *c1cc(C)ccc1C] | $C_{28}H_{24}N_5O$ [M + H] calc. 446.1975 obs. 446.1983 |
| 545 | 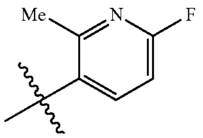 [SMILES: *c1ccc(F)nc1C] | $C_{26}H_{20}FN_6O$ [M + H] calc. 451.1677 obs. 451.1698 |
| 546 | 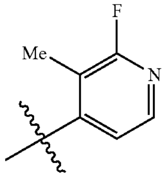 [SMILES: *c1ccnc(F)c1C] | $C_{26}H_{20}FN_6O$ [M + H] calc. 451.1677 obs. 451.1695 |
| 547 | 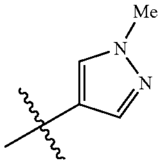 [SMILES: *c1cnn(C)c1] | $C_{24}H_{20}N_7O$ [M + H] calc. 422.1724 obs. 422.1718 |
| 548 | 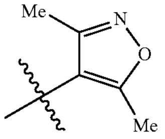 [SMILES: *c1c(C)noc1C] | $C_{25}H_{21}N_6O_2$ [M + H] calc. 437.1721 obs. 437.1713 |
| 549 | 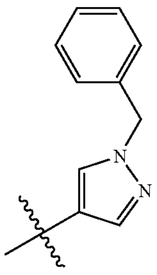 [SMILES: *c1cnn(Cc2ccccc2)c1] | $C_{30}H_{24}N_7O$ [M + H] calc. 498.2037 obs. 498.2028 |
-continued
(IR)
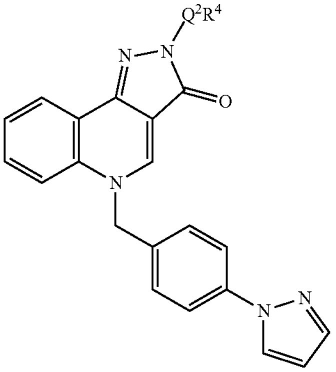
| Ex. | $Q^2R^4$ | HRMS/LRMS |
|---|---|---|
| 550 | 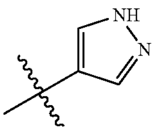 [SMILES: *c1cn[nH]c1] | $C_{23}H_{18}N_7O$ [M + H] calc. 408.1567 obs. 408.1557 |
| 551 | 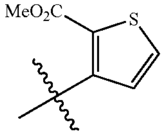 [SMILES: *c1ccsc1C(=O)OC] | $C_{26}H_{20}N_5O_3S$ [M + H] calc. 424.1629 obs. 424.1640 |
| 552 | 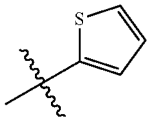 [SMILES: *c1cccs1] | $C_{24}H_{18}N_5OS$ [M + H] calc. 424.1227 obs. 424.1217 |
| 553 | 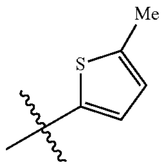 [SMILES: *c1ccc(C)s1] | $C_{25}H_{20}N_5OS$ [M + H] calc. 438.1383 obs. 437.1372 |
| 554 | 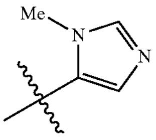 [SMILES: *c1cncn1C] | $C_{24}H_{20}N_7O$ [M + H] calc. 422.1724 obs. 422.1726 |
| 555 | 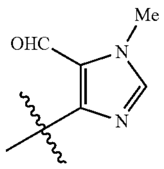 [SMILES: *c1ncn(C)c1C=O] | $C_{25}H_{20}N_7O_2$[M + H] calc. 450.1673 obs. 450.1661 |
| 556 | 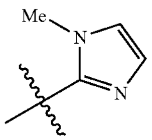 [SMILES: *c1nccn1C] | $C_{24}H_{20}N_7O$[M + H] calc. 422.1724 obs. 422.1730 |

-continued
(IR)
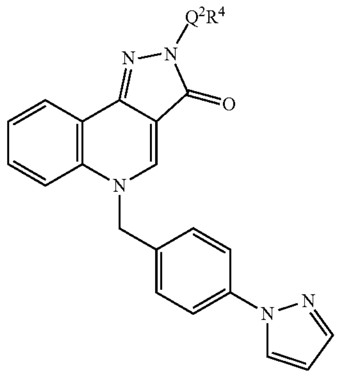
| Ex. | $Q^2R^4$ | HRMS/LRMS |
|---|---|---|
| 557 | 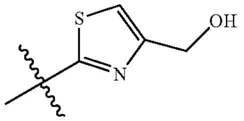 [SMILES: *c1nc(CO)cs1] | $C_{24}H_{19}N_6O_2S$ [M + H] calc. 455.1285 obs. 455.1291 |
| 558 | 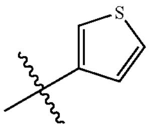 [SMILES: *c1ccsc1] | $C_{24}H_{18}N_5OS$ [M + H] calc. 424.1227 obs. 424.1234 |
| 559 | 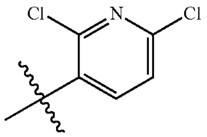 [SMILES: *c1ccc(Cl)nc1Cl] | $C_{25}H_{17}Cl_2N_6O$ [M + H] calc. 487.0835 obs. 487.0855 |
| 560 | 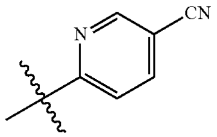 [SMILES: *c1ccc(C#N)cn1] | $C_{26}H_{18}N_7O$ [M + H] calc. 444.1567 obs. 444.1577 |
| 561 | 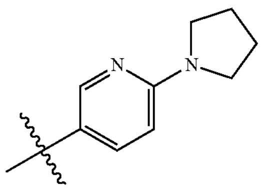 [SMILES: *c1ccc(N2CCCC2)nc1] | $C_{29}H_{26}N_7O$ [M + H] calc. 488.2193 obs. 488.2214 |
| 562 | 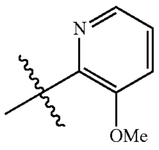 [SMILES: *c1ncccc1OC] | $C_{26}H_{21}N_6O_2$ [M + H] calc. 449.1721 obs. 449.1746 |
| 563 | 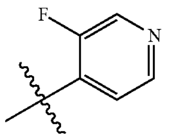 [SMILES: *c1ccncc1F] | $C_{25}H_{18}FN_6O$ [M + H] calc. 437.1521 obs. 437.1536 |
-continued
(IR)
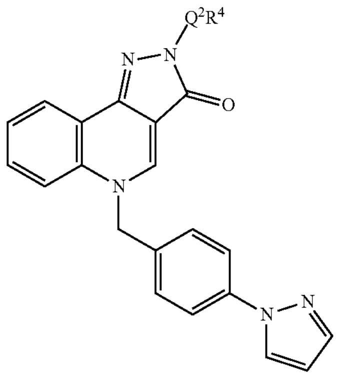
| Ex. | $Q^2R^4$ | HRMS/LRMS |
|---|---|---|
| 564 | 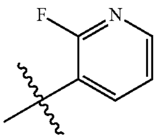 [SMILES: *c1cccnc1F] | $C_{25}H_{18}FN_6O$[M + H] calc. 437.1521 obs. 437.1539 |
| 565 | 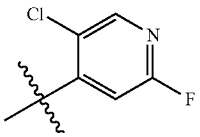 [SMILES: *c1cc(F)ncc1Cl] | $C_{25}H_{17}ClFN_6O$[M + H] calc. 471.1131 obs. 471.1156 |
| 566 | 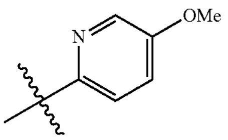 [SMILES: *c1ccc(OC)cn1] | $C_{26}H_{21}N_6O_2$ [M + H] calc. 449.1721 obs. 449.1733 |
| 567 | 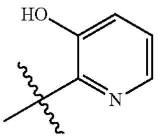 [SMILES: *c1ncccc1O] | $C_{25}H_{19}N_6O_2$ [M + H] calc. 435.1564 obs. 435.1579 |
| 568 | 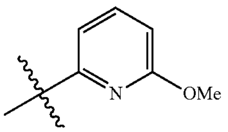 [SMILES: *c1cccc(OC)n1] | $C_{26}H_{21}N_6O_2$ [M + H] calc. 449.1721 obs. 449.1734 |
| 569 | 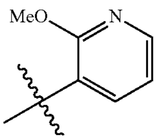 [SMILES: *c1cccnc1OC] | $C_{26}H_{21}N_6O_2$ [M + H] calc. 449.1721 obs. 449.1732 |
| 570 | 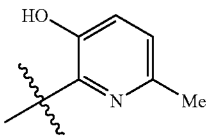 [SMILES: *c1nc(C)ccc1O] | $C_{26}H_{21}N_6O_2$ [M + H] calc. 449.1721 obs. 449.1729 |

-continued
(IR)
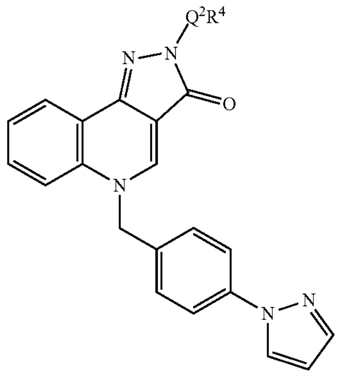
| Ex. | $Q^2R^4$ | HRMS/LRMS |
|---|---|---|
| 571 | 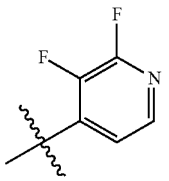 [SMILES: *c1ccnc(F)c1F] | $C_{25}H_{17}F_2N_6O$ [M + H] calc. 455.1426 obs. 455.1449 |
| 572 | 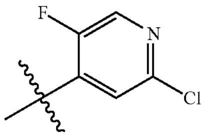 [SMILES: *c1cc(Cl)ncc1F] | $C_{25}H_{17}ClFN_6O$ [M + H] calc. 471.1131 obs. 471.1139 |
| 573 | 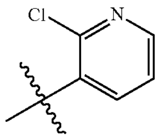 [SMILES: *c1cccnc1Cl] | $C_{25}H_{18}ClN_6O$ [M + H] calc. 453.1225 obs. 453.1209 |
| 574 | 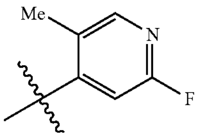 [SMILES: *c1cc(F)ncc1C] | $C_{26}H_{20}FN_6O$ [M + H] calc. 451.1677 obs. 451.1661 |
| 575 | 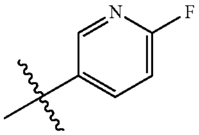 [SMILES: *c1ccc(F)nc1] | $C_{25}H_{18}FN_6O$ [M + H] calc. 437.1 obs. 437.3 |
| 576 | 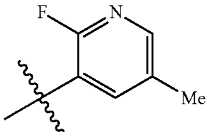 [SMILES: *c1cc(C)cnc1F] | $C_{26}H_{20}FN_6O$ [M + H] calc. 451.1677 obs. 451.1664 |
| 577 | 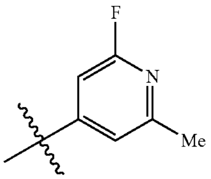 [SMILES: *c1cc(C)nc(F)c1] | $C_{26}H_{20}FN_6O$ [M + H] calc. 451.1677 obs. 451.1660 |
-continued
(IR)
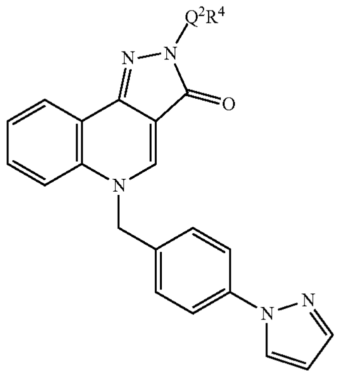
| Ex. | $Q^2R^4$ | HRMS/LRMS |
|---|---|---|
| 578 | 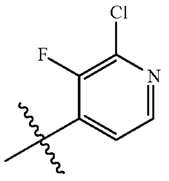 [SMILES: *c1ccnc(Cl)c1F] | $C_{25}H_{17}ClFN_6O$ [M + H] calc. 471.1131 obs. 471.1150 |
| 579 | 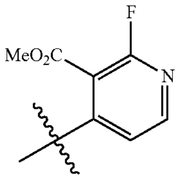 [SMILES: *c1ccnc(F)c1C(=O)OC] | $C_{27}H_{20}FN_6O_3$ [M + H] calc. 495.1575 obs. 495.1602 |
| 580 | 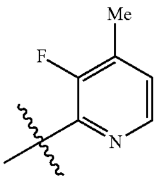 [SMILES: *c1nccc(C)c1F] | $C_{26}H_{20}FN_6O$ [M + H] calc. 451.1667 obs. 451.1682 |
| 581 | 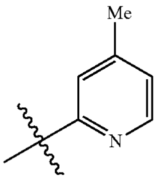 [SMILES: *c1cc(C)ccn1] | $C_{26}H_{21}N_6O$ [M + H] calc. 433.1771 obs. 433.1774 |
| 582 | 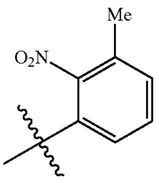 [SMILES: *c1cccc(C)c1[N+](=O)[O-]] | $C_{27}H_{21}N_6O_3$[M + H] calc. 477.1670 obs. 477.1672 |
| 583 | 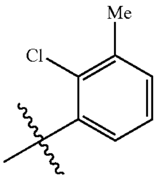 [SMILES: *c1cccc(C)c1Cl] | $C_{27}H_{21}ClN_5O$[M + H] calc. 466.1429 obs. 466.1434 |

(IR)
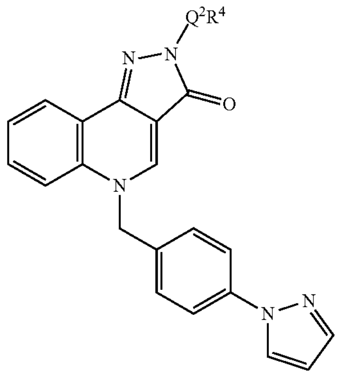
| Ex. | $Q^2R^4$ | HRMS/LRMS |
|---|---|---|
| 584 | 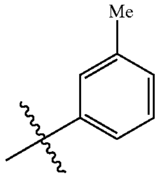 [SMILES: *c1cccc(C)c1] | $C_{27}H_{22}N_5O$ [M + H] calc. 432.1819 obs. 432.1825 |
| 585 | 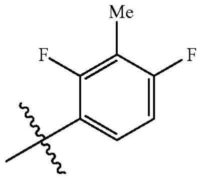 [SMILES: *c1ccc(F)c(C)c1F] | $C_{27}H_{20}F_2N_5O$ [M + H] calc. 468.1630 obs. 468.1636 |
| 586 | 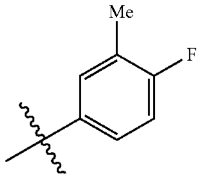 [SMILES: *c1ccc(F)c(C)c1] | $C_{27}H_{21}FN_5O$ [M + H] calc. 450.1725 obs. 450.1731 |
| 587 | 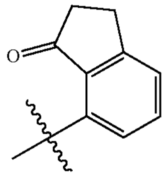 [SMILES: *c1cccc2c1C(=O)CC2] | $C_{29}H_{22}FN_5O_2$ [M + H] calc. 472.1768 obs. 472.1784 |
| 588 | 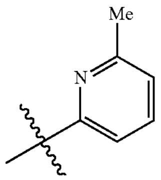 [SMILES: *c1cccc(C)n1] | $C_{26}H_{21}N_6O$ [M + H] calc. 433.1771 obs. 433.1777 |
| 589 | 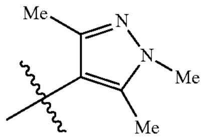 [SMILES: *c1c(C)nn(C)c1C] | $C_{26}H_{24}N_7O$ [M + H] calc. 450.2037 obs. 450.2052 |
(IR)
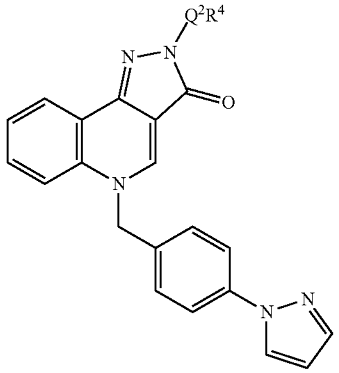
| Ex. | $Q^2R^4$ | HRMS/LRMS |
|---|---|---|
| 590 | 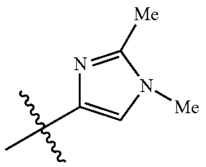 [SMILES: *c1cn(C)c(C)n1] | $C_{25}H_{22}N_7O$ [M + H] calc. 436.1880 obs. 436.1897 |
| 591 | 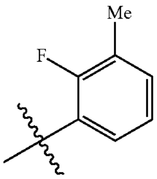 [SMILES: *c1cccc(C)c1F] | $C_{27}H_{21}FN_5O$ [M + H] calc. 450.1725 obs. 450.1749 |
| 592 | 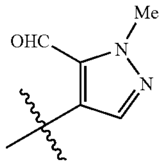 [SMILES: *c1cnn(C)c1C=O] | $C_{25}H_{20}N_7O_2$ [M + H] calc. 450.1673 obs. 450.1684 |
| 593 | 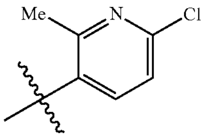 [SMILES: *c1ccc(Cl)nc1C] | $C_{26}H_{20}ClN_6O$ [M + H] calc. 467.1382 obs. 467.1390 |
| 594 | 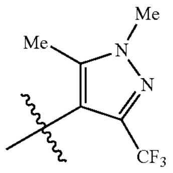 [SMILES: *c1c(C(F)(F)F)nn(C)c1C] | $C_{26}H_{21}F_3N_7O$ [M + H] calc. 504.1754 obs. 504.1761 |
| 595 | 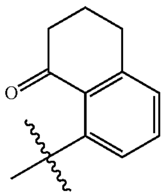 [SMILES: *c1cccc2c1C(=O)CCC2] | $C_{30}H_{23}N_5O_2$ [M + H] calc. 486.1925 obs. 486.1921 |

-continued (IR)

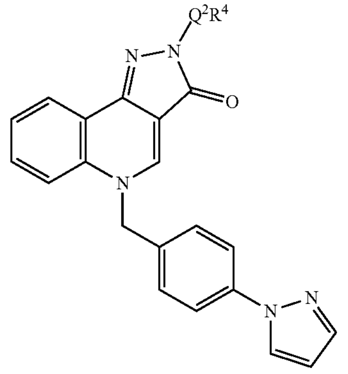

| Ex. | $Q^2R^4$ | HRMS/LRMS |
|---|---|---|
| 596 | 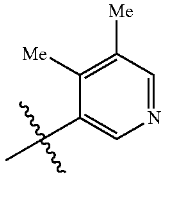 [SMILES: *c1cncc(C)c1C] | $C_{27}H_{23}N_6O$ [M + H] calc. 447.1928 obs. 447.1922 |
| 597 | 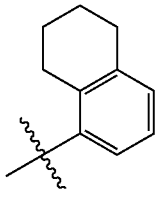 [SMILES: *c1cccc2c1CCCC2] | $C_{30}H_{26}N_5O$ [M + H] calc. 472.2132 obs. 472.2137 |
| 598 | 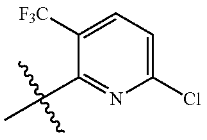 [SMILES: *c1nc(Cl)ccc1C(F)(F)F] | $C_{26}H_{17}ClF_3N_6O$ [M + H] calc. 521.1 obs. 521.3 |
| 599 | 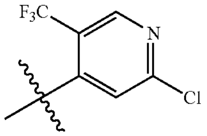 [SMILES: *c1cc(Cl)ncc1C(F)(F)F] | $C_{26}H_{17}ClF_3N_6O$ [M + H] calc. 521.1104 obs. 521.1099 |

Example 600

6-Fluoro-2-(2-fluorophenyl)-5-{[4-(1H-pyrazol-1-yl)phenyl]methyl}-2,5-dihydro-3H-pyrazolo[4,3-c]quinolin-3-one

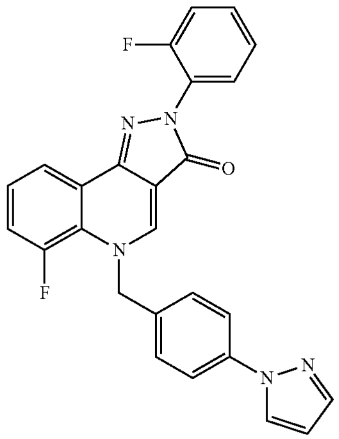 [SMILES: O=c1c2cn(Cc3ccc(-n4cccn4)cc3)c3c(F)cccc3c-2nn1-c1ccccc1F]

Using the procedures described in Example 403, substituting ethyl 8-fluoro-4-oxo-1,4-dihydroquinoline-3-carboxylate for ethyl 4-oxo-1,4-dihydroquinoline-3-carboxylate (Example 1, Step 1), and, substituting (2-fluorophenyl)hydrazine for (2,6-difluorophenyl)hydrazine (Example 403, Step 2), the titled compound was obtained: $^1$H-NMR (400 MHz, $d^6$-DMSO) δ 9.09 (1H, s), 8.44 (1H, d, J=2.2 Hz), 8.05 (1H, d, J=7.8 Hz), 7.80 (2H, d, J=8.5 Hz), 7.72 (1H, d, J=1.3 Hz), 7.61 (1H, ap t, J=7.6 Hz), 7.56-7.45 (3H, m), 7.43-7.39 (1H, m), 7.35 (1H, d, J=7.7 Hz), 7.32 (2H, d, J=8.3 Hz), 6.53-6.52 (1H, m), 5.80 (2H, s) ppm; high resolution mass spectrometry (ES+) m/z 454.1485 [$(M+H)^+$; calculated for $C_{26}H_{18}F_2N_5O$: 454.1474].

The following compound was prepared according to the general procedure described in Example 600, substituting (2-methylphenyl)hydrazine for (2-fluorophenyl)hydrazine. The starting materials are either commercially available, known in the literature or may be prepared from commercially available reagents using conventional reactions well known in the art.

(IS)

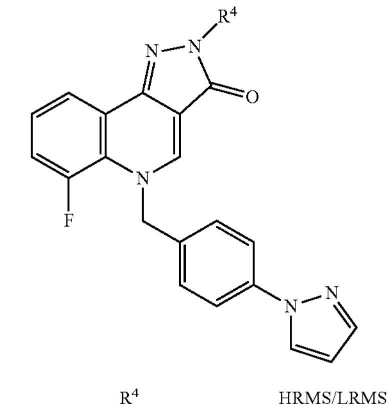

| Ex. | $R^4$ | HRMS/LRMS |
|---|---|---|
| 601 | 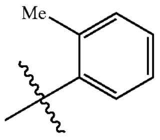 [SMILES: *c1ccccc1C] | $C_{27}H_{21}FN_5O$ [M + H] calc. 450.1725 obs. 450.1743 |

Example 602

6-Fluoro-2-(2-fluoro-3-methylpyridin-4-yl)-5-{[4-(1H-pyrazol-1-yl)phenyl]methyl}-2,5-dihydro-3H-pyrazolo[4,3-c]quinolin-3-one

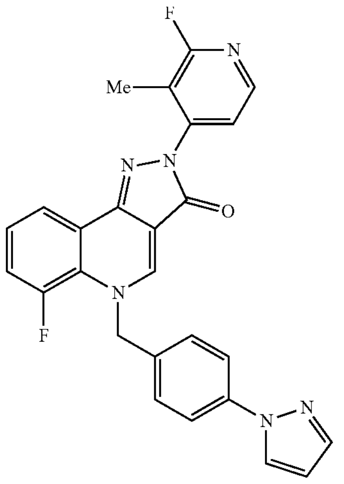 [SMILES: Cc1c(-n2nc3c4cccc(F)c4n(Cc4ccc(-n5cccn5)cc4)cc-3c2=O)ccnc1F]

Using the procedures described in Example 8, substituting ethyl 8-fluoro-4-oxo-1,4-dihydroquinoline-3-carboxylate for ethyl 4-oxo-1,4-dihydroquinoline-3-carboxylate (Step 1), and, substituting 1-[4-(bromomethyl)phenyl]-1H-pyrazole for 4-(bromomethyl)biphenyl (Step 1), and, substituting 2-fluoro-4-iodo-3-picoline for 2-fluoroiodobenzene (Step 4), the titled compound was obtained: $^1$H-NMR (400 MHz, $CDCl_3$) δ 8.36 (1H, s), 8.19 (1H, br d, J=7.9 Hz), 8.12 (1H, d, J=5.4 Hz), 7.90 (1H, d, J=2.4 Hz), 7.73-7.69 (3H, m), 7.47 (1H, dd, J=8.1, 3.5 Hz), 7.44 (1H, d, J=5.3 Hz), 7.31-7.25 (4H, m), 6.47 (1H, dd, J=2.3, 1.9 Hz), 5.66 (1H, d, J=2.5 Hz), 2.35 (3H, s) ppm; high resolution mass spectrometry (ES+) m/z 469.1591 [$(M+H)^+$; calculated for $C_{26}H_{19}F_2N_6O$: 469.1583].

The following compounds were prepared according to the general procedure described in Example 602, substituting the appropriate aryl iodide for 2-fluoro-4-iodo-3-picoline. The starting materials are either commercially available, known in the literature or may be prepared from commercially available reagents using conventional reactions well known in the art.

(IT)

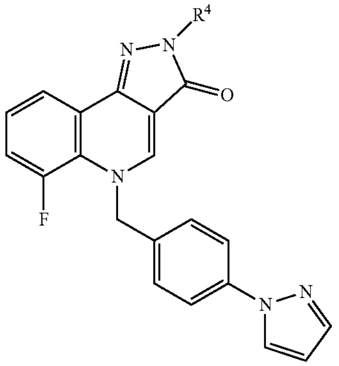

| Ex. | $R^4$ | HRMS/LRMS |
|---|---|---|
| 603 | 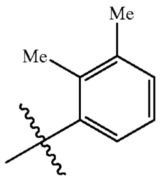 [SMILES: *c1cccc(C)c1C] | $C_{28}H_{23}FN_5O$ [M + H] calc. 464.1881 obs. 464.1888 |
| 604 | 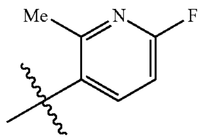 [SMILES: *c1ccc(F)nc1C] | $C_{26}H_{19}F_2N_6O$ [M + H] calc. 469.1583 obs. 469.1586 |
| 605 | 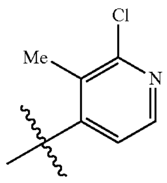 | $C_{26}H_{19}ClFN_6O$ [M + H] calc. 485.1287 obs. 485.1279 |
| 606 | 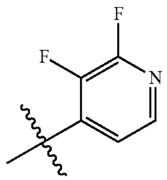 [SMILES: *c1ccnc(F)c1F] | $C_{26}H_{19}F_3N_6O$ [M + H] calc. 473.1332 obs. 473.1325 |
| 607 | 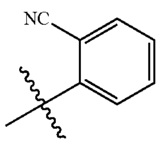 [SMILES: *c1ccccc1C#N] | $C_{27}H_{18}FN_6O$ [M + H] calc. 461.1521 obs. 461.1511 |
| 608 | 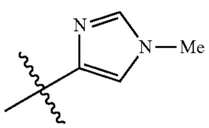 [SMILES: *c1cn(C)cn1] | $C_{26}H_{19}FN_7O$ [M + H] calc. 440.1630 obs. 440.1634 |

Example 609

9-Fluoro-2-(2-methylphenyl)-5-{[4-(1H-pyrazol-1-yl)phenyl]methyl}-2,5-dihydro-3H-pyrazolo[4,3-c]quinolin-3-one

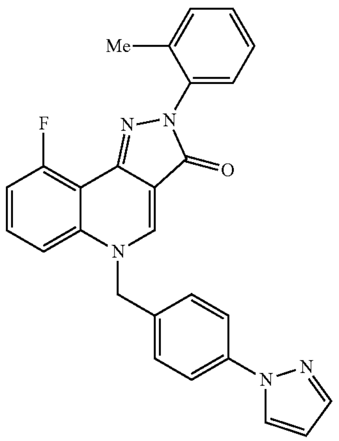 [SMILES: Cc1ccccc1-n1nc2c3c(F)cccc3n(Cc3ccc(-n4cccn4)cc3)cc-2c1=O]

Using the procedures described in Example 403, substituting ethyl 5-fluoro-4-oxo-1,4-dihydroquinoline-3-carboxylate for ethyl 4-oxo-1,4-dihydroquinoline-3-carboxylate (Example 1, Step 1), and, substituting (2-methylphenyl) hydrazine for (2,6-difluorophenyl)hydrazine (Step 2), the titled compound was obtained: $^1$H-NMR (400 MHz, d$^6$-DMSO) δ 9.12 (1H, s), 8.47 (1H, d, J=2.5 Hz), 7.83 (2H, d, J=8.5 Hz), 7.73 (1H, d, J=1.4 Hz), 7.63-7.55 (2H, m), 7.48 (2H, d, J=8.6 Hz), 7.40-7.32 (5H, m), 6.53 (1H, dd, J=2.3, 1.9 Hz), 5.75 s), 2.24 (3H, s) ppm; high resolution mass spectrometry (ES+) m/z 450.1733 [(M+H)$^+$; calculated for $C_{27}H_{21}FN_5O$: 450.1725].

Example 610

9-Bromo-6-fluoro-2-(2-fluorophenyl)-5-{[4-(1H-pyrazol-1-yl)phenyl]methyl}-2,5-dihydro-3H-pyrazolo[4,3-c]quinolin-3-one

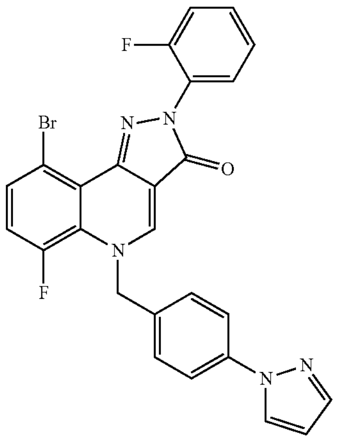 [SMILES: O=c1c2cn(Cc3ccc(-n4cccn4)cc3)c3c(F)ccc(Br)c3c-2nn1-c1ccccc1F]

Using the procedures described in Example 403, substituting ethyl 5-bromo-8-fluoro-4-oxo-1,4-dihydroquinoline-3-carboxylate for ethyl 4-oxo-1,4-dihydroquinoline-3-carboxylate (Example 1, Step 1), and, substituting (2-fluorophenyl)hydrazine for (2,6-difluorophenyl)hydrazine (Step 2), the titled compound was obtained: $^1$H-NMR (400 MHz, d$^6$-DMSO) δ 9.05 (1H, s), 8.45 (1H, d, J=2.6 Hz), 7.82-7.78 (3H, m), 7.72 (1H, d, J=1.8 Hz), 7.62 (1H, td, J=7.8, 1.6 Hz), 7.51-7.36 (4H, m), 7.32 (2H, d, J=8.6 Hz), 6.52 (1H, br m), 5.78 (2H, d, J=4.2 Hz) ppm; high resolution mass spectrometry (ES+) m/z 532.0615 [(M+H)$^+$; calculated for $C_{26}H_{17}BrF_2N_5O$: 532.0579].

Example 611

2-(3-oxo-5-{[4-(1H-pyrazol-1-yl)phenyl]methyl}-3,5-dihydro-2H-pyrazolo[4,3-c]quinolin-2-yl)benzoic acid

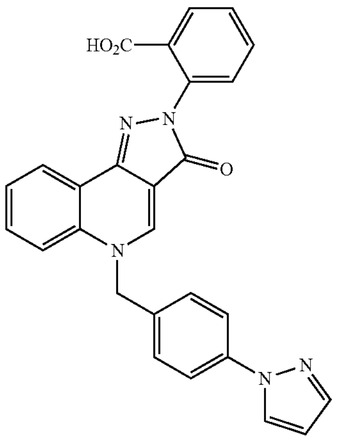 [SMILES: O=C(O)c1ccccc1-n1nc2c3ccccc3n(Cc3ccc(-n4cccn4)cc3)cc-2c1=O]

Using the procedures described in Example 403, substituting hydrazinobenzoic acid for (2,6-difluorophenyl)hydrazine (Step 2), the titled compound was obtained: $^1$H-NMR (400 MHz, d$^6$-DMSO) δ 12.33 (1H, br s), 9.09 (1H, s), 8.45 (1H, d, J=2.5 Hz), 8.21 (1H, dd, J=7.9, 1.6 Hz), 7.95 (2H, m), 7.83 (1H, d, J=8.8 Hz), 7.77 (1H, d, J=8.2 Hz), 7.73 (1H, dd, J=7.1, 1.2 Hz), 7.66 (1H, d, J=1.5 Hz), 7.65-7.60 (2H, m), 7.54 (1H, ap t, J=7.6 Hz), 7.45 (2H, d, J=8.7 Hz), 7.42 (1H, ddd, J=8.5, 6.6, 2.1 Hz), 6.53 (1H, dd, J=2.5, 1.8 Hz), 5.76 (2H, s) ppm; high resolution mass spectrometry (ES+) m/z 462.1588 [(M+H)$^+$; calculated for $C_{27}H_{20}N_5O_3$: 462.1561].

Example 612

N-Methyl-2-(3-oxo-5-{[4-(1H-pyrazol-1-yl)phenyl]methyl}-3,5-dihydro-2H-pyrazolo[4,3-c]quinolin-2-yl)benzamide

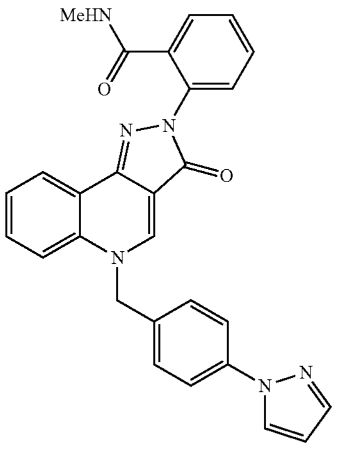 [SMILES: CNC(=O)c1ccccc1-n1nc2c3ccccc3n(Cc3ccc(-n4cccn4)cc3)cc-2c1=O]

2-(3-Oxo-5-{[4-(1H-pyrazol-1-yl)phenyl]methyl}-3,5-dihydro-2H-pyrazolo[4,3-c]quinolin-2-yl)benzoic acid (Example 611, 41 mg, 0.089 mmol) was suspended in dichloromethane (3 mL), treated with (1H-1,2,3-benzotriazol-1-yloxy) (tripyrrolidin-1-yl)phosphonium hexafluorophosphate (PyBOP, 69 mg, 0.13 mmol, 1.5 equiv) and methylamine (1.0 mL, 2 M tetrahydrofuran solution, 2.0 mmol, 22 equiv). After stirring for 1 hour, the mixture was poured into sodium bicarbonate (20 mL, aqueous saturated) and extracted with chloroform (3×25 mL). The combined organic extracts were dried with sodium sulfate, filtered and concentrated in vacuo. The residue was purified by silica gel gradient chromatography (100:0 to 0:100; hexanes:ethyl acetate), providing the titled compound: $^1$H-NMR (400 MHz, d$^6$-DMSO) δ 9.11 (1H, s), 8.45 (1H, d, J=2.5 Hz), 8.16 (1H, dd, J=7.9, 1.5 Hz), 8.11 (1H, q, J=5.0 Hz), 7.83 (2H, d, J=8.6 Hz), 7.76 (1H, d, J=8.5 Hz), 7.72 (1H, d, J=1.5 Hz), 7.70 (1H, d, J=7.9 Hz), 7.61 (1H, ddd, J=8.3, 7.3, 1.8 Hz), 7.56-7.52 (2H, m), 7.49 (1H, dd, J=7.7, 1.5 Hz), 7.46 (2H, d, J=8.9 Hz), 7.36 (1H, td, J=7.5, 1.1 Hz), 6.53 (1H, dd, J=2.4, 1.8 Hz), 5.76 (2H, s), 2.66 (3H, d, J=4.6 Hz) ppm; high resolution mass spectrometry (ES+) m/z 475.1896 [(M+H)$^+$; calculated for $C_{28}H_{23}N_6O_2$: 475.1877].

The following compounds were prepared according to the general procedure described in Example 612, substituting the appropriate amine for methylamine. The starting materials are either commercially available, known in the literature or may be prepared from commercially available reagents using conventional reactions well known in the art.

(IU)

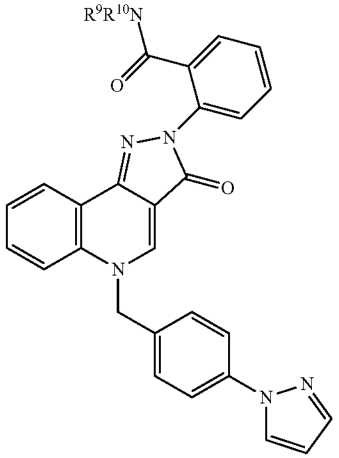

| Ex. | NR9R10 | HRMS/LRMS |
|---|---|---|
| 613 | 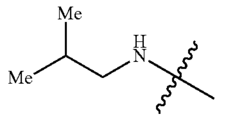 [SMILES: *NCC(C)C] | $C_{31}H_{29}N_6O_2$ [M + H] calc. 517.2347 obs. 517.2394 |
| 614 | 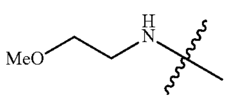 [SMILES: *NCCOC] | $C_{30}H_{27}N_6O_3$ [M + H] calc. 519.2139 obs. 519.2165 |
| 615 | 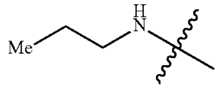 [SMILES: *NCCC] | $C_{30}H_{25}N_6O_2$ [M + H] calc. 501.2034 obs. 501.2046 |

-continued (IU)

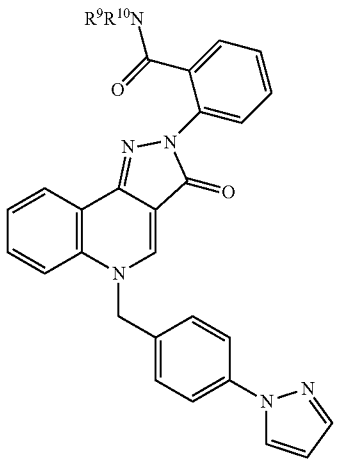

| Ex. | NR9R10 | HRMS/LRMS |
|---|---|---|
| 616 | 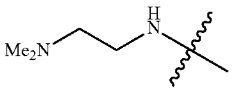 [SMILES: *NCCN(C)C] | $C_{31}H_{30}N_7O_2$ [M + H] calc. 532.2456 obs. 532.2460 |
| 617 | 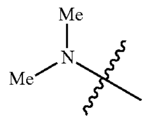 | $C_{29}H_{25}N_6O_2$ [M + H] calc. 489.2034 obs. 489.2047 |
| 618 | 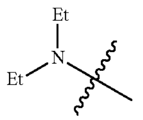 | $C_{31}H_{29}N_6O_2$ [M + H] calc. 517.2347 obs. 517.2370 |
| 619 | 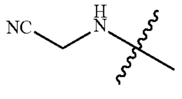 [SMILES: *NCC#N] | $C_{29}H_{22}N_7O_2$ [M + H] calc. 500.1829 obs. 500.1847 |
| 620 | 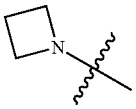 [SMILES: *N1CCC1] | $C_{30}H_{25}N_6O_2$ [M + H] calc. 501.2034 obs. 501.2049 |
| 621 | 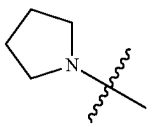 [SMILES: *N1CCCC1] | $C_{31}H_{27}N_6O_2$ [M + H] calc. 515.2190 obs. 515.2217 |
| 622 | 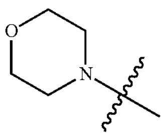 [SMILES: *N1CCOCC1] | $C_{31}H_{27}N_6O_3$ [M + H] calc. 531.2139 obs. 531.2119 |
| 623 | 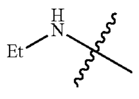 | $C_{29}H_{25}N_6O_2$ [M + H] calc. 489.2034 obs. 489.2052 |
| 624 | 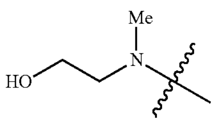 [SMILES: *N(C)CCO] | $C_{30}H_{27}N_6O_3$ [M + H] calc. 519.2145 obs. 519.2179 |

-continued (IU)

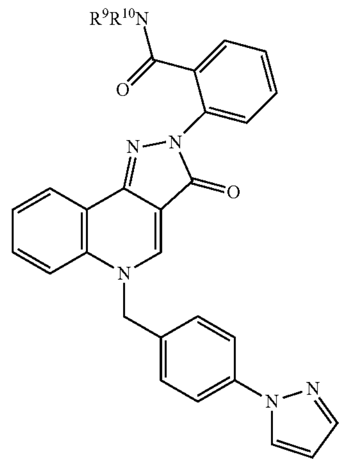

| Ex. | $NR^9R^{10}$ | HRMS/LRMS |
|---|---|---|
| 625 | 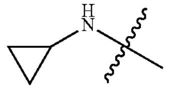 [SMILES: *NC1CC1] | $C_{30}H_{25}N_6O_2$ [M + H] calc. 501.2034 obs. 501.2048 |

Example 626

2-(2-Aminophenyl)-5-{[4-(1H-pyrazol-1-yl)phenyl]methyl}-2,5-dihydro-3H-pyrazolo[4,3-c]quinolin-3-one

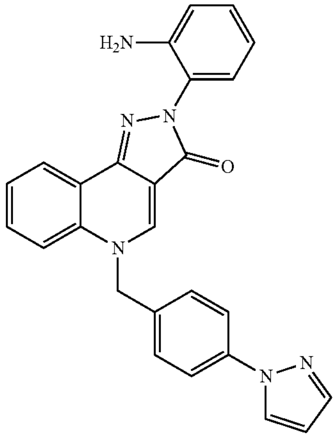 [SMILES: Nc1ccccc1-n1nc2c3ccccc3n(Cc3ccc(-n4cccn4)cc3)cc-2c1=O]

2-(2-Nitrophenyl)-5-{[4-(1H-pyrazol-1-yl)phenyl]methyl}-2,5-dihydro-3H-pyrazolo[4,3-c]quinolin-3-one (Example 427, 0.50 g, 1.1 mmol) was dissolved in methanol (20 mL) and treated with tin(II) chloride dihydrate (1.2 g, 5.4 mmol, 5 equiv) and hydrochloric acid (0.18 mL, 6 M aqueous, 1.1 mmol, 1 equiv). The mixture was placed into a preheated oil bath at 45° C. for 2 hours, cooled to ambient temperature and the pH of the mixture was brought to ~pH 7 by addition of sodium hydroxide (1 N aqueous). The mixture was extracted with ethyl acetate (2×100 mL) and the combined organic extracts were dried with sodium sulfate, filtered and concentrated in vacuo, providing the titled compound: $^1$H-NMR (400 MHz, $d^6$-DMSO) δ 9.17 (1H, s), 8.46 (1H, d, J=2.3 Hz), 8.23 (1H, d, J=7.8 Hz), 7.83 (2H, d, J=8.5 Hz), 7.79 (1H, d, J=8.8 Hz), 7.72 (1H, br s), 7.62 (1H, t, J=7.4 Hz), 7.54 (1H, t, J=7.5 Hz), 7.46 (2H, d, J=8.6 Hz), 7.33 (1H, d, J=7.6 Hz), 7.10 (1H, t, J=7.7 Hz), 6.87 (1H, d, J=8.1 Hz), 6.70 (1H, t, J=7.5 Hz), 6.53 (1H, br m), 5.80 (1H, br s), 5.76 (2H, s), 5.19 (1H, br s) ppm; high resolution mass spectrometry (ES+) m/z 433.0 [$(M+H)^+$; calculated for $C_{26}H_{21}N_6O$: 433.2].

Example 627

2-[(2-(Ethylamino)phenyl]-5-{[4-(1H-pyrazol-1-yl)phenyl]methyl}-2,5-dihydro-3H-pyrazolo[4,3-c]quinolin-3-one

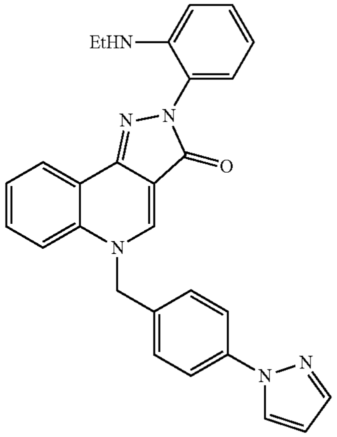

2-(2-Aminophenyl)-5-{[4-(1H-pyrazol-1-yl)phenyl]methyl}-2,5-dihydro-3H-pyrazolo[4,3-c]quinolin-3-one (Example 626, 40 mg, 0.092 mmol), acetaldehyde (4.1 mg, 0.092 mmol, 1 equiv) and acetic acid (32 μL, 0.55 mmol, 6 equiv) were combined in tetrahydrofuran (1 mL) and stirred at ambient temperature for 10 minutes. The mixture was treated with sodium borohydride (1.2 mg, 0.046 mmol, 0.5 equiv) and after 2 hours at ambient temperature, the mixture was poured into water (5 mL) and extracted with ethyl acetate (2×5 mL). The combined organic extracts were dried with sodium sulfate, filtered and concentrated in vacuo. The residue was purified by preparative reverse phase HPLC (80:20 to 5:95; water containing 0.1% trifluoroacetic acid:acetonitrile containing 0.1% trifluoroacetic acid), providing the titled compound: $^1$H-NMR (400 MHz, $d^6$-DMSO) δ 9.18 (1H, s), 8.46 (1H, d, J=2.5 Hz), 8.23 (1H, dd, J=7.7, 1.2 Hz), 7.83 (2H, d, J=8.6 Hz), 7.79 (1H, d, J=8.8 Hz), 7.72 (1H, d, J=1.2 Hz), 7.65-7.61 (1H, m), 7.55 (1H, t, J=7.8 Hz), 7.47 (2H, d, J=8.6 Hz), 7.37 (1H, dd, J=7.9, 1.2 Hz), 7.25-7.20 (1H, m), 6.82 (1H, d, J=8.1 Hz), 6.75 (1H, t, J=7.5 Hz), 6.53 (1H, br m), 5.79 (2H, s) 3.14 (2H, q, J=7.2 Hz), 1.18 (3H, t, J=7.0 Hz) ppm; low resolution mass spectrometry (ES+) m/z 461.0 [$(M+H)^+$; calculated for $C_{28}H_{25}N_6O$: 461.2].

The following compounds were prepared according to the general procedure described in Example 627, substituting the appropriate aldehyde for acetaldehyde. The starting materials are either commercially available, known in the literature or may be prepared from commercially available reagents using conventional reactions well known in the art.

(IV')

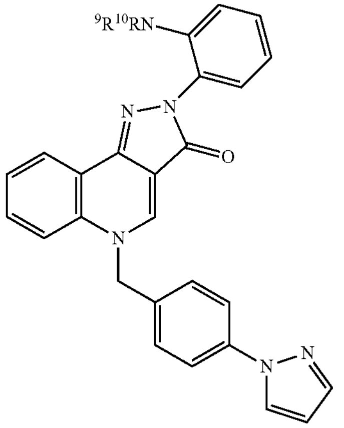

| Ex. | $NR^3R^4$ | HRMS/LRMS |
|---|---|---|
| 628 | 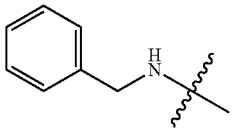 | $C_{33}H_{27}N_6O$ [M + H] calc. 523.2 obs. 523.0 |
| 629 | 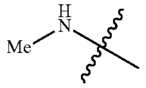 [SMILES: *NC] | $C_{27}H_{23}N_6O$ [M + H] calc. 447.1928 obs. 447.1958 |
| 630 | 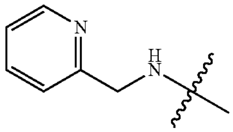 [SMILES: *NCc1ccccn1] | $C_{32}H_{26}N_7O$ [M + H] calc. 524.2194 obs. 524.2190 |
| 631 | 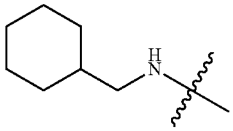 [SMILES: *NCC1CCCCC1] | $C_{33}H_{33}N_6O$ [M + H] calc. 529.2711 obs. 529.2704 |
| 632 | 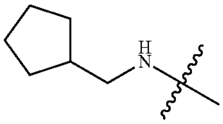 [SMILES: *NCC1CCCC1] | $C_{32}H_{31}N_6O$ [M + H] calc. 515.2554 obs. 515.2543 |
| 633 | 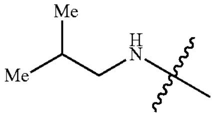 | $C_{30}H_{29}N_6O$ [M + H] calc. 489.2398 obs. 489.2391 |
| 634 | 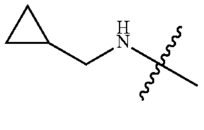 [SMILES: *NCC1CC1] | $C_{30}H_{27}N_6O$ [M + H] calc. 487.2241 obs. 487.2238 |
| 635 | 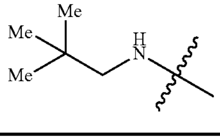 | $C_{31}H_{31}N_6O$ [M + H] calc. 503.2554 obs. 503.2552 |

Example 636

3-Methyl-N-[2-(3-oxo-5-{[4-(1H-pyrazol-1-yl)phenyl]methyl}-3,5-dihydro-2H-pyrazolo[4,3-c]quinolin-2-yl)phenyl]butanamide

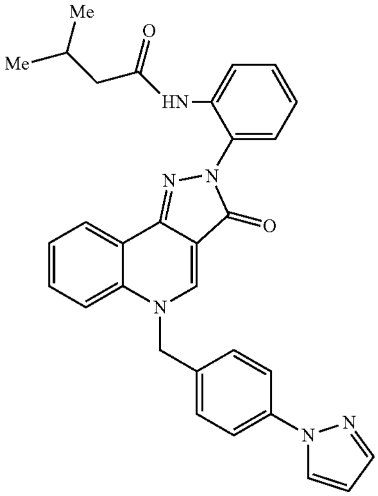 [SMILES: CC(C)CC(=O)Nc1ccccc1-n1nc2c3ccccc3n(Cc3ccc(-n4cccn4)cc3)cc-2c1=O]

2-(2-Aminophenyl)-5-{[4-(1H-pyrazol-1-yl)phenyl]methyl}-2,5-dihydro-3H-pyrazolo[4,3-c]quinolin-3-one (Example 626, 30 mg, 0.069 mmol) and diisopropylethylamine (30 μL, 0.17 mmol, 2.5 equiv) were combined in dichloromethane (1 mL) and treated with 3-methylbutanoyl chloride (9.2 mg, 0.076 mmol, 1.1 equiv). After 15 minutes at ambient temperature, the mixture was concentrated in vacuo and the residue was purified by preparative reverse phase HPLC (eluting 80:20 to 5:95; water containing 0.1% trifluoroacetic acid:acetonitrile containing 0.1% trifluoroacetic acid), providing the title compound; $^1$H-NMR (400 MHz, $d^6$-DMSO) δ 9.72 (1H, br s), 9.33 (1H, s), 8.47 (1H, d, J=2.3 Hz), 8.28 (1H, d, J=7.7 Hz), 7.93 (1H, d, 8.0 Hz), 7.84 (1H, d, J=8.9 Hz), 7.83 (2H, d, J=8.5 Hz), 7.72 (1H, br s), 7.69-7.64 (2H, m), 7.59 (1H, t, J=7.3 Hz), 7.47 (2H, d, J=8.4 Hz), 7.37 (1H, t, J=7.5 Hz), 7.27 (1H, t, J=7.5 Hz), 6.53 (1H, m), 5.83 (2H, s), 2.15 (2H, d, J=7.3 Hz), 2.09-1.94 (1H, m), 0.86 (6H, d, J=6.6 Hz) ppm; high resolution mass spectrometry (ES+) m/z 517.2391 [$(M+H)^+$; calculated for $C_{31}H_{29}N_6O_2$: 517.2347].

The following compounds were prepared according to the general procedure described in Example 636, substituting the appropriate acid chloride for 3-methylbutanoyl chloride. The starting materials are either commercially available, known in the literature or may be prepared from commercially available reagents using conventional reactions well known in the art.

(IW)

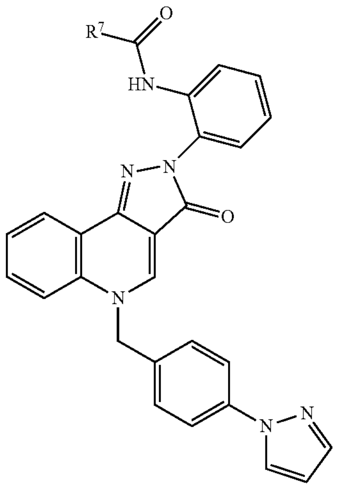

| Ex. | $R^7$ | HRMS/LRMS |
|---|---|---|
| 637 | 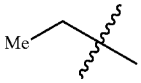 | $C_{29}H_{25}N_6O_2$<br>[M + H]<br>calc. 489.2034<br>obs. 489.2018 |
| 638 | 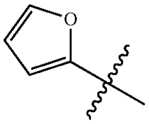 [SMILES: *c1ccco1] | $C_{31}H_{23}N_6O_3$<br>[M + H]<br>calc. 527.1826<br>obs. 527.1816 |
| 639 | 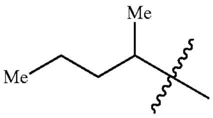 [SMILES: *C(C)CCC] | $C_{32}H_{31}N_6O_2$<br>[M + H]<br>calc. 531.2503<br>obs. 531.2506 |
| 640 | 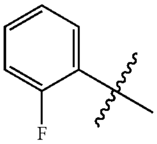 [SMILES: *c1ccccc1F] | $C_{33}H_{24}FN_6O_2$<br>[M + H]<br>calc. 555.1939<br>obs. 555.1938 |
| 641 | 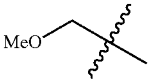 | $C_{29}H_{25}N_6O_3$<br>[M + H]<br>calc. 505.1983<br>obs. 505.1976 |
| 642 | 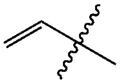 [SMILES: *C=C] | $C_{29}H_{23}N_6O_2$<br>[M + H]<br>calc. 487.1877<br>obs. 487.1903 |
| 643 | 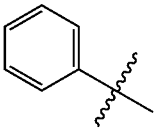 [SMILES: *c1ccccc1] | $C_{33}H_{25}N_6O_2$<br>[M + H]<br>calc. 537.2034<br>obs. 537.2042 |
| 644 | 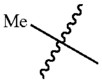 | $C_{28}H_{23}N_6O_2$<br>[M + H]<br>calc. 475.1877<br>obs. 475.1891 |
| 645 | 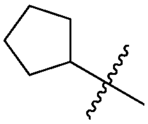 [SMILES: *C1CCCC1] | $C_{32}H_{29}N_6O_2$<br>[M + H]<br>calc. 529.2347<br>obs. 529.2360 |

-continued (IW)

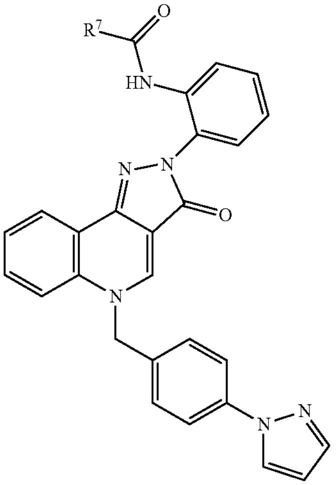

| Ex. | $R^7$ | HRMS/LRMS |
|---|---|---|
| 646 | 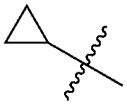 | $C_{30}H_{25}N_6O_2$<br>[M + H]<br>calc. 501.2034<br>obs. 501.2045 |
| 647 | 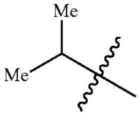 | $C_{30}H_{27}N_6O_2$<br>[M + H]<br>calc. 503.2190<br>obs. 503.2207 |

Example 648

5-{[4-(1H-Pyrazol-1-yl)phenyl]methyl}-2-[2-(pyrrolodin-1-ylmethyl)phenyl]-2,5-dihydro-3H-pyrazolo[4,3-c]quinolin-3-one

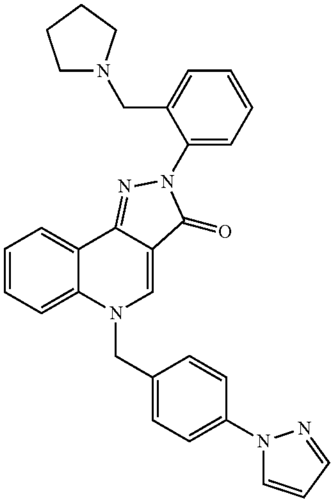 [SMILES: O=c1c2cn(Cc3ccc(-n4cccn4)cc3)c3ccccc3c-2nn1-c1ccccc1CN1CCCC1]

2-(3-Oxo-5-{[4-(1H-pyrazol-1-yl)phenyl]methyl}-3,5-dihydro-2H-pyrazolo[4,3-c]quinolin-2-yl)benzaldehyde (Example 529, 0.15 g, 035 mmol) and pyrrolidine (0.031 mL, 0.38 mmol, 1.1 equiv) were combined in 1,2-dichloroethane (2 mL) and treated with powdered 4 Å molecular sieves (0.15 g, 1 wt equiv) and acetic acid (0.099 mL, 1.7 mmol, 5 equiv). After stirring vigorously for 20 minutes at ambient temperature, the mixture was treated with sodium triacetoxyborohydride (0.11 g, 0.52 mmol, 1.5 equiv) portionwise over 2 minutes. After stirring for 90 minutes, the mixture was treated with sodium bicarbonate (7 mL, aqueous saturated) and stirred for 5 minutes. The mixture was diluted with chloroform (20 mL), filtered and the organic filtrate was washed once with sodium bicarbonate (10 mL, aqueous saturated) and brine (10 mL), dried with sodium sulfate, filtered and concentrated in vacuo. The residue was purified by silica gel gradient chromatography (100:0 to 90:10; chloroform: methanol; then 92:8; chloroform:methanol containing 10% ammonium hydroxide), providing the titled compound: $^1$H-NMR (400 MHz, d$^6$-DMSO) δ 9.12 (1H, br s), 8.46 (1H, dd, J=2.5, 0.4 Hz), 8.32 (1H, s), 8.20 (1H, d, J=8.1 Hz), 7.84 (2H, d, J=8.8 Hz), 7.78 (1H, d, J=8.3 Hz), 7.73 (1H, d, J=1.7 Hz). 7.65-7.60 (2H, m), 7.53 (1H, t, J=7.4 Hz), 7.48 (2H, d, J=8.6 Hz), 7.45-7.33 (2H, m), 6.53 (1H, dd, J=2.5, 1.8 Hz), 5.77 (2H, s), 3.63 (2H, br m), 2.36 (4H, br m), 1.63 (4H, br m) ppm; low resolution mass spectrometry (ES+) m/z 501.0 [(M+H)$^+$; calculated for $C_{31}H_{29}N_6O$: 501.2].

The following compounds were prepared according to the general procedure described in Example 648, substituting the appropriate amine for pyrrolidine. The starting materials are either commercially available, known in the literature or may be prepared from commercially available reagents using conventional reactions well known in the art.

(IX)

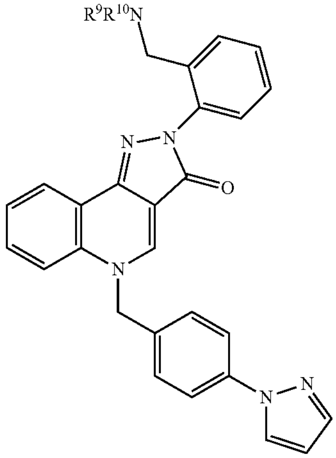

| Ex. | $NR^9NR^{10}$ | HRMS/LRMS |
|---|---|---|
| 649 | 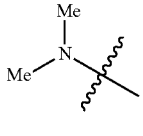 [SMILES: *N(C)C] | $C_{29}H_{27}N_6O$ [M + H] calc. 475.2 obs. 475.0 |
| 650 | 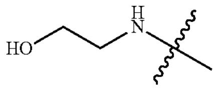 | $C_{29}H_{27}N_6O_2$ [M + H] calc. 491.2 obs. 491.0 |

-continued (IX)

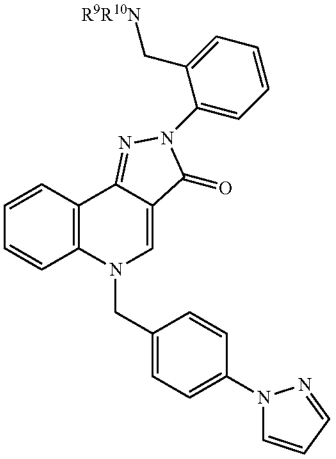

| Ex. | $NR^9NR^{10}$ | HRMS/LRMS |
|---|---|---|
| 651 | 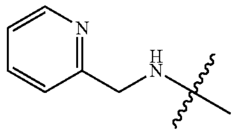 [SMILES: *NCc1ccccn1] | $C_{33}H_{28}N_7O$ [M + H] calc. 538.2 obs. 537.9 |
| 652 | 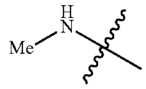 | $C_{28}H_{25}N_6O$ [M + H] calc. 461.2085 obs. 461.2061 |

Example 653

2,5-Bis{[4-(1H-pyrazol-1-yl)phenyl]methyl}-2,5-dihydro-3H-pyrazolo[4,3-c]quinolin-3-one

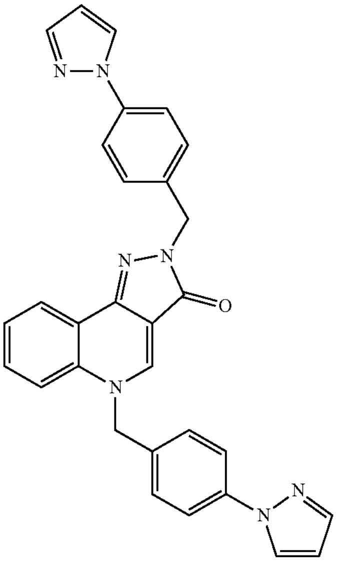 [SMILES: O=c1c2cn(Cc3ccc(-n4cccn4)cc3)c3ccccc3c-2nn1Cc1ccc(-n2cccn2)cc1]

5-{[4-(1H-Pyrazol-1-yl)phenyl]methyl}-2,5-dihydro-3H-pyrazolo[4,3-c]quinolin-3-one (Example 406, 71 mg, 0.21 mmol) was suspended in degassed N,N-dimethylformamide (3 mL), cooled to 0° C. and sodium hydride (17 mg, 0.42 mmol, 2 equiv, 60% dispersion in mineral oil) was added. After stirring for 10 minutes at 0° C., the mixture was warmed to ambient temperature and stirred for 45 minutes. 1-[4-(Bromomethyl)phenyl]-1H-pyrazole (74 mg, 0.31 mmol, 1.5 equiv) was added, the mixture as stirred for 2 hours and then poured into sodium bicarbonate (30 mL, aqueous saturated) and extracted with ethyl acetate (3×50 mL). The combined organic extracts were dried with sodium sulfate, filtered and concentrated in vacuo. The residue was purified by silica gel gradient chromatography (100:0 to 88:12; dichloromethane: methanol), providing the titled compound: $^1$H-NMR (400 MHz, d$^6$-DMSO) δ 9.09 (1H, s), 8.45-8.44 (2H, m), 8.15 (1H, d, J=7.8 Hz), 7.82-7.78 (4H, m), 7.75-7.72 (2H, m), 7.57 (1H, t, J=7.8 Hz), 7.48 (1H, t, J=7.7 Hz), 7.45-7.40 (4H, m), 6.52 (2H, s), 5.75 (2H, s), 5.14 (2H, s) ppm; high resolution mass spectrometry (ES+) m/z 498.2063 [(M+H)$^+$; calculated for $C_{30}H_{24}N_7O$: 498.2037].

Example 654

2-[2-(Hydroxymethyl)phenyl]-5-{[4-(1H-pyrazol-1-yl)phenyl]methyl}-2,5-dihydro-3H-pyrazolo[4,3-c]quinolin-3-one

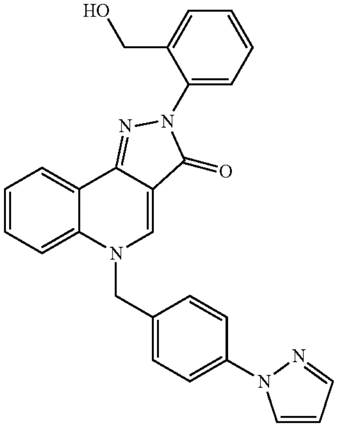 [SMILES: O=c1c2cn(Cc3ccc(-n4cccn4)cc3)c3ccccc3c-2nn1-c1ccccc1CO]

2-(3-oxo-5-{[4-(1H-pyrazol-1-yl)phenyl]methyl}-3,5-dihydro-2H-pyrazolo[4,3-c]quinolin-2-yl)benzaldehyde (Example 529, 75 mg, 0.17 mmol) was suspended in tetrahydrofuran (5 mL) and cooled to 0° C. Sodium cyanoborohydride (0.067 mL, 1 M tetrahydrofuran solution, 0.067 mmol, 0.4 equiv) was added dropwise and the mixture was stirred for 1 hour at 0° C. The mixture was diluted with dichloromethane (3 mL) until homogeneous and stirred for an additional 1 hour at 0° C. Sodium borohydride (1 spatula tip, excess) was added and the mixture was stirred at 0° C. for 30 minutes. The mixture was warmed to ambient temperature, opened to the air and treated with dichloro-5,6-dicyanobenzoquinone (DDQ, 40 mg, 0.17 mmol, 1 equiv). After stirring for 30 minutes, the mixture was poured into sodium bicarbonate (50 mL, aqueous saturated) and extracted with ethyl acetate (3×50 mL) and chloroform (3×50 mL). The combined organic extracts were dried with sodium sulfate, filtered and concentrated in vacuo. The residue was purified by silica gel gradient chromatography (100:0 to 0:100 hexanes:ethyl acetate; then 100:0 to 0:100 ethyl acetate:ethyl acetate containing 5% methanol), providing the titled compound: $^1$H-NMR (400 MHz, $CDCl_3$) δ 8.61 (1H, s), 8.35 (1H, d, J=7.4 Hz), 7.90 (1H, d, J=2.6 Hz), 7.72-7.70 (3H, m), 7.61 (1H, d, J=7.6 Hz), 7.57 (1H, d, J=7.5 Hz), 7.53 (1H, dd, J=7.6, 1.9 Hz), 7.51-7.47 (1H, m), 7.42 (1H, td, J=7.4, 1.5 Hz), 7.37 (1H, t, J=7.4 Hz), 7.29 (2H, d, J=8.6 Hz), 7.27 (1H, m), 6.47 (1H, m), 5.53 (2H, s), 5.21 (1H, br t, J=6.5 Hz), 4.53 (2H, d, J=5.8 Hz) ppm; high resolution mass spectrometry (ES+) m/z 448.1781 [(M+H)$^+$; calculated for $C_{27}H_{22}N_5O_2$: 448.1768].

Example 655

(±)-2-[2-(Hydroxyethyl)phenyl]-5-{[4-(1H-pyrazol-1-yl)phenyl]methyl}-2,5-dihydro-3H-pyrazolo[4,3-c]quinolin-3-one

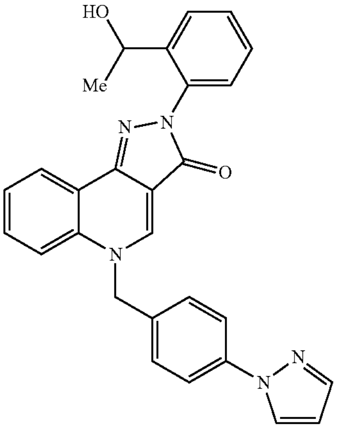 [SMILES: CC(O)c1ccccc1-n1nc2c3ccccc3n(Cc3ccc(-n4cccn4)cc3)cc-2c1=O]

2-(3-Oxo-5-{[4-(1H-pyrazol-1-yl)phenyl]methyl}-3,5-dihydro-2H-pyrazolo[4,3-c]quinolin-2-yl)benzaldehyde (Example 529, 76 mg, 0.17 mmol) was dissolved in dichloromethane (5 mL) and cooled to −78° C. Methylmagnesium bromide (0.057 mL, 3 M diethyl ether solution, 0.17 mmol, 1 equiv) was added dropwise and the mixture was stirred for 30 minutes at −78° C. Additional methylmagnesium bromide (0.057 mL, 3 M diethyl ether solution, 0.17 mmol, 1 equiv) was added and the mixture was stirred for an additional 30 minutes at −78° C. The mixture was treated with sodium bicarbonate (3 mL, aqueous saturated), warmed to ambient temperature, poured into water (10 mL) and extracted with dichloromethane (3×50 mL). The combined organic extracts were dried with sodium sulfate, filtered and concentrated in vacuo. The residue was purified via silica gel gradient chromatography (100:0 to 0:100; hexanes:ethyl acetate; then 100:0 to 0:100; ethyl acetate:ethyl acetate containing 5% methanol), providing the titled compound: $^1$H-NMR (400 MHz, d$^6$-DMSO) δ 9.13 (1H, s), 8.45 (1H, d, J=2.4 Hz), 8.18 (1H, d, J=8.0 Hz), 7.83 (2H, d, J=8.6 Hz), 7.78 (1H, d, J=8.8 Hz), 7.73 (1H, d, 1.1 Hz), 7.70 (1H, d, J=7.8 Hz), 7.65-7.60

(1H, m), 7.54 (1H, t, J=7.7 Hz), 7.48 (2H, d, 8.3 Hz), 7.44 (1H, d, J=7.8 Hz), 7.39-7.31 (2H, m), 6.53 (1H, m), 5.78 (2H, s), 5.19 (1H, d, J=4.2 Hz), 4.94-4.88 (1H, m), 1.27 (3H, d, J=6.4 Hz) ppm; high resolution mass spectrometry (ES+) m/z 462.1906 [(M+H)$^+$; calculated for $C_{29}H_{24}N_5O_2$: 462.1925].

Example 656

2-[2-(1-Hydroxy-1-methylethyl)phenyl]-5-{[4-(1H-pyrazol-1-yl)phenyl]methyl}-2,5-dihydro-3H-pyrazolo[4,3-c]quinolin-3-one

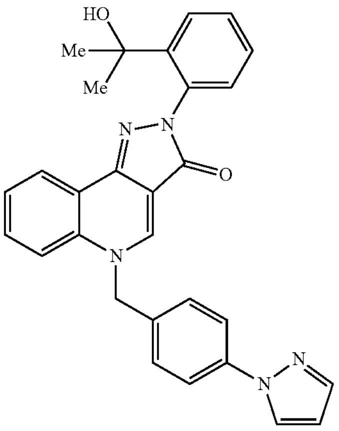 [SMILES: CC(C)(O)c1ccccc1-n1nc2c3ccccc3n(Cc3ccc(-n4cccn4)cc3)cc-2c1=O]

2-(2-acetylphenyl)-5-{[4-(1H-pyrazol-1-yl)phenyl]methyl}-2,5-dihydro-3H-pyrazolo[4,3-c]quinolin-3-one (Example 532, 77 mg, 0.17 mmol) was dissolved in dichloromethane (5 mL) and cooled to −78° C. Methylmagnesium bromide (0.056 mL, 3 M diethyl ether solution, 0.17 mmol, 1 equiv) was added dropwise and the mixture was stirred for 30 minutes at −78° C. Additional methylmagnesium bromide (0.057 mL, 3 M diethyl ether solution, 0.17 mmol, 1 equiv) was added and the mixture was stirred for an additional 30 minutes at −78° C. The mixture was treated with sodium bicarbonate (3 mL, aqueous saturated), warmed to ambient temperature, poured into water and extracted with dichloromethane (2×75 mL). The combined organic extracts were dried with sodium sulfate, filtered and concentrated in vacuo. The residue was purified via silica gel gradient chromatography (100:0 to 0:100 hexanes:ethyl acetate containing 5% methanol), providing the titled compound: $^1$H-NMR (400 MHz, d$^6$-DMSO) δ 9.12 (1H, s), 8.46 (1H, d, J=2.5 Hz), 8.15

(1H, dd, J=8.0, 1.1 Hz), 7.90 (1H, dd, J=7.9, 1.3 Hz), 7.84 (2H, d, J=8.7 Hz), 7.78 (1H, d, J=8.6 Hz), 7.73 (1H, d, J=1.4 Hz), 7.64-7.60 (1H, m), 7.53 (1H, t, J=7.6 Hz), 7.48 (2H, d, J=8.7 Hz), 7.46-7.43 (1H, m), 7.35 (1H, td, J=7.5, 1.3 Hz), 7.17 (1H, dd, J=7.5, 1.1 Hz), 6.53 (1H, dd, J=2.3, 1.9 Hz), 5.77 (2H, s), 5.28 (1H, s), 1.37 (6H, s) ppm; high resolution mass spectrometry (ES+) m/z 476.2069 [(M+H)$^+$; calculated for $C_{29}H_{26}N_5O_2$: 476.2081].

Example 657

(±)-2-[2-(Hydroxypropyl)phenyl]-5-{[4-(1H-pyrazol-1-yl)phenyl]methyl}-2,5-dihydro-3H-pyrazolo[4,3-c]quinolin-3-one

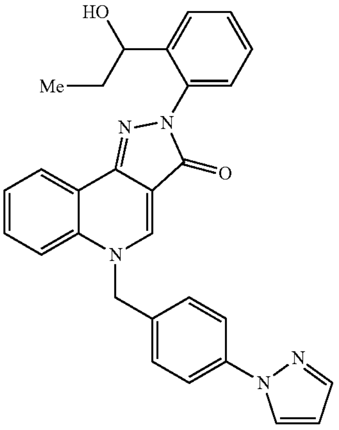 [SMILES: CCC(O)c1ccccc1-n1nc2c3ccccc3n(Cc3ccc(-n4cccn4)cc3)cc-2c1=O]

2-(3-oxo-5-{[4-(1H-pyrazol-1-yl)phenyl]methyl}-3,5-dihydro-2H-pyrazolo[4,3-c]quinolin-2-yl)benzaldehyde (Example 529, 0.14 g, 0.32 mmol) was dissolved in dichloromethane (5 mL) and cooled to −78° C. Ethylmagnesium bromide (0.10 mL, 3 M diethyl ether solution, 0.32 mmol, equiv) was added dropwise and the mixture was stirred for 30 minutes at −78° C. Additional ethylmagnesium bromide (0.10 mL, 3 M diethyl ether solution, 0.32 mmol, 1 equiv) was added and the mixture was stirred for an additional 30 minutes at −78° C. The mixture was treated with sodium bicarbonate (3 mL, aqueous saturated) and warmed to ambient temperature, poured into water and extracted with dichloromethane (3×50 mL). The combined organic extracts were dried with sodium sulfate, filtered and concentrated in vacuo. The residue was purified via silica gel gradient chromatography (100:0 to 0:100; hexanes:ethyl acetate; then 100:0 to 0:100; ethyl acetate:ethyl acetate containing 5% methanol), providing the titled compound: $^1$H-NMR (400 MHz, d$^6$-DMSO) δ 9.14 (1H, s), 8.46 (1H, d, J=2.4 Hz), 8.18 (1H, d, J=8.0 Hz), 7.84 (2H, d, J=8.7 Hz), 7.78 (1H, d, J=8.7 Hz), 7.73 (1H, m), 7.67-7.60 (2H, m), 7.53 (1H, t, J=7.7 Hz), 7.48 (2H, d, J=8.5 Hz), 7.43 (1H, br t, J=7.6 Hz), 7.38-7.33 (2H, m), 6.53 (1H, m), 5.78 (2H, s), 5.12 (1H, d, J=4.7 Hz), 4.73-4.68 (1H, m), 1.71-1.64 (1H, m), 1.5-1.43 (1H, m), 0.78 (3H, t, J=7.4 Hz) ppm; high resolution mass spectrometry (ES+) m/z 476.2061 [(M+H)$^+$; calculated for $C_{29}H_{26}N_5O_2$: 476.2081].

Example 658

2-[2-(2-Hydroxyethyl)phenyl]-5-{[4-(1H-pyrazol-1-yl)phenyl]methyl}-2,5-dihydro-3H-pyrazolo[4,3-c]quinolin-3-one

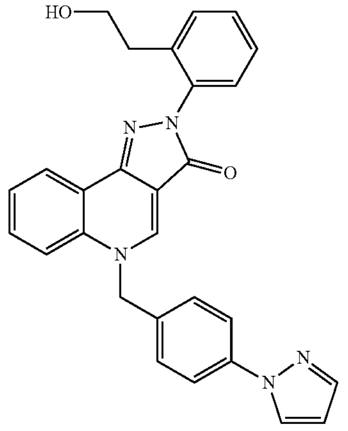 [SMILES: O=c1c2cn(Cc3ccc(-n4cccn4)cc3)c3ccccc3c-2nn1-c1ccccc1CCO]

Methyl [2-(3-oxo-5-{[4-(1H-pyrazol-1-yl)phenyl]methyl}-3,5-dihydro-2H-pyrazolo[4,3-c]quinolin-2-yl)phenyl] acetate (Example 533, 0.10 g, 0.21 mmol) was suspended in diethyl ether (6 mL) and dichloromethane (9 mL), cooled to 0° C. and treated with lithium borohydride (4.9 mg, 0.23 mmol, 1.1 equiv) and then methanol (9.2 μL, 0.23 mmol, 1.1 equiv). The mixture was stirred at 0° C. for 15 minutes and then warmed to ambient temperature. After 20 minutes, the mixture was treated with additional lithium borohydride (10 mg, 0.46 mmol, 2.2 equiv) and methanol (20 μL, 0.46 mmol, 2.2 equiv) and stirred for an additional 1 hour at ambient temperature. The mixture was treated with ammonium chloride (3 mL, aqueous saturated) and stirred at ambient temperature for 15 minutes. The mixture was poured into water (20 mL) and extracted with dichloromethane (3×50 mL). The combined organic extracts were treated with dichloro-5,6-dicyanobenzoquinone (DDQ, 52 mg, 0.46 mmol, 2.2 equiv) and stirred for 45 minutes at ambient temperature. The mixture was treated with sodium bicarbonate (50 mL, aqueous saturated) and vigorously stirred for 30 minutes, partitioned and the aqueous layer was further extracted with dichloromethane (1×50 mL). The combined organic extracts were dried with sodium sulfate, filtered and concentrated in vacuo. The residue was purified by silica gel gradient chromatography (100:0 to 0:100; hexanes:ethyl acetate containing 5% methanol), providing the titled compound: $^{1}$H-NMR (400 MHz, d$^{6}$-DMSO) δ 9.13 (1H, s), 8.46 (1H, d, J=2.5 Hz), 8.19 (1H, d, J=7.6 Hz), 7.84 (2H, d, J=8.5 Hz), 7.77 (1H, d, J=8.5 Hz), 7.73 (1H, d, J=1.4 Hz), 7.64-7.59 (1H, m), 7.53 (1H, t, J=7.2 Hz), 7.48 (2H, d, J=8.5 Hz), 7.43 (1H, br d, J=6.9 Hz), 7.39-7.33 (3H, m), 6.53 (1H, m), 5.77 (2H, s), 4.61 (1H, t, J=5.2 Hz), 3.58-3.53 (2H, m), 2.77 (2H, t, J=7.4 Hz) ppm; high resolution mass spectrometry (ES+) m/z 462.1912 [(M+H)$^{+}$; calculated for $C_{28}H_{24}N_{5}O_{2}$: 462.1925].

Example 659

2-(2-Propanoylphenyl)-5-{[4-(1H-pyrazol-1-yl)phenyl]methyl}-2,5-dihydro-3H-pyrazolo[4,3-c]quinolin-3-one

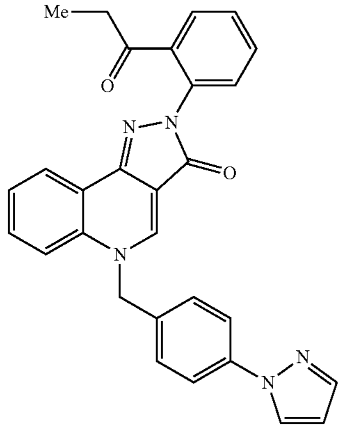 [SMILES: CCC(=O)c1ccccc1-n1nc2c3ccccc3n(Cc3ccc(-n4cccn4)cc3)cc-2c1=O]

(±)-2-[2-(Hydroxypropyl)phenyl]-5-{[4-(1H-pyrazol-1-yl)phenyl]methyl}-2,5-dihydro-3H-pyrazolo[4,3-c]quinolin-3-one (Example 657, 81 mg, 0.17 mmol), 1,1,1-tris(acetyloxy)-1,1-dihydro-1,2-benziodoxol-3-(1H)-one (Dess-Martin periodinane, 0.11 g, 0.25 mmol, 1.5 equiv), sodium bicarbonate (71 mg, 0.85 mmol, 5 equiv) and water (8.0 μL, 0.44 mmol, 2.6 equiv) were combined in dichloromethane (8 mL) and stirred vigorously for 30 minutes. Additional Dess-Martin periodinane (0.11 g, 0.25 mmol, 1.5 equiv) was added and the mixture was stirred for an additional 45 minutes. The mixture was treated with sodium bicarbonate (3 mL, aqueous saturated) and sodium thiosulfate (3 mL, aqueous saturated) and stirred vigorously for 30 minutes. The mixture was poured into sodium bicarbonate (15 mL, aqueous saturated) and extracted with dichloromethane (2×50 mL) and the combined organic extracts were dried with sodium sulfate, filtered and concentrated in vacuo. The residue was purified by silica gel gradient chromatography (100:0 to 0:100; hexanes:ethyl acetate containing 5% methanol), providing the titled compound: $^{1}$H-NMR (400 MHz, $CDCl_3$) δ 8.45 (1H, s), 8.37 (1H, dd, J=7.2, 2.2 Hz), 7.94-7.91 (2H, m), 7.74-7.72 (3H, m), 7.57-7.43 (5H, m), 7.35 (1H, d, J=7.6 Hz), 7.31 (2H, d, J=8.4 Hz), 6.47 (1H, m), 5.49 (2H, s), 2.73 (2H, q, J=7.6 Hz), 1.13 (3H, t, J=7.2 Hz) ppm; high resolution mass spectrometry (ES+) m/z 474.1919 [(M+H)$^{+}$; calculated for $C_{29}H_{24}N_{5}O_{2}$: 474.1925].

Example 660

Methyl 2-(3-oxo-5-{[4-(1H-pyrazol-1-yl)phenyl]methyl}-3,5-dihydro-2H-pyrazolo[4,3-c]quinolin-2-yl)benzoate

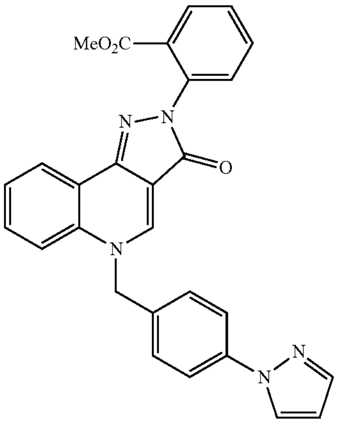 [SMILES: COC(=O)c1ccccc1-n1nc2c3ccccc3n(Cc3ccc(-n4cccn4)cc3)cc-2c1=O]

2-(3-Oxo-5-{[4-(1H-pyrazol-1-yl)phenyl]methyl}-3,5-dihydro-2H-pyrazolo[4,3-c]quinolin-2-yl)benzoic acid (Example 611, 30 mg, 0.065 mmol) was dissolved in tetrahydrofuran (1 mL) and methanol (1 mL) and treated with (trimethylsilyl)diazomethane (0.065 mL, 2 M diethyl ether solution, 0.13 mmol, 2 equiv). After stirring for 30 minutes, the mixture was concentrated in vacuo and the residue was purified by preparative reverse phase HPLC (80:20 to 5:95; water containing 0.1% trifluoroacetic acid:acetonitrile containing 0.1% trifluoroacetic acid), providing the titled compound: $^1$H-NMR (400 MHz, d$^6$-DMSO) δ 9.15 (1H s), 8.46 (1H, d, J=2.5 Hz), 8.21 (1H, dd, J=7.8, 1.4 Hz), 7.83 (2H, d, J=8.8 Hz), 7.79 (1H, m), 7.77 (1H, d, J=2.3 Hz), 7.73-7.61 (3H, m), 7.56 (1H, t, J=7.7 Hz), 7.46 (2H, d, 8.7 Hz), 7.41 (1H, td, J=7.7, 1.1 Hz), 6.53 (1H, dd, J=2.4, 1.8 Hz), 5.77 (2H, s), 3.67 (3H, s) ppm; low resolution mass spectrometry (ES+) m/z 476.0 [(M+H)$^+$; calculated for $C_{28}H_{22}N_5O_3$: 476.2].

Example 661

2-[2-(Azidomethyl)phenyl]-5-{[4-(1H-pyrazol-1-yl)phenyl]methyl}-2,5-dihydro-3H-pyrazolo[4,3-c]quinolin-3-one

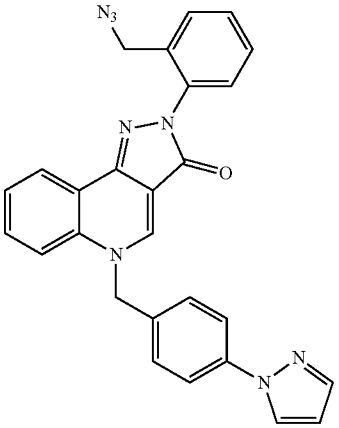 [SMILES: [N-]=[N+]=NCc1ccccc1-n1nc2c3ccccc3n(Cc3ccc(-n4cccn4)cc3)cc-2c1=O]

Step 1: Preparation of [2-(3-oxo-5-{[4-(1H-pyrazol-1-yl)phenyl]methyl}-3,5-dihydro-2H-pyrazolo[4,3-c]quinolin-2-yl)phenyl]methyl methanesulfonate 2-[2-(Hydroxymethyl)phenyl]-5-{[4-(1H-pyrazol-1-yl)phenyl]methyl}-2,5-dihydro-3H-pyrazolo[4,3-c]quinolin-3-one (Example 654, 0.23 g, 0.51 mmol) was suspended in dichloromethane (5 mL), treated with diisopropylethylamine (0.20 mL, 1.1 mmol, 2.2 equiv) and cooled to −78° C. Methanesulfonyl chloride (60 μL, 0.77 mmol, 1.5 equiv) was added and the mixture was stirred at −78° C. for 30 minutes. The dry ice/acetone bath was removed, the mixture was warmed to ambient temperature and stirred for an additional 45 minutes. The mixture was poured into ammonium chloride (20 mL, aqueous saturated) and extracted with dichloromethane (3×50 mL). The combined organic extracts were dried with sodium sulfate, filtered and concentrated in vacuo, providing the title compound.

Step 2: Preparation of 2-[2-(azidomethyl)phenyl]-5-{[4-(1H-pyrazol-1-yl)phenyl]methyl}-2,5-dihydro-3H-pyrazolo[4,3-c]quinolin-3-one

[2-(3-oxo-5-{[4-(1H-pyrazol-1-yl)phenyl]methyl}-3,5-dihydro-2H-pyrazolo[4,3-c]quinolin-2-yl)phenyl]methyl methanesulfonate (0.21 g, 0.51 mmol) was dissolved in dimethyl sulfoxide (10 mL) and treated with sodium azide (0.33 g, 5.1 mmol, 10 equiv). The mixture was stirred for 45 minutes at ambient temperature and then placed into a preheated oil bath at 80° C. for 1 hour. The mixture was cooled to ambient temperature, poured into sodium bicarbonate (100 mL, aqueous saturated) and extracted with ethyl acetate (3×100 mL). The combined organic extracts were dried with sodium sulfate, filtered and concentrated in vacuo. The residue was purified by silica gel gradient chromatography (100:0 to 0:100; hexanes:ethyl acetate containing 5% methanol), providing the titled compound: $^1$H-NMR (400 MHz, d$^6$-DMSO) δ 9.17 (1H, s), 8.46 (1H, d, J=2.5 Hz), 8.23 (1H, d, J=7.8 Hz), 7.83 (2H, d, J=8.6 Hz), 7.79 (1H, d, J=8.6 Hz), 7.72 (1H, m), 7.65-7.61 (1H, m), 7.57-7.54 (3H, m), 7.51 (1H, br d, J=7.6 Hz), 7.49-7.45 (3H, m), 6.53 (1H, m), 5.78 (2H, s), 4.60 (2H, s) ppm; high resolution mass spectrometry (ES+) m/z 473.1823 [(M+H)$^+$; calculated for $C_{27}H_{21}N_8O$: 473.1833].

Example 662

2-[2-(Aminomethyl)phenyl]-5-{[4-(1H-pyrazol-1-yl)phenyl]methyl}-2,5-dihydro-3H-pyrazolo[4,3-c]quinolin-3-one

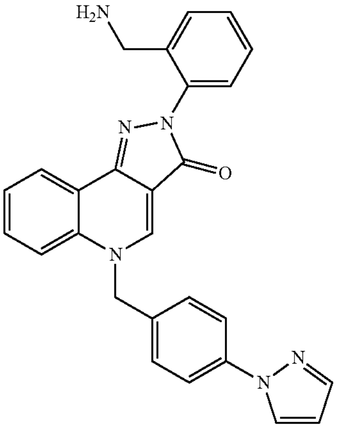

2-[2-(Azidomethyl)phenyl]-5-{[4-(1H-pyrazol-1-yl)phenyl]methyl}-2,5-dihydro-3H-pyrazolo[4,3-c]quinolin-3-one (Example 661, 92 mg, 0.19 mmol) was dissolved in tetrahydrofuran (6 mL) and cooled to 0° C. Trimethylphosphine (0.97 mL, 1 M tetrahydrofuran solution, 0.97 mmol, 5 equiv) was added, the ice bath removed and the mixture was warmed to ambient temperature and stirred for 2 hours. The mixture was treated with sodium hydroxide (1.9 mL, 1 M aqueous, 10 equiv) and stirred for an additional 1 hour. The mixture was poured into water and extracted with chloroform (4×150 mL). The combined organic extracts were dried with sodium sulfate, filtered and concentrated in vacuo. The residue was purified by silica gel gradient chromatography (100:0 to 85:15; dichloromethane:methanol containing 10% ammonium hydroxide), providing the titled compound: $^1$H-NMR (400 MHz, d$^6$-DMSO, hydrochloride salt) δ 9.27 (1H, s), 8.47 (1H, d, J=2.6 Hz), 8.33 (1H, dd, J=7.9, 1.4 Hz), 8.36-8.27 (3H, br s), 7.86-7.82 (3H, m), 7.73 (1H, d, J=1.5 Hz), 7.70-7.64 (3H, m), 7.60-7.55 (2H, m), 7.52-7.47 (3H, m), 6.54 (1H, m), 5.83 (2H, s), 4.04 (2H, q, J=5.6 Hz) ppm; high resolution mass spectrometry (ES+) m/z 447.1911 [(M+H)$^+$; calculated for $C_{27}H_{23}N_6O$: 447.1928].

Example 663

2-(2-Fluorophenyl)-5-{[2-fluoro-4-(1H-pyrazol-1-yl)phenyl]methyl}-2,5-dihydro-3H-pyrazolo[4,3-c]quinolin-3-one

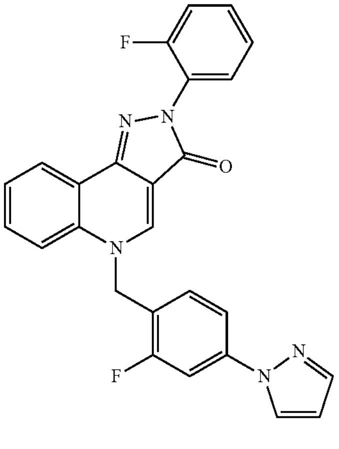 [SMILES: O=c1c2cn(Cc3ccc(-n4cccn4)cc3F)c3ccccc3c-2nn1-c1ccccc1F]

5-[(2-Fluoro-4-iodophenyl)methyl]-2-(2-fluorophenyl)-2,5-dihydro-3H-pyrazol[4,3-c]quinolin-3-one [(Example 187, Step 2), 68 mg, 0.13 mmol], pyrazole (18 mg, 0.26 mmol, 2 equiv) and copper(I) iodide (10 mg, 0.053 mmol, 0.4 equiv) were combined in a sealed tube, to which was added dimethylsulfoxide (1 mL), (±)-trans-N,N'-bismethyl-1,2-cyclohexane diamine (15 mg, 0.11 mmol, 0.8 equiv) and an aqueous (0.2 ml) solution of potassium phosphate (84 mg, 0.40 mmol, 3 equiv). The vessel was flushed with nitrogen, sealed and placed into a preheated oil bath at 100° C. for 1 hour. The mixture was cooled to ambient temperature, poured into water (15 mL) and extracted with chloroform (2×15 mL). The combined organic extracts were washed once with water (5 mL) and brine (5 mL), dried with sodium sulfate, filtered and concentrated in vacuo. The residue was purified by silica gel gradient chromatography (100:0 to 90:10; chloroform: methanol), providing the titled compound: $^1$H-NMR (400 MHz, d$^6$-DMSO) δ 9.09 (1H, s), 8.54 (1H, d, J=2.6 Hz), 8.21 (1H, dd, J=7.9, 1.5 Hz), 7.82 (1H, dd, J=11.9, 2.1 Hz), 7.73-7.73 (2H, m), 7.68-7.59 (3H, m), 7.55 (1H, t, J=7.6 Hz), 7.49-7.32 (4H, m), 6.56 (1H, dd, J=2.3, 2.0 Hz), 5.82 (2H s) ppm; high resolution mass spectrometry (ES+) m/z 454.1467 [(M+H)$^+$; calculated for $C_{26}H_{18}F_2N_5O$: 454.1474].

The following compounds were prepared according to the general procedure described in Example 663, substituting the appropriate amine for pyrazole. The starting materials are either commercially available, known in the literature or may be prepared from commercially available reagents using conventional reactions well known in the art.

(IY)

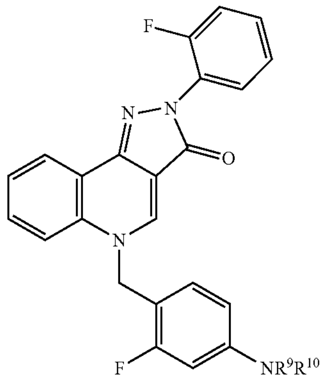

| Ex. | $NR^9R^{10}$ | HRMS/LRMS |
|---|---|---|
| 664 | 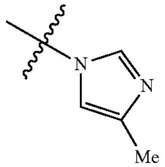 [SMILES: *n1cnc(C)c1] | $C_{27}H_{20}F_2N_5O$ [M + H] calc. 468.2 Obs. 467.9 |
| 665 | 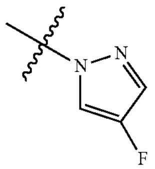 [SMILES: *n1cc(F)cn1] | $C_{26}H_{17}F_3N_5O$ [M + H] calc. 472.1380 obs. 472.1372 |

Example 666

2-(2-Bromo-6-fluorophenyl)-5-{[2-fluoro-4-(1H-pyrazol-1-yl)phenyl]methyl}-2,5-dihydro-3H-pyrazolo[4,3-c]quinolin-3-one

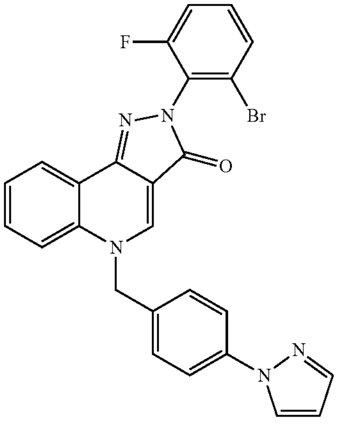 [SMILES: O=c1c2cn(Cc3ccc(-n4cccn4)cc3)c3ccccc3c-2nn1-c1c(F)cccc1Br]

Step 1: Preparation of (2-bromo-6-fluorophenyl)hydrazine hydrochloride

2-Bromo-6-fluoroaniline (2.0 g, 11 mmol) was dissolved in hydrochloric acid (7.0 mL, 12 N aqueous, 84 mmol, 8 equiv) and cooled to 0° C. An aqueous solution (10 mL) of sodium nitrite (0.80 g, 12 mmol, 1.1 equiv) was added dropwise over 30 minutes via additional funnel and the mixture was stirred for an additional 30 minutes at 0° C. A hydrochloric acid solution (10 mL, 12 N aqueous) of stannous(II) chloride dihydrate (7.1 g, 32 mmol, 3 equiv) was then added to the mixture over 45 minutes via additional funnel and the mixture was stirred for an additional 1 hour at 0° C. To the mixture, sodium hydroxide (30 mL, 1 M aqueous) was added slowly until basic by pH paper. The mixture was warmed to ambient temperature, poured into sodium hydroxide (50 mL, 25% aqueous) and the aqueous layer was extracted with diethyl ether (3×250 mL). The combined organic extracts were dried with sodium sulfate, filtered and partially concentrated in vacuo. The residue was taken up in diethyl ether and treated with gaseous hydrochloric acid. The solid was filtered and washed with diethyl ether, providing the titled compound as a white solid.

Step 2: Preparation of 2-(2-bromo-6-fluorophenyl)-5-{[2-fluoro-4-(1H-pyrazol-1-yl)phenyl]methyl}-2,5-dihydro-3H-pyrazolo[4,3-C]quinolin-3-one Using the procedures described in Example 403, substituting (2-bromo-6-fluorophenyl)hydrazine hydrochloride for (2,6-difluorophenyl)hydrazine, the titled compound was obtained: $^1$H-NMR (400 MHz, d$^6$-DMSO) δ 9.16 (1H, s), 8.46 (1H, d, J=2.5 Hz), 8.18 (1H, dd, J=7.9, 1.4 Hz), 7.84 (2H, d, J=8.5 Hz), 7.79 (1H, d, J=8.5 Hz), 7.73 (1H, d, J=1.8 Hz), 7.71-7.68 (1H, m), 7.66-7.61 (1H, m), 7.56-7.47 (5H, m), 6.53 (1H, dd, J=2.4, 1.8 Hz), 5.77 (2H, s) ppm; high resolution mass spectrometry (ES+) m/z 514.0679 [(M+H)$^+$; calculated for $C_{26}H_{18}BrFN_5O$: 514.0673].

Example 667

3-Fluoro-2-(3-oxo-5-{[4-(1H-pyrazol-1-yl)phenyl]methyl}-3,5-dihydro-2H-pyrazolo[4,3-c]quinolin-2-yl)benzonitrile

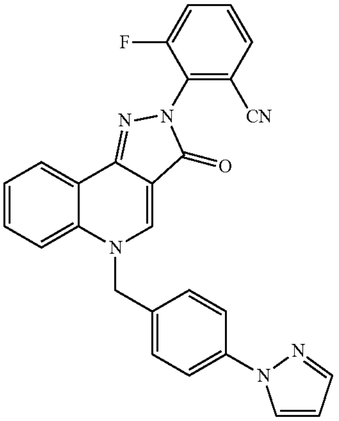 [SMILES: N#Cc1cccc(F)c1-n1nc2c3ccccc3n(Cc3ccc(-n4cccn4)cc3)cc-2c1=O]

2-(2-Bromo-6-fluorophenyl)-5-{[2-fluoro-4-(1H-pyrazol-1-yl)phenyl]methyl}-2,5-dihydro-3H-pyrazolo[4,3-c]quinolin-3-one (Example 666, 0.10 g, 0.19 mmol) and zinc (II) cyanide (46 mg, 0.39 mmol, 2 equiv) were dissolved in N,N-dimethylformamide (3.5 mL). The mixture was degassed, treated with bis(tri-tert-butylphosphine)palladium (0) (15 mg, 0.029 mmol, 0.15 equiv) and placed into an oil bath preheated to 100° C. for 1 hour. The mixture was cooled to ambient temperature, poured into sodium carbonate (15 mL, aqueous saturated) and extracted with ethyl acetate (3×50 mL). The combined organic extracts were dried with sodium sulfate, filtered and concentrated in vacuo. The residue was purified by silica gel gradient chromatography (100:0 to 0:100; hexanes:ethyl acetate containing 5% methanol), providing the titled compound: $^1$H-NMR (400 MHz, d$^6$-DMSO) δ 9.24 (1H, s), 8.46 (1H, d, J=2.5 Hz), 8.21 (1H, dd, J=7.9, 1.3 Hz), 7.91 (1H, d, J=8.0 Hz), 7.89-7.80 (4H, m), 7.76-7.70 (2H, m), 7.68-7.64 (1H, m), 7.56 (1H, ap t, J=7.3 Hz), 7.50 (2H, d, J=8.5 Hz), 6.53 (1H, m), 5.79 (2H, s) ppm; high resolution mass spectrometry (ES+) m/z 461.1503 [(M+H)$^+$; calculated for $C_{27}H_{18}FN_6O$: 461.1521].

Example 668

2-(2-Fluoro-6-methylphenyl)-5-{([4-(1H-pyrazol-1-yl)phenyl]methyl}-2,5-dihydro-3H-pyrazolo[4,3-c]quinolin-3-one

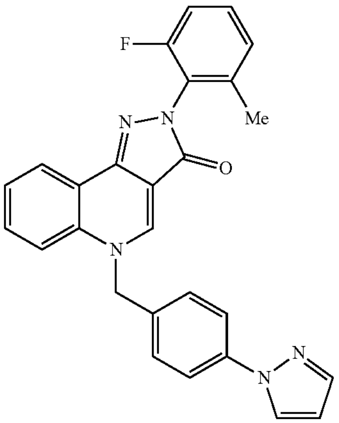

2-(2-Bromo-6-fluorophenyl)-5-{[2-fluoro-4-(1H-pyrazol-1-yl)phenyl]methyl}-2,5-dihydro-3H-pyrazolo[4,3-c]quinolin-3-one (Example 666, 0.13 g, 0.24 mmol) was suspended in tetrahydrofuran (5 mL) and treated with trimethyl aluminum (0.18 mL, 2 M toluene solution, 0.37 mmol, 1.5 equiv) and bis(tri-tert-butylphosphine)palladium(0) (19 mg, 0.037 mmol, 0.15 equiv). The mixture was placed into an oil bath preheated to 65° C. for 45 minutes, cooled to ambient temperature and poured into sodium bicarbonate (25 mL, aqueous saturated). The aqueous layer was extracted with ethyl acetate (3×100 mL) and the combined organic extracts were dried with sodium sulfate, filtered and concentrated in vacuo. The residue was purified by silica gel gradient chromatography (100:0 to 0:100; hexanes:ethyl acetate containing 5% methanol), providing the titled compound: $^1$H-NMR (400 MHz, d$^6$-DMSO) δ 9.14 (1H, s), 8.46 (1H, d, J=2.6 Hz), 8.17 (1H, d, J=7.9 Hz), 7.83 (2H, d, J=8.5 Hz), 7.77 (1H, d, J=8.8 Hz), 7.72 (1H, m), 7.64-7.60 (1H, m), 7.55-7.37 (4H, m), 7.25-7.20 (2H, m), 6.53 (1H, m), 5.77 (2H, s), 2.19 (3H, s) ppm; high resolution mass spectrometry (ES+) m/z 450.1715 [(M+H)$^+$; calculated for $C_{27}H_{21}FN_5O$: 450.1725].

Example 669

2-(2-Bromo-6-methylphenyl)-5-{[4-(1H-pyrazol-1-yl)phenyl]methyl}-2,5-dihydro-3H-pyrazolo[4,3-c]quinolin-3-one

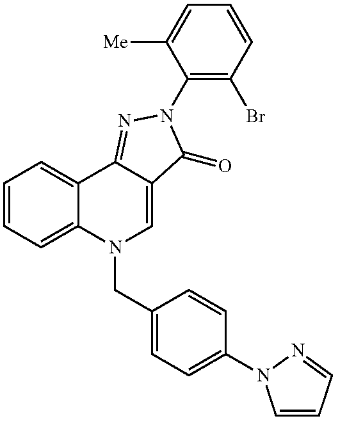 [SMILES: Cc1cccc(Br)c1-n1nc2c3ccccc3n(Cc3ccc(-n4cccn4)cc3)cc-2c1=O]

Using the procedures described in Example 666, substituting 2-bromo-6-methylaniline for 2-bromo-6-fluoroaniline (Step 1), the titled compound was obtained: $^1$H-NMR (400 MHz, d$^6$-DMSO) δ 9.12 (1H, s), 8.46 (1H, d, J=2.4 Hz), 8.18 (1H, d, J=7.9 Hz), 7.84 (2H, d, J=8.8 Hz), 7.79 (1H, d, J=8.8 Hz), 7.73 (1H, m), 7.64-7.60 (2H, m), 7.53 (1H, d, J=7.8 Hz), 7.49 (2H, d, J=8.3 Hz), 7.42 (1H, d, J=7.4 Hz), 7.34 (1H, t, J=7.9 Hz), 6.53 (1H, m), 5.76 (2H, s), 2.15 (3H, s) ppm; high resolution mass spectrometry (ES+) m/z 510.0928 [(M+H)$^+$; calculated for $C_{27}H_{21}BrN_5O$: 510.0924].

Example 670

2-(2-Cyano-6-methylphenyl)-5-{[4-(1H-pyrazol-1-yl)phenyl]methyl}-2,5-dihydro-3H-pyrazolo[4,3-c]quinolin-3-one

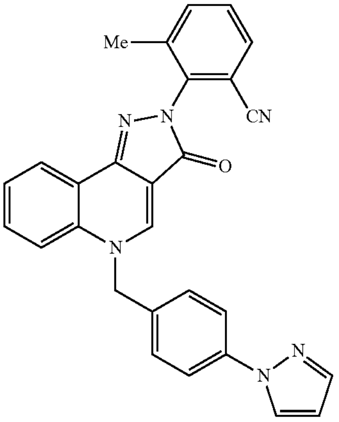 [SMILES: Cc1cccc(C#N)c1-n1nc2c3ccccc3n(Cc3ccc(-n4cccn4)cc3)cc-2c1=O]

Using the procedures described in Example 667, substituting 2-(2-bromo-6-methylphenyl)-5-{[4-(1H-pyrazol-1-yl)

phenyl]methyl}-2,5-dihydro-3H-pyrazolo[4,3-c]quinolin-3-one (Example 669) for 2-(2-bromo-6-fluorophenyl)-5-{[2-fluoro-4-(1H-pyrazol-1-yl)phenyl]methyl}-2,5-dihydro-3H-pyrazolo[4,3-c]quinolin-3-one (Example 666), the titled compound was obtained: $^1$H-NMR (400 MHz, d$^6$-DMSO) δ 9.20 (1H, s), 8.46 (1H, d, J=2.6 Hz), 8.21 (1H, dd, J=7.9, 1.4 Hz), 7.86-7.83 (3H, m), 7.81 (1H, d, J=8.7 Hz), 7.77 (1H, d, J=7.7 Hz), 7.73 (1H, d, J=1.6 Hz), 7.67-7.63 (1H, m), 7.58 (1H, t, J=7.3 Hz), 7.55 (1H, t, J=7.5 Hz), 7.50 (2H, d, J=8.7 Hz), 6.53 (1H, m), 5.79 (1H, s), 2.22 (3H, s) ppm; high resolution mass spectrometry (ES+) m/z 457.1796 [(M+H)$^+$; calculated for $C_{28}H_{21}N_6O$: 457.1771].

Example 671

2-(3-Chloropyridin-4-yl)-5-{[4-(1H-pyrazol-1-yl)phenyl]methyl}-2,5-dihydro-3H-pyrazolo[4,3-c]quinolin-3-one

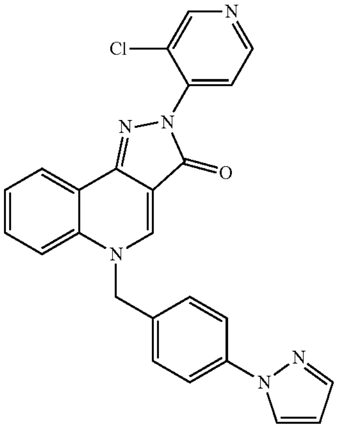 [SMILES: O=c1c2cn(Cc3ccc(-n4cccn4)cc3)c3ccccc3c-2nn1-c1ccncc1Cl]

2-(3,5-Dichloropyridin-4-yl)-5-{[4-(1H-pyrazol-1-yl)phenyl]methyl}-2,5-dihydro-3H pyrazolo[4,3-c]quinolin-3-one (Example 493, 15 mg, 0.031 mmol), ammonium formate (2.1 mg, 0.34 mmol, 1.1 equiv) and 1,1-bis(diphenylphosphino)ferrocenedichloro palladium(II) dichloromethane complex (2.2 mg, 0.00031 mmol, 0.1 equiv) were combined in methanol (2 mL) and placed into a preheated oil bath at 60° C. for 5 hours. The mixture was then heated at 70° C. for an additional 18 hours. The mixture was cooled to ambient temperature, concentrated in vacuo and the residue was purified by silica gel gradient chromatography (100:0 to 90:10; dichloromethane:methanol), providing the titled compound: $^1$H-NMR (400 MHz, d$^6$-DMSO) δ 8.94 (1H, br m), 8.75 (1H, br m), 8.71 (1H, s), 8.42 (1H, dd, J=7.7, 1.9 Hz), 8.21 (1H, br m), 7.74-7.72 (3H, m), 7.65-7.55 (4H, m), 7.35 (2H, d, J=8.7 Hz), 6.50 (1H, m), 5.62 (2H, s) ppm; high resolution mass spectrometry (ES+) m/z 453.1241 [(M+H)$^+$; calculated for $C_{25}H_{18}ClN_6O$: 453.1225].

Example 672

2-(4-Methylpyridin-3-yl)-5-{[4-(1H-pyrazol-1-yl)phenyl]methyl}-2,5-dihydro-3H-pyrazolo[4,3-c]quinolin-3-one

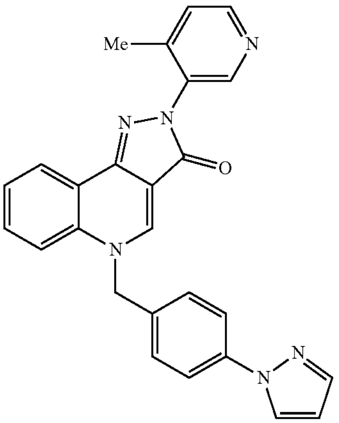 [SMILES: Cc1ccncc1-n1nc2c3ccccc3n(Cc3ccc(-n4cccn4)cc3)cc-2c1=O]

Using the procedures described in Example 668, substituting 2-(4-chloropyridin-3-yl)-5-{[4-(1H-pyrazol-1-yl)phenyl]methyl}-2,5-dihydro-3H-pyrazolo[4,3-c]quinolin-3-one (Example 509) for 2-(2-bromo-6-fluorophenyl)-5-{[2-fluoro-4-(1H-pyrazol-1-yl)phenyl]methyl}-2,5-dihydro-3H-pyrazolo[4,3-c]quinolin-3-one (Example 666), the titled compound was obtained: $^1$H-NMR (400 MHz, d$^6$-DMSO) δ 9.18 (1H, s), 8.58 (1H, br s), 8.50-8.44 (2H, m), 8.22 (1H, d, J=8.0 Hz), 7.83 (2H, d, J=8.6 Hz), 7.79 (1H, d, J=8.9 Hz), 7.73 (1H, m), 7.63 (1H, t, J=7.8 Hz), 7.54 (1H, t, J=7.7 Hz), 7.48 (2H, d, J=8.6 Hz), 7.44 (1H, d, J=4.8 Hz), 6.53 (1H, m), 5.79 (2H, s), 2.31 (3H, s) ppm; high resolution mass spectrometry (ES+) m/z 433.1779 [(M+H)$^+$; calculated for $C_{26}H_{21}N_6O$: 433.1771].

Example 673

3-(3-Oxo-5-{[4-(1H-pyrazol-1-yl)phenyl]methyl}-3,5-dihydro-2H-pyrazolo[4,3-c]quinolin-2-yl)pyridine-4-carbonitrile

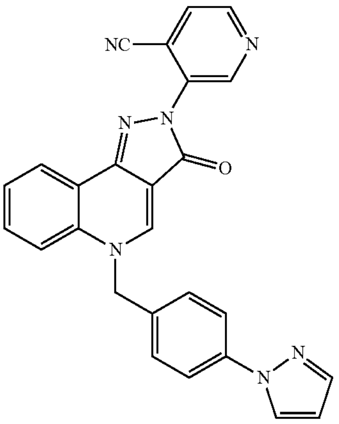 [SMILES: N#Cc1ccncc1-n1nc2c3ccccc3n(Cc3ccc(-n4cccn4)cc3)cc-2c1=O]

Using the procedures described in Example 667, substituting 2-(4-chloropyridin-3-yl)-5-{[4-(1H-pyrazol-1-yl)phenyl]methyl}-2,5-dihydro-3H-pyrazolo[4,3-c]quinolin-3-one (Example 509) for 2-(2-bromo-6-fluorophenyl)-5-{[2-fluoro-4-(1H-pyrazol-1-yl)phenyl]methyl}-2,5-dihydro-3H-pyrazolo[4,3-c]quinolin-3-one (Example 666), the titled compound was obtained: $^1$H-NMR (400 MHz, $d^6$-DMSO) δ 9.38 (1H, s), 9.30 (1H, s), 8.69 (1H, d, J=5.1 Hz), 8.46 (1H, d, J=2.8 Hz), 826 (1H, dd, J=7.8, 1.4 Hz), 8.00 (1H, d, J=4.9 Hz), 7.84-7.82 (3H, m), 7.72 (1H, d, J=1.6 Hz), 7.71-7.66 (1H, m), 7.61 (1H, t, J=7.2 Hz), 7.48 (2H, d, J=8.6 Hz), 6.53 (1H, m), 5.81 (2H, s) ppm; high resolution mass spectrometry (ES+) m/z 444.1577 [$(M+H)^+$; calculated for $C_{26}H_{18}N_7O$: 444.1567].

Example 674

2-Piperidin-4-yl-5-{[4-(1H-pyrazol-1-yl)phenyl]methyl}-2,5-dihydro-3H-pyrazolo[4,3-c]quinolin-3-one

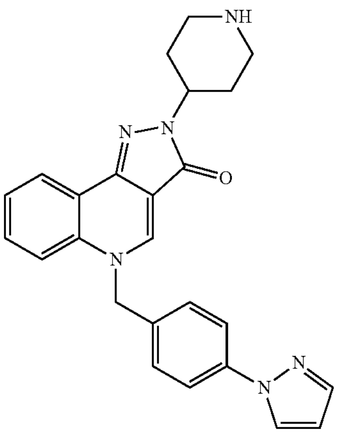 [SMILES: O=c1c2cn(Cc3ccc(-n4cccn4)cc3)c3ccccc3c-2nn1C1CCNCC1]

Phenylmethyl 4-(3-oxo-5-{[4-(1H-pyrazol-1-yl)phenyl]methyl}-3,5-dihydro-2H-pyrazolo[4,3-c]quinolin-2-yl)piperidine-1-carboxylate (Example 511, 25 mg, 0.045 mmol) was dissolved in ethyl acetate, treated with palladium(II) hydroxide on carbon (2.5 mg, 0.1 wt equiv), sparged under an atmosphere of hydrogen (1 atm) and stirred for 1 hour at ambient temperature. The mixture was sparged under an atmosphere of nitrogen, filtered through a pad of Celite and the filtrate was concentrated in vacuo. The residue was purified by silica gel gradient chromatography (100:0 to 80:20; dichloromethane:methanol), providing the titled compound: $^1$H-NMR (400 MHz, $CDCl_3$) δ 8.83 (1H, s), 8.38-8.36 (1H, m), 7.89 (1H, d, J=2.4 Hz), 7.71 (1H, d, J=1.8 Hz), 7.69 (2H, d, j=8.7 Hz), 7.52-7.43 (3H, m), 7.30-7.26 (3H, m), 6.46 (1H, m), 5.59 (2H, s), 4.61 (1H, m), 3.58-3.50 (2H, m), 3.01-2.96 (2H, m), 2.65-2.57 (2H, m), 2.13-2.05 (2H, m) ppm; low resolution mass spectrometry (ES+) m/z 424.9 [$(M+H)^+$; calculated for $C_{25}H_{25}N_6O$: 425.2].

Example 675

2-(1-Acetylpiperidin-4-yl)-5-{[4-(1H-pyrazol-1-yl)phenyl]methyl}-2,5-dihydro-3H-pyrazolo[4,3-c]quinolin-3-one5

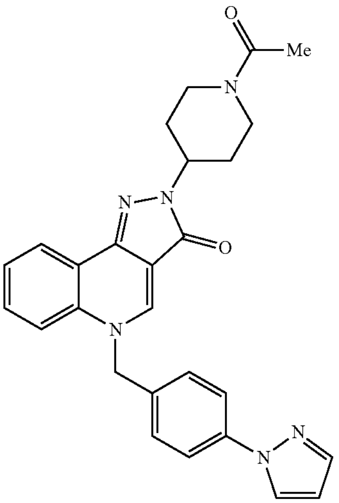 [SMILES: CC(=O)N1CCC(n2nc3c4ccccc4n(Cc4ccc(-n5cccn5)cc4)cc-3c2=O)CC1]

2-Piperidin-4-yl-5-{[4-(1H-pyrazol-1-yl)phenyl]methyl}-2,5-dihydro-3H-pyrazolo[4,3-c]quinolin-3-one (Example 674, 10 mg, 0.024 mmol) was dissolved in dichloromethane (1 mL), treated with triethylamine (8.2 μL, 0.059 mmol, 2.5 equiv) and acetyl chloride (1.8 μL, 0.026 mmol, 1.1 equiv). After stirring for 20 minutes at ambient temperature, the mixture was concentrated in vacuo and the residue was purified by silica gel gradient chromatography (100:0 to 95:5; dichloromethane:methanol), providing the titled compound: $^1$H-NMR (400 MHz, $CDCl_3$) δ 8.41 (1H, s), 8.37-8.35 (1H, m), 7.90 (1H, d, J=2.5 Hz), 7.72-7.69 (3H, m), 7.50-7.39 (3H, m), 7.28-7.25 (3H, m), 6.47 (1H, dd, J=2.5, 1.8 Hz), 5.48 (2H, s), 4.79 (1H, br d, J=13.6 Hz), 4.73-4.65 (1H, m), 3.98 (1H, br d, J=14.0 Hz), 3.28 (1H, td, J=13.1, 2.7 Hz), 2.78 (1H, td, J=12.8, 2.7 Hz), 2.16 (3H, s), 2.23-2.10 (1H, m), 2.02-1.93 (2H, m) ppm; high resolution mass spectrometry (ES+) m/z 467.2199 [$(M+H)^+$; calculated for $C_{27}H_{27}N_6O_2$: 467.2190].

The following compounds were prepared according to the general procedure described in Example 675, substituting the appropriate acylating reagent for acetyl chloride. The starting materials are either commercially available, known in the literature or may be prepared from commercially available reagents using conventional reactions well known in the art.

(IZ)

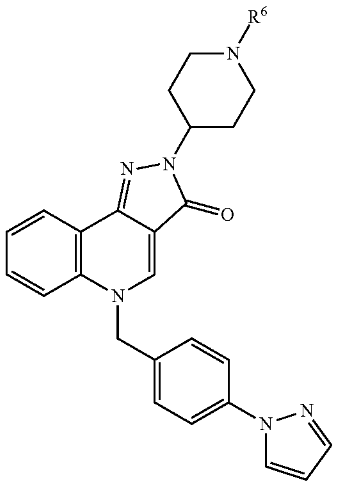

| Ex. | $R^6$ | HRMS/LRMS |
|---|---|---|
| 676 | 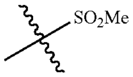 [SMILES: *S(C)(=O)=O] | $C_{27}H_{27}N_6O_3S$ [M + H] calc. 503.2 obs. 503.9 |
| 677 | 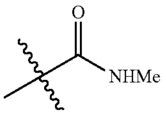 [SMILES: *C(=O)NC] | $C_{27}H_{28}N_7O_2$ [M + H] calc. 482.2299 obs. 482.2309 |
| 678 | 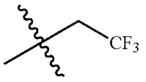 [SMILES: *CC(F)(F)F] | $C_{27}H_{26}F_3N_6O$ [M + H] calc. 507.2 obs. 507.2 |
| 679 | 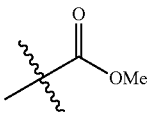 [SMILES: *C(=O)OC] | $C_{27}H_{27}N_6O_3$ [M + H] calc. 483.2139 obs. 483.2155 |

Example 680

2-(3-Chloro-5-methylpyridin-4-yl)-5-{[4-(1H-pyrazol-1-yl)phenyl]methyl}-2,5-dihydro-3H-pyrazolo[4,3-c]quinolin-3-one

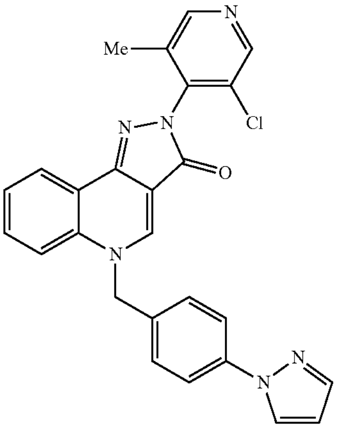 [SMILES: Cc1cncc(Cl)c1-n1nc2c3ccccc3n(Cc3ccc(-n4cccn4)cc3)cc-2c1=O]

Using the procedures described in Example 668, substituting 2-(3,5-dichloropyridin-4-yl)-5-{[4-(1H-pyrazol-1-yl)phenyl]methyl}-2,5-dihydro-3H-pyrazolo[4,3-c]quinolin-3-one (Example 493) for 2-(2-bromo-6-fluorophenyl)-5-{[2-fluoro-4-(1H-pyrazol-1-yl)phenyl]methyl}-2,5-dihydro-3H-pyrazolo[4,3-c]quinolin-3-one (Example 666), the titled compound was obtained: $^1$H-NMR (400 MHz, $CDCl_3$) δ 8.62 (1H, s), 8.50 (1H, m), 8.50 (1H, s), 8.40 (1H, dd, J=7.3, 2.1 Hz), 7.92 (1H, d, J=2.5 Hz), 7.75 (2H, d, J=8.7 Hz), 7.73 (1H, d, J=1.7 Hz), 7.57-7.48 (3H, m), 7.34 (2H, d, J=8.5 Hz), 6.48 (1H, dd, J=2.4, 1.8 Hz), 5.52 (2H, s), 2.33 (3H, s) ppm; low resolution mass spectrometry (ES+) m/z 467.2 [$(M+H)^+$; calculated for $C_{26}H_{20}ClN_6O$: 467.1].

Example 681

2-(3,5-Dimethylpyridin-4-yl)-5-{[4-(1H-pyrazol-1-yl)phenyl]methyl}-2,5-dihydro-3H-pyrazolo[4,3-c]quinolin-3-one

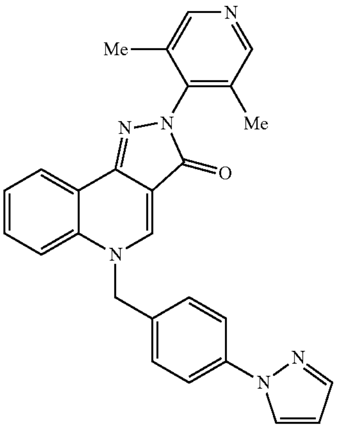 [SMILES: Cc1cncc(C)c1-n1nc2c3ccccc3n(Cc3ccc(-n4cccn4)cc3)cc-2c1=O]

Using the procedures described in Example 668, substituting 2-(3,5-dichloropyridin-4-yl)-5-{[4-(1H-pyrazol-1-yl)

phenyl]methyl}-2,5-dihydro-3H-pyrazolo[4,3-c]quinolin-3-one (Example 493) for 2-(2-bromo-6-fluorophenyl)-5-{[2-fluoro-4-(1H-pyrazol-1-yl)phenyl]methyl}-2,5-dihydro-3H-pyrazolo[4,3-c]quinolin-3-one (Example 666), the titled compound was obtained: $^1$H-NMR (400 MHz, $CDCl_3$) δ 8.49 (1H, s), 8.46 (2H, br s), 8.40 (1H, d, J=7.2 Hz), 7.92 (1H, d, J=2.4 Hz), 7.76 (2H, d, J=8.5 Hz), 7.73 (1H, m), 7.57-7.48 (3H, m), 7.35 (2H, d, J=8.3 Hz), 6.49 (1H, m), 5.52 (2H, s), 2.26 (6H, s) ppm; low resolution mass spectrometry (ES+) m/z 447.2 [$(M+H)^+$; calculated for $C_{27}H_{23}N_6O$: 447.2].

Example 682

4-{[2-(2-Fluorophenyl)-3-oxo-2,3-dihydro-5H-pyrazolo[4,3-c]quinolin-5-yl]methyl}-N-methylpiperidine-1-carboxamide

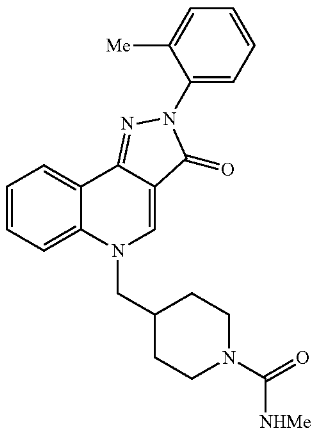 [SMILES: CNC(=O)N1CCC(Cn2cc3c(=O)n(-c4ccccc4C)nc-3c3ccccc32)CC1]

Step 1: Preparation of phenylmethyl 4-{[2-(2-fluorophenyl)-3-oxo-2,3-dihydro-5H-pyrazolo[4,3-c]quinolin-5-yl]methyl}piperidine-1-carboxylate Using the procedures described in Example 293, substituting phenylmethyl 4-(bromomethyl)piperidine-1-carboxylate for ethyl iodide (Step 2), the titled compound was obtained.

Step 2: Preparation of 2-(2-fluorophenyl)-5-(piperidin-4-ylmethyl)-2,5-dihydro-3H-pyrazolo[4,3-c]quinolin-3-one Phenylmethyl 4-{([2-(2-fluorophenyl)-3-oxo-2,3-dihydro-5H-pyrazolo[4,3-c]quinolin-5-yl]methyl}piperidine-1-carboxylate (328 mg, 0.642 mmol) was dissolved in methanol (20 mL) and tetrahydrofuran (20 mL). The mixture was treated with hydrochloric acid (10 drops from a 9" pipette, 12 N aqueous), sparged under an atmosphere of nitrogen and treated with palladium(II) hydroxide on carbon (100 mg, 20 wt % Pearllman's catalyst, 0.22 wt equiv). The mixture was sparged under an atmosphere of hydrogen (1 atm) and stirred vigorously for 5 hours. The mixture was sparged under an atmosphere of nitrogen, filtered through a pad of Celite and the solid was washed with methanol. The filtrate was concentrated in vacuo, providing the titled compound.

Step 3: Preparation of 4-{[2-(2-fluorophenyl)-3-oxo-2,3-dihydro-5H-pyrazolo[4,3-c]quinolin-5-yl]methyl}-N-methylpiperidine-1-carboxamide 2-(2-Fluorophenyl)-5-(piperidin-4-ylmethyl)-2,5-dihydro-3H-pyrazolo[4,3-c]quinolin-3-one (30 mg, 0.080 mmol) was dissolved in dichloromethane (2 ml) and tetrahydrofuran (1 ml), treated with triethylamine (0.011 ml, 0.080 mmol, 1 equiv) and methylimino(oxo)methane (4.55 mg, 0.080 mmol) were added. After 10 minutes, the mixture was concentrated in vacuo and the residue was purified by silica gel gradient chromatography (80:20 to 70:30; dichlormethane: methanol), providing the titled compound: $^1$H-NMR (400 MHz, $d^6$-DMSO) δ 8.85 (1H, s), 8.21 (1H, dd, J=, 7.9, 1.6 Hz), 7.98 (1H, d, J=8.7 Hz), 7.61-7.56 (2H, m), 7.47-7.30 (4H, m), 6.37 (1H, q, J=4.2 Hz), 5.70 (2H, br s), 4.35 (2H, d, J=6.8 Hz), 3.94 (2H, br d, J=13.6 Hz), 2.52 (3H, d, J=4.9 Hz), 2.13-2.02 (1H, m), 1.49 (2H, br d, J=12.3 Hz), 1.25-1.13 (2H, m) ppm; high resolution mass spectrometry (ES+) m/z 434.1998 [$(M+H)^+$; calculated for $C_{24}H_{25}FN_5O_2$: 434.1987].

The following compounds were prepared according to the general procedure described in Example 682, substituting the appropriate acylating reagent for methylimino(oxo)methane. The starting materials are either commercially available, known in the literature or may be prepared from commercially available reagents using conventional reactions well known in the art.

(IAA)

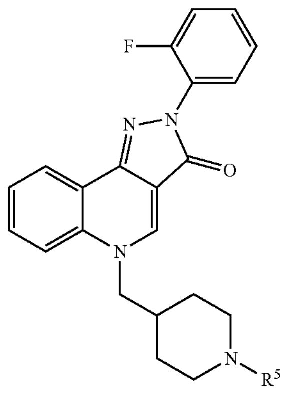

| Ex. | $R^5$ | HRMS/LRMS |
|---|---|---|
| 683 | 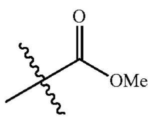 [SMILES: *C(=O)OC] | $C_{24}H_{24}FN_4O_3$ [M + H] calc. 435.1827 obs. 435.1836 |
| 684 | 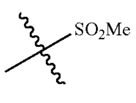 [SMILES: *S(C)(=O)=O] | $C_{23}H_{24}FN_4O_3S$ [M + H] calc. 455.1548 obs. 455.1556 |
| 685 | 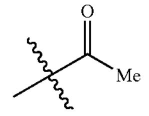 [SMILES: *C(C)=O] | $C_{24}H_{24}FN_4O_2$ [M + H] calc. 419.1878 obs. 419.1875 |

Example 686

2-(2-Fluorophenyl)-5-{[2-(hydroxymethyl)phenyl]methyl}-2,5-dihydro-3H-pyrazolo[4,3-c]quinolin-3-one

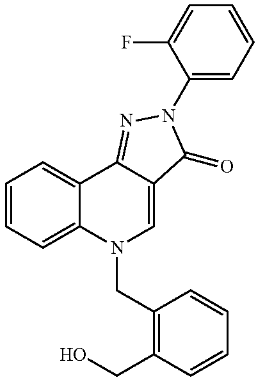 [SMILES: O=c1c2cn(Cc3ccccc3CO)c3ccccc3c-2nn1-c1ccccc1F]

Using the procedures described hi Example 658, substituting ethyl 2-{[2-(2-fluorophenyl)-3-oxo-2,3-dihydro-5H-pyrazolo[4,3-c](quinolin-5-yl]methyl}benzoate (Example 341) for methyl[2-(3-oxo-5-{[4-(1H-pyrazol-1-yl)phenyl]methyl}-3,5-dihydro-2H-pyrazolo[4,3-c]quinolin-2-yl)phenyl]acetate (Example 533), the titled compound was obtained: $^1$H-NMR (400 MHz, $d^6$-DMSO) δ 8.96 (1H, s), 8.22 (1H, dd, J=7.3, 1.6 Hz), 7.63-7.52 (3H, m), 7.50-7.32 (5H, m), 7.29 (1H, t, J=7.5 Hz), 7.16 (1H, td, J=7.4, 1.4 Hz), 6.69 (1H, d, J=7.7 Hz), 5.80 (2H, s), 5.44 (1H, t, J=5.3 Hz), 4.72 (2H, d, J=5.2 Hz) ppm; high resolution mass spectrometry (ES+) m/z 400.1451 [(M+H)$^+$; calculated for $C_{24}H_{19}FN_3O_2$: 400.1456].

The following compounds were prepared according to the general procedure described in Example 686, substituting the appropriate ester for ethyl 2-{([2-(2-fluorophenyl)-3-oxo-2,3-dihydro-5H-pyrazolo[4,3-c]quinolin-5-yl]methyl}benzoate. The starting materials are either commercially available, known in the literature or may be prepared from commercially available reagents using conventional reactions well known in the art.

(IBB)

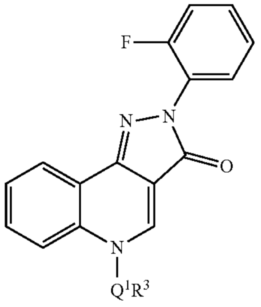

| Ex. | $Q^1R^3$ | HRMS/LRMS |
|---|---|---|
| 687 | 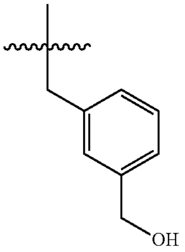 [SMILES: *Cc1cccc(CO)c1] | $C_{24}H_{19}FN_3O_2$ [M + H] calc. 400.1456 obs. 400.1461 |
| 688 | 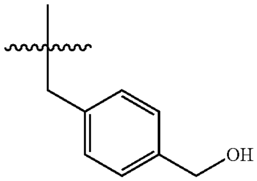 [SMILES: *Cc1ccc(CO)cc1] | $C_{24}H_{19}FN_3O_2$ [M + H] calc. 400.1456 obs. 400.1463 |

Example 689

(3-Oxo-5-{[4-(1H-pyrazol-1-yl)phenyl]methyl}-3,5-dihydro-2H-pyrazol[4,3-c]quinolin-2-yl)acetic acid

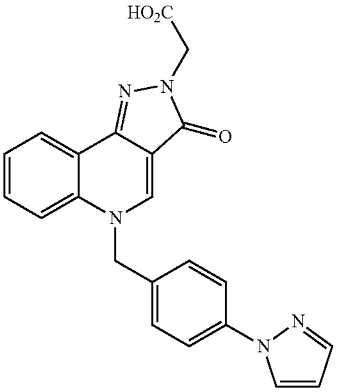 [SMILES: O=C(O)Cn1nc2c3ccccc3n(Cc3ccc(-n4cccn4)cc3)cc-2c1=O]

Ethyl (3-oxo-5-{[4-(1H-pyrazol-1-yl)phenyl]methyl}-3,5-dihydro-2H-pyrazol[4,3-c]quinolin-2-yl)acetate (Example 524, 10 mg, 0.023 mmol) was suspended in dioxane (2 mL), treated with an lithium hydroxide (22 μL, 1 N aqueous, 0.023 mmol, 1.05 equiv) and stirred vigorously for 18 hours. The mixture was diluted with dichloromethane until homogeneous (2 mL) and stirred for an additional 6 hours. The mixture was treated with hydrochloric acid (1 drop from 9" pipette, 12 N aqueous) and concentrated in vacuo, providing the titled compound: $^1$H-NMR (400 MHz, $d^6$-DMSO) δ 9.06 (1H, s), 8.44 (1H, d, J=2.7 Hz), 8.15 (1H, d, J=7.9 Hz), 7.81 (2H, d, J=8.8 Hz), 7.74 (1H, d, J=8.5 Hz), 7.71 (1H, d, J=1.3 Hz), 7.58 (1H, t, 7.8 Hz), 7.50 (1H, t, J=7.3 Hz), 7.43 (2H, d, J=8.5 Hz), 7.14 (1H, hr s), 6.52 (1H, m), 5.74 (2H, s), 4.59 (2H, s) ppm; high resolution mass spectrometry (ES+) m/z 400.1412 [$(M+H)^+$; calculated for $C_{22}H_{18}N_5O_3$: 400.1404].

Example 690

N,N-Diethyl-2-(3-oxo-5-{[4-(1H-pyrazol-1-yl)phenyl]methyl}-3,5-dihydro-2H-pyrazol[4,3-c]quinolin-2-yl)acetamide

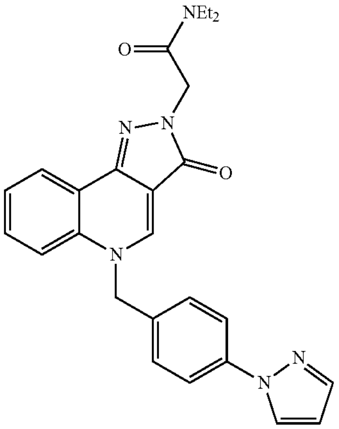

Using the procedures described in Example 612, substituting (3-oxo-5-{[4-(1H-pyrazol-1-yl)phenyl]methyl}-3,5-dihydro-2H-pyrazol[4,3-c]quinolin-2-yl)acetic acid (Example 689) for 2-(3-oxo-5-{[4-(1H-pyrazol-1-yl)phenyl]methyl}-3,5-dihydro-2H-pyrazolo[4,3-c]quinolin-2-yl)benzoic acid (Example 611), and, substituting diethylamine for methylamine, the titled compound was obtained: $^1$H-NMR (400 MHz, $CDCl_3$) δ 8.37-8.34 (1H, m), 833 (1H, s), 7.90 (1H, d, J=2.4 Hz), 7.72 (1H, d, J=1.6 Hz), 7.69 (2H, d, J=8.6 Hz), 7.47-7.40 (3H, m), 7.29 (2H, d, J=8.7 Hz), 6.46 (1H, dd, J=2.3, 1.9 Hz), 5.46 (2H, s), 4.90 (2H, s), 3.43 (4H, qd, J=7.1, 1.8 Hz), 1.27 (3H, t, J=7.2 Hz), 1.16 (3H, t, J=7.2 Hz) ppm; high resolution mass spectrometry (ES+) m/z 455.2198 [$(M+H)^+$; calculated for $C_{26}H_{27}N_6O_2$: 455.2190].

The following compounds were prepared according to the general procedure described in Example 690, substituting the appropriate amine for diethylamine. The starting materials are either commercially available, known in the literature or may be prepared from commercially available reagents using conventional reactions well known in the art.

(ICC)

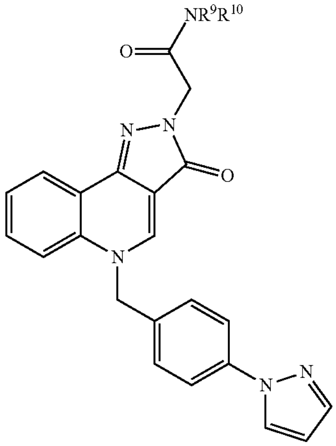

| Ex. | $NR^9R^{10}$ | HRMS/LRMS |
|---|---|---|
| 691 | 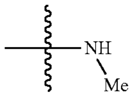 | $C_{23}H_{21}N_6O_2$ [M + H] calc. 413.1721 obs. 413.1730 |
| 692 | 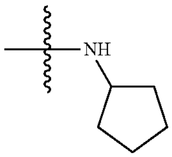 [SMILES: *NC1CCCC1] | $C_{27}H_{27}N_6O_2$ [M + H] calc. 467.2190 obs. 467.2197 |
| 693 | 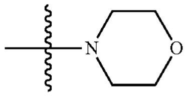 | $C_{26}H_{25}N_6O_3$ [M + H] calc. 469.1983 obs. 469.1991 |
| 694 | 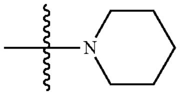 | $C_{27}H_{27}N_6O_2$ [M + H] calc. 467.2190 obs. 467.2192 |
| 695 | 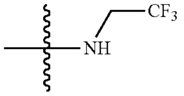 | $C_{24}H_{20}F_3N_6O_2$ [M + H] calc. 481.1594 obs. 481.1600 |
| 696 | 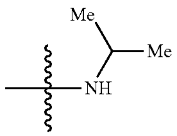 [SMILES: *NC(C)C] | $C_{25}H_{25}N_6O_2$ [M + H] calc. 441.2034 obs. 441.2050 |
| 697 | 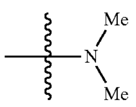 [SMILES: *N(C)C] | $C_{24}H_{23}N_6O_2$ [M + H] calc. 427.1877 obs. 427.1888 |
| 698 | 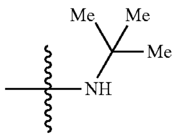 [SMILES: *NC(C)(C)C] | $C_{26}H_{27}N_6O_2$ [M + H] calc. 455.2190 obs. 455.2195 |
| 699 | 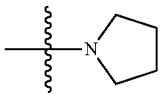 [SMILES: *N1CCCC1] | $C_{26}H_{25}N_6O_2$ [M + H] calc. 453.2034 obs. 453.2027 |

-continued (ICC)

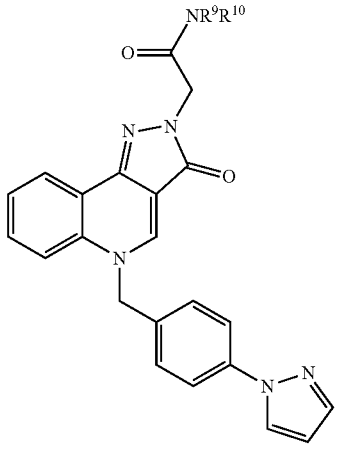

| Ex. | $NR^9R^{10}$ | HRMS/LRMS |
|---|---|---|
| 700 | 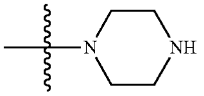 [SMILES: *N1CCNCC1] | $C_{26}H_{26}N_7O_2$ [M + H] calc. 468.2143 obs. 468.2148 |
| 701 | 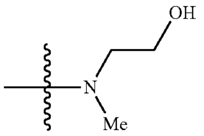 [SMILES: *N(C)CCO] | $C_{25}H_{25}N_6O_3$ [M + H] calc. 457.1983 obs. 457.1991 |
| 702 | 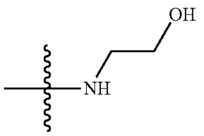 [SMILES: *NCCO] | $C_{24}H_{23}N_6O_3$ [M + H] calc. 443.1826 obs. 443.1821 |
| 703 | 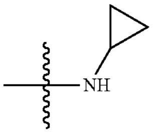 [SMILES: *NC1CC1] | $C_{25}H_{25}N_6O_2$ [M + H] calc. 439.1877 obs. 439.1886 |
| 704 | 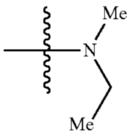 [SMILES: *N(C)CC] | $C_{25}H_{25}N_6O_2$ [M + H] calc. 441.2034 obs. 441.2036 |
| 705 | 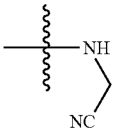 [SMILES: *NCC#N] | $C_{24}H_{20}N_7O_2$ [M + H] calc. 438.1673 obs. 438.1671 |

Example 706

6-Bromo-9-fluoro-2-(2-methylphenyl)-5-{[4-(1H-pyrazol-1-yl)phenyl]methyl}-2,5-dihydro-3H-pyrazolo[4,3-c]quinolin-3-one

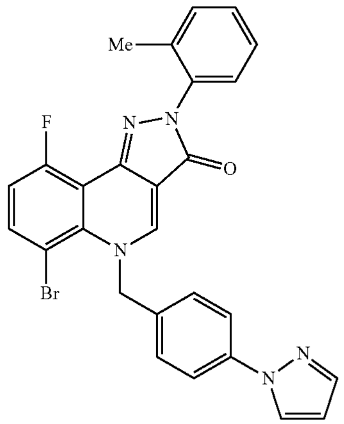 [SMILES: Cc1ccccc1-n1nc2c3c(F)ccc(Br)c3n(Cc3ccc(-n4cccn4)cc3)cc-2c1=O]

Using the procedures described in Example 1, substituting ethyl 8-bromo-5-fluoro-4-oxo-1,4-dihydroquinoline-3-carboxylate for ethyl 4-oxo-1,4-dihydroquinoline-3-carboxylate, and, substituting 1-[4-(bromomethyl)phenyl]-1H-pyrazole for 4-methoxybenzylchloride (Step 1), and substituting Lawesson's Reagent for phosphorous pentasulfide (Step 2), and, substituting and toluene for pyridine (Step 2), and, substituting 2-methylphenylhydrazine hydrochloride for 2-fluorophenylhydrazine hydrochloride (Step 3), the titled compound was obtained: $^1$H-NMR (400 MHz, $CDCl_3$) δ 8.52 (1H, br s), 7.90 (1H, d, J=2.6 Hz), 7.78 (OH, dd, J=8.8, 5.8 Hz), 7.72 (1H, d, J=1.4 Hz), 7.67 (2H, d, J=8.5 Hz), 7.44-7.40 m), 7.33-7.25 (5H, m), 7.11 (1H, t, J=8.8 Hz), 6.47 (1H, m), 5.92 (2H, s), 2.30 (3H, s) ppm; high resolution mass spectrometry (ES+) m/z 528.0829 [$(M+H)^+$; calculated for $C_{27}H_{20}BrFN_5O$: 528.0830].

Example 707

9-Fluoro-6-methyl-2-(2-methylphenyl)-5-{[4-(1H-pyrazol-1-yl)phenyl]methyl}-2,5-dihydro-3H-pyrazolo[4,3-c]quinolin-3-one

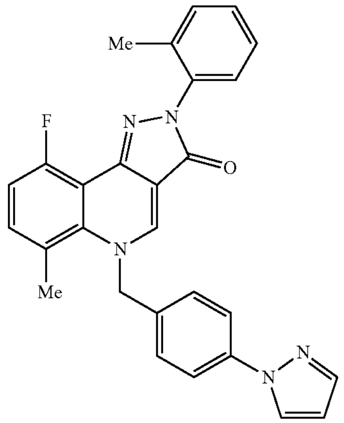 [SMILES: Cc1ccccc1-n1nc2c3c(F)ccc(C)c3n(Cc3ccc(-n4cccn4)cc3)cc-2c1=O]

Using the procedures described in Example 668, substituting 6-bromo-9-fluoro-2-(2-methylphenyl)-5-{[4-(1H-pyrazol-1-yl)phenyl]methyl}-2,5-dihydro-3H-pyrazolo[4,3-c]quinolin-3-one (Example 706) for 2-(2-bromo-6-fluorophenyl)-5-{[2-fluoro-4-(1H-pyrazol-1-yl)phenyl]methyl}-2,5-dihydro-3H-pyrazolo[4,3-c]quinolin-3-one (Example 666), the titled compound was obtained: $^1$H-NMR (400 MHz, $CDCl_3$) δ 8.29 (1H, s), 7.90 (1H, d, J=2.6 Hz), 7.72 (1H, m), 7.70 (2H, d, J=8.5 Hz), 7.48-7.45 (1H, m), 7.32-7.24 (4H, m), 7.17-7.11 (3H, m), 6.48 (1H, dd, J=2.5, 1.7 Hz), 5.60 (2H, s), 2.66 (3H, s), 2.33 (3H, s) ppm; high resolution mass spectrometry (ES+) m/z 464.1876 [(M+H)$^+$; calculated for $C_{28}H_{23}FN_5O$: 464.1881].

Example 707

9-Fluoro-2-(2-methylphenyl)-3-oxo-5-{[4-(1H-pyrazol-1-yl)phenyl]methyl}-3,5-dihydro-2H-pyrazolo[4,3-c]quinoline-6-carbonitrile

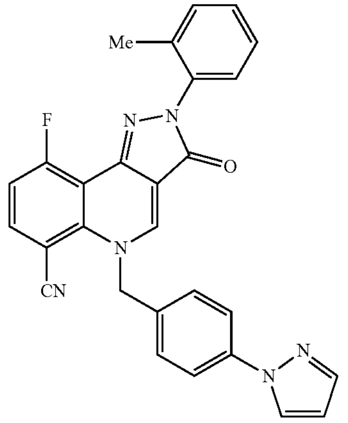 [SMILES: Cc1ccccc1-n1nc2c3c(F)ccc(C#N)c3n(Cc3ccc(-n4cccn4)cc3)cc-2c1=O]

Using the procedures described in Example 667, substituting 6-bromo-9-fluoro-2-(2-methylphenyl)-5-{[4-(1H-pyrazol-1-yl)phenyl]methyl}-2,5-dihydro-3H-pyrazolo[4,3-c]quinolin-3-one (Example 706) for 2-(2-bromo-6-fluorophenyl)-5-{[2-fluoro-4-(1H-pyrazol-1-yl)phenyl]methyl}-2,5-dihydro-3H-pyrazolo[4,3-c]quinolin-3-one (Example 666), the titled compound was obtained: $^1$H-NMR (400 MHz, $CDCl_3$) δ 8.31 (1H, s), 7.92 (1H, d, J=2.6 Hz), 7.84 (1H, dd, J=8.6, 5.6 Hz), 7.76-7.62 (3H, m), 7.45-7.41 (1H, m), 7.35-7.27 (6H, m), 6.48 (1H, dd, J=2.5, 1.9 Hz), 6.00 (2H, s), 2.32 (3H, s) ppm; high resolution mass spectrometry (ES+) m/z 475.1700 [(M+H)$^+$; calculated for $C_{28}H_{24}FN_6O$: 475.1677].

Example 708

5-{[3-Chloro-4-(6-morpholin-4-ylpyridin-3-yl)phenyl]methyl}-2-(2-fluorophenyl)-2,5-dihydro-3H-pyrazolo[4,3-c]quinolin-3-one

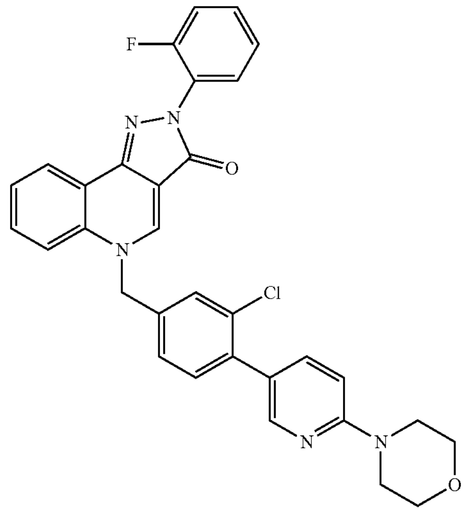 [SMILES: O=c1c2cn(Cc3ccc(-c4ccc(N5CCOCC5)nc4)c(Cl)c3)c3ccccc3c-2nn1-c1ccccc1F]

Using the procedures described in Example 95, substituting 5-[(4-bromo-3-chlorophenyl)methyl]-2-(2-fluorphenyl)-2,5-dihydro-3H-pyrazolo[4,3-c]quinolin-3-one (Example 185) for 5-[(4-bromo-2-fluorophenyl)methyl-6,9-difluoro-2-(2-fluorophenyl)-2,5-dihydro-3H-pyrazolo[4,3-c]quinolin-3-one (Example 78), and substituting 4-[5-(4,4,5,5-tetramethyl-1,3,2-dioxaborolan-2-yl)pyridin-2-yl]morpholine for 1-iso-butyl-4-(4,4,5,5-tetramethyl-1,3,2-dioxaborolan-2-yl)-1H-pyrazole, the titled compound was obtained: $^1$H-NMR (400 MHz, $CDCl_3$) δ 9.00 (1H, s), 8.50 (1H, dd, J=7.7, 1.6 Hz), 8.26 (1H, d, J=2.1 Hz), 8.03 (1H, dd, J=9.5, 2.2 Hz), 7.69-7.59 (3H, m), 7.53 (1H, d, J=8.2 Hz), 7.46-7.37 (3H, m), 7.32-7.24 (3H, m), 7.02 (1H, d, J=9.7 Hz), 5.60 (2H, s), 3.92-3.90 (4H, m), 3.78-3.75 (4H, m) ppm; high resolution mass spectrometry (ES+) m/z 566.1751 [(M+H)$^+$; calculated for $C_{32}H_{26}ClFN_5O_2$: 566.1754].

The following compounds were prepared according to the general procedure described in Example 708, substituting the appropriate boronic acid or ester for 4-[5-(4,4,5,5-tetramethyl-1,3,2-dioxaborolan-2-yl)pyridin-2-yl]morpholine. The starting materials are either commercially available, known in the literature or may be prepared from commercially available reagents using conventional reactions well known in the art.

(IDD)

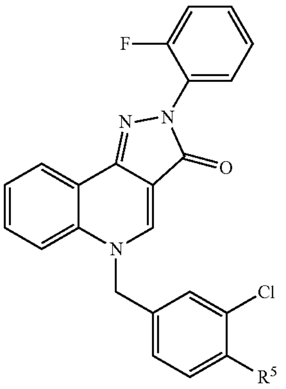

| Ex. | $R^5$ | HRMS/LRMS |
|---|---|---|
| 709 | 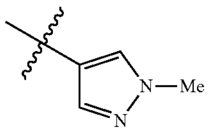 [SMILES: *c1cnn(C)c1] | $C_{27}H_{20}ClFN_5O$[M + H] calc. 484.1335 obs. 484.1355 |
| 710 | 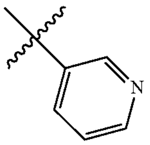 [SMILES: *c1cccnc1] | $C_{28}H_{19}ClFN_4O$[M + H] calc. 481.1226 obs. 481.1222 |
| 711 | 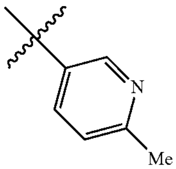 [SMILES: *c1ccc(C)nc1] | $C_{29}H_{21}ClFN_4O$[M + H] calc. 495.1382 obs. 495.1369 |
| 712 | 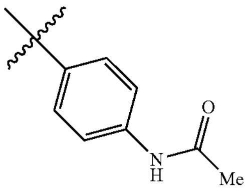 [SMILES: *c1ccc(NC(C)=O)cc1] | $C_{31}H_{23}ClFN_4O_2$[M + H] calc. 537.1488 obs. 537.1487 |

Example 713

(±)-2-[trans-2-(Methyloxy)cyclohexyl]-5-{[4-(1H-pyrazol-1-yl)phenyl]methyl}-2,5-dihydro-3H-pyrazolo[4,3-c]quinolin-3-one

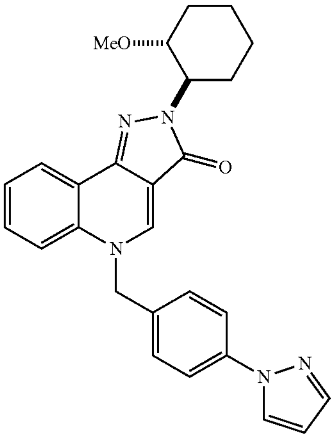 [SMILES: CO[C@@H]1CCCC[C@H]1n1nc2c3ccccc3n(Cc3ccc(-n4cccn4)cc3)cc-2c1=O]

(±)-2-(trans-2-Hydroxycyclohexyl)-5-{[4-(1H-pyrazol-1-yl)phenyl]methyl}-2,5-dihydro-3H-pyrazolo[4,3-c]quinolin-3-one (Example 508, 73 mg, 0.17 mmol) was dissolved in degassed N,N-dimethylformamide (3 mL), cooled to 0° C. and treated with sodium hydride (10 mg, 0.25 mmol, 1.5 equiv). After stirring for 15 minutes, the mixture was warmed to ambient temperature, stirred for 15 minutes and cooled to 0° C. The mixture was treated with methyl iodide (0.026 mL, 0.41 mmol, 2.5 equiv) and stirred at 0° C. for 1 hour. The mixture was treated with sodium bicarbonate (1.5 mL, aqueous saturated) and then poured into sodium bicarbonate (25 mL, aqueous saturated). The aqueous layer was extracted with ethyl acetate (2×100 mL), dried with sodium sulfate, filtered and concentrated in vacuo. The mixture was purified by silica gel gradient chromatography (100:0 to 90:10; dichloromethane:methanol), providing the titled compound: $^1$H-NMR (400 MHz, $CDCl_3$) δ 8.40-8.37 (1H, m), 7.89 (1H, d, J=2.4 Hz), 7.72-7.68 (3H, m), 7.46-7.42 (2H, m), 7.40-736 (1H, m), 7.28 (2H, d, J=8.9 Hz), 6.46 (1H, m), 5.44 (2H, s), 4.39 (1H, td, J=10.2, 5.5 Hz), 3.83-3.77 (1H, m), 3.22 (3H, s), 2.27-2.23 (1H, m), 2.04-1.93 (2H, m), 1.86-1.77 (2H, m), 1.48-1.34 (4H, m) ppm; high resolution mass spectrometry (ES+) m/z 454.2250 [$(M+H)^+$; calculated for $C_{27}H_{28}N_5O_2$: 454.2238].

Example 714

(±)-2-(cis-2-Fluorocyclohexyl)-5-{[4-(1H-pyrazol-1-yl)phenyl]methyl}-2,5-dihydro-3H-pyrazolo[4,3-c]quinolin-3-one

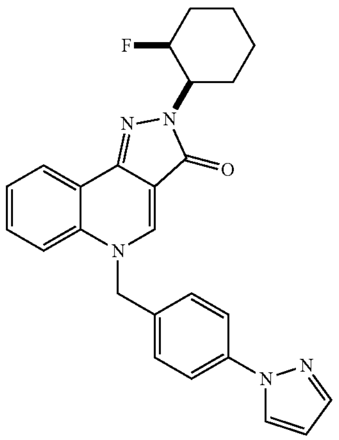 [SMILES: O=c1c2cn(Cc3ccc(-n4cccn4)cc3)c3ccccc3c-2nn1[C@@H]1CCCC[C@@H]1F]

(±)-2-(trans-2-Hydroxycyclohexyl)-5-{[4-(1H-pyrazol-1-yl)phenyl]methyl}-2,5-dihydro-3H-pyrazolo[4,3-c]quinolin-3-one (Example 508, 0.15 g, 0.35 mmol) was dissolved in dichloromethane (5 mL), cooled to 0° C. and treated with bis(2-methoxyethyl)aminosulfur trifluoride (0.15 mL, 0.70 mmol, 2 equiv). The mixture was stirred at 0° C. for 30 minutes and then treated with additional bis(2-methoxyethyl)aminosulfur trifluoride (75 μL, 0.35 mmol, 1 equiv). After stirring for an additional 30 minutes, the mixture was treated with sodium bicarbonate (5 mL, aqueous saturated) and stirred vigorously for 15 minutes. The mixture was poured into sodium bicarbonate (75 mL, aqueous saturated) and extracted with dichloromethane (2×75 mL). The combined organic extracts were dried with sodium sulfate, filtered and concentrated in vacuo. The residue was purified by silica gel gradient chromatography (100:0 to 85:15; ethyl acetate:methanol), providing the titled compound: $^1$H-NMR (400 MHz, $CDCl_3$) δ 8.39 (1H, s), 8.38-8.35 (1H, m), 7.89 (1H, d, J=2.5 Hz), 7.71 (1H, d, J=1.8 Hz), 7.69 (2H, d, J=8.6 Hz), 7.47-7.42 (2H, m), 7.40-7.36 (1H, m), 7.28-7.26 (2H, m), 6.46 (1H, dd, J=2.4, 1.8 Hz), 5.45 (2H, s), 5.03 (1H, dtd, J=49.9, 10.6, 5.0 Hz), 4.61-4.52 (1H, m), 2.34-2.27 (1H, m), 2.06-1.98 (2H, m), 1.91-1.80 (2H, m), 1.74-1.59 (1H, m), 1.52-1.43 (2H, m) ppm; high resolution mass spectrometry (ES+) m/z 442.2051 [$(M+H)^+$; calculated for $C_{26}H_{25}FN_5O$: 442.2038].

Example 715

(±)-2-(Cyclohex-2-en-1-yl)-5-{[4-(1H-pyrazol-1-yl)phenyl]methyl}-2,5-dihydro-3H-pyrazolo[4,3-c]quinolin-3-one

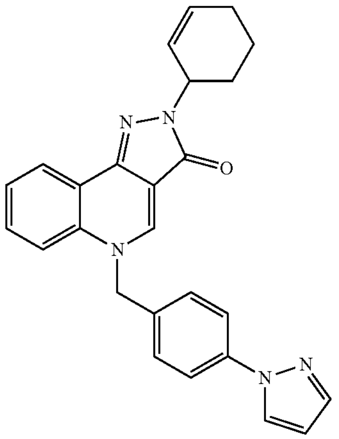 [SMILES: O=c1c2cn(Cc3ccc(-n4cccn4)cc3)c3ccccc3c-2nn1C1C=CCCC1]

(±)-2-(trans-2-Hydroxycyclohexyl)-5-{[4-(1H-pyrazol-1-yl)phenyl]methyl}-2,5-dihydro-3H-pyrazolo[4,3-c]quinolin-3-one (Example 508, 78 mg, 0.18 mmol) was suspended in dichloromethane (3 mL) and treated with bis[α,α-bis(trifluoromethyl)benzyloxy]diphenylsulfur (Martin's sulfurane, 0.18 g, 0.27 mmol, 1.5 equiv). After stirring for 1 hour, additional Martin's sulfurane (75 mg, 0.18 mmol, 1 equiv) was added and the mixture was stirred at ambient temperature for an additional 16 hours. The mixture was then placed into an oil bath preheated to 45° C. for 6 hours, cooled to ambient temperature, treated with sodium bicarbonate (1.5 mL, aqueous saturated) and stirred vigorously for 30 minutes. The mixture was poured into sodium bicarbonate (50 mL, aqueous saturated) and extracted with dichloromethane (2×75 mL). The combined organic extracts were dried with sodium sulfate, filtered and concentrated in vacuo. The residue was purified by silica gel gradient chromatography (100:0 90:10; dichloromethane:methanol), providing partially purified material. The mixture was purified by preparative reverse phase HPLC (80:20 to 25:75; water containing 0.1% trifluoroacetic acid:acetonitrile containing 0.1% trifluoroacetic acid). The appropriate fractions were poured into sodium bicarbonate (15 mL, aqueous saturated) and extracted once with ethyl acetate (30 mL). The organic layer was dried with sodium sulfate, filtered and concentrated in vacuo, providing the titled compound: $^1$H-NMR (400 MHz, $CDCl_3$) δ 8.44 (1H, dd, J=4.6, 2.0 Hz), 8.42 (1H, s), 7.89 (1H, d, J=2.6 Hz), 7.72 (1H, d, J=1.8 Hz), 7.70 (2H, d, J=8.6 Hz), 7.46-7.43 (2H, m), 7.41-7.37 (1H, m), 7.28-7.28 (2H, m), 6.47 (1H, dd, J=2.4, 1.9 Hz), 6.03-5.98 (1H, m), 5.75 (1H, br d, J=9.8 Hz), 5.47 (2H, s), 5.29-5.22 (1H, m), 2.30-2.20 (1H, m), 2.14-1.98 (4H, m), 1.85-1.73 (1H, m) ppm; high resolution mass spectrometry (ES+) m/z 422.1981 [$(M+H)^+$; calculated for $C_{26}H_{24}N_5O$: 422.1975].

Example 716

(±)-2-(3-Oxo-5-{[4-(1H-pyrazol-1-yl)phenyl]methyl}-3,5-dihydro-2H-pyrazolo[4,3-c]quinolin-2-yl) cyclohexyl acetate

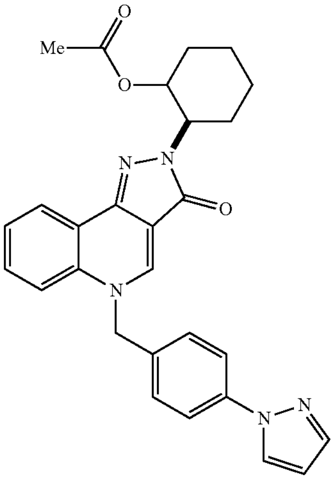 [SMILES: CC(=O)OC1CCCC[C@H]1n1nc2c3ccccc3n(Cc3ccc(-n4cccn4)cc3)cc-2c1=O]

(±)-2-(trans-2-Hydroxycyclohexyl)-5-{[4-(1H-pyrazol-1-yl)phenyl]methyl}-2,5-dihydro-3H-pyrazolo[4,3-c]quinolin-3-one (Example 508, 50 mg, 0.11 mmol) was dissolved in dichloromethane (2 ml) and treated sequentially with diisopropylethylamine (0.028 ml, 0.16 mmol, 1.4 equiv), dimethyl-4-aminopyridine (1.4 mg, 0.011 mmol, 0.1 equiv) and acetyl chloride (0.014 ml, 0.19 mmol, 1.7 equiv). After stirring for 20 minutes, additional acetyl chloride (0.014 ml, 0.19 mmol, 1.7 equiv) was added and the mixture was stirred for an additional 20 minutes. The mixture was poured into water (15 mL) and extracted with dichloromethane (2×15 mL). The organic extracts were washed once with hydrochloric acid (10 mL, 1 N aqueous) and sodium bicarbonate (10 mL, aqueous saturated), dried with sodium sulfate, filtered and concentrated in vacuo. The residue was purified by silica gel gradient chromatography (100:0 to 80:20; dichloromethane:methanol), providing the titled compound: $^1$H-NMR (400 MHz, $CDCl_3$) δ 8.38 (1H, dd, J=6.1, 3.4 Hz), 8.36 (1H, s), 7.90 (1H, d, J=2.4 Hz), 7.72-7.70 (3H, m), 7.46-7.42 (2H, m), 7.39-7.36 (1H, m), 7.29-7.26, (2H, m), 6.47 (1H, dd, J=2.2, 1.9 Hz), 5.47 (1H, d, J=16.7 Hz), 5.42 (1H, d, J=16.2 Hz), 5.32-5.26 (1H, m), 4.56-4.49 (1H, m), 216-2.19 (2H, m), 2.13-1.99 (2H, m), 1.87 (3H, s), 1.89-1.81 (2H, m), 1.54-1.47 (2H, m) ppm; high resolution mass spectrometry (ES+) m/z 482.2202 [(M+H)$^+$; calculated for $C_{28}H_{28}N_5O_3$: 482.2187].

The following compounds were prepared according to the general procedure described in Example 716, substituting the appropriate acid chloride for acetyl chloride. The starting materials are either commercially available, known in the literature or may be prepared from commercially available reagents using conventional reactions well known in the art.

(IEE)

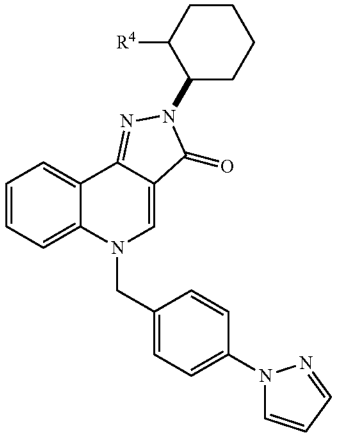

| Ex. | $R^4$ | HRMS/LRMS |
|---|---|---|
| 717 | 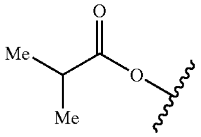 [SMILES: *OC(=O)C(C)C] | $C_{30}H_{32}N_5O_3$[M + H] calc. 510.2500 obs. 510.2521 |
| 718 | 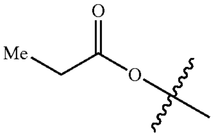 [SMILES: *OC(=O)CC] | $C_{29}H_{30}N_5O_3$[M + H] calc. 496.2343 obs. 496.2331 |
| 719 | 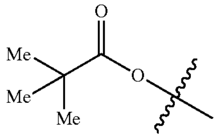 [SMILES: *OC(=O)C(C)(C)C] | $C_{31}H_{34}N_5O_3$[M + H] calc. 524.2656 obs. 524.2669 |

Example 720

(±)-2-(2-Oxocyclohexyl)-5-{[4-(1H-pyrazol-1-yl)phenyl]methyl}-2,5-dihydro-3H-pyrazolo[4,3-c]quinolin-3-one

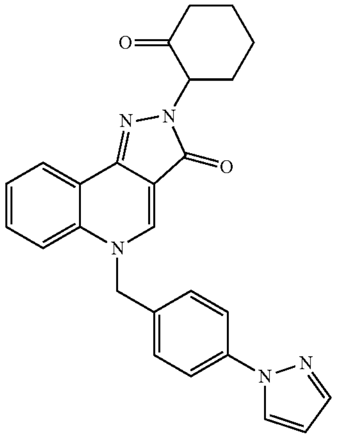 [SMILES: O=C1CCCCC1n1nc2c3ccccc3n(Cc3ccc(-n4cccn4)cc3)cc-2c1=O]

(±)-2-(trans-2-Hydroxycyclohexyl)-5-{([4-(1H-pyrazol-1-yl)phenyl]methyl}-2,5-dihydro-3H-pyrazolo[4,3-c]quinolin-3-one (Example 508, 0.40 g, 0.92 mmol), 1,1,1-tris(acetyloxy)-1,1-dihydro-1,2-benziodoxol-3-(1H)-one (Dess-Martin periodinane, 0.49 g, 1.1 mmol, 1.25 equiv), sodium bicarbonate (0.38 g, 4.6 mmol, 5 equiv) and water (0.021 mL, 1.1 mmol, 1.25 equiv) were combined in dichloromethane (9 mL) and stirred vigorously for 3 hours. Additional Dess-Martin periodinane (0.20 g, 0.46 mmol, 0.5 equiv) was added and the mixture was stirred for an additional 1 hour. The mixture was treated with a 1:1 mixture of sodium bicarbonate:sodium thiosulfate (15 mL, aqueous saturated) and stirred for 30 minutes at ambient temperature. The mixture was poured into water and extracted with ethyl acetate (3×40 mL). The combined organic extracts were dried with sodium sulfate, filtered and concentrated in vacuo. The residue was purified by silica gel gradient chromatography (100:0 to 80:20; ethyl acetate:methanol), providing the titled compound: $^{1}$H-NMR (400 MHz, $CDCl_3$) δ 8.39 (1H, s), 8.37-8.34 (1H, m), 7.90 (1H, d, J=2.6 Hz), 7.72 (1H, d, J=1.6 Hz), 7.70 (2H, d, J=8.6 Hz), 7.45-7.38 (3H, m), 7.28 (2H, d, J=8.6 Hz), 6.46 (1H, dd, J=2.4, 1.9 Hz), 5.48 (1H, d, J=16.7 Hz), 5.43 (1H, d, J=16.7 Hz), 5.19 (1H, dd, J=13.0, 6.1 Hz), 2.67-2.57 (2H, m), 2.51 (1H, td, J=13.5, 6.3 Hz), 2.37 (1H, ddd, J=12.9, 5.9, 3.0 Hz), 2.19-2.10 (2H, m), 1.97-1.83 (2H, m) ppm; high resolution mass spectrometry (ES+) m/z 438.1932 [(M+H)$^+$; calculated for $C_{26}H_{24}N_5O_2$: 438.1925].

Example 721

(±)-2-[trans-2-(Methylamino)cyclohexyl]-5-{[4-(1H-pyrazol-1-yl)phenyl]methyl}-2,5-dihydro-3H-pyrazolo[4,3-c]quinolin-3-one

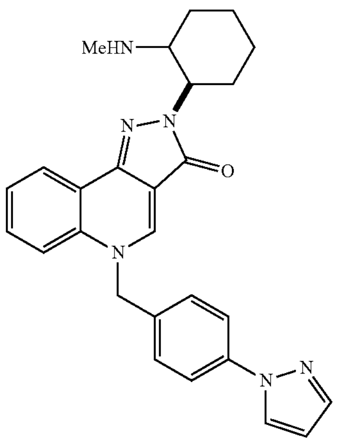 [SMILES: CNC1CCCC[C@H]1n1nc2c3ccccc3n(Cc3ccc(-n4cccn4)cc3)cc-2c1=O]

(±)-2-(2-Oxocyclohexyl)-5-{[4-(1H-pyrazol-1-yl)phenyl]methyl}-2,5-dihydro-3H-pyrazolo[4,3-c]quinolin-3-one (Example 720, 45 mg, 0.10 mmol) was dissolved in 1,2-dichloroethane (3 mL) and treated with acetic acid (0.029 mL, 0.51 mmol, 5 equiv) and methylamine (0.057 mL, 0.11 mmol, 1.1 equiv). After stirring for 20 minutes at ambient temperature, sodium triacetoxyborohydride (30 mg, 0.14 mmol, 1.4 equiv) was added and the mixture was vigorously stirred for 4 hours. The mixture was treated with methanol (1 mL), poured into water (15 mL) and extracted once with ethyl acetate (20 mL). The organic layer was discarded and the aqueous layer was treated with sodium bicarbonate (15 mL, aqueous saturated) and extracted with ethyl acetate (2×30 mL). The combined organic extracts were dried with sodium sulfate, filtered and concentrated in vacuo, providing the titled compound: $^{1}$H-NMR (400 MHz, $CDCl_3$) δ 8.45 (1H, s), 8.41-8.38 (1H, m), 7.89 (1H, d, J=2.5 Hz), 7.71 (1H, d, J=1.6 Hz), 7.70 (2H, d, J=8.5 Hz), 7.49-7.43 (2H, m), 7.41-7.38 (1H, m), 7.27 (2H, d, J=8.5 Hz), 6.47-6.46 (1H, m), 5.50 (1H, d, J=16.5 Hz), 5.44 (1H, d, J=16.5 Hz), 4.75 (1H, dt, J=10.5, 3.8 Hz), 3.02 (1H, m), 2.49-2.33 (1H, m), 2.37 (3H, s), 2.14-2.09 (1H, m), 1.98-1.92 (1H, m), 1.87-1.80 (1H, m), 1.70-1.59 (2H, m), 1.57-1.42 (2H, m) ppm; high resolution mass spectrometry (ES+) m/z 453.2387 [(M+H)$^+$; calculated for $C_{27}H_{29}N_6O$: 453.2397].

Example 722

5-[(4-Iodophenyl)methyl]-9-(methyloxy)-2-(2-methylphenyl)-2,5-dihydro-3H-pyrazolo[4,3-c]quinolin-3-one

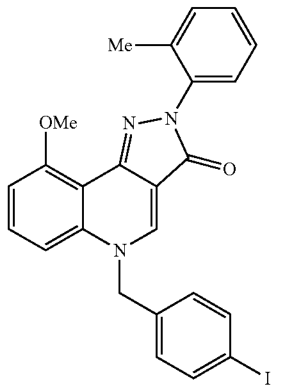 [SMILES: COc1cccc2c1c1nn(-c3ccccc3C)c(=O)c-1cn2Cc1ccc(I)cc1]

Step 1: Preparation of ethyl 3-[2-fluoro-6-(methyloxy)phenyl]-3-oxopropanoate

Potassium ethylmalonate (2.1 g, 12 mmol, 2.1 equiv) was suspended in acetonitrile (20 mL), cooled to 5° C. and treated with successively with triethylamine (2.6 mL, 18 mmol, 3.2 equiv) and magnesium(II) chloride (1.4 g, 14 mmol, 2.5 equiv). The ice bath was removed and the mixture was warmed and stirred at ambient temperature for 2.5 hours. An acetonitrile solution (5 mL) of 2-fluoro-6-(methyloxy)benzoyl chloride (1.1 g, 5.8 mmol) was added and the mixture was stirred for 2 hours at ambient temperature. The mixture was concentrated in vacuo and the residue was suspended in toluene (50 mL), cooled to 0° C. and treated with hydrochloric acid (20 mL, 12 N aqueous) with vigorous stirring. The ice bath was removed after 10 minutes and the mixture was warmed to ambient temperature and stirred for an additional 15 minutes. The mixture was poured into water (50 mL) and extracted with ethyl acetate (3×75 mL). The combined organic extracts were dried with sodium sulfate, filtered and concentrated in vacuo. The residue was purified by silica gel gradient chromatography (100:0 to 1:1; hexanes:ethyl acetate), providing the titled compound.

Step 2: Preparation of 5-[(4-iodophenyl)methyl]-9-(methyloxy)-2-(2-methylphenyl)-2,5-dihydro-3H-pyrazolo[4,3-C]quinolin-3-one Using the procedures described in Example 107, substituting 2-methylphenyl hydrazine for 2-fluorophenyl hydrazine (Step 1), and ethyl 3-[2-fluoro-6-(methyloxy)phenyl]-3-oxopropanoate for ethyl 3-(2-fluorophenyl)-3-oxopropanoate (Step 1), and, substituting 1-(4-iodophenyl)methanamine for 1-[4-(1H-pyrazol-1-yl)phenyl]methanamine (Step 3), the titled compound was obtained: $^1$H-NMR (400 MHz, $CDCl_3$) δ 8.35 (1H, s), 7.71 (2H, d, J=8.5 Hz), 7.53-7.51 (1H, m), 7.41 (1H, t, J=8.5 Hz), 7.34-7.26 (4H, m), 6.97-6.92 (4H, m), 5.36 (2H, s), 4.04 (3H, s), 2.37 (3H, s) ppm; high resolution mass spectrometry (ES+) m/z 522.0678 $[(M+H)^+]$; calculated for $C_{25}H_{21}IN_3O_2$: 522.0673].

Example 723

9-(Methyloxy)-2-(2-methylphenyl)-5-{[4-(1H-pyrazol-1-yl)phenyl]methyl}-2,5-dihydro-3H-pyrazolo[4,3-c]quinolin-3-one

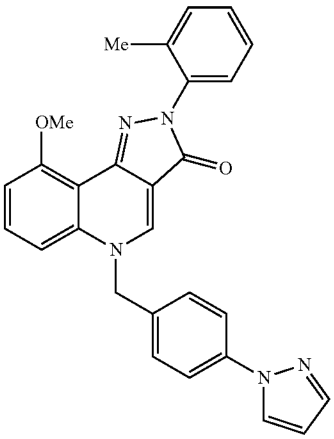 [SMILES: COc1cccc2c1c1nn(-c3ccccc3C)c(=O)c-1cn2Cc1ccc(-n2cccn2)cc1]

Using the procedure described in Example 54, substituting 5-[(4-iodophenyl)methyl]-9-(methyloxy)-2-(2-methylphenyl)-2,5-dihydro-3H-pyrazolo[4,3-c]quinolin-3-one (Example 722) for 6,9-difluoro-2-(1-iodophenyl)-5-{[4-(1H-pyrazol-1-yl)phenyl]methyl}-2,5-dihydro-3H-pyrazolo[4,3-c]quinolin-3-one (Example 53), the titled compound was obtained: $^1$H-NMR (400 MHz, $CDCl_3$) δ 8.38 (1H, s), 7.88 (1H, d, J=2.5 Hz), 7.70-7.67 (3H, m), 7.51-7.49 (1H, m), 7.37 (1H, t, J=8.5 Hz), 7.29-7.23 (6H, m), 6.99 (1H, d, J=8.8 Hz), 6.93 (1H, d, J=8.4 Hz), 6.45-6.43 (1H, m), 5.42 (2H, s), 4.01 (3H, s), 2.34 (3H, s) ppm; high resolution mass spectrometry (ES+) m/z 462.1923 $[(M+H)^+]$; calculated for $C_{28}H_{24}N_5O_2$: 462.1925].

Example 724

9-Hydroxy-2-(2-methylphenyl)-5-{[4-(1H-pyrazol-1-yl)phenyl]methyl}-2,5-dihydro-3H-pyrazolo[4,3-c]quinolin-3-one

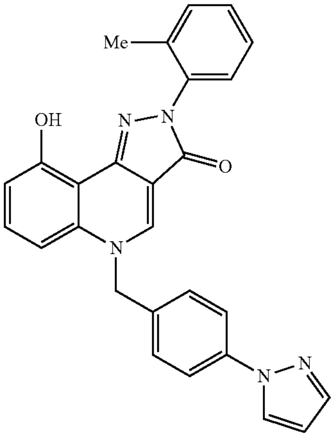 [SMILES: Cc1ccccc1-n1nc2c3c(O)cccc3n(Cc3ccc(-n4cccn4)cc3)cc-2c1=O]

9-(Methyloxy)-2-(2-methylphenyl)-5-{[4-(1H-pyrazol-1-yl)phenyl]methyl}-2,5-dihydro-3H-pyrazolo[4,3-c]quinolin-3-one (Example 723, 37 mg, 0.80 mmol) was dissolved in dichloromethane (5 mL) and cooled to −78° C. Boron tribromide (0.24 mL, 1 M dichloromethane solution, 0.24 mmol, 3 equiv) was added and the mixture was stirred for 3 hours at −78° C. The mixture was then warmed to −40° C. and stirred for an additional 30 minutes. The acetonitrile/dry ice bath was removed, the mixture was warmed to ambient temperature and stirred for 30 minutes. Additional boron tribromide (0.24 mL, 1 M dichloromethane solution, 0.24 mmol, 3 equiv) was added and the mixture was stirred for an additional 45 minutes at ambient temperature. The mixture was treated with sodium bicarbonate (6 mL, aqueous saturated) slowly over 5 minutes, stirred for 30 minutes at ambient temperature and then poured into sodium bicarbonate (50 mL, aqueous saturated). The aqueous layer was extracted with dichloromethane (3×100 mL) and the combined organic extracts were dried with sodium sulfate, filtered and concentrated in vacuo. The residue was purified by silica gel gradient chromatograph (100:0 to 90:10 dichloromethane:methanol), providing the titled compound: $^1$H-NMR (400 MHz, $CDCl_3$) δ 9.71 (1H, s), 8.51 (1H, s), 7.91 (1H, d, J=1.9 Hz), 7.74-7.72 (3H, m), 7.47-7.45 (1H, m), 7.39 (1H, t, J=8.5 Hz), 7.36-7.30 (5H, m), 7.01 (1H, d, J=8.3 Hz), 6.94 (1H, d, J=8.6 Hz), 6.48 (1H, m), 5.46 (2H, s), 2.35 (3H, s) ppm; high resolution mass spectrometry (ES+) m/z 448.1785 $[(M+H)^+]$; calculated for $C_{27}H_{22}N_5O_2$: 448.1768].

Example 725

2-(2-Methylphenyl)-3-oxo-5-{[4-(1H-pyrazol-1-yl)phenyl]methyl}-3,5-dihydro-2H-pyrazolo[4,3-c]quinolin-9-yl trifluoromethanesulfonate

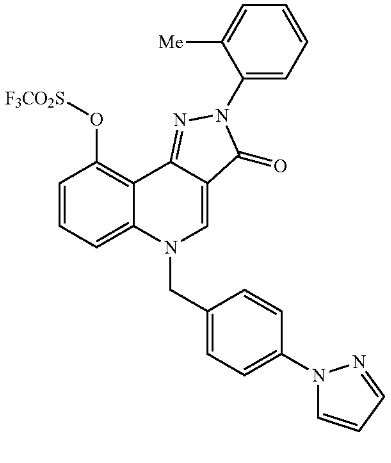

9-Hydroxy-2-(2-methylphenyl)-5-{[4-(1H-pyrazol-1-yl)phenyl]methyl}-2,5-dihydro-3H-pyrazolo[4,3-c]quinolin-3-one (Example 724, 0.10 g, 0.23 mmol) was dissolved in pyridine (3 mL), cooled to 0° C. and treated with trifluoromethanesulfonic anhydride (0.076 mL, 0.45 mmol, 2 equiv). The mixture was slowly warmed to ambient temperature and after 18 hours, the mixture was poured into sodium bicarbonate (50 mL, aqueous saturated) and extracted with dichloromethane (2×25 mL). The combined organic extracts were washed with hydrochloric acid (3×50 mL, 1 N aqueous), dried with sodium sulfate, filtered and concentrated in vacuo. The residue was purified by silica gel gradient chromatography (100:0 to 0:100; hexanes:ethyl acetate containing 5% methanol), providing the titled compound: $^1$H-NMR (400 MHz, $CDCl_3$) δ 8.44 (1H, s), 7.93 (1H, d, J=2.6 Hz), 7.77 (2H, d, J=8.6 Hz), 7.74 (1H, d, J=1.6 Hz), 7.54-7.45 (3H, m), 7.41-7.22 (6H, m), 6.50 (1H, dd, J=2.4, 1.8 Hz), 5.48 (2H, s), 2.37 (3H, s) ppm; high resolution mass spectrometry (ES+) m/z 580.1284 [$(M+H)^+$; calculated for $C_{28}H_{21}F_3N_5O_4S$: 580.1261].

Example 726

9-Methyl-2-(2-methylphenyl)-5-{[4-(1H-pyrazol-1-yl)phenyl]methyl}-2,5-dihydro-3H-pyrazolo[4,3-c]quinolin-3-one

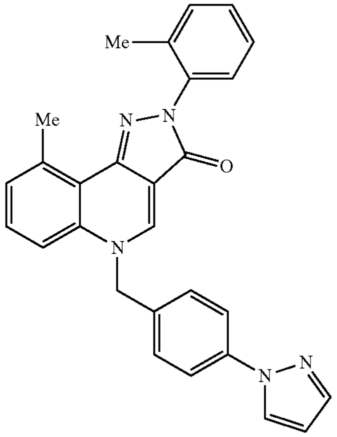 [SMILES: Cc1ccccc1-n1nc2c3c(C)cccc3n(Cc3ccc(-n4cccn4)cc3)cc-2c1=O]

Using the procedures described in Example 668, substituting 2-(2-methylphenyl)-3-oxo-5-{[4-(1H-pyrazol-1-yl)phenyl]methyl}-3,5-dihydro-2H-pyrazolo[4,3-c]quinolin-9-yl trifluoromethanesulfonate (Example 725) for 2-(2-bromo-6-fluorophenyl)-5-{[2-fluoro-4-(1H-pyrazol-1-yl)phenyl]methyl}-2,5-dihydro-3H-pyrazolo[4,3-c]quinolin-3-one (Example 666), the titled compound was obtained: $^1$H-NMR (400 MHz, $CDCl_3$) δ 8.52 (1H, s), 7.88 (1H, d, J=2.7 Hz), 7.72 (1H, d, J=1.7 Hz), 7.69 (2H, d, J=8.5 Hz), 7.52-7.48 (1H, m), 736-7.25 (8H, m), 6.47-6.46 (1H, m), 5.47 (2H, s), 2.94 (3H, s), 2.36 (3H, s) ppm; high resolution mass spectrometry (ES+) m/z 446.2000 [$(M+H)^+$; calculated for $O_{28}H_{24}N_5O$: 446.1975].

Example 727

2-(2-Methylphenyl)-3-oxo-5-{[4-(1H-pyrazol-1-yl)phenyl]methyl}-3,5-dihydro-2H-pyrazolo[4,3-c]quinolin-9-yl acetate

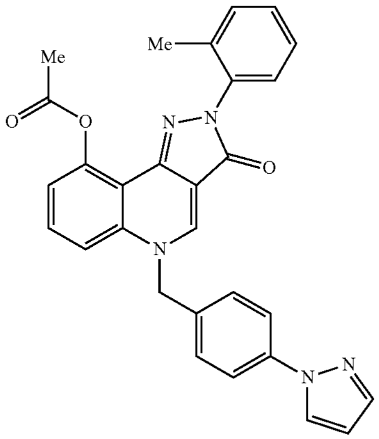 [SMILES: CC(=O)Oc1cccc2c1c1nn(-c3ccccc3C)c(=O)c-1cn2Cc1ccc(-n2cccn2)cc1]

9-Hydroxy-2-(2-methylphenyl)-5-{[4-(1H-pyrazol-1-yl)phenyl]methyl}-2,5-dihydro-3H-pyrazolo[4,3-c]quinolin-3-one (Example 724, 56 mg, 0.12 mmol) was dissolved in dichloromethane (2.5 mL), treated with N,N-dimethyl-4-aminopyridine (1.5 mg, 0.013 mmol, 0.1 equiv) and N,N-diisopropylethylamine (0.033 mL, 0.19 mmol, 1.5 equiv) and cooled to 0° C. To the mixture was added acetyl chloride (0.012 mL, 0.17 mmol, 1.4 equiv), and after 15 minutes the mixture was warmed to ambient temperature. After 15 minutes at ambient temperature, the mixture was poured into sodium bicarbonate (5 mL, aqueous saturated) and extracted with dichloromethane (2×15 mL). The combined organic extracts were washed with hydrochloric acid (2×15 mL, 1 N aqueous) and brine (1×10 mL), dried with sodium sulfate, filtered and concentrated in vacuo. The residue was purified by silica gel gradient chromatography (100:0 to 0:100; hexanes:ethyl acetate containing 5% methanol), providing the titled compound: $^1$H-NMR (400 MHz, $CDCl_3$) δ 8.47 (1H, s), 7.91 (1H, d, J=2.6 Hz), 7.73 (1H, d, J=1.7 Hz), 7.72 (2H, d, J=8.6 Hz), 7.47 (1H, t, J=8.2 Hz), 7.44-7.42 (1H, m), 7.34-7.26 (6H, m), 7.17 (1H, d, J=7.9 Hz), 6.47 (1H, dd, J=2.3, 1.9 Hz), 5.45 (2H, s), 2.33 (3H, s), 2.32 (3H, s) ppm; high resolution mass spectrometry (ES+) m/z 490.1900 [$(M+H)^+$; calculated for $C_{29}H_{24}N_5O_3$: 490.1874].

Example 728

9-Hydroxy-5-[(iodophenyl)methyl]-2-(2-methylphenyl)-2,5-dihydro-3H-pyrazolo[4,3-c]quinolin-3-one

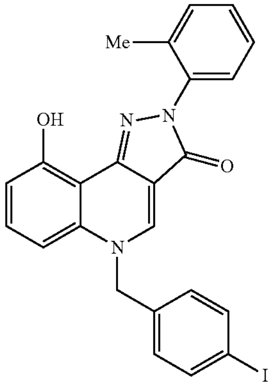 [SMILES: Cc1ccccc1-n1nc2c3c(O)cccc3n(Cc3ccc(I)cc3)cc-2c1=O]

Using the procedure described in Example 724, substituting 5-[(4-iodophenyl)methyl]-9-(methyloxy)-2-(2-methylphenyl)-2,5-dihydro-3H-pyrazolo[4,3-c]quinolin-3-one (Example 722) for 9-(methyloxy)-2-(2-methylphenyl)-5-{[4-(1H-pyrazol-1-yl)phenyl]methyl}-2,5-dihydro-3H-pyrazolo[4,3-c]quinolin-3-one (Example 723), the titled compound was obtained: $^1$H-NMR (400 MHz, $CDCl_3$) δ 9.69 (1H, s), 8.50 (1H, s), 7.70 (2H, d, J=8.4 Hz), 7.45-7.43 (1H, m), 7.38 (1H, t, J=8.5 Hz), 7.35-7.29 (3H, m), 7.00 (1H, d, J=8.2 Hz), 6.94 (2H, d, J=8.2 Hz), 6.87 (1H, d, J=8.6 Hz), 5.37 (2H, s), 2.33 (3H, s) ppm; high resolution mass spectrometry (ES+) m/z 508.0520 [$(M+H)^+$; calculated for $C_{24}H_{19}IN_3O_2$: 508.0516].

Example 729

9-Hydroxy-2-(2-methylphenyl)-5-{[4-(6-methylpyridin-3-yl)phenyl]methyl}-2,5-dihydro-3H-pyrazolo[4,3-c]quinolin-3-one

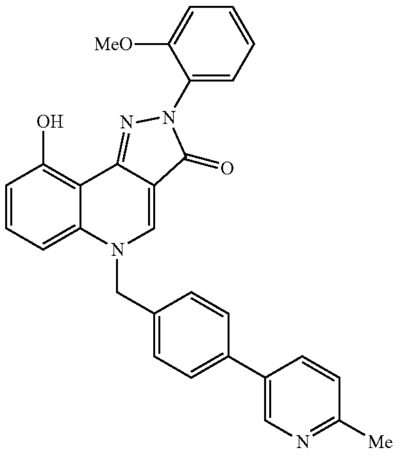 [SMILES: COc1ccccc1-n1nc2c3c(O)cccc3n(Cc3ccc(-c4ccc(C)nc4)cc3)cc-2c1=O]

9-Hydroxy-5-[(iodophenyl)methyl]-2-(2-methylphenyl)-2,5-dihydro-3H-pyrazolo[4,3-c]quinolin-3-one (Example 728, 0.28 g, 0.56 mmol) was dissolved in tetrahydrofuran (5 mL) and treated with bis(tri-tert-butylphosphine)palladium (0) (57 mg, 0.11 mmol, 0.2 equiv), copper(I) chloride (55 mg, 0.56 mmol, 1 equiv), 2-methyl-5-pyridinylboronic acid (0.15 g, 1.1 mmol, 2 equiv) and an aqueous solution (2 mL) of cesium carbonate (0.45 g, 1.4 mmol, 2.5 equiv). The mixture was placed into a preheated oil bath at 70° C. for 2 hours, charged with additional boronic acid 2-methyl-5-pyridinylboronic acid (75 mg, 0.56 mmol, 1 equiv) and bis(tri-tert-butylphosphine)palladium(0) (27 mg, 0.056 mmol, 0.1 equiv). The mixture was heated for an additional 3 hours at 70° C., cooled to ambient temperature, poured into sodium bicarbonate (50 mL, aqueous saturated) and water (100 mL) and extracted with ethyl acetate (2×75 mL). The combined organic extracts were dried with sodium sulfate, filtered and concentrated in vacuo. The residue was purified by silica gel gradient chromatography (100:0 to 0:100; hexanes:ethyl acetate containing 10% methanol), providing the titled compound as a light yellow solid: $^1$H-NMR (400 MHz, $CDCl_3$) δ 9.72 (1H, br s), 8.70 (1H, d, J=2.1 Hz), 8.45 (1H, s), 7.74 (1H, dd, J=8.0, 2.3 Hz), 7.58 (2H, d, J=8.0 Hz), 7.50-7.21 (4H, br m), 7.46 (1H, br m), 7.33 (2H, d, J=8.2 Hz), 7.23 (1H, d, J=8.0 Hz), 7.01 (1H, br s), 5.46 (2H, s), 2.60 (3H, s), 2.35 (3H, s) ppm; high resolution mass spectrometry (ES+) m/z 473.1985 [$(M+H)^+$; calculated for $C_{30}H_{25}N_4O_2$: 473.1972].

Example 730

9-(Methyloxy)-2-(2-methylphenyl)-5-{[4-(6-methylpyridin-3-yl)phenyl]methyl}-2,5-dihydro-3H-pyrazolo[4,3-c]quinolin-3-one

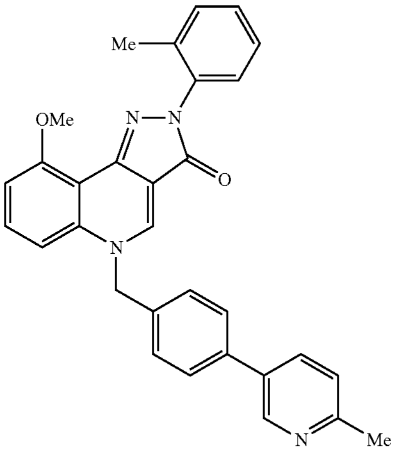 [SMILES: COc1cccc2c1c1nn(-c3ccccc3C)c(=O)c-1cn2Cc1ccc(-c2ccc(C)nc2)cc1]

Using the procedure described in Example 729, substituting 5-[(4-iodophenyl)methyl]-9-(methyloxy)-2-(2-methylphenyl)-2,5-dihydro-3H-pyrazolo[4,3-c]quinolin-3-one (Example 722) for 9-hydroxy-5-[(iodophenyl)methyl]-2-(2-methylphenyl)-2,5-dihydro-3H-pyrazolo[4,3-c]quinolin-3-one (Example 728), the titled compound was obtained: $^1$H-NMR (400 MHz, $CDCl_3$) δ 830 (1H, d, J=2.2 Hz), 8.47 (1H, s), 7.74 (1H, dd, J=8.1, 2.4 Hz), 7.56 (2H, d, J=8.3 Hz), 7.53-7.51 (1H, m), 7.43 (1H, t, J=8.5 Hz), 7.32-7.26 (5H, m), 7.22 (1H, d, J=8.1 Hz), 7.05 (1H, d, 8.5 Hz), 6.96 (1H, d, J=8.2 Hz), 5.47 (2H, s), 4.04 (3H, s), 2.60 (3H, s), 2.37 (3H, s) ppm; high resolution mass spectrometry (ES+) m/z 487.2142 [(M+H)$^+$; calculated for $C_{31}H_{27}N_4O_2$: 487.2129].

Example 731

2-[5-(Hydroxymethyl)-1-methyl-1H-imidazol-4-yl]-5-{[4-(1H-pyrazol-1-yl)phenyl]methyl}-2,5-dihydro-3H-pyrazolo[4,3-c]quinolin-3-one

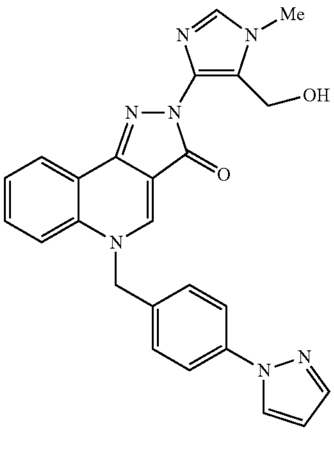 [SMILES: Cn1cnc(-n2nc3c4ccccc4n(Cc4ccc(-n5cccn5)cc4)cc-3c2=O)c1CO]

1-Methyl-4-(3-oxo-5-{[4-(1H-pyrazol-1-yl)phenyl]methyl}-3,5-dihydro-2H-pyrazolo[4,3-c]quinolin-2-yl)-1H-imidazole-5-carbaldehyde (Example 555, 50 mg, 0.11 mmol) was dissolved in tetrahydrofuran (2 mL) and dichloromethane (15 mL), cooled to 0° C. and treated with sodium cyanoborohydride (0.033 mL, 1 M tetrahydrofuran solution, 0.033 mmol, 0.3 equiv). After stirring for 5 minutes at 0° C., the mixture was warmed to ambient temperature and stirred for 1 hour. Additional sodium cyanoborohydride (0.033 mL, 1 M tetrahydrofuran solution, 0.033 mmol, 0.3 equiv) was added and after 1 hour, the mixture was concentrated in vacuo. The residue was purified by preparative reverse phase HPLC (85:15 to 40:60; water containing 0.5% trifluoroacetic acid:acetonitrile containing 0.5% trifluoroacetic acid). The appropriate fractions were concentrated in vacuo, providing the titled compound: $^1$H-NMR (400 MHz, d$^6$-DMSO) δ 9.04 (1H, br s), 8.37 (1H, br d, J=4.7 Hz), 8.20 (1H, m), 7.85 (1H, d, J=8.8 Hz), 7.77 (2H, d, J=8.3 Hz), 7.74-7.65 (4H, m), 7.61 (1H, br t, J=6.7 Hz), 7.44 (2H, d, J=7.6 Hz), 6.51 (1H, m), 5.82 (2H, s), 4.00 (2H, s) 2.65 (3H, s) ppm; high resolution mass spectrometry (ES+) m/z 452.1842 [(M+H)$^+$; calculated for $C_{25}H_{22}N_7O_2$: 452.1829].

Example 732

2-{1-Methyl-5-[(methylamino)methyl]-1H-imidazol-4-yl]-5-{[4-(1H-pyrazol-1-yl)phenyl]methyl}-2,5-dihydro-3H-pyrazolo[4,3-c]quinolin-3-one

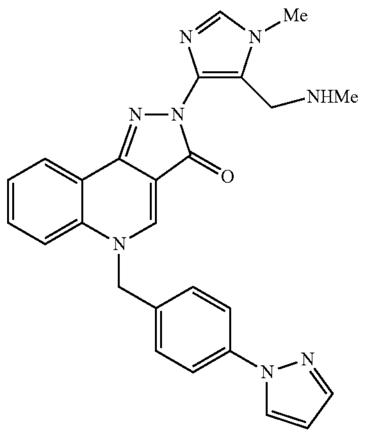 [SMILES: CNCc1c(-n2nc3c4ccccc4n(Cc4ccc(-n5cccn5)cc4)cc-3c2=O)ncn1C]

Using the procedure described in Example 721, substituting 1-methyl-4-(3-oxo-5-{[4-(1H-pyrazol-1-yl)phenyl]methyl}-3,5-dihydro-2H-pyrazolo[4,3-c]quinolin-2-yl)-1H-imidazole-5-carbaldehyde (Example 555) for (±)-2-(2-oxocyclohexyl)-5-{[4-(1H-pyrazol-1-yl)phenyl]methyl}-2,5-dihydro-3H-pyrazolo[4,3-c]quinolin-3-one (Example 720), the titled compound was obtained: $^1$H-NMR (400 MHz, d$^6$-DMSO) δ 9.25 (1H, br s), 8.93 (2H, br s), 8.47 (1H, d, J=2.4 Hz), 8.27 (1H, br s), 7.86-7.82 (3H, m), 7.73 (1H, d, J=1.6 Hz), 7.68 (1H, t, J=7.5 Hz), 7.63-7.59 (1H, m), 7.45 (2H, d, J=8.5 Hz), 6.53 (1H, dd, J=2.4, 1.8 Hz), 5.84 (2H, s), 4.27 (2H, m), 3.79 (3H, s), 2.67 (3H, s) ppm; high resolution mass spectrometry (ES+) m/z 465.2154 [(M+H)$^+$; calculated for $C_{26}H_{25}N_5O$: 465.2146].

Example 733

(±)-8-Fluoro-2-(3-fluoro-4-methylpyridin-2-yl)-5-trans-2-[(3-fluoro-4-methylpyridin-2-yl)amino]cyclohexy}-9-({[4-(1H-pyrazol-1-yl)phenyl]methyl}amino)-2,5-dihydro-3H-pyrazolo[4,3-c]quinolin-3-one

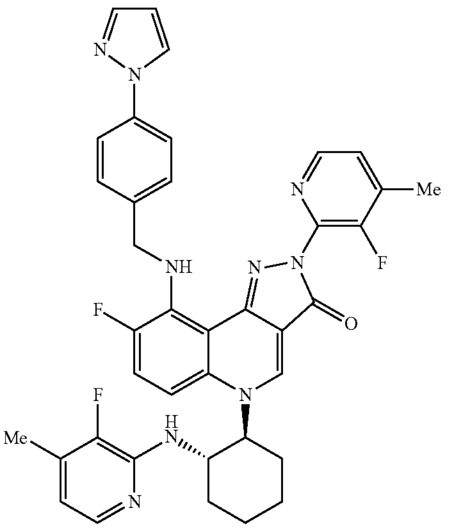 [SMILES: Cc1ccnc(N[C@H]2CCCC[C@@H]2n2cc3c(=O)n(-c4nccc(C)c4F)nc-3c3c(NCc4ccc(-n5cccn5)cc4)c(F)ccc32)c1F]

6,9-Difluoro-5-{[4-(1H-pyrazol-1-yl)phenyl]methyl}-2,5-dihydro-3H-pyrazolo[4,3-c]quinolin-3-one [(See Example 24 for preparation) 70 mg, 0.19 mmol], 2-bromo-3-fluoro-4-methylpyridine (56 mg, 0.30 mmol, 1.6 equiv), copper(I) iodide (35 mg, 0.19 mmol, 1 equiv), (±)-trans-1,2-diaminocyclohexane (54 mg, 0.47 mmol, 2.55 equiv) and potassium carbonate (0.15 g, 1.1 mmol, 6 equiv) were combined in dimethylsulfoxide (3 mL), the vessel was sealed and irradiated in a μW reactor (high setting) for 90 minutes. The mixture was cooled to ambient temperature, filtered and purified by preparative reverse phase HPLC (90:10 to 5:95: water containing 0.5% trifluoroacetic acid:acetonitrile containing 0.5% trifluoroacetic acid), providing the titled compound: $^1$H-NMR (400 MHz, $CDCl_3$) δ 8.69 (1H, s), 8.35 (1H, t, J=5.6 Hz), 8.24 (1H, d, J=4.8 Hz), 7.85 (1H, d, J=2.5 Hz), 7.69 (1H, d, J=1.7 Hz), 7.64 (1H, d, J=5.2 Hz), 7.57 (2H, d, J=8.6 Hz), 7.46 (2H, d, J=8.6 Hz), 7.14-7.07 (2H, m), 6.81 (1H, dd, J=9.6, 3.2 Hz), 6.43-6.42 (1H, m), 6.27 (1H, t, J=5.2 Hz), 4.82-4.66 (3H, m), 4.52 (1H, td, J=11.5, 3.4 Hz), 4.27 (1H, dd, J=9.2, 2.5 Hz), 3.48 (1H, br s), 2.38-2.31 (1N, m), 2.36 (3H, d, J=1.4 Hz), 2.24 (1H, br d, J=13.2 Hz), 2.04 (3H, d, J=1.6 Hz), 2.00-1.92 (2H, m), 1.88-1.76 (2H, m), 1.65-1.50 (1H, m) ppm; high resolution mass spectrometry (ES+) m/z 690.2930 $[(M+H)^+$; calculated for $C_{38}H_{35}F_3N_9O$: 690.2911].

Example 734

8-Fluoro-5-{[4-(methyloxy)phenyl]methyl}-2-(2-methylphenyl)-9-({[4-(1H-pyrazol-1-yl)phenyl]methyl}amino)-2,5-dihydro-3H-pyrazolo[4,3-c]quinolin-3-one

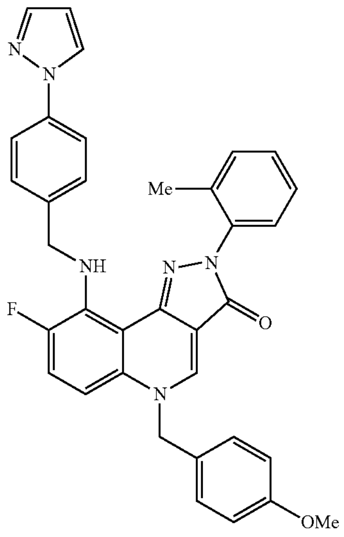 [SMILES: COc1ccc(Cn2cc3c(=O)n(-c4ccccc4C)nc-3c3c(NCc4ccc(-n5cccn5)cc4)c(F)ccc32)cc1]

6,9-Difluoro-2-(2-methylphenyl)-5-{[4-(1H-pyrazol-1-yl)phenyl]methyl}-2,5-dihydro-3H-pyrazolo[4,3-c]quinolin-3-one (Example 29, 12 mg, 0.026 mmol), 1-[4-(methyloxy)phenyl]methanamine (5.3 mg, 0.039 mmol, 1.5 equiv) and cesium carbonate (12 mg, 0.039 mmol, 1.5 equiv) were combined in dimethylsulfoxide (2 mL) and placed into an oil bath preheated at 70° C. for 1 hour. The mixture was cooled to ambient temperature, poured into sodium bicarbonate (50 mL, aqueous saturated) and extracted with ethyl acetate (2×75 mL). The combined organic extracts were dried with sodium sulfate, filtered and concentrated in vacuo. The residue was purified by preparative HPLC (80:20 to 5:95; water containing 0.5% trifluoroacetic acid:acetonitrile containing 0.5% trifluoroacetic acid). The appropriate fractions were poured into sodium bicarbonate (75 mL, aqueous saturated) and extracted with ethyl acetate (1×100 mL). The organic extract was dried with sodium sulfate, filtered and concentrated in vacuo, providing the titled compound as a yellow foam: $^1$H-NMR (4001 MHz, $CDCl_3$) δ 8.35 (1H, s), 8.35-8.29 (1H, m), 7.85 (1H, d, J=2.5 Hz), 7.69 (1H, d, J=1.6 Hz), 7.56 (2H, d, J=8.5 Hz), 7.45 (1H, dd, J=5.3, 4.1 Hz), 7.42 (2H, d, J=8.5 Hz), 7.33-7.27 (3H, m), 7.14 (2H, d, J=8.7 Hz), 7.05 (1H, dd, J=13.2, 9.0 Hz), 6.90 (2H, d, J=8.7 Hz), 6.68 (1H, dd, J=9.4, 3.4 Hz), 6.44-6.43 (1H, m), 5.29 (2H, s), 4.77 (2H, m), 3.80 (3H, s), 2.31 (3H, s) ppm; high resolution mass spectrometry (ES+) m/z 585.2417 $[(M+H)^+$; calculated for $C_{35}H_{30}FN_6O_2$: 585.2409].

Example 735

(±)-2-(2-Fluorophenyl)-5-{trans-2-[(3-fluoropyridin-2-yl)amino]cyclohexyl}-9-({[4-(1H-pyrazol-1-yl)phenyl]methyl}amino)-2,5-dihydro-3H-pyrazolo[4,3-c]quinolin-3-one

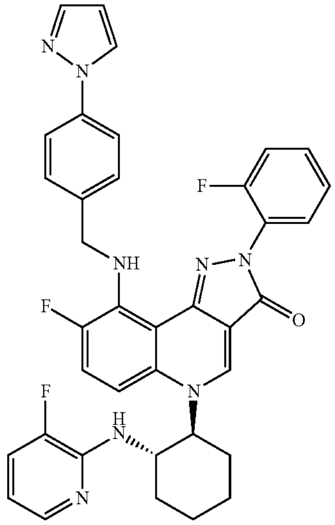 [SMILES: O=c1c2cn([C@H]3CCCC[C@@H]3Nc3ncccc3F)c3ccc(F)c(NCc4ccc(-n5cccn5)cc4)c3c-2nn1-c1ccccc1F]

Step 1: Preparation of (±)-1,1-dimethylethyl{trans-2-[(3-fluoropyridin-2-yl)amino]cyclohexyl}carbamate-methane (1:1)

2,3-Difluoropyridine (637 mg, 5.54 mmol) and (±)-trans-1,2-diaminocyclohexane (632 mg, 5.54 mmol, 1 equiv) were combined in N,N-dimethylformamide (5.5 mL) and placed into an oil bath preheated to 120° C. for 30 minutes. The mixture was cooled to ambient temperature and concentrated in vacuo. The residue was dissovled in dichloromethane (10 mL), treated with bis(1,1-dimethylethyl)dicarbonate (1.28 g, 5.54 mmol, 1 equiv) and stirred for 18 hours at ambient temperature. The mixture was concentrated in vacuo and the residue was purified by silica gel gradient chromatography (100:0 to 0:100; hexanes:ethyl acetate), providing the titled compound. Step 2: Preparation of (±)-trans-N-(3-fluoropyridin-2-yl)cyclohexane-1,2-diamine bishydrochloride: (±)-1,1-Dimethylethyl {trans-2[(3-fluoropyridin-2-yl)amino]cyclohexyl}carbamate-methane (1:1) (1.1 g, 3.5 mmol) was dissolved in methanol (10 mL) and ethyl acetate (30 mL), cooled to 0° C. and the mixture was saturated with gaseous hydrochloric acid. After aging for 1 hour, the mixture was concentrated in vacuo and the residue was concentrated from toluene (2×30 mL), providing the titled compound.

Step 3: (±)-2-(2-Fluorophenyl)-5-{trans-2-[(3-fluoropyridin-2-yl)amino]cyclohexyl}-9-({[4-(1H-pyrazol-1-yl)-phenyl]methyl}amino)-2,5-dihydro-3H-pyrazolo[4,3-c]quinolin-3-one 6,9-Difluoro-2-(2-fluorophenyl)-5-{[4-(1H pyrazol-1-yl)phenyl]methyl}-2,5-dihydro-3H-pyrazolo[4,3-c]quinolin-3-one (Example 28, 74 mg, 0.16 mmol), (±)-trans-N-(3-fluoropyridin-2-yl)cyclohexane-1,2-diamine bishydrochloride (43 mg, 0.19 mmol, 1.2 equiv) and potassium carbonate (0.22 g, 1.6 mmol, 10 equiv) were combined in degassed dimethylsulfoxide (5 mL) and placed into an oil bath preheated at 95° C. for 1 hour. Additional (±)-trans-N-(3-fluoropyridin-2-yl)cyclohexane-1,2-diamine bishydrochloride (0.10 g, 0.44 mmol, 2.3 equiv) and potassium carbonate (0.42 g, 3.0 mmol, 16 equiv) were added and the mixture was heated at 95° C. for an additional 2 hours. The mixture was cooled to ambient temperature, filtered and purified by preparative reverse phase HPLC (eluting 70:30 to 5:95; water containing 0.1% TFA: acetonitrile containing 0.1% TFA). The appropriate fractions were poured into sodium bicarbonate (100 mL, aqueous saturated) and extracted with ethyl acetate (1×50 mL). The organic extract was dried with sodium sulfate, filtered and concentrated in vacuo, providing the titled compound as a light yellowish-green solid: $^1$H-NMR (400 MHz, $CDCl_3$) δ 8.73 (1H, s), 8.32 (1H, br s), 7.85 (1H, d, J=2.8 Hz), 7.77 (1H, d, J=4.6 Hz), 7.69 (1H, d, J=1.8 Hz), 7.61-7.56 (3H, m), 7.44 (2H, d, J=8.6 Hz), 7.30-7.24 (1H, m), 7.21-7.15 (2H, m), 7.11 (1H, dd, J=13.6, 9.8 Hz), 6.90 (1H, ddd, J=11.2, 7.9, 1.3 Hz), 6.83 (1H, dd, J=9.4, 3.0 Hz), 6.44 (1H, dd, J=2.4, 1.9 Hz), 6.39 (1H, ddd, J=7.9, 5.0, 3.5 Hz), 4.77-4.67 (3H, m), 4.56 (1H, br t, J=10.2 Hz), 4.35 (1H, br m), 2.33 (1H, br d, J=10.9 Hz), 2.23 (1H, br d, J=12.8 Hz), 2.01-1.79 (3H, m), 1.67-1.51 (3H, m) ppm; high resolution mass spectrometry (ES+) m/z 661.2621 [$(M+H)^+$; calculated for $C_{37}H_{32}F_3N_8O$: 661.2646].

The following compounds were prepared according to the general procedure described in Example 735, substituting the appropriate amine for (±)-trans-N-(3-fluoropyridin-2-yl)cyclohexane-1,2-diamine bishydrochloride. The starting materials are either commercially available, known in the literature or may be prepared from commercially available reagents using conventional reactions well known in the art.

(IFF)

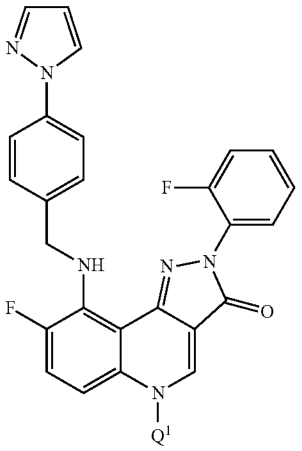

| Ex. | $Q^1R^3$ | HRMS/LRMS |
|---|---|---|
| 736 | 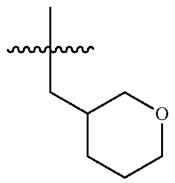 [SMILES: *CC1CCCOC1] | $C_{32}H_{29}F_2N_6O_2$[M + H] calc. 567.2315 obs. 567.2347 |

-continued
(IFF)
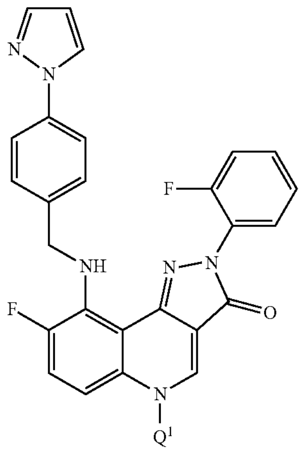
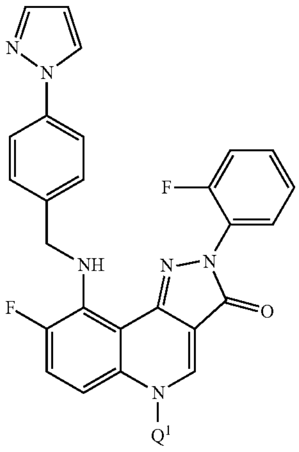
| Ex. | $Q^1R^3$ | HRMS/LRMS |
|---|---|---|
| 737 | 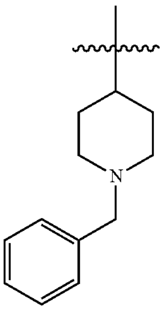 [SMILES: *C1CCN(Cc2ccccc2)CC1] | $C_{38}H_{34}F_2N_7O$[M + H] calc. 642.2787 obs. 642.2781 |
| 738 | 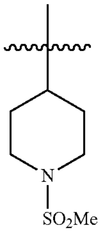 | $C_{32}H_{30}F_2N_7O_3S$[M + H calc. 567.2315 obs. 567.2347 |
| 739 | 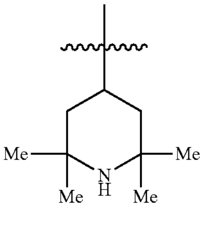 [SMILES: *C1CC(C)(C)NC(C)(C)C1] | $C_{35}H_{36}F_2N_7O$[M + H] calc. 608.2944 obs. 608.2969 |
| 740 | 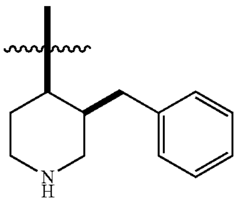 [SMILES: *[C@@H]1CCNC[C@@H]1Cc1ccccc1] | $C_{39}H_{36}F_2N_7O$[M + H] calc. 656.2933 obs. 656.2933 |
| 741 | 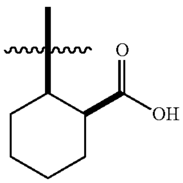 [SMILES: *[C@@H]1CCCC[C@@H]1C(=O)O] | $C_{33}H_{29}F_2N_6O_3$[M + H] calc. 595.2264 obs. 595.2237 |
| 742 | 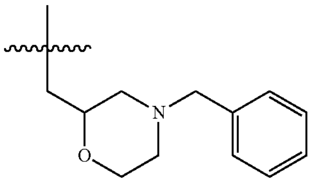 [SMILES: *CC1CN(Cc2ccccc2)CCO1] | $C_{38}H_{34}F_2N_7O_2$[M + H] calc. 658.2737 obs. 658.2752 |
Example 743
5-[(5-Bromopyridin-2-yl)methyl]-2-(2-methylphenyl)-2,5-dihydro-3H-pyrazolo[4,3-c]quinolin-3-one
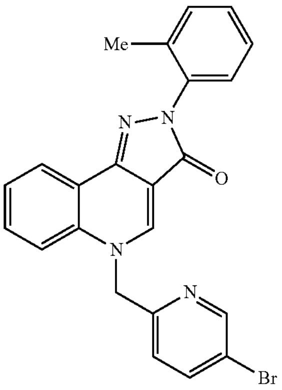 [SMILES: Cc1ccccc1-n1nc2c3ccccc3n(Cc3ccc(Br)cn3)cc-2c1=O]

Step 1: Preparation of (5-bromopyridin-2-yl)methyl methanesulfonate

Using the procedures described in Example 103, substituting 5-bromo-2-(hydroxymethyl)pyridine for (5-bromo-3-fluoropyridin-2-yl)methanol (Step 4), the title compound was obtained.

Step 2: Preparation of ethyl 1-[(5-bromopyridin-2-yl)methyl]-4-oxo-1,4-dihydroquinoline-3-carboxylate Using the procedure described in Example 8, substituting (5-bromopyridin-2-yl)methyl methanesulfonate for 4-(bromomethyl)biphenyl (Step 1), the title compound was obtained.

Step 3: Preparation of 1-[(5-bromopyridin-2-yl)methyl]-4-chloro-3-(ethoxycarbonyl)quinolinium salt Ethyl 1-[(5-bromopyridin-2-yl)methyl]-4-oxo-1,4-dihydroquinoline-3-carboxylate (7.00 g, 18.1 mmol) was dissolved in phosphorous oxychloride (50.5 mL, 542 mmol, 30 equiv) and stirred at ambient temperature for 20 hours. The mixture was concentrated in vacuo and the residue was concentrated with toluene (2×50 mL), providing the title compound.

Step 4: Preparation of 5-[(5-bromopyridin-2-yl)methyl]-2-(2-methylphenyl)-2,5-dihydro-3H-pyrazolo[4,3-c]quinolin-3-one 1-[(5-Bromopyridin-2-yl)methyl]-4-chloro-3-(ethoxycarbonyl)quinolinium salt (1.55 g, 3.51 mmol), potassium carbonate (2.63 g, 19.1 mmol, 5.4 equiv), and (2-methylphenyl) hydrazine hydrochloride (1.33 g, 8.38 mmol, 2.4 equiv) were combined in a mixture (1:1) of N,N-dimethylformamide:1,2-dimethoxyethane (25 mL) and placed into an oil bath preheated at 80° C. for 3 hours. The mixture was cooled to ambient temperature, poured into water (100 mL) and extracted with dichloromethane (2×100 mL). The combined organic extracts were dried with sodium sulfate, filtered, and concentrated in vacuo. The residue was purified by silica gel gradient chromatography (100:0 to 90:10; dichloromethane: methanol), providing the titled compound as a yellow solid: $^1$H-NMR (400 MHz, $CD_3OD$) δ 8.97 (1H, s), 8.59 (1H, s), 8.33 (1H, d, J=7.8 Hz), 8.02-8.00 (1H, m), 7.78 (1H, d, J=9.0 Hz), 7.66-7.56 (2H, m), 7.48-7.37 (5H, m), 5.85 (2H, s), 2.28 (3H, s), ppm; low resolution mass spectrometry (ES+) m/z 446.8 [(M+H)$^+$; calculated for $C_{23}H_{17}BrN_4O$: 446.3].

The following compounds were prepared according to the general procedure described in Example 743, substituting the appropriate hydrazine for (2-methylphenyl)hydrazine hydrochloride. The starting materials are either commercially available, known in the literature or may be prepared from commercially available reagents using conventional reactions well known in the art.

(IFF)

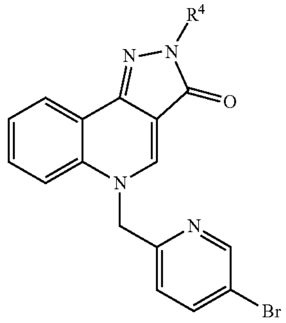

| Ex. | $R^4$ | HRMS/LRMS |
|---|---|---|
| 744 | 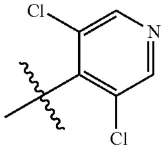 [SMILES: *c1c(Cl)cncc1Cl] | $C_{21}H_{12}BrCl_2N_5O$ [M + H] calc. 501.2 obs. 501.7 |
| 745 | 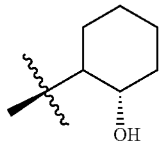 [SMILES: *C1CCCC[C@@H]1O] | $C_{21}H_{21}BrN_4O_2$ [M + H] calc. 454.1 obs. 454.8 |

Example 746

2-(2-Methylphenyl)-5-[(5-phenylpyridin-2-yl)methyl]-2,5-dihydro-3H-pyrazolo[4,3-c]quinolin-3-one

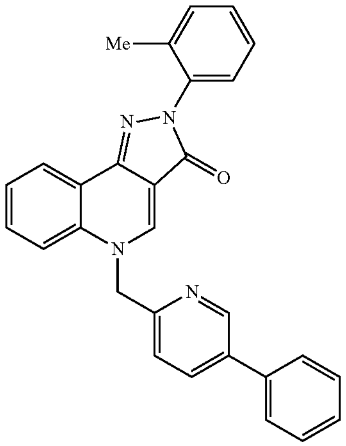 [SMILES: Cc1ccccc1-n1nc2c3ccccc3n(Cc3ccc(-c4ccccc4)cn3)cc-2c1=O]

Using the procedure described in Example 95, substituting 5-[5-bromopyridin-2-yl)methyl]-2-(2-methylphenyl)-2,5-dihydro-3H-pyrazolo[4,3-c]quinolin-3-one for 5-[(4-bromo-2-fluorophenyl)methyl-6,9-difluoro-2-(2-fluorophenyl)-2,5-dihydro-3H-pyrazolo[4,3-c]quinolin-3-one, and, substituting phenylboronic acid for 1-iso-butyl-4-(4,4,5,5-tetramethyl-1,3,2-dioxaborolan-2-yl)-1H-pyrazole, the titled compound was obtained: $^1$H-NMR (400 MHz, $CD_3OD$) δ 9.03 (1H, s), 8.77 (1H, s), 8.36-8.33 (1H, m), 8.10-8.07 (1H, m), 7.85 (1H, d, J=8.8 Hz), 7.68-7.37 (12H, m), 5.93 (2H, s), 2.29 (3H, s), ppm; low resolution mass spectrometry (ES+) m/z 442.9 [(M+H)$^+$; calculated for $C_{29}H_{22}N_4O$: 443.2].

The following compounds were prepared according to the general procedure described in Example 746, substituting the appropriate boronic acid, boronate ester, or potassium trifluoroborate salt for phenylboronic acid. The starting materials are either commercially available, known in the literature or may be prepared from commercially available reagents using conventional reactions well known in the art.

(IHH)

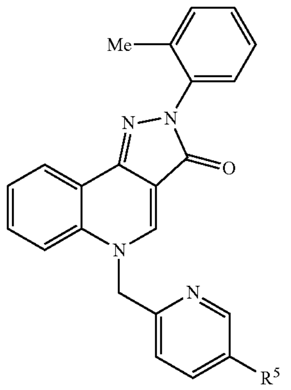

| Ex. | $R^5$ | HRMS/LRMS |
|---|---|---|
| 747 | 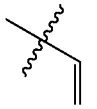 [SMILES: *C=C] | $C_{25}H_{20}N_4O$ [M + H] calc. 393.2 obs. 393.0 |
| 748 | 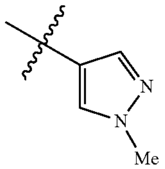 [SMILES: *c1cnn(C)c1] | $C_{27}H_{23}N_6O$ [M + H] calc. 447.1928 obs. 447.1928 |
| 749 | 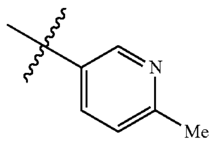 [SMILES: *c1ccc(C)nc1] | $C_{29}H_{24}N_5O$ [M + H] calc. 458.1975 obs. 458.1976 |

Example 750

2-(2-Methylphenyl)-5-(pyridin-2-ylmethyl)-2,5-dihydro-3H-pyrazolo[4,3-c]quinolin-3-one

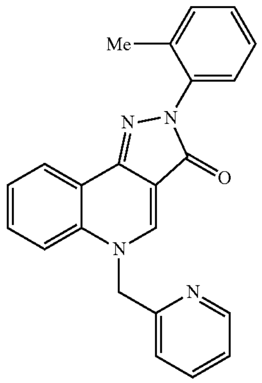 [SMILES: Cc1ccccc1-n1nc2c3ccccc3n(Cc3ccccn3)cc-2c1=O]

Using the procedure described in Example 746, substituting 2-thiopheneboronic acid for phenylboronic acid, the titled compound, resulting from protodehalogenation, was obtained: $^1$H-NMR (400 MHz, $CD_3OD$) δ 9.00 (1H, s), 8.53 (1H, d, J=4.6 Hz), 8.34 (1H, d, J=8.0 Hz), 7.90-7.86 (1H, m), 7.79 (1H, d, J=8.6 Hz), 7.66-7.56 (2H, m), 7.51 (1H, d, J=7.7 Hz), 7.42-7.37 (5H, m), 5.90 (2H, s), 2.28 (3H, s), ppm; low resolution mass spectrometry (ES+) m/z 367.0 [$(M+H)^+$; calculated for $C_{23}H_{18}N_4O$: 3 67.2].

Example 751

2-(3,5-Dichloropyridin-4-yl)-5-[(pyridin-2-yl)methyl]-2,5-dihydro-3H-pyrazolo[4,3-c]quinolin-3-one

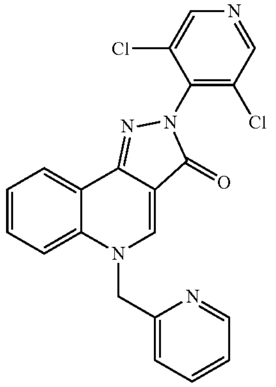 [SMILES: O=c1c2cn(Cc3ccccn3)c3ccccc3c-2nn1-c1c(Cl)cncc1Cl]

Using the procedure described in Example 750, substituting 5-[(5-bromopyridin-2-yl)methyl]-2-(3,5-dichloropyridin-4-yl)-2,5-dihydro-3H-pyrazolo[4,3-c]quinolin-3-one (Example 744) for 5-[(5-bromopyridin-2-yl)methyl]-2-(2-methylphenyl)-2,5-dihydro-3H-pyrazolo[4,3-c]quinolin-3-one (Example 743), the titled compound was obtained: $^1$H-NMR (400 MHz, $CD_3OD$) δ 9.03 (1H, s), 8.79 (2H, s), 8.52 (1H, d, J=5.1 Hz), 8.33-8.30 (1H, m), 7.88-7.84 (1H, m), 7.79 (1H, d, J=8.4 Hz), 7.68-7.57 (2H, m), 7.52 (1H, d, J=7.9 Hz), 7.37-7.34 (1H, m), 5.88 (2H, s), ppm; low resolution mass spectrometry (ES+) m/z 421.8 [$(M+H)^+$; calculated for $C_{21}H_{13}Cl_2N_5O$: 422.0].

Example 752

2-(2-Methylphenyl)-5-[(5-methylpyridin-2-yl)methyl]-2,5-dihydro-3H-pyrazolo[4,3-c]quinolin-3-one

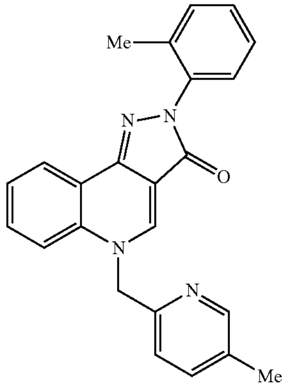 [SMILES: Cc1ccc(Cn2cc3c(=O)n(-c4ccccc4C)nc-3c3ccccc32)nc1]

5-[(5-Bromopyridin-2-yl)methyl]-2-(2-methylphenyl)-2,5-dihydro-3/1-pyrazolo[4,3-c]quinolin-3-one (Example 743, 40 mg, 0.090 mmol) was dissolved in tetrahydrofuran (2 mL), and the mixture was sparged under an atmosphere of nitrogen. Dimethyl zinc (0.49 mL, 2.0 Min toluene, 0.90 mmol, 10 equiv) and tetrakis(triphenylphosphine) palladium (0) (1.0 mg, 0.01 mmol, 0.1 equiv) were added and the mixture was placed into an oil bath preheated to 60° C. for 4 hours. Additional dimethyl zinc (0.49 mL, 2.0 M in toluene, 0.90 mmol, 10 equiv) and tetrakis(triphenylphosphine) palladium (0) (1.0 mg, 0.01 mmol, 0.1 equiv) were added and the mixture was heated at 70° C. for an additional 3 hours. The mixture was cooled to ambient temperature, treated with ammonium chloride (0.2 mL, aqueous saturated), and concentrated in vacuo. The residue was purified by preparative reverse phase HPLC (90:10 to 5:95; water containing 0.1% trifluoroacetic acid: acetonitrile containing 0.1% trifluoroacetic acid), providing the titled compound: $^{1}$H-NMR (400 MHz, $CD_3OD$) δ 8.98 (1H, s), 8.39 (1H, s), 8.35-8.32 (1H, m), 7.78 (1H, d, J=8.5 Hz), 7.73 (1H, d, J=6.2 Hz), 7.66-7.56 (2H, m), 7.42-7.35 (5H, m), 5.86 (2H, s), 234 (3H, s), 2.28 (3H, s), ppm; low resolution mass spectrometry (ES+) m/z 381.0 $(M+H)^+$; calculated for $C_{24}H_{20}N_4O$: 381.2].

The following compounds were prepared according to the general procedure described in Example 749, substituting the appropriately substituted organozinc reagent for dimethyl zinc. The starting materials are either commercially available, known in the literature or may be prepared from commercially available reagents using conventional reactions well known in the art.

(IJJ)

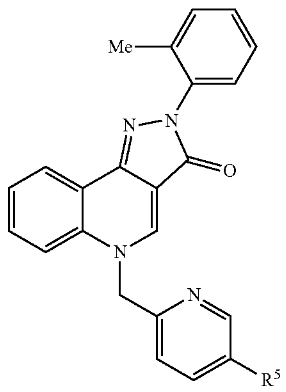

| Ex. | $R^5$ | HRMS/LRMS |
|---|---|---|
| 753 | Et | $C_{25}H_{22}N_4O$ [M + H] calc. 395.2 obs. 395.0 |
| 754 | CN | $C_{24}H_{17}N_5O$ [M + H] calc. 392.2 obs. 392.0 |

Example 755

2-(2-Methylphenyl)-5-(4-nitrobenzyl)-2,5-dihydro-3H-pyrazolo[4,3-c]quinolin-3-one

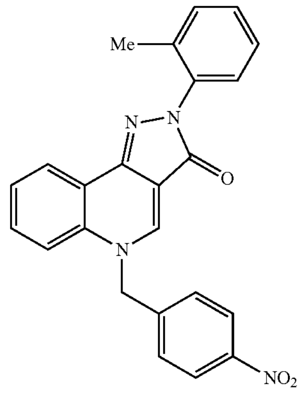

Using the procedure described in Example 743, substituting 1-(bromomethyl)-4-nitrobenzene for (5-bromopyridin-2-yl)methyl methanesulfonate, the titled compound was obtained: $^{1}$H-NMR (400 MHz, $CD_3OD$) δ 9.00 (1H, s), 8.35 (1H, d, J=5.8 Hz), 8.25 (2H, d, J=8.8 Hz), 7.72 (1H, d, J=8.6 Hz), 7.66-7.58 (2H, m), 7.53 (2H, d, J=8.4 Hz), 7.42-7.39 (4H, m), 5.95 (2H, s), 2.28 (s, 3H), ppm; low resolution mass spectrometry (ES+) m/z 410.9 [$(M+H)^+$; calculated for $C_{24}H_{18}N_4O_3$: 411.1].

Example 756

5-(4-Aminobenzyl)-2-(2-methylphenyl)-2,5-dihydro-3H-pyrazolo[4,3-c]quinolin-3-one

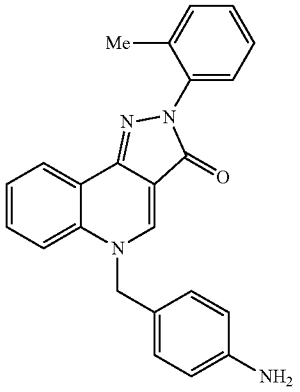 [SMILES: Cc1ccccc1-n1nc2c3ccccc3n(Cc3ccc([N+](=O)[O-])cc3)cc-2c1=O]

2-(2-Methylphenyl)-5-(4-nitrobenzyl)-2,5-dihydro-3H-pyrazolo[4,3-c]quinolin-3-one (Example 755, 50 mg, 0.12 mmol) was suspended in methanol (5 mL) and the mixture was sparged under an atmosphere of nitrogen. The mixture was treated with Raney Ni (~20 mg, spatula tip) and sparged under an atmosphere of hydrogen (1 atm). The mixture was, stirred vigorously for 6 hours at ambient temperature, sparged under an atmosphere of nitrogen, filtered and the filtrate was concentrated in vacuo. The residue was purified by preparative reverse phase HPLC (90:10 to 5:95; water containing 0.1% trifluoroacetic acid:acetonitrile containing 0.1% trifluoroacetic acid), providing the titled compound: $^1$H-NMR (400 MHz, $CD_3OD$) δ 8.96 (1H, s), 8.34 (1H, d, J=6.4 Hz), 7.82 (1H, d, J=8.6 Hz), 7.67-7.58 (2H, m), 7.44-7.36 (6H, m), 7.29 (2H, d, J=8.2 Hz), 5.82 (2H, s), 2.27 (3H, s), ppm; low resolution mass spectrometry (ES+) m/z 381.0 $(M+H)^+$; calculated for $C_{24}H_{20}N_4O$: 381.2].

Example 757

5-[4-(Dimethylamino)benzyl]-2-(2-methylphenyl)-2,5-dihydro-3H-pyrazolo[4,3-c]quinolin-3-one

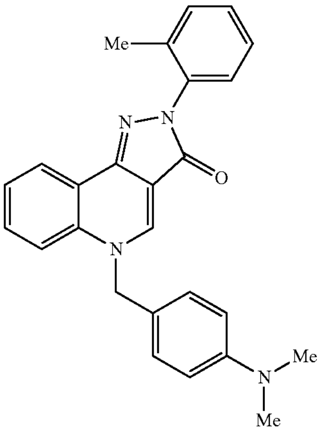 [SMILES: Cc1ccccc1-n1nc2c3ccccc3n(Cc3ccc(N(C)C)cc3)cc-2c1=O]

Using the procedure described in Example 627, substituting 5-(4-aminobenzyl)-2-(2-methylphenyl)-2,5-dihydro-3H-pyrazolo[4,3-c]quinolin-3-one (Example 756) for 2-(2-aminophenyl)-5-{[4-(1H-pyrazol-1-yl)phenyl]methyl}-2,5-dihydro-3H-pyrazolo[4,3-c]quinolin-3-one and, substituting formaldehyde for acetaldehyde, the titled compound was obtained: $^1$H-NMR (400 MHz, $CD_3OD$) δ 8.90 (1H, s), 8.33 (1H, d, J=8.0 Hz), 7.93 (1H, d, J=8.2 Hz), 7.70-7.66 (1H, m), 7.62-7.58 (1H, m), 7.53-7.36 (4H, m), 7.31 (2H, d, J=8.7 Hz), 7.02 (2H, d, J=8.4 Hz), 5.71 (2H, s), 3.03 (6H, s), 2.26 (3H, s) ppm; low resolution mass spectrometry (ES+) m/z 409.0 [$(M+H)^+$; calculated for $C_{26}H_{24}N_4O$: 409.2]

Example 758

N-(4-{[2-(2-Methylphenyl)-3-oxo-2,3-dihydro-5H-pyrazolo[4,3-c]quinolin-5-yl]methyl}phenyl)methanesulfonamide

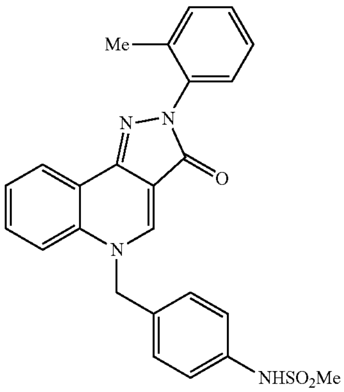

5-(4-Aminobenzyl)-2-(2-methylphenyl)-2,5-dihydro-3H-pyrazolo[4,3-c]quinolin-3-one (Example 756, 35 mg, 0.092 mmol) and sodium bicarbonate (23 mg, 0.28 mmol, 3 equiv) were combined in dichloromethane (2 mL) and cooled to 0° C. The mixture was treated with methanesulfonyl chloride (0.071 mL, 0.92 mmol, 10 equiv), stirred for 4 hours and treated with ammonium chloride (0.2 mL, aqueous saturated). The mixture was diluted with dichloromethane (15 mL) and washed with brine (15 mL). The organic extract was dried with sodium sulfate, filtered, and concentrated in vacuo. The residue was purified by preparative reverse phase HPLC (eluting 80:20 to 5:95; water containing 0.1% trifluoroacetic acid:acetonitrile containing 0.1% trifluoroacetic acid), providing the title compound: $^1$H-NMR (400 MHz, $CD_3OD$) δ 8.95 (1H, s), 8.34 (1H, d, J=7.8 Hz), 7.88 (1H, d, J=8.5 Hz), 7.70-7.66 (1H, m), 7.62-7.58 (1H, m), 7.47-7.38 (4H, m), 7.33-7.26 (4H, m), 5.76 (2H, s), 2.94 (3H, s), 2.27 (3H, s), ppm; low resolution mass spectrometry (ES+) m/z 458.9 [$(M+H)^+$; calculated for $C_{23}H_{22}N_4O_3S$: 459.1].

The following compounds were prepared according to the general procedure described in Example 758, substituting the appropriate acid chloride, anhydride, or sulfonyl chloride for methanesulfonyl chloride. The starting materials are either commercially available, known in the literature or may be prepared from commercially available reagents using conventional reactions well known in the art.

(IKK)

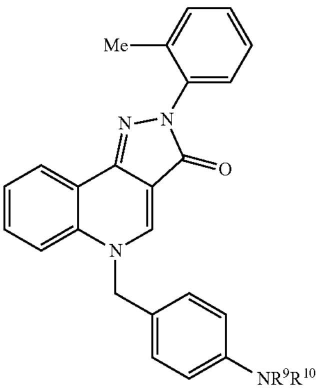

| Ex. | $NR^9R^{10}$ | HRMS/LRMS |
|---|---|---|
| 759 | $NHSO_2Ph$ | $C_{30}H_{24}N_4O_3S$[M + H] calc. 521.1, obs. 520.9 |
| 760 | NHCOMe | $C_{26}H_{22}N_4O_2$[M + H] calc. 423.2, obs. 422.9 |
| 761 | NHCOPh | $C_{31}H_{24}N_4O_2$[M + H] calc. 485.2, obs. 484.9 |
| 762 | $N(SO_2Me)_2$ | $C_{26}H_{24}N_4O_5S_2$[M + H] calc. 538.1, obs. 536.8 |

Example 763

2-Allyl-5-[(5-bromopyridin-2-yl)methyl]-2,5-dihydro-3H-pyrazolo[4,3-c]quinolin-3-one

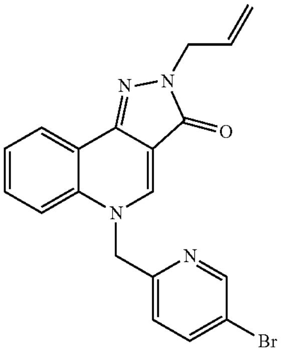 [SMILES: C=CCn1nc2c3ccccc3n(Cc3ccc(Br)cn3)cc-2c1=O]

Step 1: Preparation of ethyl (4Z)-1-[(5-bromopyridin-2-yl)methyl]-4-[(tert-butoxycarbonyl)hydrazono]-1,4-dihydroquinoline-3-carboxylate 1-[(5-Bromopyridin-2-yl)methyl]-4-chloro-3-(ethoxycarbonyl)quinolinium salt ([Example 743, Step 3], 4.25 g, 9.61 mmol), potassium carbonate (4.33 g, 31.4 mmol, 3.3 equiv), and tert-butyl carbonate (3.04 g, 23.0 mmol, 2.4 equiv) were combined in a 1:1 mixture (25 mL) of N,N-dimethylformamide:1,2-dimethoxyethane and stirred at ambient temperature for 2 hours. The mixture was poured into water (100 mL) and extracted with dichloromethane (2×100 mL). The combined organic extracts were dried with sodium sulfate, filtered, and concentrated in vacuo. The residue was washed with dichloromethane (2×10 mL), providing the titled compound as a yellow solid.

Step 2: Preparation of 5-[(5-bromopyridin-2-yl)methyl]-2,5-dihydro-3H-pyrazolo[4,3-c]quinolin-3-one Ethyl (4Z)-1-[(5-bromopyridin-2-yl)methyl]-4-[(tert-butoxycarbonyl)hydrazono]-1,4-dihydroquinoline-3-carboxylate (2.86 g, 5.70 mmol) was dissolved in toluene (30 mL), treated with hydrochloric acid (0.950 mL, 12 N aqueous, 11 mmol, 2 equiv) and placed into an oil bath preheated to 100° C. for 3 hours. The mixture was cooled to ambient temperature. The mixture was filtered and the yellow solid was collected and washed with toluene (2×10 mL), providing the titled compound.

Step 3: Preparation of 2-allyl-5-[(5-bromopyridin-2-yl)methyl]-2,5-dihydro-3H-pyrazolo[4,3-c]quinolin-3-one 5-[(5-Bromopyridin-2-yl)methyl]-2,5-dihydro-3H-pyrazolo[4,3-c]quinolin-3-one (250 mg, 0.704 mmol) was dissolved in dimethylsulfoxide (3 mL) and treated with sodium hydride (70.4 mg, 1.76 mmol, 2.5 equiv) and allyl bromide (170 mg, 1.41 mmol, 2.0 equiv). The mixture was stirred at ambient temperature for 18 hours, poured into dichloromethane (50 mL) and washed with sodium bicarbonate (2×50 mL, aqueous saturated) and brine (1×50 mL). The organic extract was dried with sodium sulfate, filtered, and concentrated in vacuo. The residue was purified by preparative reverse phase HPLC (eluting 80:20 to 5:95; water containing 0.1% trifluoroacetic acid:acetonitrile containing 0.1% trifluoroacetic acid), providing the title compound: $^1$H-NMR (400 MHz, $CD_3OD$) δ 8.90 (1H, s), 8.56 (1H, s), 8.34 (1H, d, J=9.0 Hz), 7.99 (1H, d, J=6.2 Hz), 7.74 (1H, d, J=8.2 Hz), 7.63-7.55 (2H, m), 7.42 (1H, d, J=8.4 Hz), 6.07-5.98 (1H, m), 5.81 (2H, s), 5.24-5.16 (2H, m), 4.86 (2H, s), ppm; low resolution mass spectrometry (ES+) m/z 396.8 ($^{81}$Br) [(M+H)$^+$; calculated for $C_{19}H_{15}BrN_4O$: 397.0].

Example 764

2-Allyl-5-(4-fluorobenzyl)-2,5-dihydro-3H-pyrazolo[4,3-c]quinolin-3-one

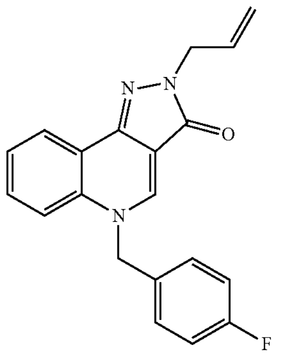 [SMILES: C=CCn1nc2c3ccccc3n(Cc3ccc(F)cc3)cc-2c1=O]

Using the procedure described in Example 743, substituting 4-fluorobenzyl bromide for 5-bromo-2-(hydroxymethyl)pyridine, and, substituting allylhydrazine for (2-methylphenyl)hydrazine hydrochloride, the title compound was obtained: $^1$H-NMR (400 MHz, $CD_3OD$) δ 8.88 (1H, s), 8.36 (1H, d, J=7.8 Hz), 7.80 (1H, d, J=8.3 Hz), 7.66-7.56 (2H, m), 7.34-7.30 (2H, m), 7.11 (2H, t, J=8.8 Hz), 6.06-5.98 (1H, m), 5.74 (2H, s), 5.25-5.15 (2H, m), 4.66 (2H, d, J=5.3 Hz), ppm;

low resolution mass spectrometry (ES+) m/z 334.0 [$(M+H)^+$; calculated for $C_{20}H_{16}FN_3O$: 334.1].

The following compounds were prepared according to the general procedure described in Example 764, substituting the appropriate hydrazine or hydrazine hydrochloride for allylhydrazine. The starting materials are either commercially available, known in the literature or may be prepared from commercially available reagents using conventional reactions well known in the art.

(ILL)

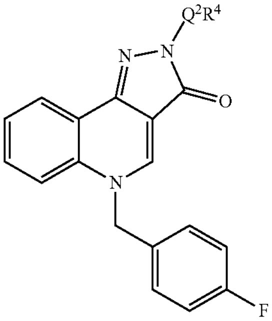

| Ex. | $Q^2R^4$ | HRMS/LRMS |
|---|---|---|
| 765 | 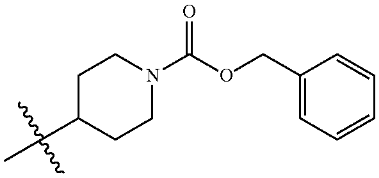 [SMILES: *C1CCN(C(=O)OCc2ccccc2)CC1] | $C_{30}H_{27}FN_4O_3$ [M + H] calc. 511.2 obs. 510.9 |
| 766 | 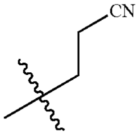 [SMILES: *CCC#N] | $C_{20}H_{15}FN_4O$ [M + H] calc. 347.1303 obs. 347.1309 |
| 767 | 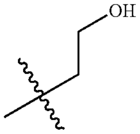 [SMILES: *CCO] | $C_{19}H_{16}FN_3O_2$ [M + H] calc. 338.1299 obs. 338.1298 |
| 768 | 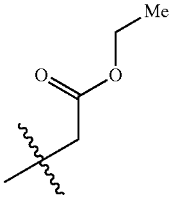 [SMILES: *CC(=O)OCC] | $C_{21}H_{18}FN_3O_3$ [M + H] calc. 380.1405 obs. 380.1401 |
| 769 | 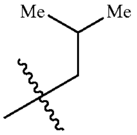 [SMILES: *CC(C)C] | $C_{21}H_{20}FN_3O$ [M + H] calc. 350.1663 obs. 350.1662 |
| 770 | 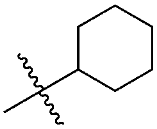 [SMILES: *C1CCCCC1] | $C_{23}H_{22}FN_3O$ [M + H] calc. 376.1820 obs. 376.1820 |

-continued (ILL)

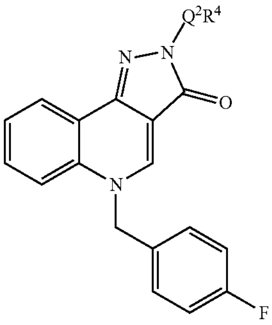

| Ex. | $Q^2R^4$ | HRMS/LRMS |
|---|---|---|
| 771 | 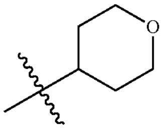 [SMILES: *C1CCOCC1] | $C_{22}H_{20}FN_3O_2$ [M + H] calc. 378.1612 obs. 378.1610 |
| 772 | 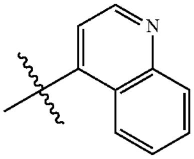 [SMILES: *c1ccnc2ccccc12] | $C_{26}H_{17}FN_4O$ [M + H] calc. 421.1459 obs. 421.1456 |
| 773 | 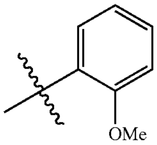 [SMILES: *c1ccccc1OC] | $C_{24}H_{18}FN_3O_2$ [M + H] calc. 400.1456 obs. 400.1453 |
| 774 | 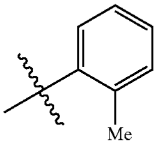 [SMILES: *c1ccccc1C] | $C_{24}H_{18}FN_3O$ [M + H] calc. 384.1507 obs. 384.1510 |
| 775 | 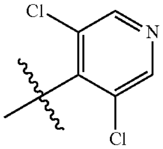 [SMILES: *c1c(Cl)cncc1Cl] | $C_{22}H_{13}Cl_2N_4O$ [M + H] calc. 439.0523 obs. 439.0538 |
| 776 | 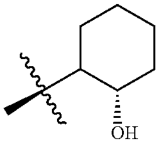 [SMILES: *C1CCCC[C@@H]1O] | $C_{23}H_{22}FN_3O_2$ [M + H] calc. 392.1769 obs. 392.1771 |
| 777 | 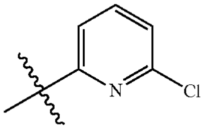 [SMILES: *c1cccc(Cl)n1] | $C_{22}H_{14}ClFN_4O$ [M + H] calc. 405.0913 obs. 405.0922 |
| 778 | 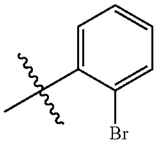 [SMILES: *c1ccccc1Br] | $C_{23}H_{15}BrFN_3O$ [M + H] calc. 448.0455 obs. 448.0455 |

-continued (ILL)

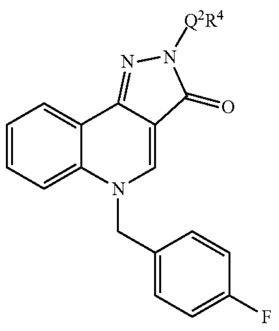

| Ex. | $Q^2R^4$ | HRMS/LRMS |
|---|---|---|
| 779 | 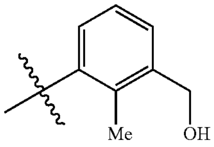 [SMILES: *c1cccc(CO)c1C] | $C_{25}H_{20}FN_3O_2$ [M + H] calc. 414.2 obs. 413.9 |

Example 780

5-(4-Fluorobenzyl)-2-pyridin-4-yl-2,5-dihydro-3H-pyrazolo[4,3-c]quinolin-3-one

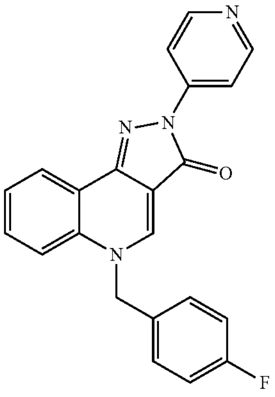 [SMILES: O=c1c2cn(Cc3ccc(F)cc3)c3ccccc3c-2nn1-c1ccncc1]

Using the procedure described in Example 8, substituting 4-fluorobenzyl bromide for 4-(bromomethyl)biphenyl, and, substituting 4-iodopyridine for 2-fluoroiodobenzene, the titled compound was obtained: $^1$H-NMR (400 MHz, $CD_3OD$) δ 9.30 (1H, s), 8.80-8.74 (2H, m), 8.60-8.57 (2H, m), 8.34 (1H, d, J=7.9 Hz), 7.83 (1H, d, J=8.4 Hz), 7.75-7.71 (1H, m), 7.66-7.62 (1H, m), 7.46-7.40 (2H, m), 7.22-7.18 (2H, m), 5.76 (2H, s) ppm; low resolution mass spectrometry (ES+) m/z 370.9 [$(M+H)^+$; calculated for $C_{22}H_{15}FN_4O$: 371.1].

The following compounds were prepared according to the general procedure described in Example 780, substituting the appropriate iodide or bromide for 4-iodopyridine. The starting materials are either commercially available, known in the literature or may be prepared from commercially available reagents using conventional reactions well known in the art.

(IMM)

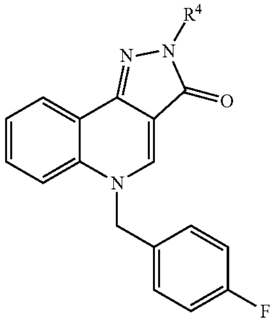

| Ex. | $R^4$ | HRMS/LRMS |
|---|---|---|
| 781 | 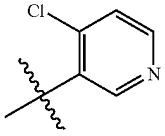 [SMILES: *c1cnccc1Cl] | $C_{22}H_{14}ClFN_4O$ [M + H] calc. 405.1 obs. 405.1 |
| 782 | 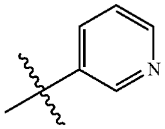 [SMILES: *c1cccnc1] | $C_{22}H_{15}FN_4O$ [M + H] calc. 371.1 obs. 370.9 |
| 783 | 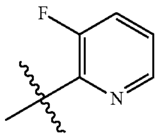 [SMILES: *c1ncccc1F] | $C_{22}H_{14}F_2N_4O$ [M + H] calc. 389.1 obs. 388.9 |
| 784 | 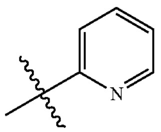 [SMILES: *c1ccccn1] | $C_{22}H_{15}FN_4O$ [M + H] calc. 371.1 obs. 371.0 |
| 785 | 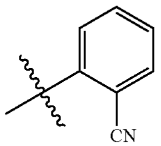 [SMILES: *c1ccccc1C#N] | $C_{24}H_{15}FN_4O$ [M + H] calc. 395.1 obs. 394.9 |
| 786 | 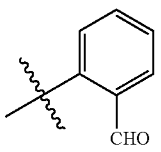 [SMILES: *c1ccccc1C=O] | $C_{24}H_{16}FN_3O_2$ [M + H] calc. 398.1 obs. 398.1 |

Example 787

5-(4-Fluorobenzyl)-2-piperidin-4-yl-2,5-dihydro-3H-pyrazolo[4,3-c]quinolin-3-one

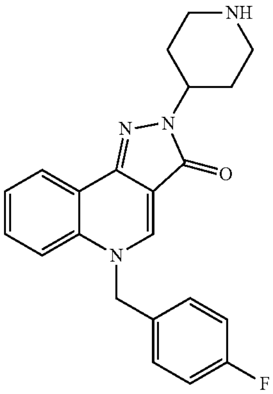 [SMILES: O=c1c2cn(Cc3ccc(F)cc3)c3ccccc3c-2nn1C1CCNCC1]

Using the procedure described in Example 674, substituting benzyl 4-[5-(4-fluorobenzyl)-3-oxo-3,5-dihydro-2H-pyrazolo[4,3-c]quinolin-2-yl]piperidine-1-carboxylate (Example 765) for phenylmethyl 4-(3-oxo-5-{[4-(1H-pyrazol-1-yl)phenyl]methyl}-3,5-dihydro-2H-pyrazolo[4,3-c]quinolin-2-yl)piperidine-1-carboxylate, the titled compound was obtained: $^1$H-NMR (400 MHz, $CD_3OD$) δ 8.87 (1H, s), 8.33 (1H, d, J=7.7 Hz), 7.79 (1H, d, J=8.4 Hz), 7.65-7.61 (2H, m), 7.32-7.29 (2H, m), 7.12 (2H, d, J=8.8 Hz), 5.73 (2H, s), 4.83-4.79 (1H, m), 3.63-3.60 (2H, m), 3.28-3.24 (2H, m), 3.24-3.13 (2H, m), 2.47-2.36 (2H, m), ppm; low resolution mass spectrometry (ES+) m/z 377.0 [(M+H)$^+$; calculated for $C_{22}H_{21}FN_4O$: 377.2].

Example 788

Methyl 4-[5-(4-fluorobenzyl)-3-oxo-3,5-dihydro-2H-pyrazolo[4,3-c]quinolin-2-yl]piperidine-1-carboxylate

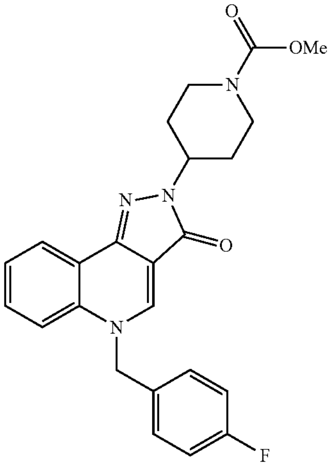 [SMILES: COC(=O)N1CCC(n2nc3c4ccccc4n(Cc4ccc(F)cc4)cc-3c2=O)CC1]

Using the procedure described in Example 679, substituting 5-(4-fluorobenzyl)-2-piperidin-4-yl-2,5-dihydro-3H-pyrazolo[4,3-c]quinolin-3-one for 2-piperidin-4-yl-5-{[4-(1H-pyrazol-1-yl)phenyl]methyl}-2,5-dihydro-3H-pyrazolo[4,3-c]quinolin-3-one, the titled compound was obtained: $^1$H-NMR (400 MHz, $CD_3OD$) δ 8.86 (1H, s), 8.40 (1H, br s), 7.78 (1H, d, J=8.6 Hz), 7.63-7.60 (2H, m), 7.33-7.30 (2H, m), 7.10 (2H, d, J=8.7 Hz), 5.74 (2H, s), 4.75-4.63 (1H, m), 4.28-4.21 (2H, m), 3.74 (3H, s), 3.21-3.05 (2H, m), 2.15-2.10 (2H, m), 1.91-1.87 (2H, m), ppm; low resolution mass spectrometry (ES+) m/z 434.9 [(M+H)$^+$; calculated for $C_{24}H_{23}FN_4O_3$: 435.2].

Example 789

5-[(4-Fluorophenyl)methyl]-2-(1-methylpiperidin-4-yl)-2,5-dihydro-3H-pyrazolo[4,3-c]quinolin-3-one

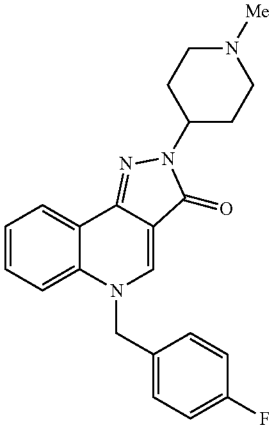 [SMILES: CN1CCC(n2nc3c4ccccc4n(Cc4ccc(F)cc4)cc-3c2=O)CC1]

Using the procedure described in Example 757, substituting 5-(4-fluorobenzyl)-2-piperidin-4-yl-2,5-dihydro-3H-pyrazolo[4,3-c]quinolin-3-one for 5-(4-aminobenzyl)-2-(2-methylphenyl)-2,5-dihydro-3H-pyrazolo[4,3-c]quinolin-3-one, the titled compound was obtained: $^1$H-NMR (400 MHz, $CD_3OD$) δ 8.87 (1H, s), 8.32 (1H, d, J=7.7 Hz), 7.79 (1H, d, J=8.4 Hz), 7.65-7.56 (2H, m), 7.33-7.29 (2H, m), 7.13-7.08 (2H, m), 5.73 (2H, s), 4.75-7.68 (1H, m), 3.75-3.63 (2H, m), 2.96 (3H, s), 2.64-2.61 (2H, m), 2.54-2.44 (2H, m), 2.20-2.17 (2H, m), ppm; low resolution mass spectrometry (ES+) m/z 391.0 [(M+H)$^+$; calculated for $C_{23}H_{23}FN_4O$: 391.2].

Example 790

(±)-5-(4-Fluorobenzyl)-2-[2-(1-hydroxyethyl)phenyl]-2,5-dihydro-3H-pyrazolo[4,3-c]quinolin-3-one

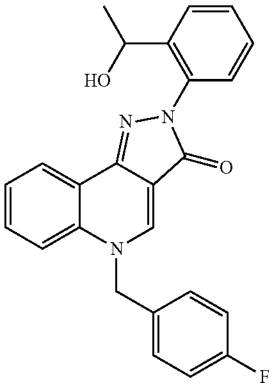 [SMILES: CC(O)c1ccccc1-n1nc2c3ccccc3n(Cc3ccc(F)cc3)cc-2c1=O]

Using the procedure described in Example 655, substituting 2-[5-(4-fluorobenzyl)-3-oxo-3,5-dihydro-2H-pyrazolo[4,3-c]quinolin-2-yl]benzaldehyde (Example 786) for 2-(3-oxo-5-{[4-(1H-pyrazol-1-yl)phenyl]methyl}-3,5-dihydro-2H-pyrazolo[4,3-c]quinolin-2-yl)benzaldehyde, the titled compound was obtained: $^1$H-NMR (400 MHz, $d^6$-DMSO) δ 9.11 (1H, s), 8.16 (1H, d, J=7.4 Hz), 7.75 (1H, d, J=7.0 Hz), 7.69 (1H, d, J=7.8 Hz), 7.63-7.60 (1H, m), 7.55-7.51 (1H, m), 7.44-7.40 (2H, m), 7.38-7.30 (2H, m), 7.23-7.18 (3H, m), 7.08 (1H, s), 6.95 s), 5.72 (2H, s), 4.91-4.89 (1H, m), 1.25 (3H, d, J=6.4 Hz), ppm; low resolution mass spectrometry (ES+) m/z 413.9 $[(M+H)^+]$; calculated for $C_{24}H_{20}FN_3O_2$: 414.2].

Example 791

5-(4-Fluorobenzyl)-2-propyl-2,5-dihydro-3H-pyrazolo[4,3-c]quinolin-3-one

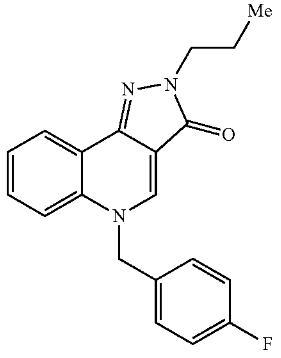 [SMILES: CCCn1nc2c3ccccc3n(Cc3ccc(F)cc3)cc-2c1=O]

2-Allyl-5-(4-fluorobenzyl)-2,5-dihydro-3H-pyrazolo[4,3-c]quinolin-3-one (Example 764, 20 mg, 0.060 mmol) was dissolved in methanol (3 mL), treated with palladium on carbon (2 mg, 10 wt % on activated carbon, 0.1 wt equiv) sparged under an atmosphere of hydrogen (1 atm) and stirred for 4 hours at ambient temperature. The mixture was sparged under an atmosphere of nitrogen, filtered through a pad of Celite and the filtrate was concentrated in vacuo, providing the titled compound: $^1$H-NMR (400 MHz, $CD_3OD$) δ 9.07 (1H, s), 8.42 (1H, d, J=7.7 Hz), 7.96 (1H, d, J=8.5 Hz), 7.78-7.68 (2H, m), 7.38-7.37 (2H, m), 7.16-7.11 (2H, m), 5.85 (2H, s), 4.10 (2H, t, J=7.0 Hz), 1.95-1.89 (2H, m), 0.99 (3H, t, J=7.5 Hz), ppm; low resolution mass spectrometry (ES+) m/z 336.0 $[(M+H)^+]$; calculated for $C_{20}H_{18}FN_3O$: 336.1].

Example 792

5-(4-Fluorobenzyl)-2-[2-(hydroxymethyl)phenyl]-2,5-dihydro-3H-pyrazolo[4,3-c]quinolin-3-one

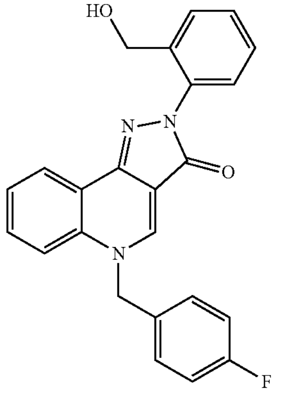 [SMILES: O=c1c2cn(Cc3ccc(F)cc3)c3ccccc3c-2nn1-c1ccccc1CO]

2-[5-(4-Fluorobenzyl)-3-oxo-3,5-dihydro-2H-pyrazolo[4,3-c]quinolin-2-yl]benzaldehyde (Example 786) (60 mg, 0.15 mmol) was dissolved in dichloromethane (3 mL), treated with sodium borohydride (7.4 mg, 0.20 mmol, 1.3 equiv) and stirred at ambient temperature for 24 hours. The mixture was washed with brine (5 mL), dried with sodium sulfate, filtered, and concentrated in vacuo. The residue was dissolved in dichloromethane (3 mL), treated with 2,3-dichloro-5,6-dicyano-1,4-benzoquinone (56 mg, 0.25 mmol, 1.6 equiv) and stirred at ambient temperature for 3 hours. The mixture was concentrated in vacuo and the residue was purified by preparative reverse phase HPLC (eluting 80:20 to 5:95; water containing 0.1% trifluoroacetic acid:acetonitrile containing 0.1% trifluoroacetic acid), providing the title compound: $^1$H-NMR (400 MHz, $CD_3OD$) δ 9.12 (1H, s), 8.19 (1H, d, J=7.9 Hz), 7.75 (1H, d, J=8.6 Hz), 7.66-7.60 (2H, m), 7.55-7.51 (1H, m), 7.44-7.38 (5H, m), 7.20 (2H, d, J=8.8 Hz), 5.73 (2H, s), 4.45 (2H, s), ppm; low resolution mass spectrometry (ES+) m/z 399.9 $[(M+H)^+]$; calculated for $C_{24}H_{18}FN_3O_2$: 400.1].

Biological Utility

The utility of the compounds as M1 receptor positive allosteric modulators may be demonstrated by methodology known in the art, including by the assay described below. The assay is designed to select compounds that possess modulator activity at the acetylcholine muscarinic M1 receptor or other muscarinic receptors expressed in CHOnfat cells by measuring the intracellular calcium with a $FLIPR^{384}$ Fluorometric Imaging Plate Reader System. The assay studies the effect of one or several concentrations of test compounds on basal or acetylcholine-stimulated $Ca^{2+}$ levels using FLIPR.

Compounds are prepared and subjected to a preincubation period of 4 min. Thereafter, a single $EC_{20}$ concentration of acetylcholine is added to each well (3 nM final). The intracellular $Ca^{2+}$ level of each sample is measured and compared to an acetylcholine control to determine any modulatory activity.

Cells: CHOnfat/hM1, hM2, hM3 or hM4 cells are plated 24 hr before the assay at a density of 18,000 cells/well (100 μL) in a 384 well plate. CHOnfat/hM1 and CHOnfat/hM3 Growth Medium: 90% DMEM (Hi Glucose); 10% HI FBS; 2 mM L-glutamine; 0.1 mM NEAA; Pen-Strep; and 1 mg/ml Geneticin, are added. For M2Gqi5CHOnfat and M4Gqi5CHOnfat cells, an additional 600 ug/ml hygromycin is added.

Equipment: 384 well plate, 1204 addition plate; 96-well Whatman 2 ml Uniplate Incubator, 37° C., 5% $CO_2$; Skatron EMBLA-384 Plate Washer; Multimek Pipetting System; Genesis Freedom 200 System; Mosquito System; Temo Nanoliter Pipetting System; and FLIPR$^{384}$ Fluorometric Imaging Plate Reader System are used.

Buffers. Assay Buffer: Hanks Balanced Salt Solution, with 20 mM Hepes, 2.5 mM Probenecid (Sigma P-8761) first dissolved in 1 N NaOH, 1% Bovine Serum Albumin (Sigma A-9647). Dye Loading Buffer: Assay Buffer plus 1% Fetal Bovine Serum and Fluo-4AM/Pluronic Acid Mixture. 2 mM Fluo-4AM ester stock in DMSO (Molecular Probes F-14202) Concentration of 2 μM in buffer for a final concentration of 1 μM in Assay. 20% Pluronic Acid Solution stock, with concentration of 0.04% in Buffer, 0.02% in Assay.

65 μL of 2 mM Fluo-4AM are mixed with 130 μL of 20% Pluronic Acid. The resulting solution and 650 μL FBS is added to the assay buffer for a total volume of 65 mL. Positive Controls: 4-Br-A23187: 10 mM in DMSO; final concentration 10 μM. Acetylcholine: 10 mM in water, working stock at both 20 μM and 30 μM in assay buffer, final concentration of 10 μM. This is used to check the maximum stimulation of the CHOK1/hM1 cells, 20 μM (2×) acetylcholine is added in the preincubation part of the assay, and the 30 μM (3×) stock is added in the second part. ($EC_{20}$)Acetylcholine: 10 mM in water, working stock of 9 nM (3×), and final concentration in assay is 3 nM. This is used after the preincubation with test compounds. Addition of the $EC_{20}$ Acetylcholine to each well with a test compound will ascertain any modulator activity. 24 wells contain 3 nM Acetylcholine alone as a control.

Determining Activity of Putative Compounds:

Screening Plate Compounds are titrated in 96-well plates (columns 2-11), 100% DMSO, started at a concentration of 15 mM (150× stock concentration), and 3-fold serial dilutions using Genesis Freedom200 System. Four 96-well plates are combined into a 384-well plate using Mosquito Nanoliter Pipetting System by transferring 1 μl of serial diluted compounds to each well, and 1 mM acetylcholine (100× stock concentration) were added as a control. Using Temo, 49 μl assay buffer is added to each well of the 384-well plate right before assay.

In a 96-well Whatman 2 ml Uniplate, 9 nM Acetylcholine (3×) is pipetted into wells corresponding to the screening compounds, and into control wells. The 30 μM acetylcholine control (3×) is added into control wells, and the 3× agonist plate is transferred into a 384 well plate.

Cells are washed three times with 100 μl, of buffer, leaving 30 μl of buffer in each well. Using Multimek, 30 μL of Dye Loading Buffer is added into each well and incubated at 37° C., 5% $CO_2$ for up to one hr.

After 60 min, the cells are washed three times with 100 μl of buffer, leaving 30 μl, of buffer in each well. The cell plate, screening plate, and agonist addition plates are placed on the platform in the FLIPR and the door closed. A signal test to check background fluorescence and basal fluorescence signal is performed. Laser intensity is adjusted if necessary.

4 min of preincubation with the test compounds is provided to determine any agonist activity on the M1 receptor by comparison to the 1 mM acetylcholine control. After preincubation, the $EC_{20}$ value of acetylcholine (3 nM final) is added to determine any modulator activity.

A further description of the muscarinic FLIPR assay can be found in International patent application WO2004/073639.

In particular, the compounds of the following examples had activity in the aforementioned assay, generally with an IP (inflection point) of 30 μM (10,000 nM) or less. The inflection point is calculated from the FLIPR values, and is a measure of activity. Such a result is indicative of the intrinsic activity of the compounds in use as M1 allosteric modulators.

IP values from the aforementioned assay for representative exemplary compounds of the invention (as described herein) are provided below in Table 1 below:

| Example | IP Value (nM) |
|---|---|
| 1 | 415 |
| 8 | 1990 |
| 24 | 103 |
| 55 | 204 |
| 56 | 123 |
| 77 | 65 |
| 84 | 348 |
| 107 | 59 |
| 109 | 90 |
| 128 | 1286 |
| 187 | 1643 |
| 242 | 159 |
| 258 | 246 |
| 294 | 824 |
| 381 | 900 |
| 428 | 359 |
| 508 | 33 |
| 587 | 4.8 |
| 612 | 4874 |
| 648 | 179 |
| 667 | 22 |
| 675 | 664 |
| 690 | 1249 |
| 720 | 135 |
| 733 | 653 |

The following abbreviations are used throughout the text:

TEOF triethylorthoformate
DDQ 2,3-dichloro-5,6-dicyanobenzoquinone
Pd/C palladium on activated carbon
DMF.DMA N,N-dimethylformamide dimethyl acetal
DME 1,2-dimethoxyethane
DMSO dimethylsulfoxide
DMF N,N-dimethylformamide
Me: methyl
Et: ethyl
Bu: butyl
t-Bu: tert-butyl
Ar: aryl
Ph: phenyl
Bn: benzyl
DMF: dimethylformamide
Ac: acetyl
DMSO: dimethylsulfoxide
DMEM: Dulbecco's Modified Eagle Medium (High Glucose)
FBS: fetal bovine serum
dba: dibenzylideneacetone
dppa: diphenylphosphoryl azide
dppf: (diphenylphosphino)ferrocenez
THF: tetrahydrofuran
$PCy_3$: trichcyclohexylphosphine
mCPBA: meta-chloroperoxybenzoic acid
PBSF: perfluoro-1-butanesulfonyl fluoride
TEA: triethylamine
BOP: Benzotriazolyloxytris(dimethylamino)phosphonium hexafluorophosphate
DIBAL: diisobutylaluminum hydride
TBAF: tetra-n-butylammonium fluoride
DAST: diethylaminosulfur trifluoride
TBS: tert-butyldimethylsilyl DMAD: dimethyl acetylenedicarboxylate
TBSOTf: tert-butyldimethylsilyl triflate
TMS: trimethylsilyl
rt: room temperature
aq: aqueous
HPLC: high performance liquid chromatography
MS: mass spectrometry While the invention has been described and illustrated with reference to certain particular embodiments thereof, those skilled in the art will appreciate that various adaptations, changes, modifications, substitutions, deletions, or additions of procedures and protocols may be made without departing from the spirit and scope of the invention. It is intended, therefore, that the invention be defined by the scope of the claims that follow and that such claims be interpreted as broadly as is reasonable.

What is claimed is:

1. A compound of formula (I):

(II)

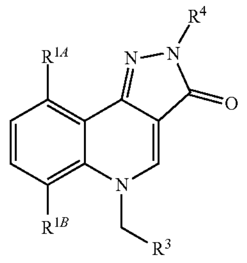

or a pharmaceutically acceptable salt thereof, wherein $R^{1A}$ and $R^{1B}$ are either hydrogen or selected from the group consisting of
(1) halogen,
(2) —$C_{1-6}$ alkyl,
(3) —O—$C_{1-6}$ alkyl,
(4) —CN;

$R^3$ is selected from the group consisting of
(1) —$C_{6-10}$ aryl,
(2) heteroaryl, wherein the heteroaryl is an aromatic cyclic group, having from five to ten ring atoms, said ring atoms selected from C, O, N, N→O, C(═O) or S, at least one of which is O, N, N→O or S,
(3) a heterocyclic group having 4 to 8 ring atoms selected from C, O, N, N→O, C(═O), $SO_2$ or S, at least one of which is O, N, N→O, $SO_2$ or S,
(4) —$C_{3-8}$ cycloalkyl,
wherein each aryl, heteroaryl or heterocyclic is substituted with one or more of $R^5$ group;

$R^5$ is selected from the group consisting of
(1) halogen,
(2) —$C_{2-8}$ alkenyl,
(3) —O—$C_{1-6}$ alkyl,
(4) —C(═O)—$(O)_m$—$R^7$,
(5) —NH—C(═O)—$R^7$,
(6) —$C_{3-8}$ cycloalkyl,
(7) —S(═O)$_2$—$R^7$,
(8) —NH—S(═O)$_2$—$R^7$,
(9) —$NO_2$,
(10) —CN;
(11) $C_{6-10}$ aryl,
(12) heteroaryl, which is an aromatic cyclic or polycyclic group, having from five to ten ring atoms, said ring atoms selected from C, O, N, N→O, C(═O) or S, at least one of which is O, N, N→O or S,
(13) —$NR^9R^{10}$,
(14) —$B(OH)_2$,
wherein said cycloalkyl, aryl or heteroaryl $R^5$ group is optionally substituted with one or more
(a) halogen,
(b) —$C_{1-6}$ alkyl,
(c) —$C_{3-8}$ cycloalkyl,
(d) —$NR^{11}R^{12}$,
(e) —O—$C_{1-6}$ alkyl,
(f) $C_{6-10}$ aryl,
(g) CN,
(h) hydroxyl
(i) —C(═O)—O—$R^7$,
(j) —NH—C(═O)—$R^7$,
(k) —S(═O)$_2$—$R^7$,
(l) —NH—S(═O)$_2$—$R^7$,
wherein said alkyl or aryl is optionally substituted with one or more
(i) halogen,
(ii) hydroxyl,
(iii) —$NR^{13}R^{14}$;

$R^4$ is selected from the group consisting of
(1) —$C_{6-10}$ aryl,
(2) heteroaryl, which is an aromatic cyclic or polycyclic group, having from five to ten ring atoms, said ring atoms selected from C, O, N, N→O, C(═O) or S, at least one of which is O, N, N→O or S,
(3) a heterocyclic group having 4 to 8 ring atoms selected from C, O, N, N→O, C(═O), $SO_2$ or S, at least one of which is O, N, N→O, $SO_2$ or S,
wherein each aryl, heteroaryl or heterocyclic is optionally substituted with one or more $R^6$ group;

$R^6$ is selected from the group consisting of
(1) halogen,
(2) —$C_{1-6}$ alkyl,
(3) —$C_{2-8}$ alkenyl,
(4) —O—$C_{1-6}$ alkyl,
(5) hydroxyl,
(6) —C(═O)—$(O)_m$—$R^7$,
(7) —C(═O)—$NR^9R^{10}$,
(8) —O—C(═O)—$R^7$,
(9) —NH—C(═O)—$R^7$,
(10) —NH—C(═O)—$OR^7$,
(11) —$C_{3-8}$ cycloalkyl,
(12) —S(═O)$_2$—$R^7$,
(13) —S(═O)$_2$—$OR^7$,
(14) —S(═O)$_2$—$NR^9R^{10}$,
(15) —NH—S(═O)$_2$—$R^7$,
(16) —$NO_2$,
(17) —CN;
(18) —$C_{6-10}$ aryl,
(19) —O—$C_{6-10}$ aryl,
(20) heteroaryl, which is an aromatic cyclic or polycyclic group, having from five to ten ring atoms, said ring atoms selected from C, O, N, N→O, C(═O) or S, at least one of which is O, N, N→O or S,
(21) —$NR^9R^{10}$,
wherein said alkyl, cycloalkyl, aryl or heteroaryl $R^5$ group is optionally substituted with one or more
(a) halogen,
(b) —$C_{1-6}$ alkyl,
(c) —$NR^{11}R^{12}$,
(d) —O—$C_{1-6}$ alkyl,
(f) —$C_{6-10}$ aryl,
(g) heteroaryl, which is an aromatic cyclic or polycyclic group, having from five to ten ring atoms, said ring atoms selected from C, O, N, N→O, C(═O) or S, at least one of which is O, N, N→O or S,
(h) CN,
(i) hydroxyl
wherein said alkyl, aryl or heteroaryl is optionally substituted with one or more
(i) halogen,
(ii) hydroxyl,
(iii) —$NR^{13}R^{14}$;

$R^7$ is selected from the group consisting of
(1) hydrogen,
(2) —$C_{1-6}$ alkyl;
(3) —$C_{3-8}$ cycloalkyl;
(2) —$C_{2-6}$ alkenyl;
(3) —$C_{0-2}$ alkyl-$C_{6-10}$ aryl,
(4) —$C_{0-2}$ alkyl-heteroaryl group, wherein the heteroaryl is an aromatic cyclic or polycyclic group, having from five to ten ring atoms, said ring atoms selected from C, O, N, N→O, C(═O) or S, at least one of which is O, N, N→O or S, wherein said alkyl, alkenyl, aryl or heteroaryl $R^7$ group is optionally substituted with one or more
(a) halogen,
(b) hydroxy,
(c) —O—$C_{1-6}$ alkyl,
(d) —$C_{1-6}$ alkyl, optionally substituted with halogen;

$R^9$ and $R^{10}$, or $R^{11}$ and $R^{12}$, or $R^{13}$ and $R^{14}$ are each independently selected from the group consisting of
(1) hydrogen,
(2) —$C_{1-6}$ alkyl,
(3) —$C_{3-8}$ cycloalkyl, or
(4) —$C_{6-10}$ aryl,
wherein said alkyl, cycloalkyl or aryl is optionally substituted with one or more
(a) halogen,
(b) —$C_{1-6}$ alkyl,
(c) —$C_{3-8}$ cycloalkyl,
(d) —N(—$C_{1-6}$ alkyl)$_2$,
(e) —O—$C_{1-6}$ alkyl,
(f) —$C_{6-10}$ aryl,
(g) heteroaryl, which is an aromatic cyclic or polycyclic cyclic, having from five to ten ring atoms, said ring atoms selected from C, O, N, N→O, C(═O) or S, at least one of which is O, N, N→O or S,
(h) CN,
(i) hydroxyl
(i) —C(═O)—O—$R^7$,
(j) —NH—C(═O)—$R^7$,
(k) —S(═O)$_2$—$R^7$,
(l) —NH—S(═O)$_2$—$R^7$,
or $R^9$ and $R^{10}$, or $R^{11}$ and $R^{12}$, or $R^{13}$ and $R^{14}$ are linked together with the nitrogen to which they are both attached to form a 4-8 membered carbocyclic ring, wherein one or two of the ring carbon atoms is replaced by a nitrogen, oxygen or sulfur, and the carbocyclic is optionally substituted with one or more
(a) halogen,
(b) —$C_{1-6}$ alkyl,
(c) —O—$C_{1-6}$ alkyl, or
(d) —$C_{6-10}$ aryl, m is 0 or 1;

or a pharmaceutically acceptable salt thereof.

2. The compound of claim 1 wherein $R^{1A}$ and $R^{1B}$ are both hydrogen.

3. The compound of claim 1 wherein $R^3$ is selected from the group consisting of
(1) phenyl,
(2) heteroaryl, which is an aromatic cyclic or polycyclic group, having from five to ten ring atoms, said ring atoms selected from C, O, N, N→O, C(═O), $SO_2$ or S, at least one of which is O, N, N→O, $SO_2$ or S,
(3) a heterocyclic group having 4 to 8 ring atoms selected from C, O, N, N→O, C(═O), $SO_2$ or S, at least one of which is O, N, N→O, $SO_2$ or S,
wherein phenyl, heteroaryl or heterocyclic is optionally substituted with one or more $R^5$.

4. The compound of claim 1 wherein $R^5$ is present at one or more of the ring atoms and is selected from the group consisting of
(1) halogen,
(2) —O—$C_{1-6}$ alkyl,
(3) hydroxyl,
(4) —C(═O)—(O)$_m$—$R^7$,
(5) —NH—C(═O)—$R^7$,
(6) —NH—S(═O)$_2$—$R^7$,
(7) —$NO_2$,
(8) —CN;
(9) $C_{6-10}$ aryl,
(10) heteroaryl, which is an aromatic cyclic or polycyclic group, having from five to ten ring atoms, said ring atoms selected from C, O, N, N→O, C(═O) or S, at least one of which is O, N, N→O or S, and
(11) —$NR^9R^{10}$,
wherein said alkyl, cycloalkyl, aryl or heteroaryl $R^5$ group is optionally substituted with one or more
(d) halogen,
(e) —$C_{1-6}$ alkyl,
(f) —$C_{3-8}$ cycloalkyl,
(d) —$NR^{11}R^{12}$,
(f) —O—$C_{1-6}$ alkyl,
(f) $C_{6-10}$ aryl,
(g) CN,
(h) hydroxyl
(i) —C(═O)—O—$R^7$,
(j) —NH—C(═O)—$R^7$,
(k) —S(═O)$_2$—$R^7$, or
(l) —NH—S(═O)$_2$—$R^7$,
wherein said alkyl or aryl is optionally substituted with one or more
(i) halogen,
(ii) hydroxyl, or
(iii) —$NR^{11}R^{12}$.

5. The compound of claim 1 wherein $R^4$ is selected from the group consisting of
(1) phenyl,
(2) heteroaryl, which is an aromatic cyclic or polycyclic group, having from five to ten ring atoms, said ring atoms selected from C, O, N, N→O, C(═O) or S, at least one of which is O, N, N→O or S,
(3) a heterocyclic group having 4 to 8 ring atoms selected from C, O, N, N→O, C(═O), $SO_2$ or S, at least one of which is O, N, N→O, $SO_2$ or S,
wherein phenyl, heteroaryl or heterocyclic is optionally substituted with one or more $R^6$ group.

6. The compound of claim 1 wherein $R^3$ is phenyl substituted by a heteroaryl, which is an aromatic cyclic or polycyclic group, having from five to ten ring atoms, said ring atoms selected from C, O, N, N→O, C(═O), $SO_2$ or S, at least one of which is O, N, N→O, $SO_2$ or S.

7. The compound of claim 1 represented by structural formula (IV):

(IV)

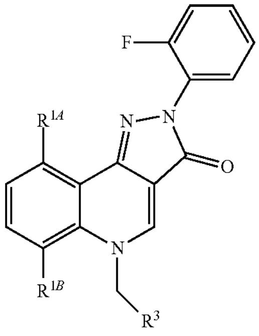

or pharmaceutically acceptable salt thereof, wherein $R^3$, $R^{1A}$ and $R^{1B}$ are defined in claim 1.

8. A compound which is selected from the group consisting of 2-(2-Fluorophenyl)-5-{[4-(methoxy)phenyl]methyl}-2,5-dihydro-3H-pyrazolo[4,3-c]quinolin-3-one;

2-(2-Fluorophenyl)-5-(biphenyl-4-ylmethyl)-2,5-dihydro-3H-pyrazolo[4,3-c]quinolin-3-one;

5-(Biphenyl-4-ylmethyl)-2-phenyl-2,5-dihydro-3H-pyrazolo[4,3-c]quinolin-3-one;

5-(Biphenyl-4-ylmethyl)-2-(phenylmethyl)-2,5-dihydro-3H-pyrazolo[4,3-c]quinolin-3-one;

6,9-Difluoro-2-(1-methyl-1H-imidazol-4-yl)-5-{[4-(1H-pyrazol-1-yl)phenyl]methyl}-2,5-dihydro-3H-pyrazolo[4,3-c]quinolin-3-one;

6,9-Difluoro-2-(1-iodophenyl)-5-{[4-(1H-pyrazol-1-yl)phenyl]methyl}-2,5-dihydro-3H-pyrazolo[4,3-c]quinolin-3-one;

6,9-Difluoro-2-[2-(1H-pyrazol-1-yl)phenyl]-5-{[4-(1H-pyrazol-1-yl)phenyl]methyl}-2,5-dihydro-3H-pyrazolo[4,3-c]quinolin-3-one;

6,9-Difluoro-2-[2-(hydroxymethyl)phenyl]-5-{[4-(1H-pyrazol-1-yl)phenyl]methyl}-2,5-dihydro-3H-pyrazolo[4,3-c]quinolin-3-one;

2-{2-[(Ethylamino)methyl]phenyl-6,9-difluoro-5-{[4-(1H-pyrazol-1-yl)phenyl]methyl}-2,5-dihydro-3H-pyrazolo[4,3-c]quinolin-3-one;

6,9-Difluoro-5-{[4-(1H-pyrazol-1-yl)phenyl]methyl}-2-[3-(trifluoromethyl)pyridin-2-yl]-2,5-dihydro-3H-pyrazolo[4,3-c]quinolin-3-one;

5-[(4-Bromo-2-fluorophenyl)methyl-6,9-difluoro-2-(2-fluorophenyl)-2,5-dihydro-3H-pyrazolo[4,3-c]quinolin-3-one;

6,9-Difluoro-2-(2-fluorophenyl)-5-{[2-fluoro-4-(1H-pyrazol-1-yl)phenyl]methyl}-2,5-dihydro-3H-pyrazolo[4,3-c]quinolin-3-one;

5-[(4-Iodo-2-fluorophenyl)methyl-6,9-difluoro-2-(2-fluorophenyl)-2,5-dihydro-3H-pyrazolo[4,3-c]quinolin-3-one;

6,9-Difluoro-2-(2-fluorophenyl)-5-{[2-fluoro-4-(1H-1,2,4-triazol-1-yl)phenyl]methyl}-2,5-dihydro-3H-pyrazolo[4,3-c]quinolin-3-one;

6,9-Difluoro-5-({2-fluoro-4-[1-(2-methylpropyl)-1H-pyrazol-4-yl]phenyl}methyl)-2-(2-fluorophenyl)-2,5-dihydro-3H-pyrazolo[4,3-c]quinolin-3-one;

5-[(5-Bromo-3-fluoropyridin-2-yl)methyl]-6,9-difluoro-2-(2-fluorophenyl)-2,5-dihydro-3H-pyrazolo[4,3-c]quinolin-3-one;

6,9-Difluoro-5-{[3-fluoro-5-(1-methyl-1H-pyrazol-4-yl)pyridin-2-yl]methyl}-2-(2-fluorophenyl)-2,5-dihydro-3H-pyrazolo[4,3-c]quinolin-3-one;

6,9-Difluoro-5-[(5-fluoro-6'-morpholin-4-yl-3,3'-bipyridin-6-yl)methyl]-2-(2-fluorophenyl)-2,5-dihydro-3H-pyrazolo[4,3-c]quinolin-3-one;

6,9-Difluoro-2-(2-fluorophenyl)-5-{3-fluoro-5-(1H-pyrazol-1-yl)pyridin-2-yl}methyl}-2,5-dihydro-3H-pyrazolo[4,3-c]quinolin-3-one;

2-Fluorophenyl-5-{[4-(1H-pyrazol-1-yl)phenyl]methyl}-2,5-dihydro-3H-pyrazolo[4,3-c]quinolin-3-one;

5-{[4-(3-Methyl-1H-pyrazol-1-yl)phenyl]methyl}-2-phenyl-2,5-dihydro-3H-pyrazolo[4,3-c]quinolin-3-one;

2-(2-Fluorophenyl)-5-(1H-indol-5-ylmethyl)-2,5-dihydro-3H-pyrazolo[4,3-c]quinolin-3-one;

2-(2-Fluorophenyl)-5-[(2-oxo-1-phenylpiperidin-4-yl)methyl]-2,5-dihydro-3H-pyrazolo[4,3-c]quinolin-3-one;

5{[2-Fluoro-4-(1H-indol-5-yl)phenyl]methyl}-2-(2-fluorophenyl)-2,5-dihydro-3H-pyrazolo[4,3-c]quinolin-3-one;

5-[(6-Chloropyridin-3-yl)methyl]-2-(2-fluorophenyl)-2,5-dihydro-3H-pyrazolo[4,3-c]quinolin-3-one;

2-(2-Fluorophenyl)-5-{[6-(1-methyl-1H-pyrazol-4-yl)pyridin-4-yl]methyl}-2,5-dihydro-3H-pyrazolo[4,3-c]quinolin-3-one;

2-(2-Fluorophenyl)-5-[(2'-methyl-3,3'-bipyridin-6-yl)methyl]-2,5-dihydro-3H-pyrazolo[4,3-c]quinolin-3-one;

2-(2-Fluorophenyl)-5-{[5-(4-methyl-1H-imidazol-1-yl)pyridin-2-yl]methyl}-2,5-dihydro-3H-pyrazolo[4,3-c]quinolin-3-one;

5-Ethyl-2-(2-fluorophenyl)-2,5-dihydro-3H-pyrazolo[4,3-c]quinolin-3-one;

2-(2-Fluorophenyl)-5-{[4-(1,3-oxadiazol-2-yl)phenyl]methyl}-2,5-dihydro-3H-pyrazolo[4,3-c]quinolin-3-one;

2-(2-Fluorophenyl)-5-{[4-(1-methyl-1H-pyrazol-4-yl)phenyl]methyl}-2,5-dihydro-3H-pyrazolo[4,3-c]quinolin-3-one;

2-(2-Fluorophenyl)-5-{[4-(1-methyl-1H-pyrazol-4-yl)phenyl]methyl}-2,5-dihydro-3H-pyrazolo[4,3-c]quinolin-3-one;

2-(2,6-Difluorophenyl)-5-{[4-(1H-pyrazol-1-yl)phenyl]methyl}-2,5-dihydro-3H-pyrazolo[4,3-c]quinolin-3-one;

2-(3-Oxo-5-{[4-(1H-pyrazol-1-yl)phenyl]methyl}-3,5-dihydro-2H-pyrazolo[4,3-c]quinolin-2-yl)benzonitrile;

6-Fluoro-2-(2-fluorophenyl)-5-{[4-(1H-pyrazol-1-yl)phenyl]methyl}-2,5-dihydro-3H-pyrazolo[4,3-c]quinolin-3-one;

6-Fluoro-2-(2-fluoro-3-methylpyridin-4-yl)-5-{[4-(1H-pyrazol-1-yl)phenyl]methyl}-2,5-dihydro-3H-pyrazolo[4,3-c]quinolin-3-one;

9-Fluoro-2-(2-methylphenyl)-5-{[4-(1H-pyrazol-1-yl)phenyl]methyl}-2,5-dihydro-3H-pyrazolo[4,3-c]quinolin-3-one;

9-Bromo-6-fluoro-2-(2-fluorophenyl)-5-{[4-(1H-pyrazol-1-yl)phenyl]methyl}-2,5-dihydro-3H-pyrazolo[4,3-c]quinolin-3-one;

2-(3-Oxo-5-{[4-(1H-pyrazol-1-yl)phenyl]methyl}-3,5-dihydro-2H-pyrazolo[4,3-c]quinolin-2-yl)benzoic acid;

N-Methyl-2-(3-oxo-5-{[4-(1H-pyrazol-1-yl)phenyl]methyl}-3,5-dihydro-2H-pyrazolo[4,3-c]quinolin-2-yl)benzamide;

2-(2-Aminophenyl)-5-{[4-(1H-pyrazol-1-yl)phenyl]methyl}-2,5-dihydro-3H-pyrazolo[4,3-c]quinolin-3-one;

2-[2-(Ethylamino)phenyl]-5-{[4-(1H-pyrazol-1-yl)phenyl]methyl}-2,5-dihydro-3H-pyrazolo[4,3-c]quinolin-3-one;

3-Methyl-N-[2-(3-oxo-5-{[4-(1H-pyrazol-1-yl)phenyl]methyl}-3,5-dihydro-2H-pyrazolo[4,3-c]quinolin-2-yl)phenyl]butanamide;

5-{[4-(1H-Pyrazol-1-yl)phenyl]methyl}-2-[2-(pyrrolodin-1-ylmethyl)phenyl]-2,5-dihydro-3H-pyrazolo[4,3-c]quinolin-3-one;

2,5-Bis {[4-(1H-pyrazol-1-yl)phenyl]methyl}-2,5-dihydro-3H-pyrazolo[4,3-c]quinolin-3-one;

2-[2-(Hydroxymethyl)phenyl]-5-{[4-(1H-pyrazol-1-yl)phenyl]methyl}-2,5-dihydro-3H-pyrazolo[4,3-c]quinolin-3-one;

(±)-2-[2-(Hydroxyethyl)phenyl]-5-{[4-(1H-pyrazol-1-yl)phenyl]methyl}-2,5-dihydro-3H-pyrazolo[4,3-c]quinolin-3-one;

2-[2-(1-Hydroxy-1-methylethyl)phenyl]-5-{[4-(1H-pyrazol-1-yl)phenyl]methyl}-2,5-dihydro-3H-pyrazolo[4,3-c]quinolin-3-one;

(±)-2-[2-(Hydroxypropyl)phenyl]-5-{[4-(1H-pyrazol-1-yl)phenyl]methyl}-2,5-dihydro-3H-pyrazolo[4,3-c]quinolin-3-one;

2-[2-(2-Hydroxyethyl)phenyl]-5-{[4-(1H-pyrazol-1-yl)phenyl]methyl}-2,5-dihydro-3H-pyrazolo[4,3-c]quinolin-3-one;

2-(2-Propanoylphenyl)-5-{[4-(1H-pyrazol-1-yl)phenyl]methyl}-2,5-dihydro-3H-pyrazolo[4,3-c]quinolin-3-one;

Methyl 2-(3-oxo-5-{[4-(1H-pyrazol-1-yl)phenyl]methyl}-3,5-dihydro-2H-pyrazolo[4,3-c]quinolin-2-yl)benzoate;

2-[2-(Azidomethyl)phenyl]-5-{[4-(1H-pyrazol-1-yl)phenyl]methyl}-2,5-dihydro-3H-pyrazolo[4,3-c]quinolin-3-one;

2-[2-(Aminomethyl)phenyl]-5-{[4-(1H-pyrazol-1-yl)phenyl]methyl}-2,5-dihydro-3H-pyrazolo[4,3-c]quinolin-3-one;

2-(2-Fluorophenyl)-5-{[2-fluoro-4-(1H-pyrazol-1-yl)phenyl]methyl}-2,5-dihydro-3H-pyrazolo[4,3-c]quinolin-3-one;

2-(2-Bromo-6-fluorophenyl)-5-{[2-fluoro-4-(1H-pyrazol-1-yl)phenyl]methyl}-2,5-dihydro-3H-pyrazolo[4,3-c]quinolin-3-one;

3-Fluoro-2-(3-oxo-5-{[4-(1H-pyrazol-1-yl)phenyl]methy}-3,5-dihydro-2H-pyrazolo[4,3-c]quinolin-2-yl)benzonitrile;

2-(2-Fluoro-6-methylphenyl)-5-{[4-(1H-pyrazol-1-yl)phenyl]methyl}-2,5-dihydro-3H-pyrazolo[4,3-c]quinolin-3-one;

2-(2-Bromo-6-methylphenyl)-5-{[4-(1H-pyrazol-1-yl)phenyl]methyl}-2,5-dihydro-3H-pyrazolo[4,3-c]quinolin-3-one;

2-(2-Bromo-6-methylphenyl)-5-{[4-(1H-pyrazol-1-yl)phenyl]methyl}-2,5-dihydro-3H-pyrazolo[4,3-c]quinolin-3-one;

2-(3-Chloropyridin-4-yl)-5-{[4-(1H-pyrazol-1-yl)phenyl]methyl}-2,5-dihydro-3H-pyrazolo[4,3-c]quinolin-3-one;

2-(4-Methylpyridin-3-yl)-5-{[4-(1H-pyrazol-1-yl)phenyl]methyl}-2,5-dihydro-3H-pyrazolo[4,3-c]quinolin-3-one;

3-(3-Oxo-5-{[4-(1H-pyrazol-1-yl)phenyl]methyl}-3,5-dihydro-2H-pyrazolo[4,3-c]quinolin-2-yl)pyridine-4-carbonitrile;

2-Piperidin-4-yl-5-{[4-(1H-pyrazol-1-yl)phenyl]methyl}-2,5-dihydro-3H-pyrazolo[4,3-c]quinolin-3-one;

2-(1-Acetylpiperidin-4-yl)-5-{[4-(1H-pyrazol-1-yl)phenyl]methyl}-2,5-dihydro-3H-pyrazolo[4,3-c]quinolin-3-one;

2-(3-Chloro-5-methylpyridin-4-yl)-5-{[4-(1H-pyrazol-1-yl)phenyl]methyl}-2,5-dihydro-3H-pyrazolo[4,3-c]quinolin-3-one;

2-(3,5-Dimethylpyridin-4-yl)-5-{[4-(1H-pyrazol-1-yl)phenyl]methyl}-2,5-dihydro-3H-pyrazolo[4,3-c]quinolin-3-one;

4-{[2-(2-Fluorophenyl)-3-oxo-2,3-dihydro-5H-pyrazolo[4,3-c]quinolin-5-yl]methyl}-N-methylpiperidine-1-carboxamide;

2-(2-Fluorophenyl)-5-{[2-(hydroxymethyl)phenyl]methyl}-2,5-dihydro-3H-pyrazolo[4,3-c]quinolin-3-one;

(3-Oxo-5-{[4-(1H-pyrazol-1-yl)phenyl]methyl}-3,5-dihydro-2H-pyrazol[4,3-c]quinolin-2-yl)acetic acid;

N,N-Diethyl-2-(3-oxo-5-{[4-(1H-pyrazol-1-yl)phenyl]methyl}-3,5-dihydro-2H-pyrazol[4,3-c]quinolin-2-yl)acetamide;

6-Bromo-9-fluoro-2-(2-methylphenyl)-5-{[4-(1H-pyrazol-1-yl)phenyl]methyl}-2,5-dihydro-3H-pyrazolo[4,3-c]quinolin-3-one;

9-Fluoro-6-methyl-2-(2-methylphenyl)-5-{[4-(1H-pyrazol-1-yl)phenyl]methyl}-2,5-dihydro-3H-pyrazolo[4,3-c]quinolin-3-one;

9-Fluoro-2-(2-methylphenyl)-3-oxo-5-{[4-(1H-pyrazol-1-yl)phenyl]methyl}-3,5-dihydro-2H-pyrazolo[4,3-c]quinoline-6-carbonitrile;

5-{[3-Chloro-4-(6-morpholin-4-ylpyridin-3-yl)phenyl]methyl}-2-(2-fluorophenyl)-2,5-dihydro-3H-pyrazolo[4,3-c]quinolin-3-one;

(±)-2-[trans-2-(Methyloxy)cyclohexyl]-5-{[4-(1H-pyrazol-1-yl)phenyl]methyl}-2,5-dihydro-3H-pyrazolo[4,3-c]quinolin-3-one;

(±)-2-(cis-2-Fluorocyclohexyl)-5-{[4-(1H-pyrazol-1-yl)phenyl]methyl}-2,5-dihydro-3H-pyrazolo[4,3-c]quinolin-3-one;

(±)-2-(Cyclohex-2-en-1-yl)-5-{[4-(1H-pyrazol-1-yl)phenyl]methyl}-2,5-dihydro-3H-pyrazolo[4,3-c]quinolin-3-one;

(±)-2-(3-Oxo-5-{[4-(1H-pyrazol-1-yl)phenyl]methyl}-3,5-dihydro-2H-pyrazolo[4,3-c]quinolin-2-yl)cyclohexyl acetate;

(±)-2-(2-Oxocyclohexyl)-5-{[4-(1H-pyrazol-1-yl)phenyl]methyl}-2,5-dihydro-3H-pyrazolo[4,3-c]quinolin-3-one;

(±)-2-[trans-2-(Methylamino)cyclohexyl]-5-{[4-(1H-pyrazol-1-yl)phenyl]methyl}-2,5-dihydro-3H-pyrazolo[4,3-c]quinolin-3-one;

5-[(4-Iodophenyl)methyl]-9-(methyloxy)-2-(2-methylphenyl)-2,5-dihydro-3H-pyrazolo[4,3-c]quinolin-3-one;

9-(Methyloxy)-2-(2-methylphenyl)-5-{[4-(1H-pyrazol-1-yl)phenyl]methyl}-2,5-dihydro-3H-pyrazolo[4,3-c]quinolin-3-one;

9-Hydroxy-2-(2-methylphenyl)-5-{[4-(1H-pyrazol-1-yl)phenyl]methyl}-2,5-dihydro-3H-pyrazolo[4,3-c]quinolin-3-one;

2-(2-Methylphenyl)-3-oxo-5-{[4-(1H-pyrazol-1-yl)phenyl]methyl}-3,5-dihydro-2H-pyrazolo[4,3-c]quinolin-9-yl trifluoromethanesulfonate;

9-Methyl-2-(2-methylphenyl)-5-{[4-(1H-pyrazol-1-yl)phenyl]methyl}-2,5-dihydro-3H-pyrazolo[4,3-c]quinolin-3-one;

2-(2-Methylphenyl)-3-oxo-5-{[4-(1H-pyrazol-1-yl)phenyl]methyl}-3,5-dihydro-2H-pyrazolo[4,3-c]quinolin-9-yl acetate;

9-Hydroxy-5-[(iodophenyl)methyl]-2-(2-methylphenyl)-2,5-dihydro-3H-pyrazolo[4,3-c]quinolin-3-one;

9-Hydroxy-2-(2-methylphenyl)-5-{[4-(6-methylpyridin-3-yl)phenyl]methyl}-2,5-dihydro-3H-pyrazolo[4,3-c]quinolin-3-one;

9-(Methyloxy)-2-(2-methylphenyl)-5-{[4-(6-methylpyridin-3-yl)phenyl]methyl}-2,5-dihydro-3H-pyrazolo[4,3-c]quinolin-3-one;

2-[5-(Hydroxymethyl)-1-methyl-1H-imidazol-4-yl]-5-{[4-(1H-pyrazol-1-yl)phenyl]methyl}-2,5-dihydro-3H-pyrazolo[4,3-c]quinolin-3-one;

2-{1-Methyl-5-[(methylamino)methyl]-1H-imidazol-4-yl]-5-{[4-(1H-pyrazol-1-yl)phenyl]methyl}-2,5-dihydro-3H-pyrazolo[4,3-c]quinolin-3-one;

(±)-2-(3-Fluoro-4-methylpyridin-2-yl)-5-trans-2-[(3-fluoro-4-methylpyridin-2-yl)amino]cyclohexy}-9-({[4-(1H-pyrazol-1-yl)phenyl]methyl}amino)-2,5-dihydro-3H-pyrazolo[4,3-c]quinolin-3-one;

8-Fluoro-5-{[4-(methyloxy)phenyl]methyl}-2-(2-methylphenyl)-9-({[4-(1H-pyrazol-1-yl)phenyl]methyl}amino)-2,5-dihydro-3H-pyrazolo[4,3-c]quinolin-3-one;

(±)-2-(2-Fluorophenyl)-5-{trans-2-[(3-fluoropyridin-2-yl)amino]cyclohexyl}-9-({[4-(1H-pyrazol-1-yl)phenyl]methyl}amino)-2,5-dihydro-3H-pyrazolo[4,3-c]quinolin-3-one;

5-[(5-Bromopyridin-2-yl)methyl]-2-(2-methylphenyl)-2,5-dihydro-3H-pyrazolo[4,3-c]quinolin-3-one;

2-(2-Methylphenyl)-5-[(5-phenylpyridin-2-yl)methyl]-2,5-dihydro-3H-pyrazolo[4,3-c]quinolin-3-one;

2-(2-Methylphenyl)-5-(pyridin-2-ylmethyl)-2,5-dihydro-3H-pyrazolo[4,3-c]quinolin-3-one;

2-(3,5-Dichloropyridin-4-yl)-5-[(pyridin-2-yl)methyl]-2,5-dihydro-3H-pyrazolo[4,3-c]quinolin-3-one;

2-(2-Methylphenyl)-5-[(5-methylpyridin-2-yl)methyl]-2,5-dihydro-3H-pyrazolo[4,3-c]quinolin-3-one;

2-(2-Methylphenyl)-5-(4-nitrobenzyl)-2,5-dihydro-3H-pyrazolo[4,3-c]quinolin-3-one;

5-(4-Aminobenzyl)-2-(2-methylphenyl)-2,5-dihydro-3H-pyrazolo[4,3-c]quinolin-3-one;

5-[4-(Dimethylamino)benzyl]-2-(2-methylphenyl)-2,5-dihydro-3H-pyrazolo[4,3-c]quinolin-3-one;

N-(4-{[2-(2-Methylphenyl)-3-oxo-2,3-dihydro-5H-pyrazolo[4,3-c]quinolin-5-yl]methyl}phenyl)methanesulfonamide;

2-Allyl-5-[(5-bromopyridin-2-yl)methyl]-2,5-dihydro-3H-pyrazolo[4,3-c]quinolin-3-one;

2-Allyl-5-(4-fluorobenzyl)-2,5-dihydro-3H-pyrazolo[4,3-c]quinolin-3-one;

5-(4-Fluorobenzyl)-2-pyridin-4-yl-2,5-dihydro-3H-pyrazolo[4,3-c]quinolin-3-one;

5-(4-Fluorobenzyl)-2-piperidin-4-yl-2,5-dihydro-3H-pyrazolo[4,3-c]quinolin-3-one;

Methyl 4-[5-(4-fluorobenzyl)-3-oxo-3,5-dihydro-2H-pyrazolo[4,3-c]quinolin-2-yl]piperidine-1-carboxylate;

5-[(4-Fluorophenyl)methyl]-2-(1-methylpiperidin-4-yl)-2,5-dihydro-3H-pyrazolo[4,3-c]quinolin-3-one;

(±)-5-(4-Fluorobenzyl)-2-[2-(1-hydroxyethyl)phenyl]-2,5-dihydro-3H-pyrazolo[4,3-c]quinolin-3-one;

5-(4-Fluorobenzyl)-2-propyl-2,5-dihydro-3H-pyrazolo[4,3-c]quinolin-3-one;

5-(4-Fluorobenzyl)-2-[2-(hydroxymethyl)phenyl]-2,5-dihydro-3H-pyrazolo[4,3-c]quinolin-3-one;

or a pharmaceutically acceptable salt thereof.

9. The compound of claim 1, wherein the compound of formula (I) is a compound of formula (IA), (IB), (IC), or (ID)

(IA)

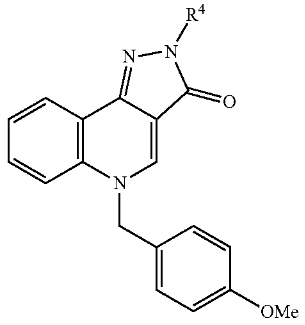

(IB)

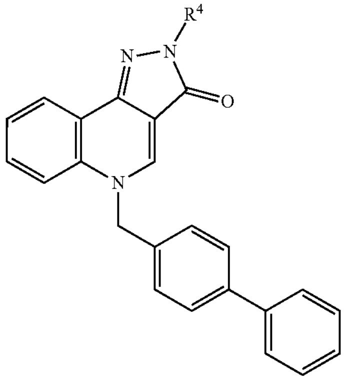

(IC)

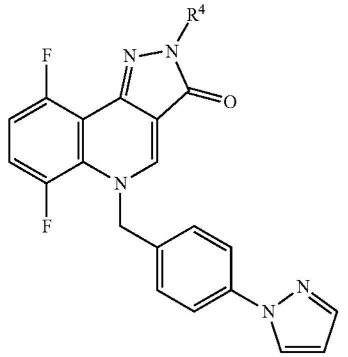

(ID)

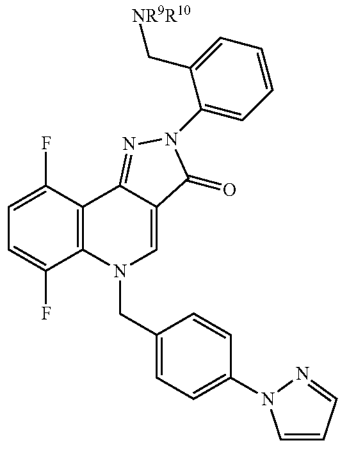

or a pharmaceutically acceptable salt thereof, wherein $R^4$ in (IA) is selected from the group consisting of
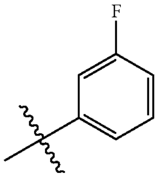 and 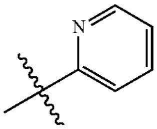;
$R^4$ in (IB) is selected from the group consisting of:
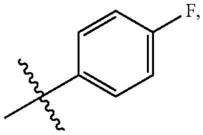 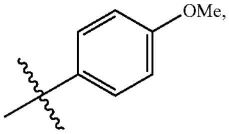 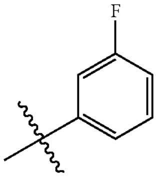, 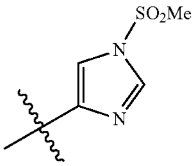, 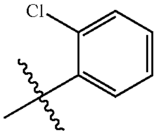, 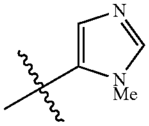 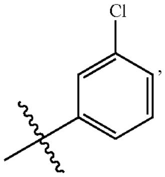, 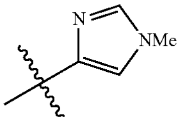 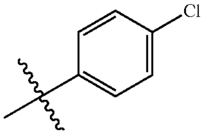, 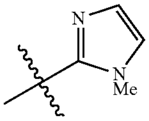, 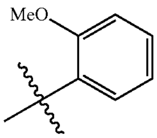, 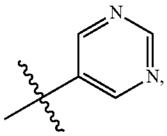 and 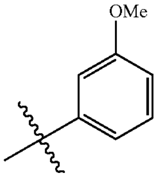,
$R^4$ in (IC) is selected from the group consisting of
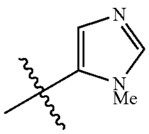, 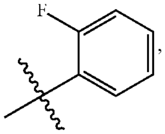, 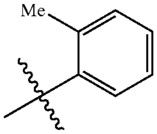, 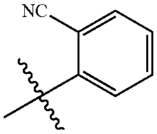, 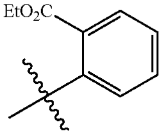 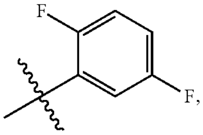
-continued
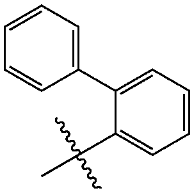, 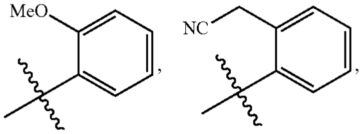, 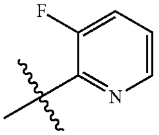, 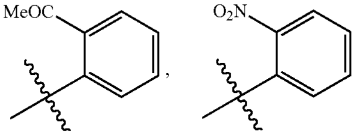, 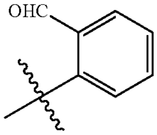, 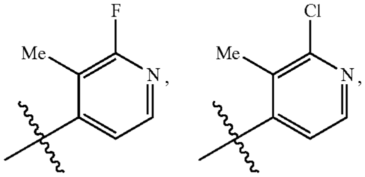, 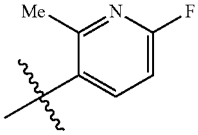, 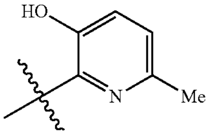 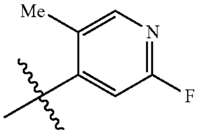, 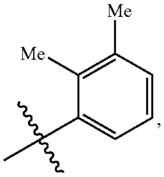, 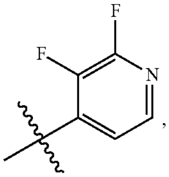, 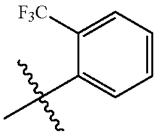, 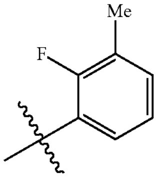, 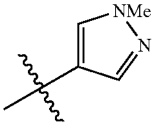 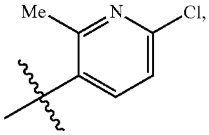 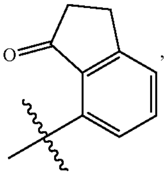, 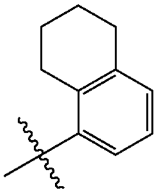, 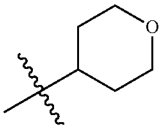, and 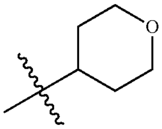
wherein $NR^9R^{10}$ in (ID) is selected from the group consisting of

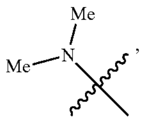, 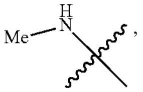, 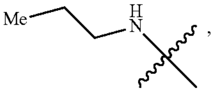,
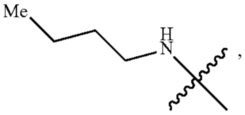,
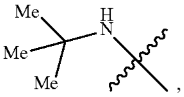, 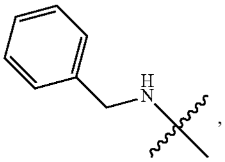,
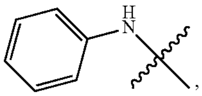, 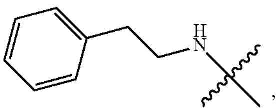,
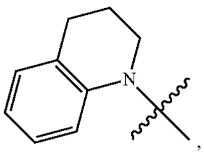, 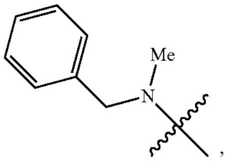,
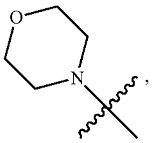, 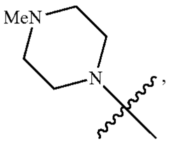, 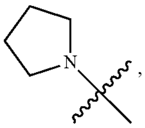,
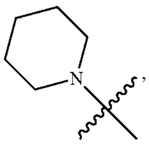, 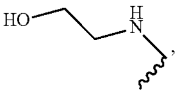, 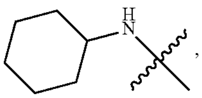,
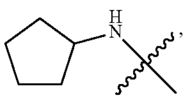, 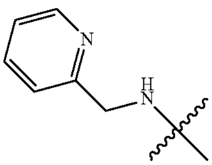,
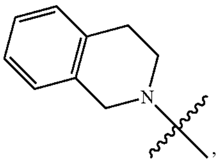, and 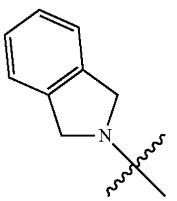.
10. A compound represented by formula (IF), (IG), (IH), (IJ), or (IK)
(IF)
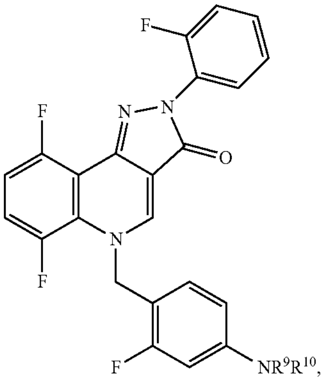
(IG)
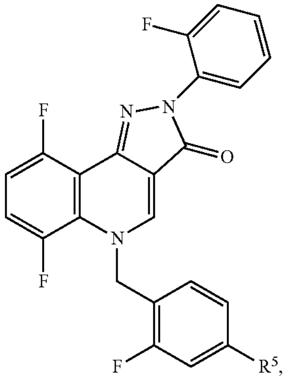
(IH)
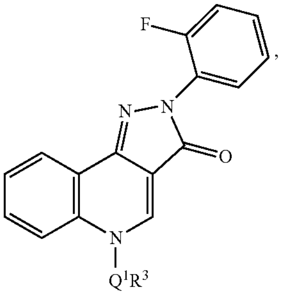
(IJ)
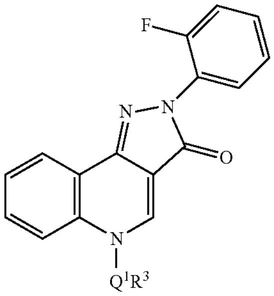

-continued
(IK)
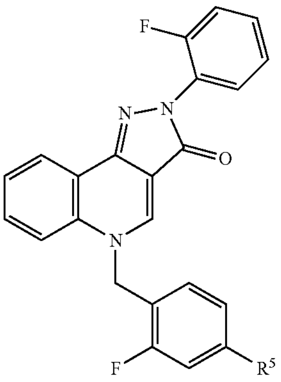
wherein $NR^9R^{10}$ in (IF) is selected from the group consisting of
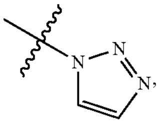
,
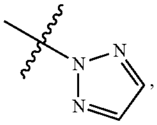
,
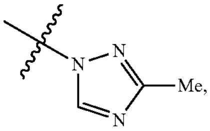
,
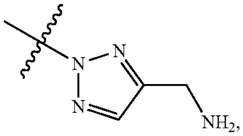
,
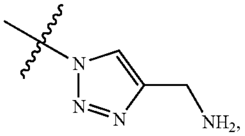
,
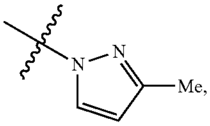
,
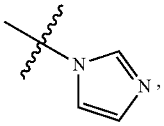
,
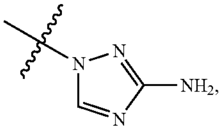
,
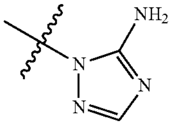
and
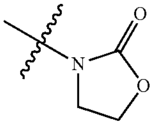
$R^5$ in (IG) is selected from the group consisting of
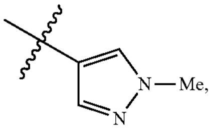
,
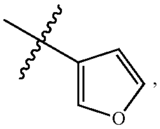
,
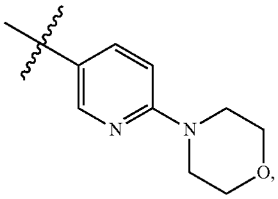
,
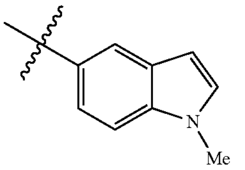
,
-continued
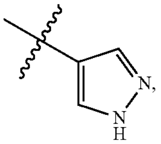
,
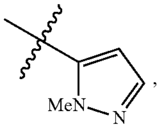
, and
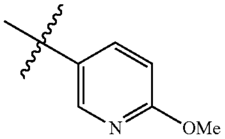
$Q^1R^3$ in (IH) is selected from the group consisting of
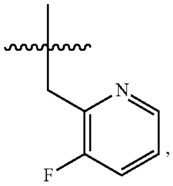
,
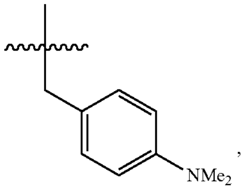
,
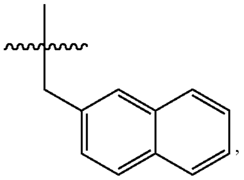
,
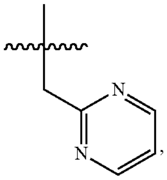
,
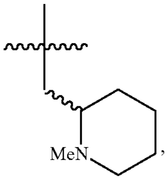
,
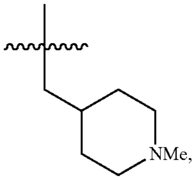
,
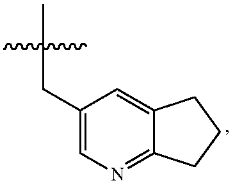
,
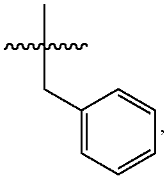
,
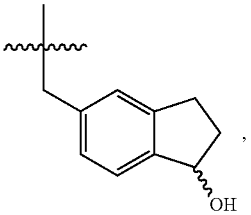
, and
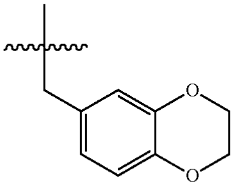

Q¹R³ in (IJ) is selected from the group consisting of
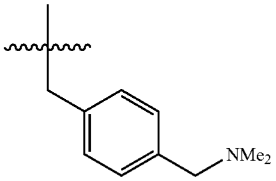, 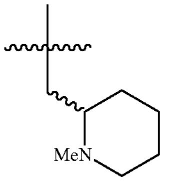, 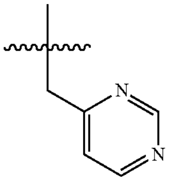, 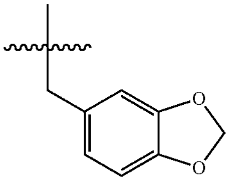
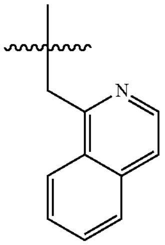, 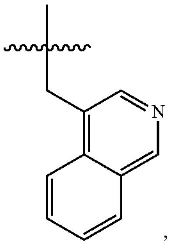,
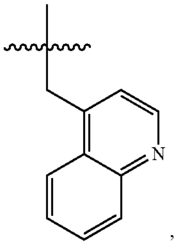, 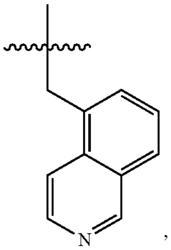, 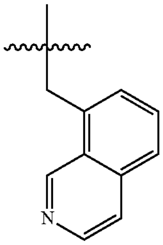,
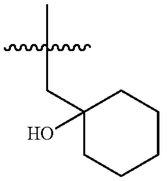, 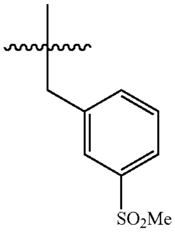,
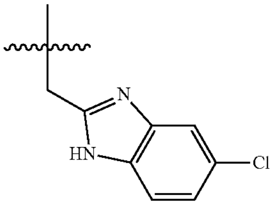, 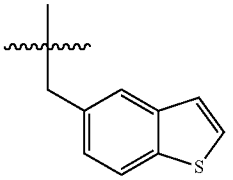,
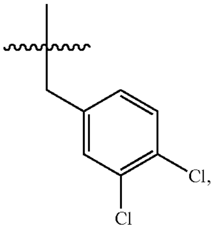 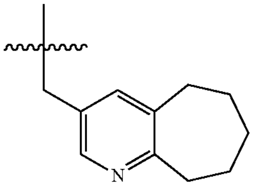,
-continued
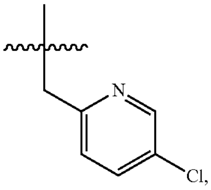 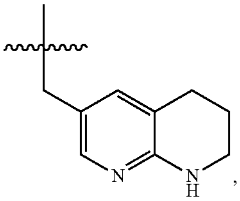,
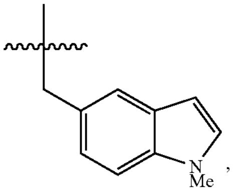,
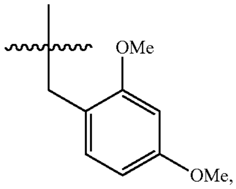 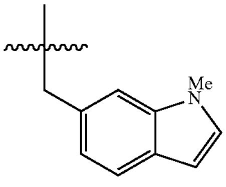,
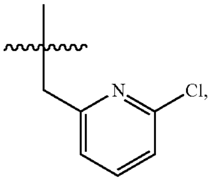 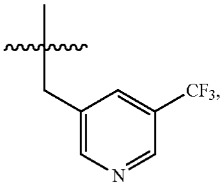
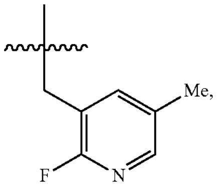 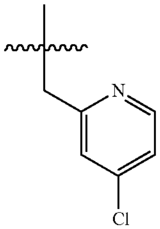,
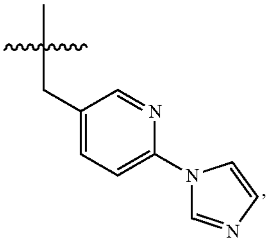 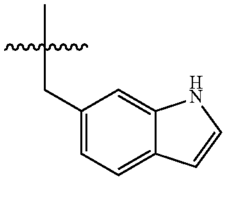,
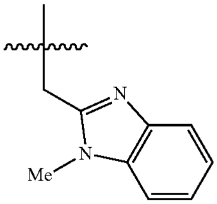, 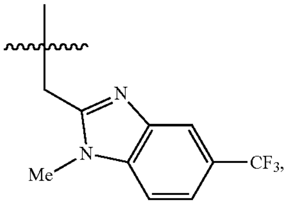
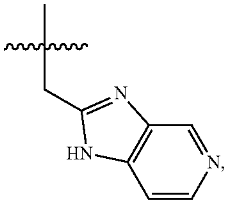 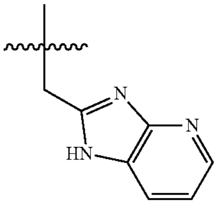, -continued
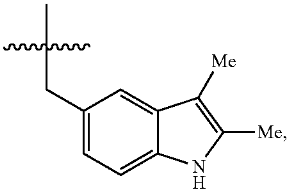
,
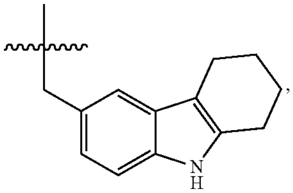
,
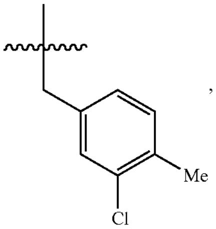
,
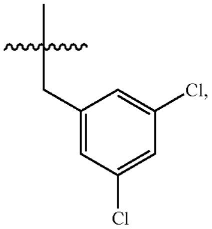
,
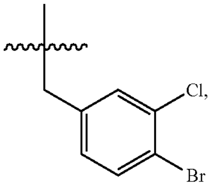
and
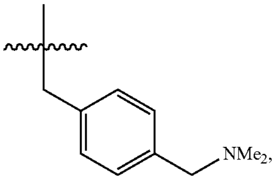
,
$R^5$ in (IK) is selected from the group consisting of
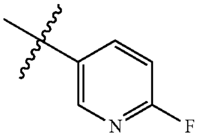
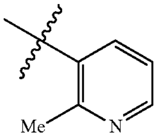
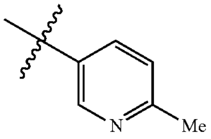
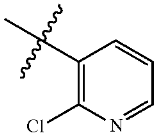
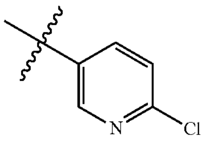
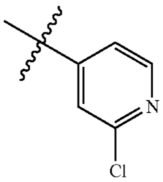
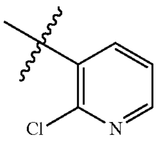
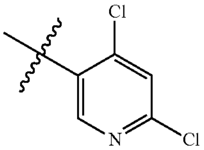
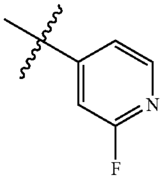
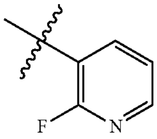
-continued
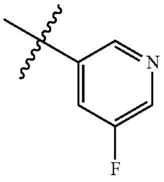
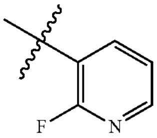
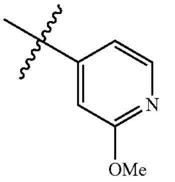
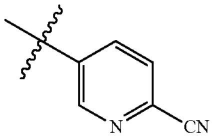
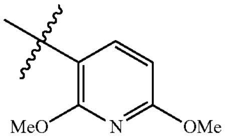
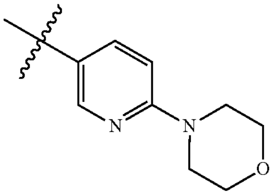
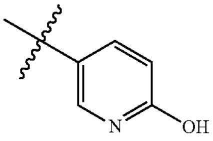
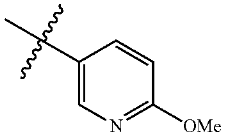
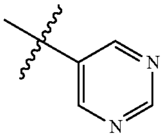
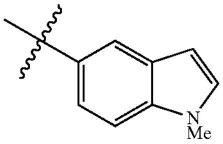
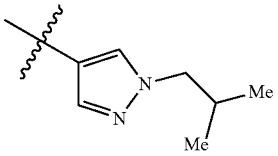
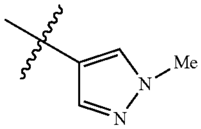
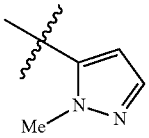
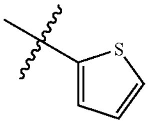
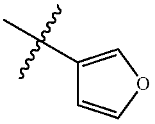
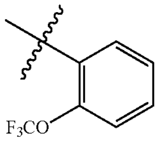
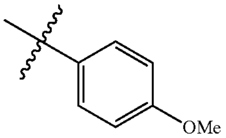
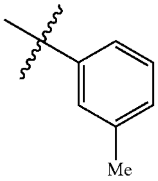
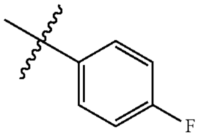
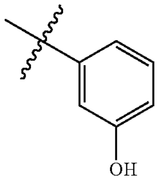
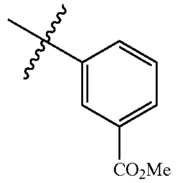
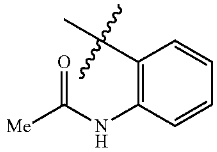
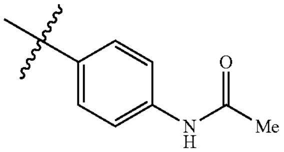
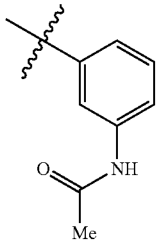

-continued
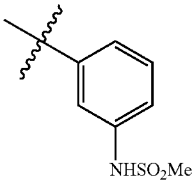
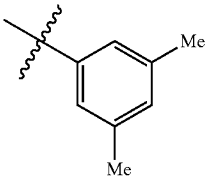
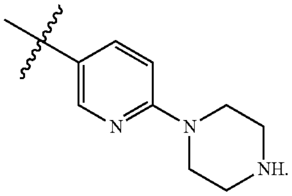
or a pharmaceutically acceptable salt thereof.
11. A compound represented by formula (IL), (IM), (IN), (IO),
(IL)
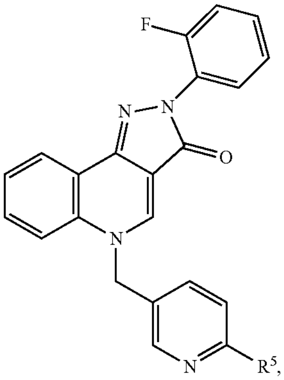
(IM)
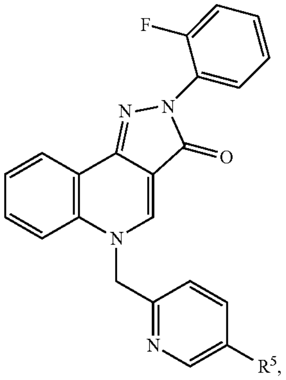
(IN)
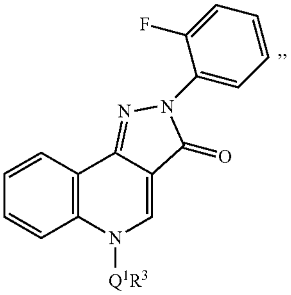
-continued
(IO)
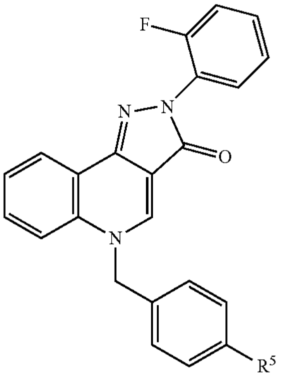
wherein $R^5$ in (IL) is selected from the group consisting of:
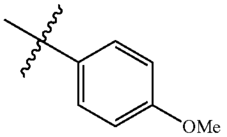
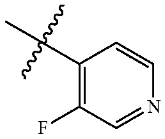
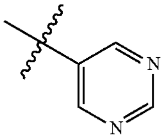
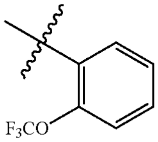
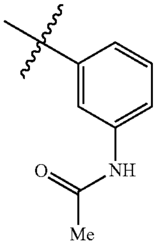
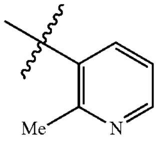
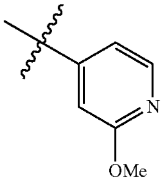
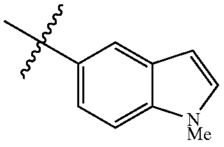
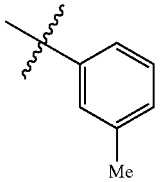
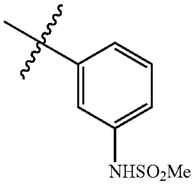
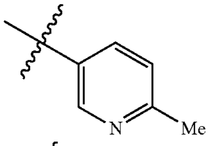
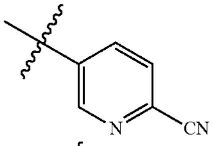
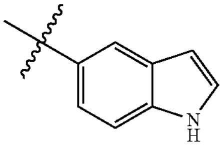
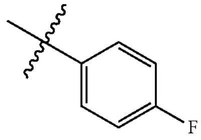
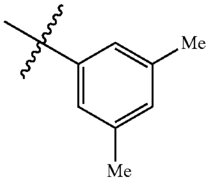
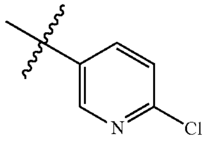

-continued
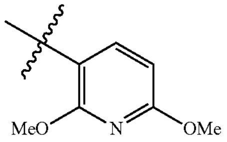
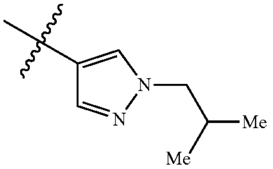
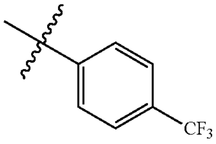
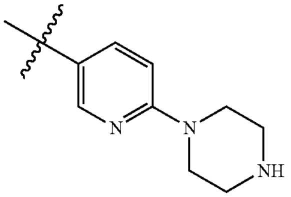
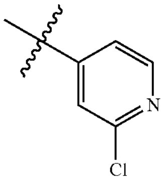
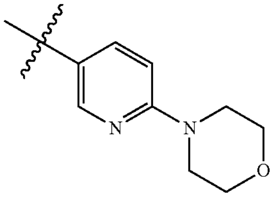
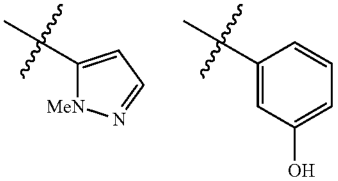
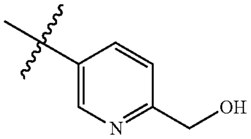
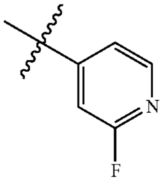
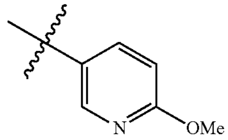
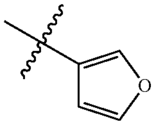
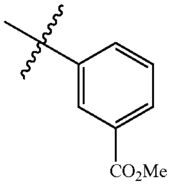
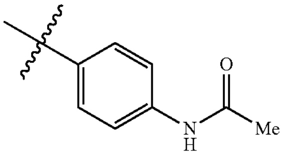
$R^5$ in (IM) is selected from the group consisting of
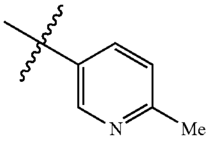
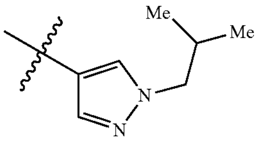
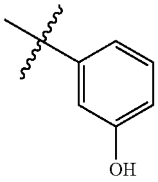
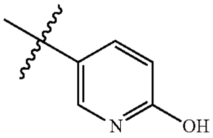
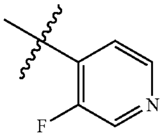
-continued
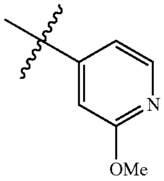
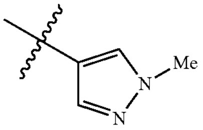
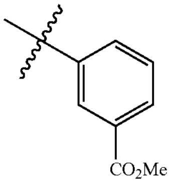
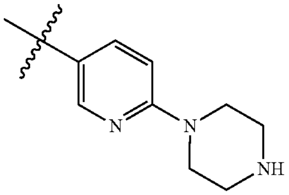
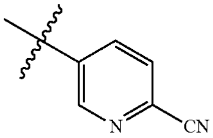
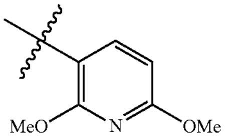
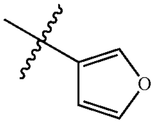
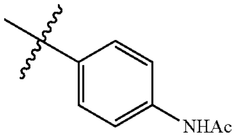
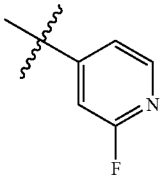
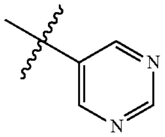
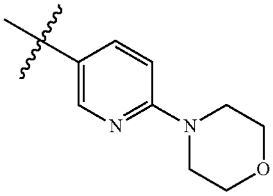
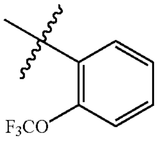
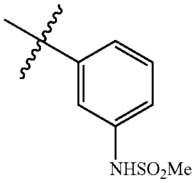
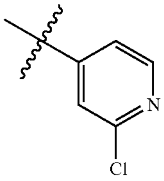
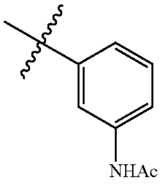
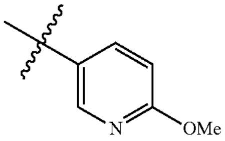
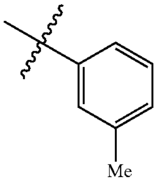
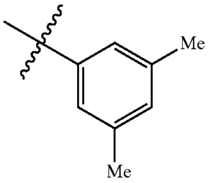
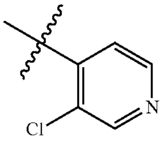
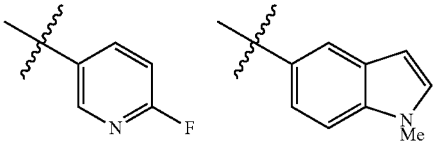
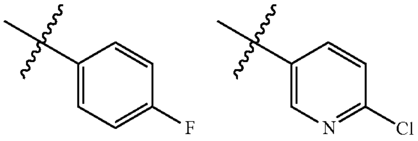

-continued
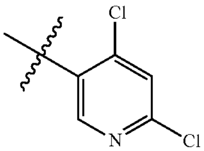
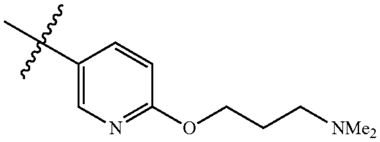
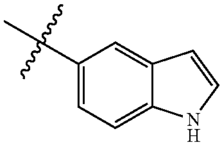
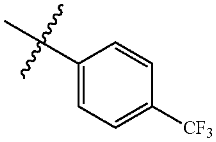
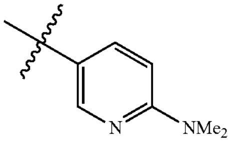
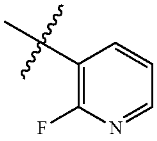
wherein $Q^1R^3$ in (IN) is selected from the group consisting of
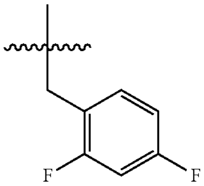
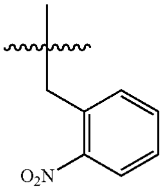
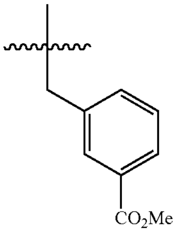
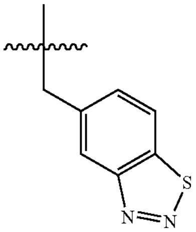
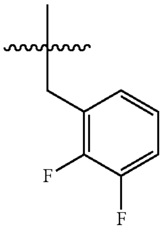
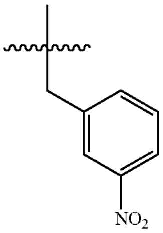
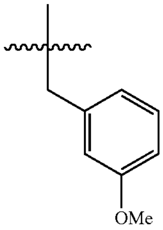
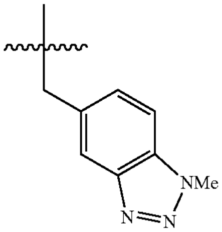
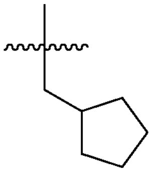
-continued
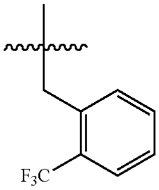
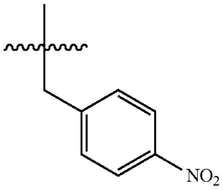
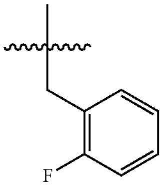
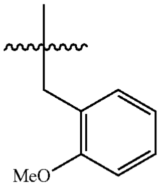
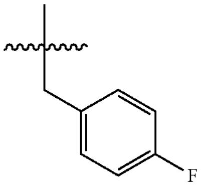
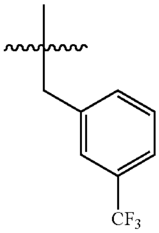
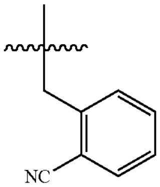
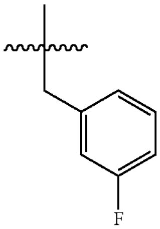
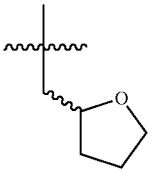
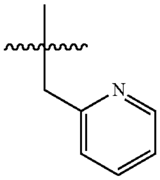
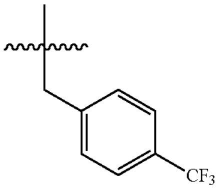
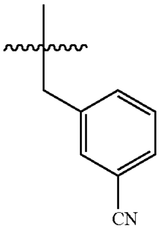
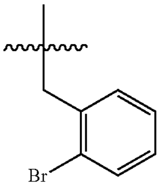
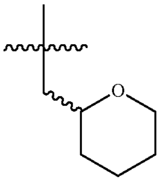
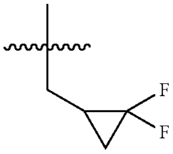
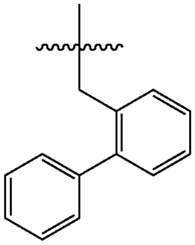
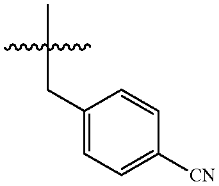
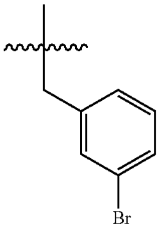
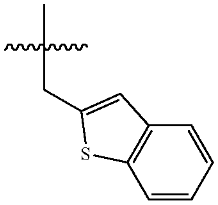
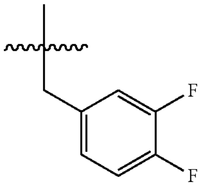

-continued
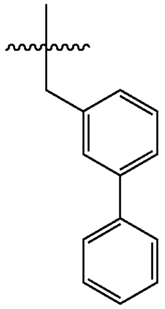
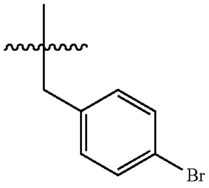
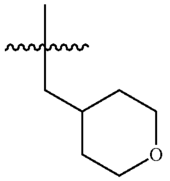
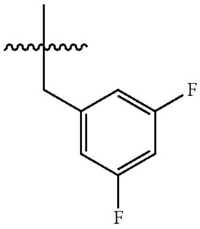
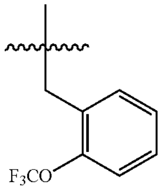
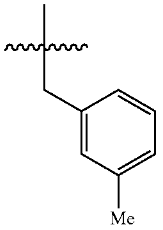
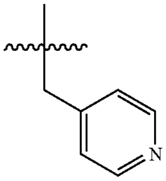
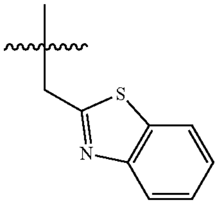
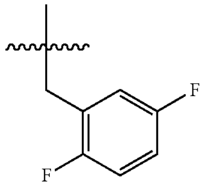
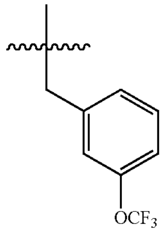
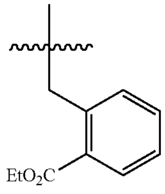
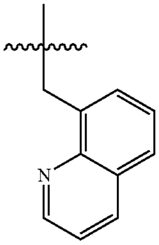
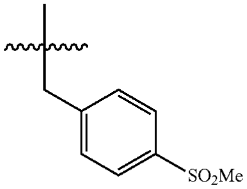
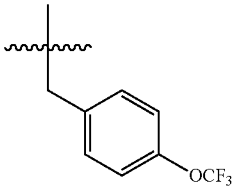
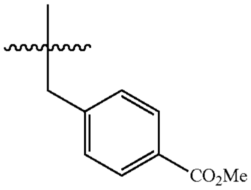
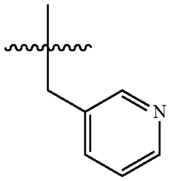
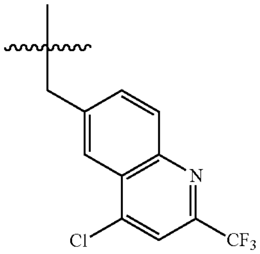
-continued
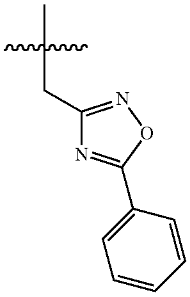
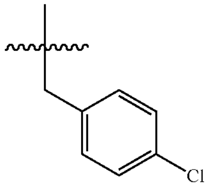
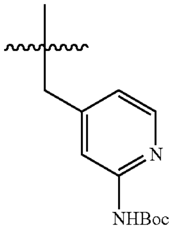
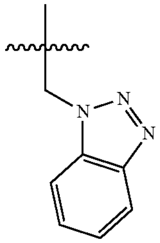
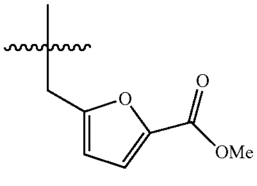
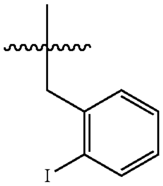
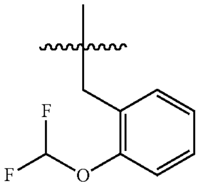
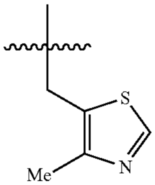
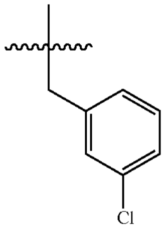
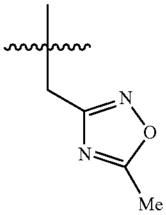
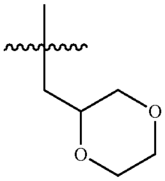
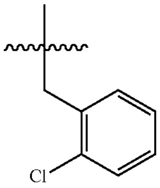
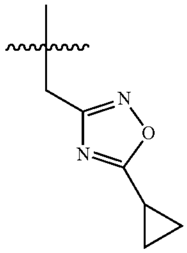
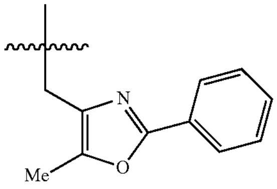
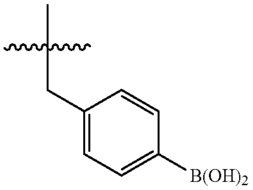

-continued
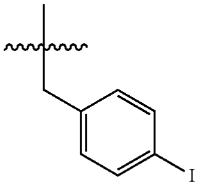
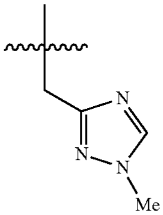
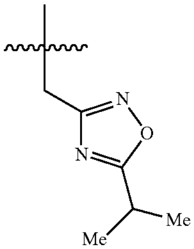
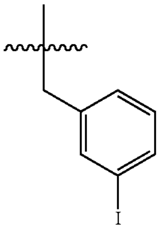
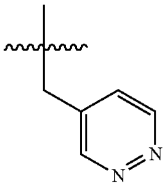
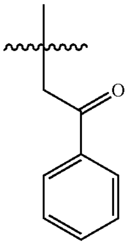
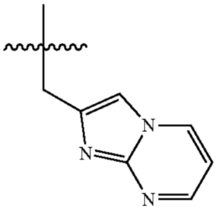
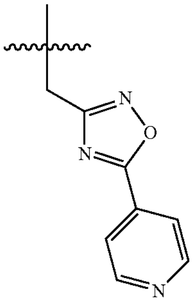
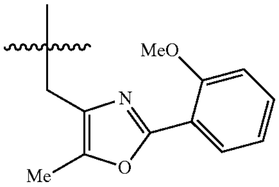
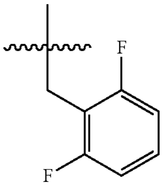
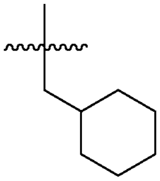
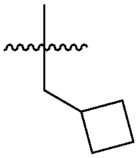
wherein $R^5$ in (IO) is selected from the group consisting of
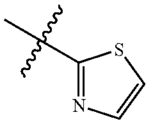
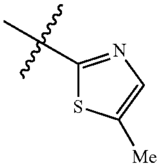
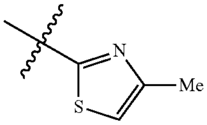
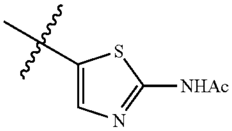
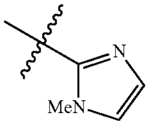
-continued
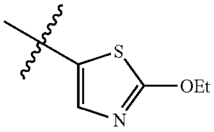
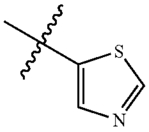
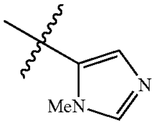
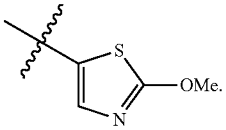
12. A compound represented by formula (IP), (IQ), (IR), (IS), (IT)
(IP)
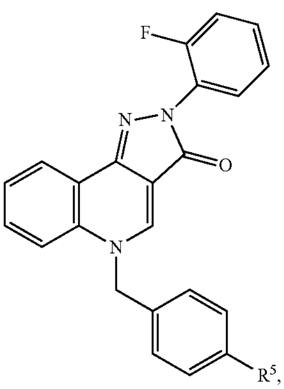
(IQ)
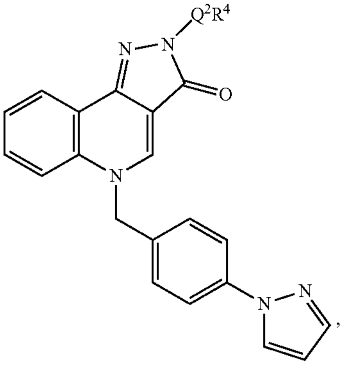
(IR)
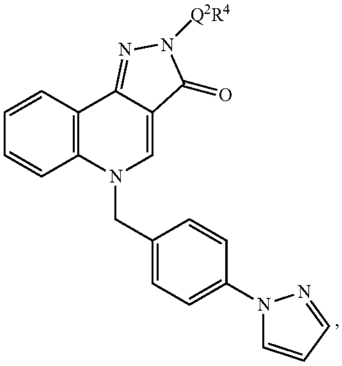

-continued
(IS)
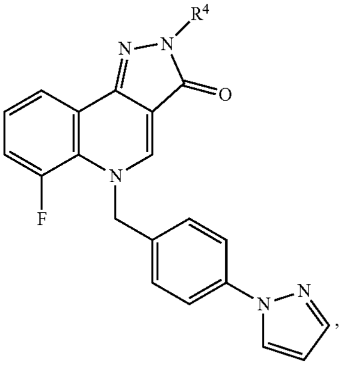
(IT)
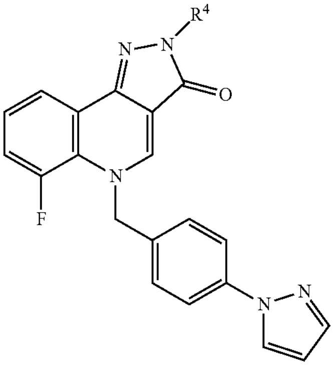
or a pharmaceutically acceptable salt thereof,
wherein $R^5$ in (IP) is selected from the group consisting of
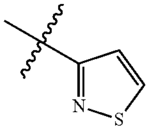
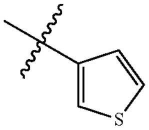
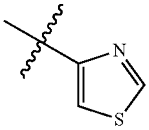
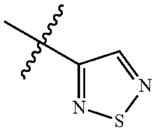
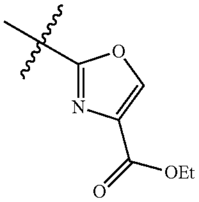
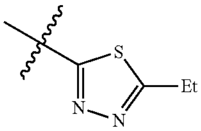
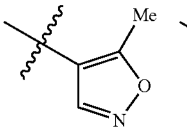
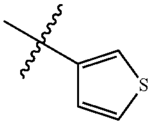
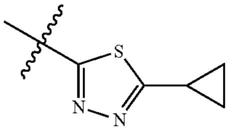
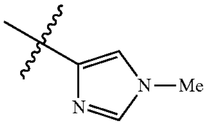
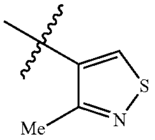
wherein $Q^2R^4$ in (IQ) is selected from the group consisting of
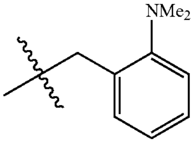
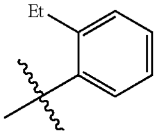
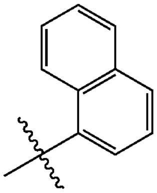
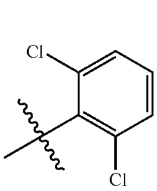
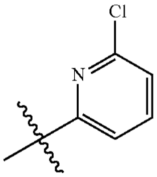
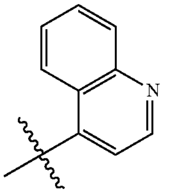
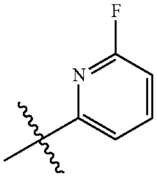
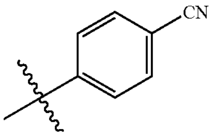
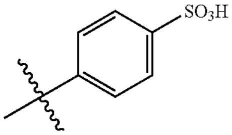
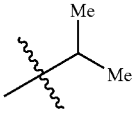
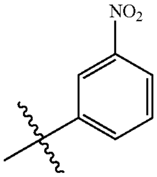
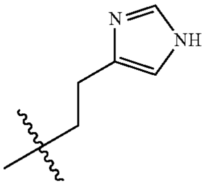
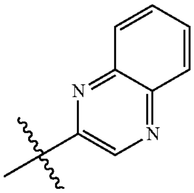
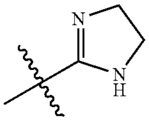
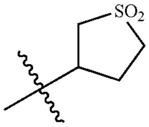
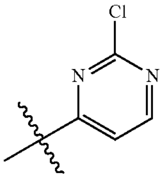
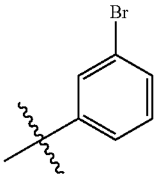
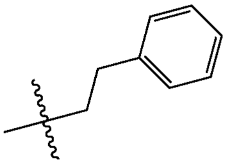
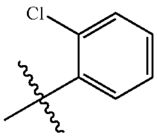
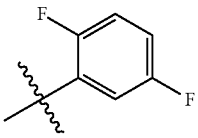
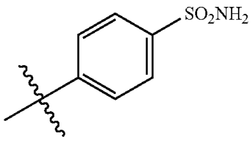

-continued
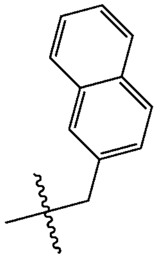
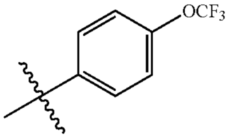
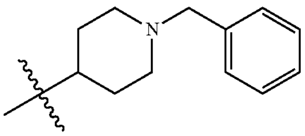
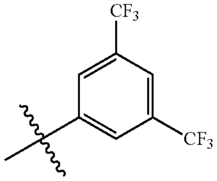
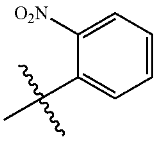
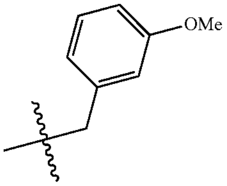
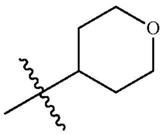
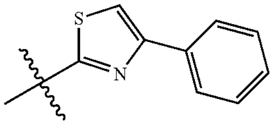
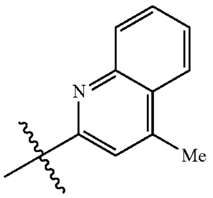
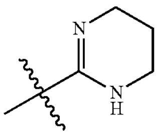
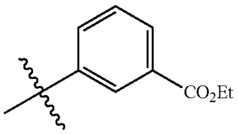
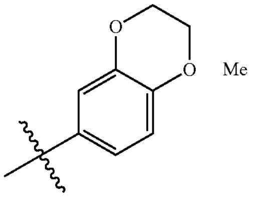
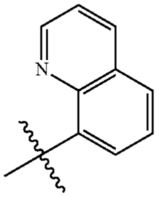
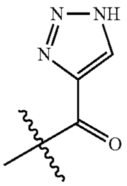
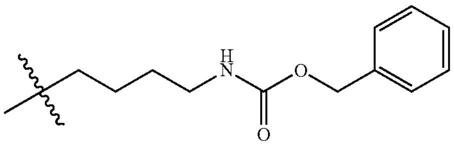
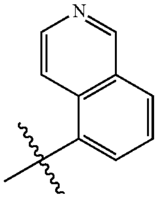
-continued
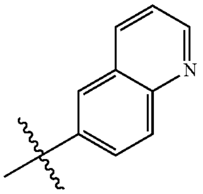
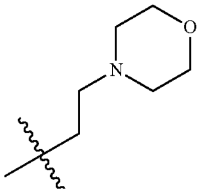
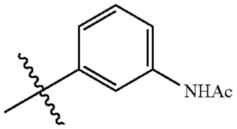
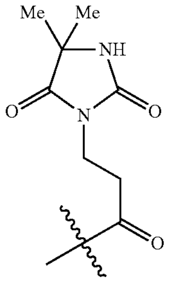
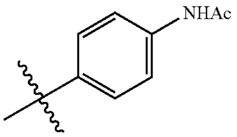
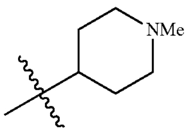
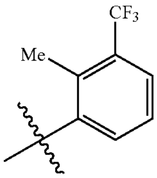
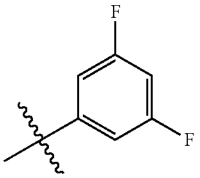
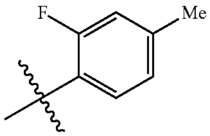
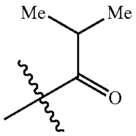
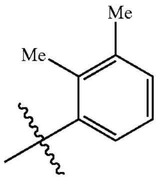
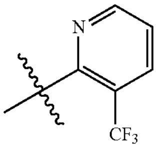
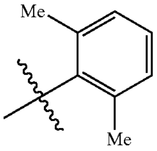
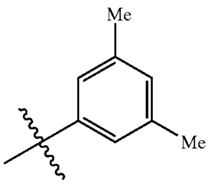
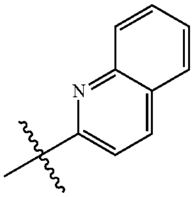
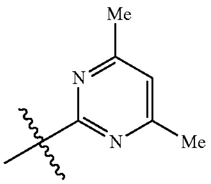
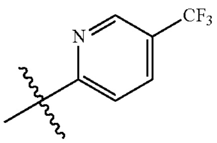
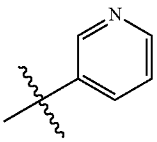
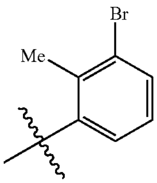
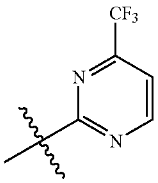

-continued
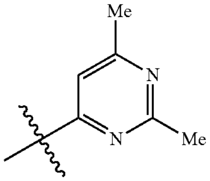
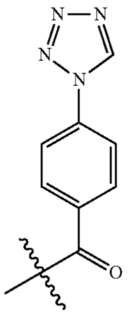
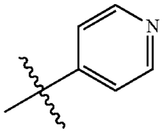
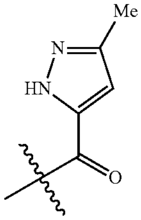
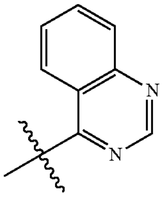
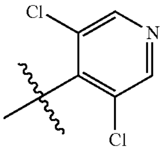
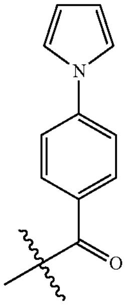
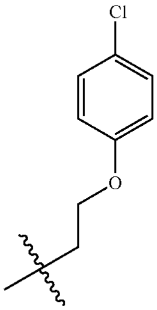
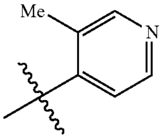
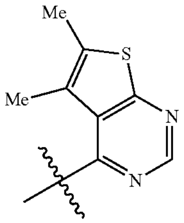
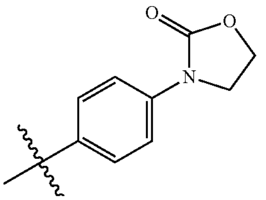
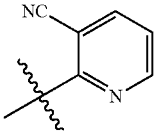
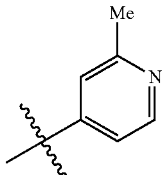
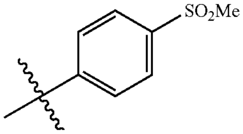
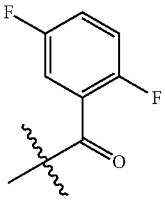
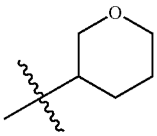
-continued
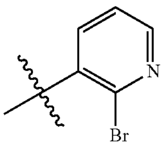
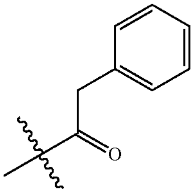
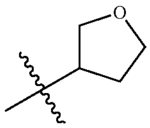
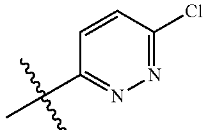
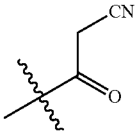
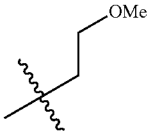
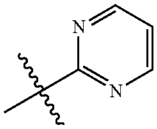
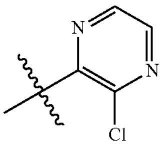
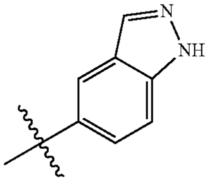
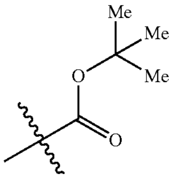
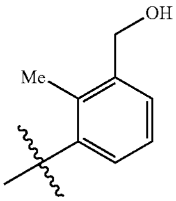
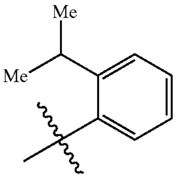
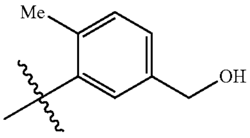
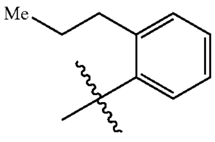
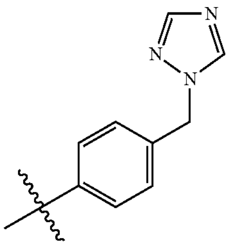
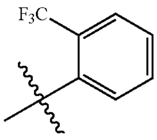
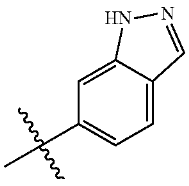
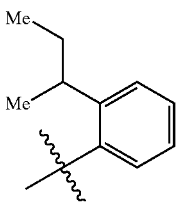
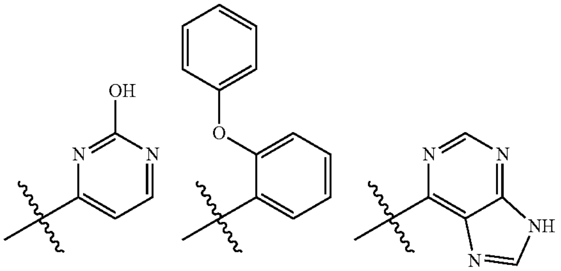

-continued
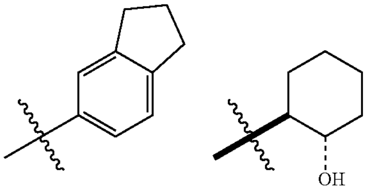
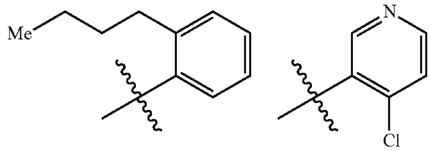
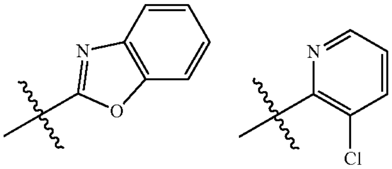
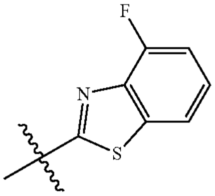
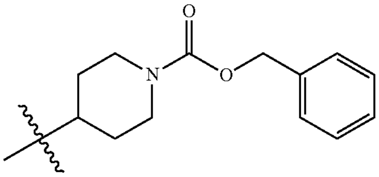
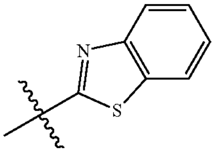 [SMILES: *c1nc2ccccc2s1]
wherein $Q^2R^4$ in (IR) is selected from the group consisting of
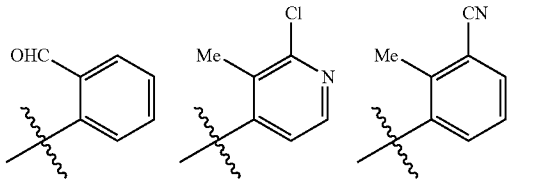
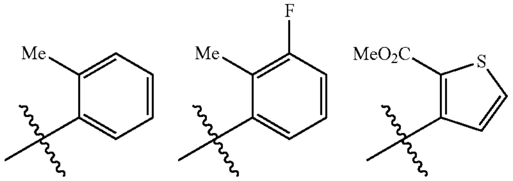
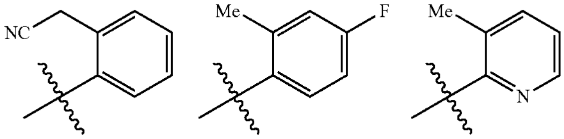
-continued
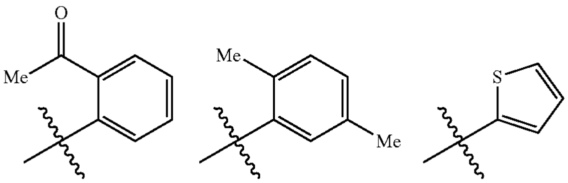
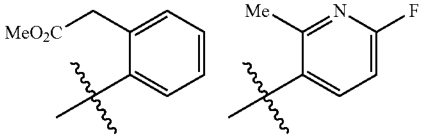
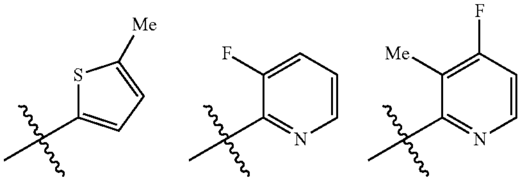
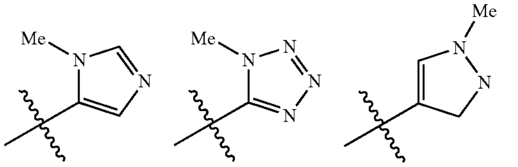
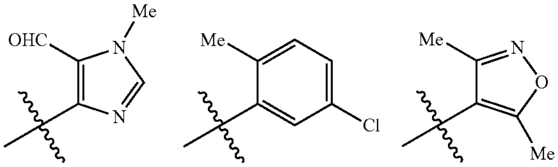
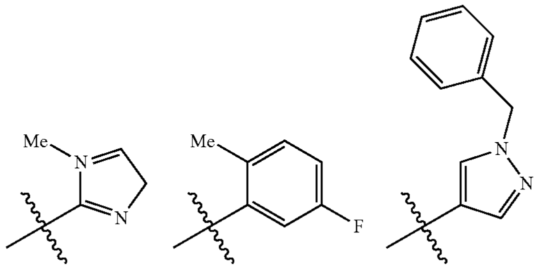
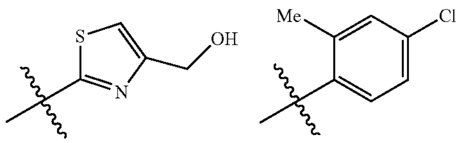
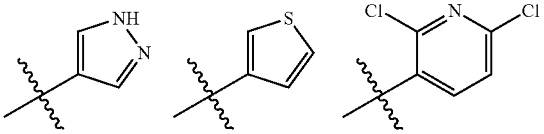
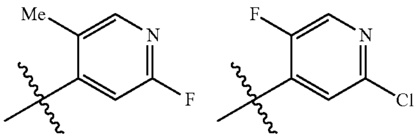
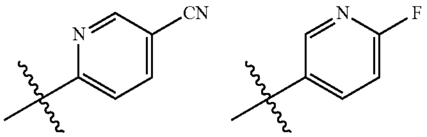

-continued
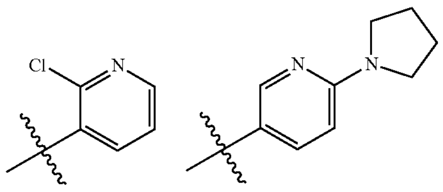
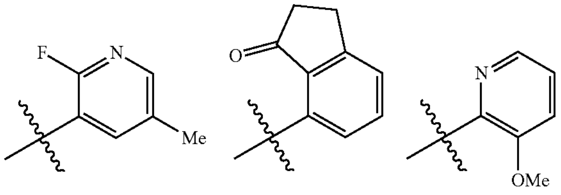
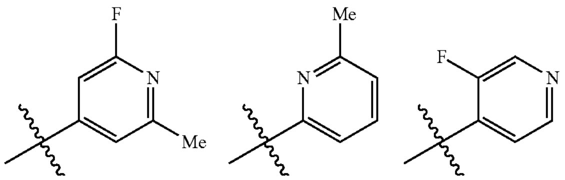
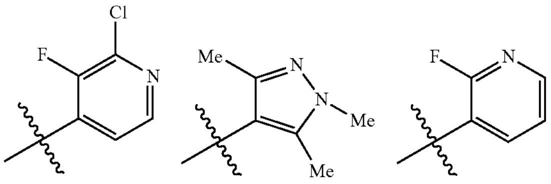
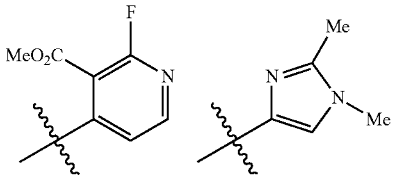
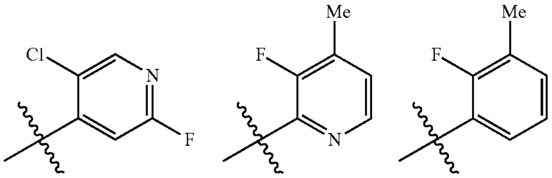
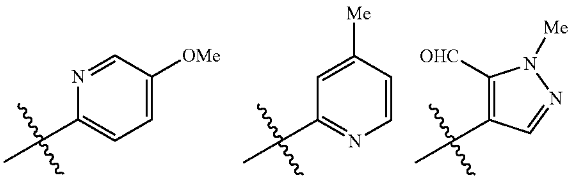
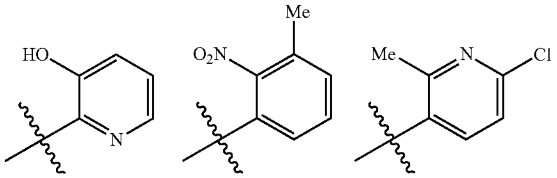
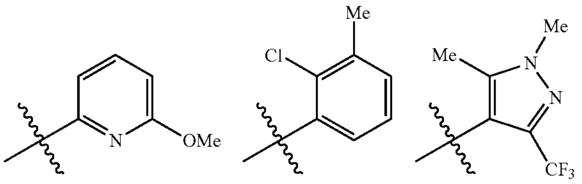
-continued
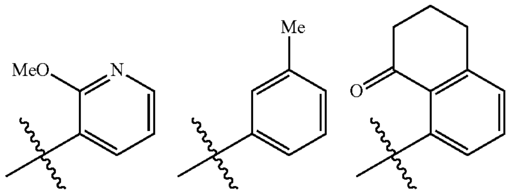
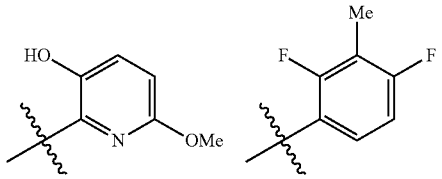
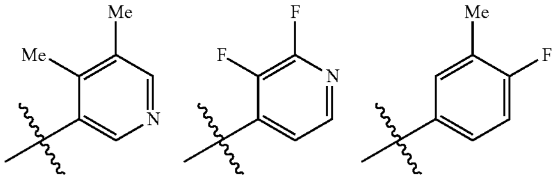
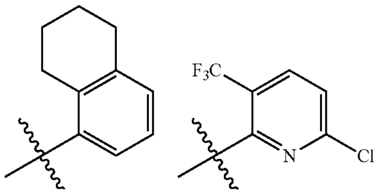
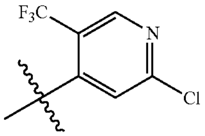
wherein $R^4$ in (IS) is selected from the group consisting of
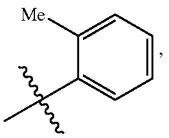 [SMILES: *c1ccccc1C]
wherein $R^4$ in (IT) is selected from the group consisting of:
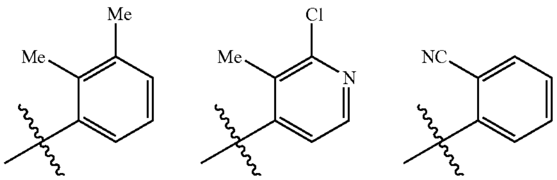
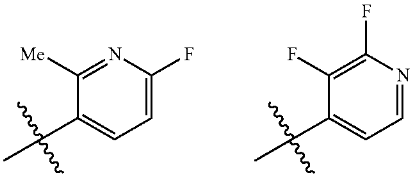

-continued
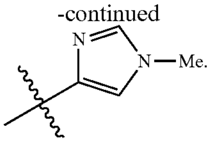
13. The compound of claim 1, wherein the compound of formula (I) is a compound of formula (IU), (IV), (IW), (IX), or (IY)
(IU)
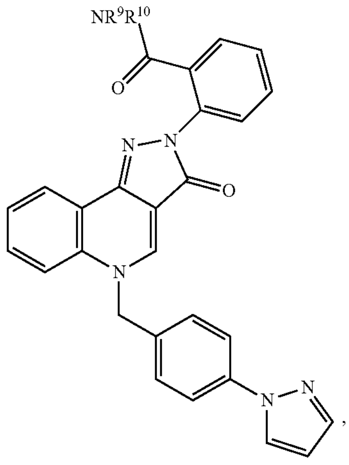
(IV)
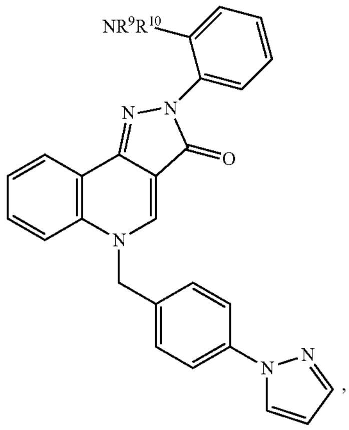
(IW)
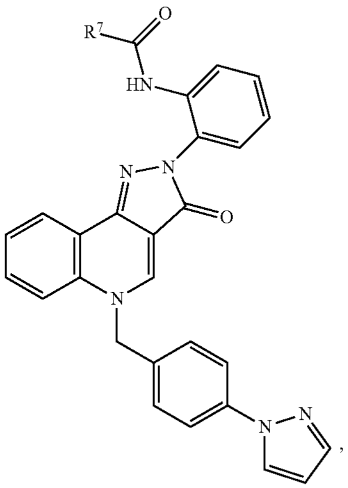
-continued
(IX)
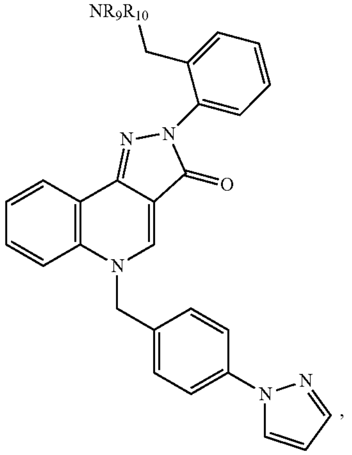
(IY)
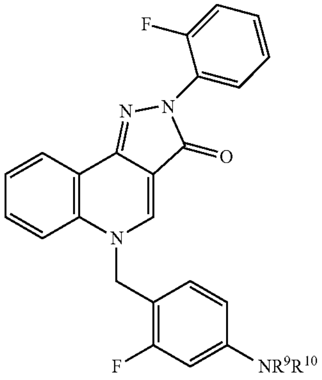
or a pharmaceutically acceptable salt thereof,
wherein $NR^9R^{10}$ in (IU) is selected from the group consisting of
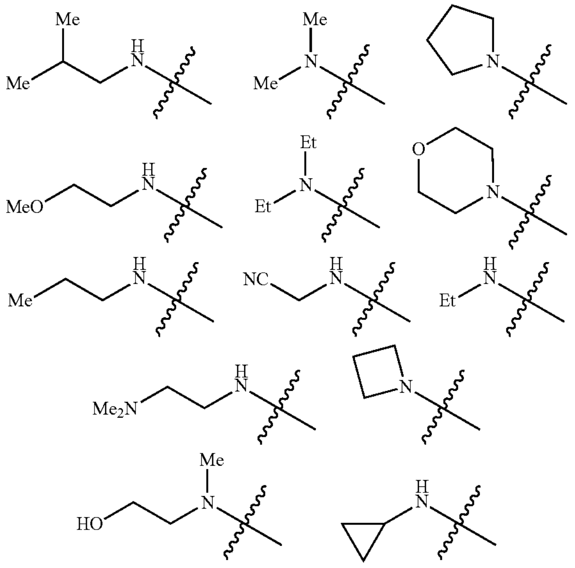

wherein $NR^9R^{10}$ in (IV) is selected from the group consisting of:
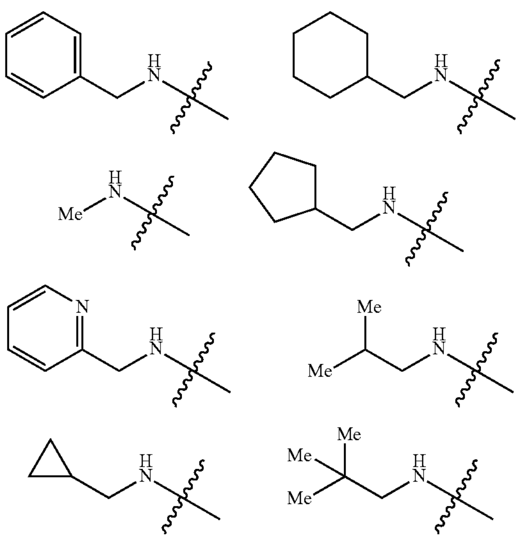
wherein $R^7$ in (IW) is selected from the group consisting of
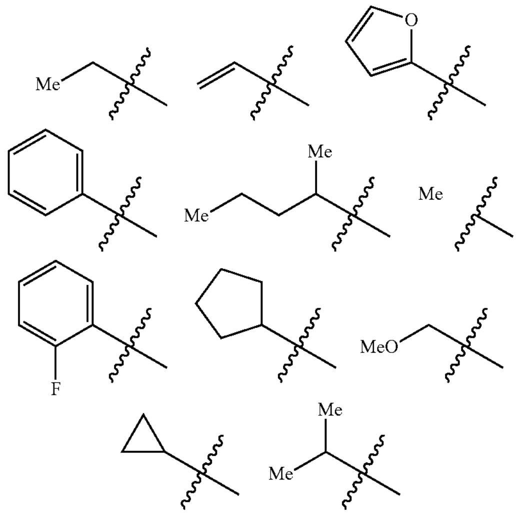
wherein $NR^9R^{10}$ in (IX) is selected from the group consisting of
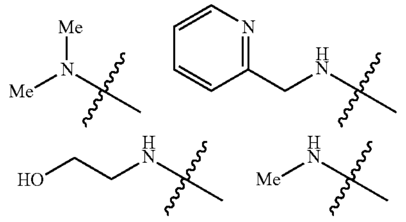
wherein $NR^9R^{10}$ in (IY) is selected from the group consisting of
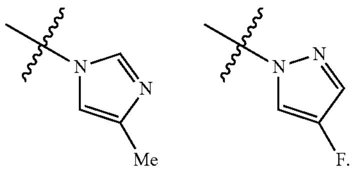 [SMILES: *n1cnc(C)c1 ; *n1cc(F)cn1]
14. A compound represented by structural formula (IZ), (IAA), (IBB), or (IDD)
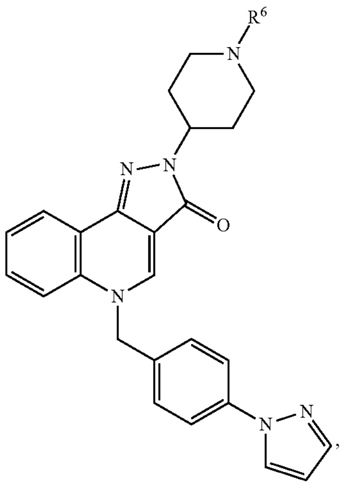
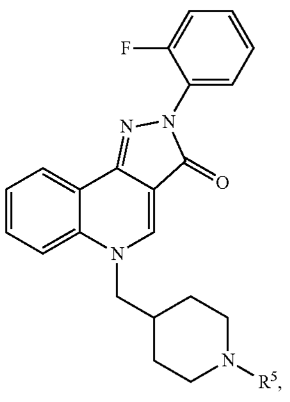
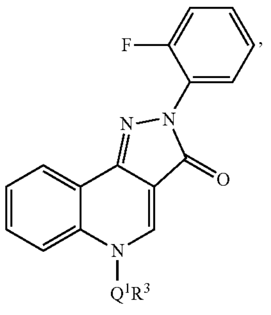

-continued

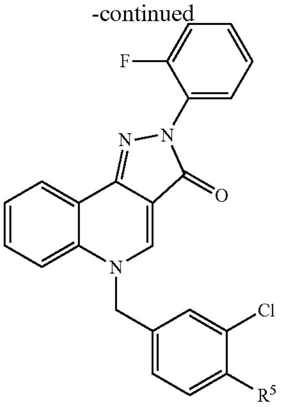

or a pharmaceutically acceptable salt thereof, (IZ) (IAA) (IBB) (IDD)

wherein $R^6$ in (IZ) is selected from the group consisting of

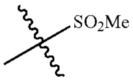
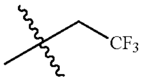
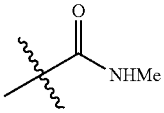
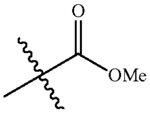

wherein $R^5$ in (IAA) is selected from the group consisting of

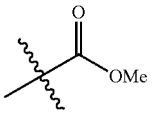
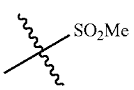
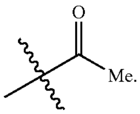

wherein $Q^1R^3$ in (IBB) is selected from the group consisting of

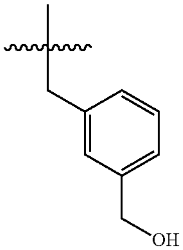
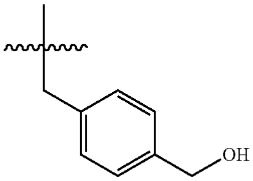

wherein $R^5$ in (IDD) is selected from the group consisting of

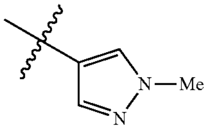
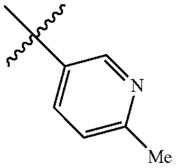
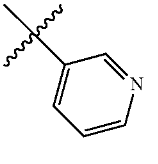
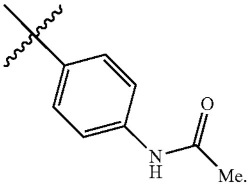

15. A compound of claim 1, wherein the compound of formula (I) is a compound of formula (IFF), (IGG), (IHH), (IJJ)

(IGG)

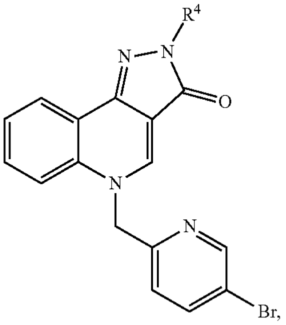

(IHH)

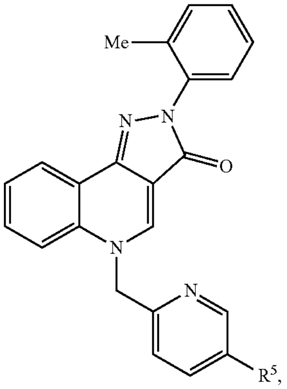

(IJJ)

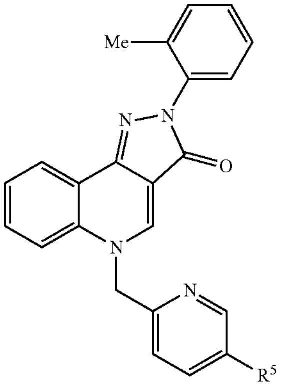

or a pharmaceutically acceptable salt thereof, wherein $R^4$ in (IGG) is selected from the group consisting of

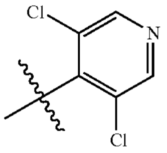 [SMILES: *c1c(Cl)cncc1Cl]

wherein $R^5$ in (IHH) is selected from the group consisting of

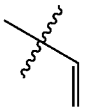
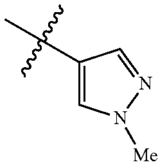
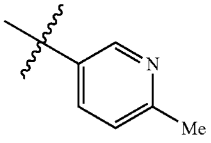

and wherein $R^5$ in (IJJ) is selected from the group consisting of Et, and CN.

16. A compound represented by structural formula (IKK), (ILL), (IMM)

(IKK)

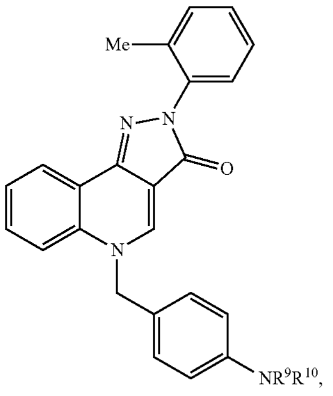

(ILL)

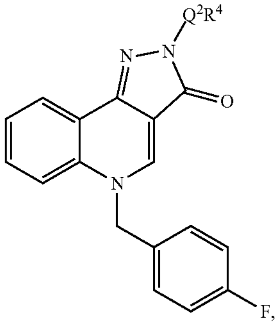

-continued (IMM)

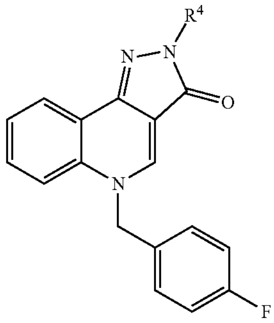

or a pharmaceutically acceptable salt thereof, wherein $NR^9R^{10}$ in (IKK) is selected from the group consisting of $NHSO_2Ph$, NHCOMe, NHCOPh, and $N(SO_2Me)_2$, wherein $Q^2R^4$ in (ILL) is selected from the group consisting of

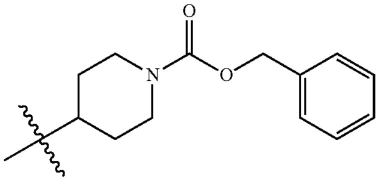
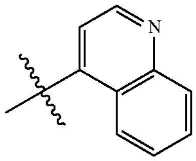
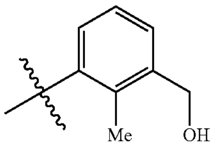
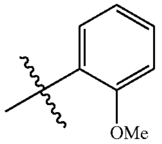
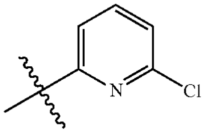
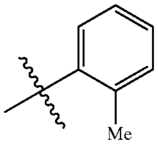
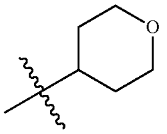
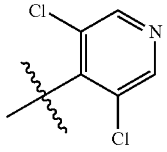
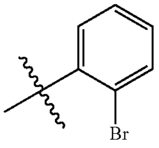

wherein $R^4$ in (IMM) is selected from the group consisting of

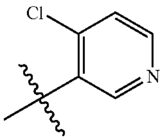
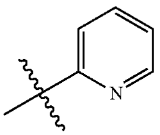
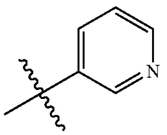

-continued
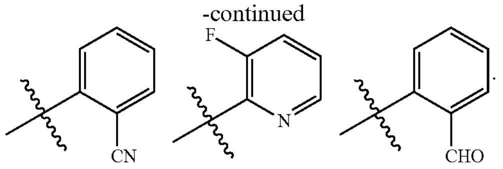
17. A pharmaceutical composition comprising a therapeutically effective amount of a compound of claim 1, or a pharmaceutically acceptable salt thereof, and a pharmaceutically acceptable carrier.
* * * * *